United States Patent [19]

Mori et al.

[11] Patent Number: 4,902,811
[45] Date of Patent: Feb. 20, 1990

[54] BENZODIOXANE PROSTACYCLIN ANALOGS

[75] Inventors: Sachio Mori; Shozo Takechi, both of Hyogo, Japan

[73] Assignee: Shionogi & Co., Ltd., Osaka, Japan

[21] Appl. No.: 208,728

[22] Filed: Jun. 20, 1988

[30] Foreign Application Priority Data

Jul. 1, 1987 [JP] Japan .................. 62-164288

[51] Int. Cl.$^4$ ............................ C07D 319/14
[52] U.S. Cl. ...................... 549/359; 549/214
[58] Field of Search ....................... 549/359, 214

[56] References Cited

FOREIGN PATENT DOCUMENTS 88619 9/1983 European Pat. Off. .
159784 10/1985 European Pat. Off. .

Primary Examiner—Nicky Chan
Attorney, Agent, or Firm—Wenderoth, Lind & Ponack

[57] ABSTRACT

Benzodioxane prostacyclin analogs represented by the formula:

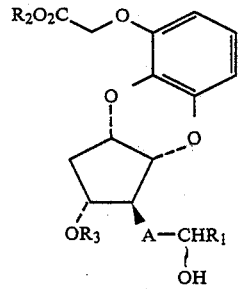

wherein $R_1$ is alkyl, alkenyl, alkynyl, cycloalkyl, cycloalkylalkyl, or phenoxyalkyl; $R_2$ is hydrogen, lower alkyl, or aralkyl; $R_3$ is hydrogen or a protecting group; A is ethylene or vinylene; and the wavy line indicates α or β configuration or their mixture; or a salt thereof having an antiulcer activity and platelet aggregation inhibitory activity.

9 Claims, No Drawings

BENZODIOXANE PROSTACYCLIN ANALOGS

Background of the Invention

(1) Field of the Invention

The compounds of the present invention are related to novel benzodioxane prostacyclin analogues and intermediates thereof. In more detail, this invention relates to the compounds represented by the general formula (I) or the salts thereof, which have prostacyclin (prostaglandin $I_2$; prostaglandin is abbreviated to PG hereinafter) like antiulcer activity and platelet aggregation inhibitory activity, and the intermediate thereof.

General formula:

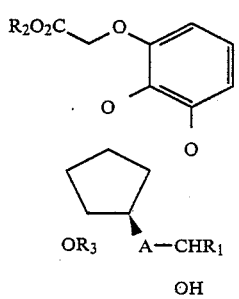

(wherein $R_1$ is alkyl, alkenyl, alkynyl, cycloalkyl, cycloalkylalkyl, or phenoxyalkyl; $R_2$ is hydrogen, lower alkyl or aralkyl; $R_3$ is hydrogen or a protecting group; A is ethylene or vinylene; the wavy line indicates α or β configuration or their mixture)

(2) Prior Art

It is said that a peptic ulcer is formed by the action of gastric juice on the weak part of gastric mucosa which is generated by local nutrition disorder. Though the origin of peptic ulcers is uncertain, it is thought that various factors such as local factor (e.g., mechanical stimulation, chemical stimulation, gastric juice digestion, gastritis, gastric mucous parasecretion) and systemic factor (e.g., stress, neurovegetative disease, cryptorrhea, systemic cacotrophy, allergy, anomalous constitution) are responsible. Such idea is summarized in the Shay's theory, concerning balance between aggressive and defensive factors, that postulates ulceration is induced by the imbalance between mucous aggressive factor (e.g., supersecretion of hydrochloric acid, pepsin, or gastrin, vagotonia, increasing of number of gastric parietal cells, or Zollinger-Ellison syndrome) and mucous defensive factor (e.g., gastric mucosal barrier, mucosal resistance, hyposecretion of duodenal gastric juice). Therefore, a ulcer is treated by such a method that the mucous defensive factor is activated and the mucosa is protected from aggressive factor. In the pharmacotherapy of ulcers the medication has been by the administration of, for example, (1) tranquilizer, (2) parasympatholytic, (3) antacid, (4) antipepsin, (5) antigastrin, (6) gastric mucosa protectant (e.g., mucin preparation) or (7) gastric anagenetic accelerator.

Since Robert et al., found that PG $E_2$, PG $I_2$ and the like inhibited acid secretion and/or had cytoprotection effect, these PGs or their derivatives have been noted because they may be useful for the medication of peptic ulcers.

As PG $I_2$ analogues having antiulcer activity, such compounds as nileprost (U.S. Pat. No. 4,219,479), Hoe-892 (S. J. Konturek et al., Prostaglandins, 28, 443, (1984)), U-68215 (A. Robert et al., Prostaglandins, 30, 619, (1985)) and compounds disclosed in JP Kokai 83-164585 are cited.

After being discovered as a new arachidonic acid metabolite, PG $I_2$ has caught considerable attention because of its various interesting biological activity, e.g., gastric mucosa protective activity (gastric antisecretory and cytoprotective effect), platelet aggregation inhibition, vasodilation or broncosmooth muscle relaxation or the like.

It is thought that the acid hyposecretive or cytoprotective action of PG $I_2$ (mucous secretion, supersecretion, stabilization of membrane, maintenance of sodium pomp, bicarbonate ion secretion, increasing of gastric mucosal blood flow or the like) protects the gastric mucosa from various aggressive factors.

However, the naturally occurring PG $I_2$ has some problems, that is, (1) inactiveness in oral administration and a short duration of action when administered parenterally because of rapid metabolism (2) incidence of numerous side effects and (3) chemical instability. PG $I_2$ analogues which are fully satisfactory as antiulcer agent have not been developed yet.

SUMMARY

The invention provides benzodioxane prostacyclin analogues represented by the formula (I):

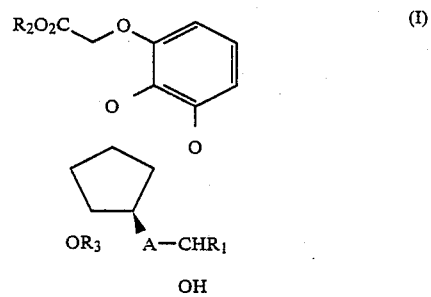

wherein $R_1$ is alkyl, alkenyl, alkynyl, cycloalkyl, cycloalkylalkyl or phenoxyalkyl; $R_2$ is hydrogen, lower alkyl or aralkyl; $R_3$ is hydrogen or a protecting group; A is ethylene or vinylene; the wavy line indicates α or β configuration or their mixture; or a salt thereof. Said compounds have antiulcer and platelet aggregation inhibitory activities.

DESCRIPTION OF THE PREFERRED EMBODIMENTS

The present invention conducted an investigation to resolve these problems and prepared the benzodioxane prostacyclin analogues represented by the formula (I). They found that the novel compounds had potent protective effect for gastric mucosa and were chemically stable and long acting, and completed the invention.

The following definitions are given for various terms used throughout this specification.

The term "lower alkyl" refers to straight or branched $C_1$ to $C_6$ alkyl, e.g., methyl, ethyl, propyl, isopropyl, butyl, isobutyl, tert-butyl, pentyl, and hexyl.

The term "alkyl" refers to straight or branched $C_1$ to $C_{10}$ alkyl, e.g., methyl, ethyl, propyl, isopropyl, butyl, isobutyl, tert-butyl, pentyl, 1-methylpentyl, 1,1-dimethylpentyl, 2-methylpentyl, hexyl, 1-methylhexyl, 1,1-dimethylhexyl, 2-methylhexyl, heptyl, octyl, nonyl, and decyl.

The term "alkenyl" refers to straight or branched $C_2$ to $C_{10}$ alkenyl, e.g., vinyl, 1-propenyl, 2-propenyl, 2-butyl-2-propenyl, 1-butenyl, 2-butenyl, 2-pentenyl, 1-methyl-3-pentenyl, 3-hexenyl, 2-methyl-5-hexenyl, 2,6-dimethyl-5-heptenyl, 3-octenyl, and 3-nonyl.

The term "alkynyl" refers to straight or branched $C_2$ to $C_{10}$ alkynyl, e.g., ethynyl, 1-propynyl, 2-propynyl, 1-butynyl, 2-butynyl, 2-pentynyl, 2-methyl-3-pentynyl, 3-hexynyl, 2-methyl-5-heptynyl, 3-octynyl, and 3-nonynyl.

The term "cycloalkyl" refers to $C_3$ to $C_8$ cycloalkyl, e.g., cyclopropyl, cyclobutyl, cyclopentyl, cyclohexyl, cycloheptyl, and cyclooctyl.

The term "cycloalkylalkyl" refers to lower alkyl substituted by $C_3$ to $C_8$ cycloalkyl, e.g., cyclopropylmethyl, cyclobutylmethyl, cyclopentylmethyl, cyclopentylethyl, cyclohexylmethyl, cyclohexylethyl, cycloheptylmethyl, and cyclooctylmethyl.

The term "phenoxyalkyl" refers to lower alkyl substituted by phenoxy, e.g., phenoxymethyl, phenoxyethyl, 1-phenoxypropyl, 2-phenoxypropyl, 1-phenoxy-2-methylpropyl, 1-phenoxybutyl, 2-phenoxybutyl, 1-phenoxypentyl, 1-phenoxyhexyl, 1-phenoxyheptyl, and 1-phenoxyoctyl.

The term "aralkyl" refers to lower alkyl substituted by aryl, e.g., benzyl, substituted benzyl (2,4,6-trimethylbenzyl, 4-bromobenzyl, 4-methoxybenzyl or the like), diphenylmethyl, triphenylmethyl, bis(2-nitrophenyl)methyl or 9-anthrylmethyl.

In the general formula (I), especially preferably $R_1$ is alkyl (e.g., pentyl, 1-methylpentyl, 1,1-dimethylpentyl, 2-methylhexyl), alkenyl (e.g., 2,6-dimethyl-5-heptenyl, 2-methyl-5-hexenyl, 2-butyl-2-propenyl), alkynyl (e.g., 1-methyl-3-pentynyl, 3-hexynyl), cycloalkyl (e.g., cyclopentyl, cyclohexyl) or cycloalkylalkyl (e.g., cyclohexylmethyl), phenoxyalkyl (e.g., phenoxy-2-propyl, phenoxy-2-methylpropyl). Especially preferable $R_2$ is hydrogen, lower alkyl (e.g., methyl) or aralkyl (e.g., 9-anthrylmethyl). Especially preferable $R_3$ is hydrogen or ordinarily used protecting group (e.g., trimethylsilyl, tert-butyldimethylsilyl or tert-butyldiphenylsilyl). Especially preferable A is ethylene or vinylene (trans).

The salts which may be formed when $R_2$ is hydrogen in the general formula (I) include, for example, salts with alkali metal (e.g., lithium, sodium, potassium), salts with alkaline earth metal (e.g., calcium), ammonium salts, salts with organic base (e.g., triethylamine, N-methylmorpholine, dicyclohexylamine, pyridine, trimethylamine), or amino acid (e.g., glycine, valine, alanine).

Illustrative compounds (I) of the present invention are as follows:

[2-hydroxy-1-(3-hydroxy-1-octenyl)-2,3,3a,9a-tetrahydro-1H-cyclopenta[b][1,4]benzodioxin-5-yl]oxyacetic acid,

[2-hydroxy-1-(3-cyclohexyl-3-hydroxy-1-propenyl)-2,3,3a,9a-tetrahydro-1H-cyclopenta[b][1,4]benzodioxin-5-yl]oxyacetic acid,

[2-hydroxy-1-(3-hydroxy-1-nonen-6-ynyl)-2,3,3a,9a-tetrahydro-1-H-cyclopenta[b][1,4]benzodioxin-5-yl]oxyacetic acid,

[2-hydroxy-1-(3-hydroxy-5-methyl-1-nonenyl)-2,3,3a,9a-tetrahydro-1H-cyclopenta[b][1,4]benzodioxin-5-yl]oxyacetic acid,

[2-hydroxy-1-(3-hydroxy-4-methyl-1-octenyl)-2,3,3a,9a-tetrahydro-1H-cyclopenta[b][1,4]benzodioxin-5-yl]oxyacetic acid,

[2-hydroxy-1-(3-hydroxy-4,4-dimethyl-1-octenyl)-2,3,3a,9a-tetrahydro-1H-cyclopenta[b][1,4]benzodioxin-5-yl]oxyacetic acid,

[2-hydroxy-1-(3-hydroxy-4-methyl-1-octen-6-ynyl)-2,3,3a,9a-tetrahydro-1H-cyclopenta[b][1,4]benzodioxin-5-yl]oxyacetic acid,

[2-hydroxy-1-(3-cyclopentyl-3-hydroxy-1-propenyl)-2,3,3a,9a-tetrahydro-1H-cyclopenta[b][1,4]benzodioxin-5-yl]oxyacetic acid,

[2-hydroxy-1-(4-cyclohexyl-3-hydroxy-1-butenyl)-2,3,3a,9a-tetrahydro-1H-cyclopenta[b][1,4]benzodioxin-5-yl]oxyacetic acid,

[2-hydroxy-1-(3-hydroxy-5,9-dimethyl-1,8-decadienyl)-2,3,3a,9a-tetrahydro-1H-cyclopenta[b][1,4]benzodioxin-5-yl]oxyacetic acid,

[2-hydroxy-1-(3-hydroxy-5-phenoxy-1-hexenyl)-2,3,3a,9a-tetrahydro-1H-cyclopenta[b][1,4]benzodioxin-5-yl]oxyacetic acid,

[2-hydroxy-1-(3-hydroxy-5-phenoxymethyl-1-hexenyl)-2,3,3a,9a-tetrahydro-1H-cyclopenta[b][1,4]benzodioxin-5-yl]oxyacetic acid,

[2-hydroxy-1-(3-hydroxy-5-methyl-1,8-nonadienyl)-2,3,3a,9a-tetrahydro-1H-cyclopenta[b][1,4]benzodioxin-5-yl]oxyacetic acid,

[2-hydroxy-1-(5-butyl-3-hydroxy-1,5-hexadienyl)-2,3,3a,9a-tetrahydro-1H-cyclopenta[b][1,4]benzodioxin-5-yl]oxyacetic acid,

[2-hydroxy-1-(3-hydroxyoctyl)-2,3,3a,9a-tetrahydro-1H-cyclopenta[b][1,4]benzodioxin-5-yl]oxyacetic acid,

[2-hydroxy-1-(3-cyclohexyl-3-hydroxypropyl)-2,3,3a,9a-tetrahydro-1H-cyclopenta[b][1,4]benzodioxin-5-yl]oxyacetic acid,

[2-hydroxy-1-(3-hydroxy-4-methyloctyl)-2,3,3a,9a-tetrahydro-1H-cyclopenta[b][1,4]benzodioxin-5-yl]oxyacetic acid,

[2-hydroxy-1-(3-cyclopentyl-3-hydroxypropyl)-2,3,3a,9a-tetrahydro-1H-cyclopenta[b][1,4]benzodioxin-5-yl]oxyacetic acid, and

[2-hydroxy-1-(4-cyclohexyl-3-hydroxybutyl)-2,3,3a,9a-tetrahydro-1H-cyclopenta[b][1,4]benzodioxin-5-yl]oxyacetic acid.

The above compounds can be converted into the desired esters or their salts.

The compounds of the present invention are racemates or optically active compounds whose one enantiomer is represented by the general formula (I). Therefore, the present invention includes all of the stereoisomers or their mixture shown by the general formula (I).

The compounds of the present invention can be prepared according to the following scheme.

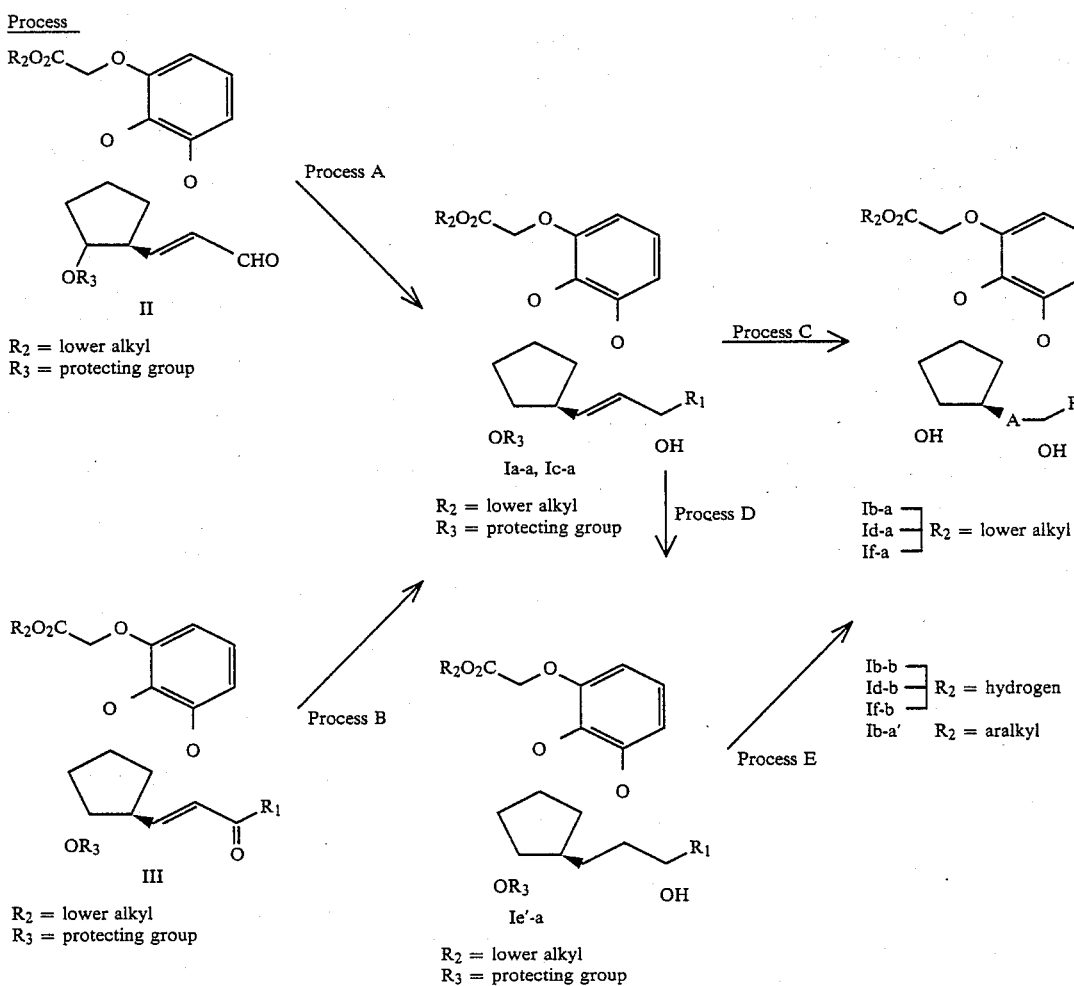

PROCESS A

In this process, the aldehyde II is treated with a Grignard reagent to give the compounds of the present invention Ia-a and Ic-a.

The reaction is carried out in a usual manner of Grignard reaction in an etherial solvent (e.g., diethyl ether, tetrahydrofuran) for a period of several tens of minutes to several hours under cooling. The Grignard reagent used in the reaction is exemplified by a magnesium halide having a desired side chain, such as alkylmagnesium halide (e.g., n-pentyl-magnesium bromide, 1-methylpentylmagnesium bromide, 1,1-dimethylpentylmagnesium chloride, n-hexylmagnesium bromide, 2-methylhexylmagnesium bromide), alkenylmagnesium halide (e.g., 2, 6-dimethyl-5-heptenylmagnesium bromide), alkynylmagnesium halide (e.g., 3-hexynylmagnesium bromide, 1-methyl-3-pentynylmagnesium bromide), cycloalkylmagnesium halide (e.g., cyclopentylmagnesium bromide, cyclohexylmagnesium bromide) or cycloalkylalkylmagnesium halide (e.g., cyclohexylmethylmagnesium bromide).

PROCESS B

In this process, the enone III is reduced to give the unsaturated alcohol Ia-a and Ic-a.

A reducing agent such as aluminium isopropoxide, diisobornyl aluminium isopropoxide, sodium cyanoborohydride, potassium tri-sec-butylborohydride, zinc borohydride, sodium borohydride, a combination of sodium borohydride and cerium (III) chloride, 2,6-di-tert-butyl-4-methylphenoxidodiisobutyl aluminium, lithium hexyllimonylborohydride or BINAL-H [prepared from binaphthol, lithium aluminium hydride and ethanol (J. Am. Chem. Soc., 106,6709, (1984))]can be used.

As a solvent ether (e.g., diethyl ether, tetrahydrofuran), alcohol (e.g., methanol, ethanol), aromatic hydrocarbon (e.g., benzene, toluene) or chlorinated hydrocarbon (e.g., dichloromethane, chloroform) is used alone or as a mixture depending on the reagent used. The reaction is carried out at room temperature or under cooling for several tens of minutes.

When the allyl alcohol thus prepared contains a phenylselenyl moiety, it is subjected to oxidative elimination to give a dienyl alcohol.

The phenylselenyl allyl alcohol is oxidized with ozone, sodium periodate, peroxide (e.g., hydrogen peroxide, peracetic acid, m-chloroperbenzoice acid) or the like to give the selenoxide which is then refluxed in chlorinated hydrocarbon (e.g., carbon tetrachloride, chloroform, dichloromethane), if necessary, in the presence of an amine such as diisopropylamine to give the dienyl alcohol.

The alcohol prepared in this process is a mixture of the epimers.

In this process the compounds Ia-a and Ic-a, the hydroxy protected compounds of the present invention, are prepared.

PROCESS C

In this process, the hydroxy-protecting groups of the compounds Ia—a and Ic-a are removed to give the compound Ib-a and Id-a, respectively.

The reaction can be achieved using a reagent such as acetic acid, hydrochloric acid, p-toluenesulfonic acid, hydrogen fluoride and pyridine, tetrabutylammonium fluoride or the like in a solvent such as alcohol (e.g., methanol, ethanol), ether (e.g., diethyl ether, tetrahydrofuran), acetonitrile or water at room temperature or under heating within a period of several tens of minutes to several hours. In this reaction, the methyl ester of carboxylic acid is sometimes hydrolyzed; in such a case, the resulting carboxylic acid may be esterified, for example, with diazomethane, if necessary.

In this process the compound Ib-a and Id-a, the hydroxy-deprotected compounds of the present invention, are prepared.

PROCESS D

In this process the compound Ia-a is catalytically hydrogenated to give the compound Ie-a.

The hydrogenation is performed at atmospheric pressure or higher pressure in the presence of metal catalyst itself (e.g., palladium, platinum, nickel) or metal catalyst absorbed on a carrier (e.g., active carbon, alumina, barium sulfate, calcium carbonate, strontium carbonate), or nickel boride or rhodium chlorotris(triphenylphosphine).

A solvent such as alcohol (e.g., methanol, ethanol), ether (e.g., diethyl ether, tetrahydrofuran, dioxane) or ester (e.g., ethyl acetate) is used alone or as a mixture.

The reaction is carried out at room temperature for a period of several hours to several tens of hours.

PROCESS E

In this process the hydroxy-protecting group of the compound Ie-a is removed to give the compound If-a.

The reaction can be carried out in the same manner as in Process C.

In this process, the compound If-a, the hydroxy-deprotected compound of the present invention, is prepared.

PROCESS F

In this process, the esters of the carboxylic acids Ib-a, Id-a and If-a are hydrolyzed to give the free carboxylic acids Ib-b, Id-b and If-b, respectively.

The hydrolysis may be carried out in the conventional manner.

In this process, the free carboxylic acids Ib-b, Id-b and If-b, compounds of the present invention, are prepared.

PROCESS G

In this process, the free carboxylic acid Ib-b is esterified to give the compound Ib-a', aralkyl ester of the carboxylic acid.

The esterification is carried out by the following conventional methods, (1) the reaction of a carboxylic acid with an alcohol, (2) the reaction of an acid chloride with an alcohol, (3) the reaction of a carboxylate salt with a halide, (4) the reaction of a carboxylic acid with a diazo compound or the like.

The aralkyl moiety constituting a part of the alcohol, halide or diazo-compound which is used for ester formation includes, for example, benzyl, substituted benzyl (e.g., 2,4,6-trimethylbenzyl, 4-bromobenzyl, 4-methoxybenzyl), diphenylmethyl, triphenylmethyl, bis(2-nitrophenyl)methyl, 9-anthrylmethyl or the like.

The definitions of $R_1$, $R_2$, $R_3$ and A are the same as mentioned above unless special limitation is given.

The wavy line indicates α or β configuration or their mixture.

The starting compound (II) and (III) can be prepared by the methods shown in the following figures.

FIG. 1

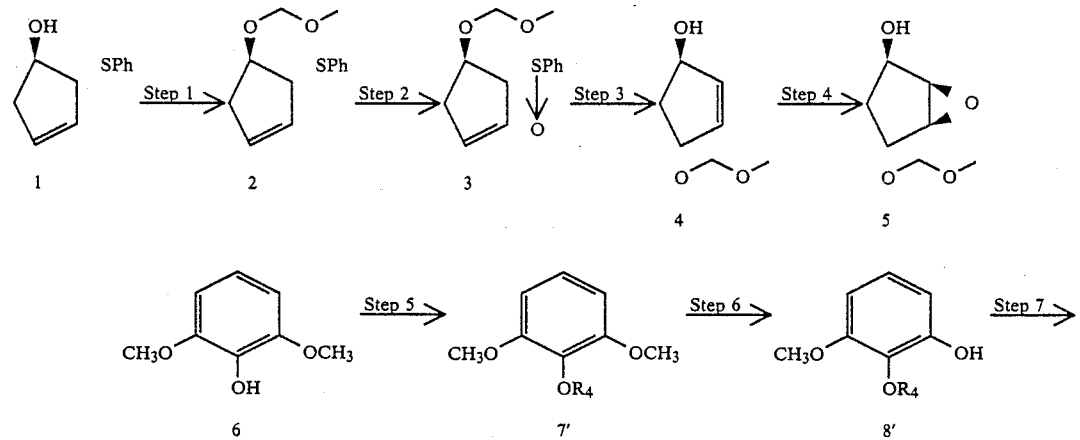

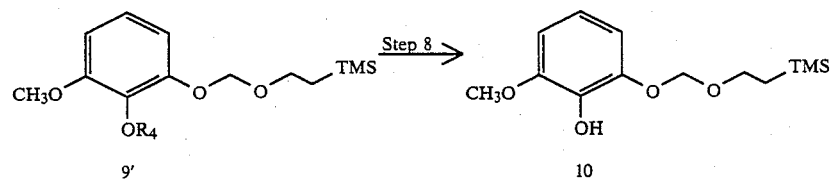
FIG. 2
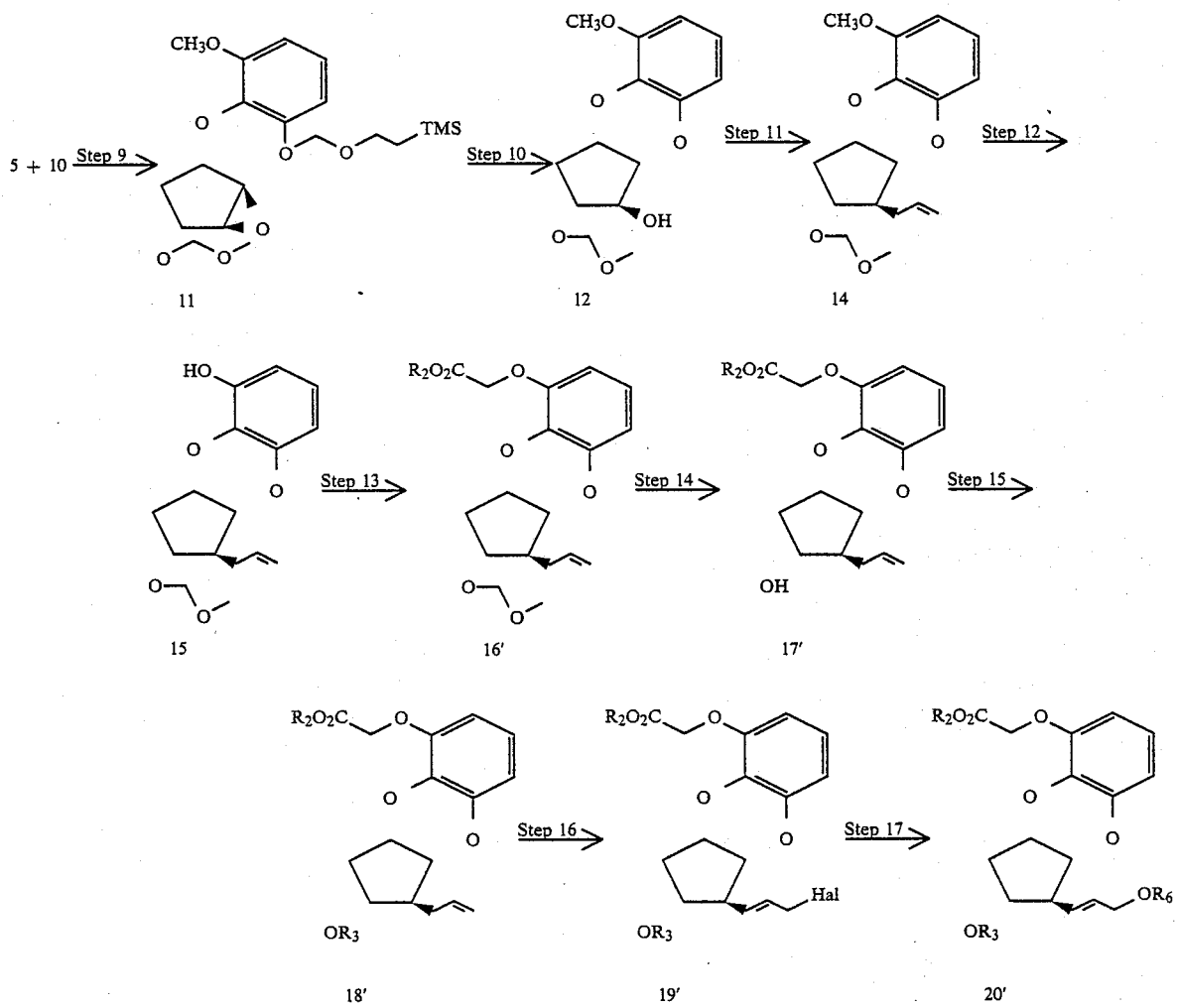
FIG. 3
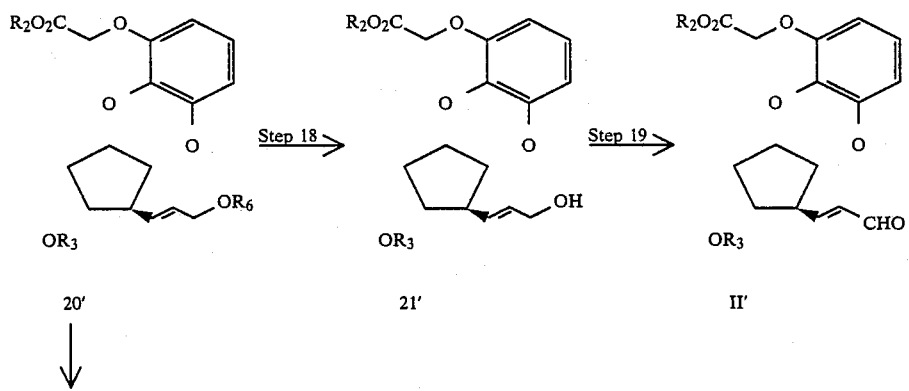

REACTION STEPS

Step 1

In this step, the hydroxy of the compound 1 is alkylated for protection with an alkyl halide in the presence of a base to give the ether 2.

The reaction is carried out using an alkyl halide such as methoxymethyl chloride, methoxymethyl bromide or the like in a solvent such as ether (e.g., dimethyl ether, tetrahydrofuran), chlorinated hydrocarbon (e.g., dichloromethane, chloroform), dimethylsulfoxide or dimethylformamide under cooling or at room temperature for a period of several hours to several tens of hours. As a base, sodium amide, potassium carbonate, triethylamine, diisopropylethylamine, sodium hydroxide, barium oxide, silver oxide, sodium hydride or the like is exemplified.

Step 2

In this step, the sulfide 2 is oxidized to the sulfoxide 3.

The reaction is carried out using an oxidizing agent such as hydrogen peroxide, tert-butyl hydroperoxide, performic acid, peracetic acid, perbenzoic acid, m-chloroperbenzoic acid, p-nitroperbenzoic acid or the like in a solvent such as alcohol (e.g., methanol, ethanol), ether (e.g., diethyl ether, tetrahydrofuran) or chlorinated hydrocarbon (e.g., dichloromethane, chloroform) under cooling for a period of several tens of minutes to several hours.

Step 3

In this step, the sulfoxide 3 is rearranged to the sulfenate ester which is further converted to the alcohol 4 by ester exchange.

In order to facilitate the rearrangement of the sulfoxide 3 into the sulfenate ester, a reagent such as phosphine (e.g., triphenylphosphine) or phosphate (e.g., trimethylphosphate, triethylphosphate) is used.

The reaction is carried out in a mixed solvent such as aromatic hydrocarbon (e.g., benzene, toluene) and alcohol (e.g., methanol, ethanol) under heating for several tens of hours.

Step 4

In this step, the double bond of the compound 4 is oxidized to give the compound 5.

The reaction is carried out using an oxidizing agent such as peroxide (e.g., hydrogen peroxide, tert-butyl hydroperoxide, performic acid, peracetic acid, perbenzoic acid, m-chloroperbenzoic acid, p-nitroperbenzoic acid) in a solvent such as alcohol (e.g., methanol, ethanol), ether (e.g., diethyl ether, tetrahydrofuran) or chlorinated hydrocarbon (e.g., dichloromethane, chloroform) under cooling for a period of several tens of minutes to several hours.

Step 5

In this step, the hydroxy group of the compound 6 is protected.

As a compound which is used for protection, methanesulfonyl chloride, p-toluenesulfonyl chloride or the like is exemplified. The reaction is carried out in the presence of a base such as sodium hydroxide, triethylamine, pyridine or the like in a solvent such as ether (e.g., diethyl ether, tetrahydrofuran), chlorinated hydrocarbon (e.g., dichloromethane, chloroform), dimethylsulfoxide or dimethylformamide under cooling for a period of several tens of minutes to several hours.

Step 6

In this step, the methyl group of the compound 7' is removed to give the compound 8'.

The reaction is carried out using a boron trichloride or boron tribromide in a solvent such as chlorinated hydrocarbon (e.g., dichloromethane, chloroform) under cooling for a period of several tens of minutes to several hours.

There are some other methods, for example, oxidation of the methyl ether with chromium trioxide-acetic acid to the formate ester, which is followed by hydrolysis to give the phenol; or a method by of heating with hydroiodic acid or hydrobromic acid.

Step 7

In this step, the hydroxy group of the compound 8' is alkylated for protection with an alkyl halide in the presence of a base to give the ether 9'.

As an alkyl halide, (2-trimethylsilyl)ethoxymethyl chloride or (2-trimethylsilyl)ethoxymethyl bromide is used. The reaction is carried out in the same manner as in Step 1.

Step 8

In this step, the sulfonate ester 9' is converted into the phenol 10.

The reaction is carried out by, first, preparing a metal adduct using a nucleophilic reagent such as alkyllithium (e.g., methyllithium, ethyllithium, isopropyllithium, n-butyllithium), alkylmagnesium halide (Grignard reagent) (e.g., methylmagnesium bromide, ethylmagensium bromide, isopropylmagensium bromide, n-butylmagnesium bromide) or the like in an ether solvent such as diethyl ether, or tertrahydrofuran under cooling for a period of several tens of minutes to several hours and then decomposing the resulting metal adduct with water.

Step 9

In this step, the compound 5 and the compound 10 are condensed.

The reaction is carried out by reacting the compound 5 with the acidic compound 10 in the presence of triphenylphosphine and diethyl azodicarboxylate under cooling or at room temperature for a period of several tens of minutes to several days. A dry solvent such as aromatic hydrocarbon (e.g., benzene), chlorinated hydrocarbon (e.g., dichloromethane, chloroform) or ether (e.g., diethyl ether, tetrahydrofuran) is used.

Step 10

In this step, the hydroxy-protecting group of the compound 11 is removed to give the compound 12.

The reaction is carried out in a conventional manner for removing the hydroxy-protecting group, for example, using a reagent such as hydrogen fluoride-pyridine or tetrabutylammonium fluoride in a solvent such as ether (e.g., diethyl ether, tetrahydrofuran) at room temperature or under heating for a period of several hours to several days. When the hydroxy-protecting group of the compound 11 is removed, cyclization to the compound 12 occurs spontaneously.

Step 11

In this step, the hydroxy group of the compound 12 is allylated to give the compound 14.

This step can be carried out by the method as described in Tetrahedron, 41, 4079-4094 (1985). First, the compound 12 is converted into the precursor of a carbon radical such as thioacyl derivative, and then, the precursor is irradiated in the presence of allyl stannane such as allyl-tri-n-butyl stannane.

The acylation is carried out using phenyl chlorothionocarbonate, diimidazole thionocarbonate or carbon disulfide-methyl iodide in a solvent such as ether (e.g., diethyl ether, tetrahydrofuran) in the presence of a base such as methyl lithium, n-butyl lithium or the like.

The photo-reaction is carried out by irradiation in an argon atmosphere using a 450 W high pressure mercury lamp equipped with a pyrex filter for a period of several hours to several tens of hours. A solvent such as aromatic hydrocarbon (e.g., benzene, toluene) or ester (e.g., ethyl acetate) is used alone or as a mixture.

Step 12

In this step, the methyl ether 14 is demethylated to give the compound 15.

As a reagent, a metal salt (e.g., lithium, sodium) of thiol such as lithium methylthiolate, sodium ethylthiolate, lithium n-propylthiolate, lithium n-butylthiolate or the like is exemplified. The reaction is carried out in an aprotic polar solvent such as dimethylformamide, hexamethylphosphoric triamide, dimethylsulfoxide for a period of several tens of minutes to several hours.

Step 13

In this step, the compound 15 is alkylated with an alkyl halide in the presence of a base to give the compound 16'.

An alkyl halide such as methyl bromoacetate or methyl iodoacetate is used for the reaction.

This step can be carried out in the same manner as in Step 1.

Step 14

In this step, the hydroxy-protecting group of the compound 16' is removed to give the compound 17'.

As a reagent, a combination of a Lewis acid and sulfide, or thiol is used. As the Lewis acid, boron trifluoride diethyl etherate, aluminium chloride, aluminium bromide or the like is exemplified. As the sulfide, dimethylsulfide, diethylsulfide diphenylsulfide or the like, and as the thiol, methanethiol, ethanethiol, benzenethiol or the like are respectively exemplified. The reaction is carried out at $-10°$ C. or at room temperature in a chlorinated hydrocarbon such as dichloromethane or chloroform.

This step can also be achieved by hydrolysis with an acidic catalyst (e.g., hydrochloric acid, acetic acid).

Step 15

In this step, the hydroxy group of the compound 17' is protected from the subsequent reactions.

The reaction is achieved using a tert-butyldimethylsilyl chloride, tert-butyldiphenylsilyl chloride, trimethylsilyl chloride or the like in the presence of a base such as triethylamine, pyridine, 4-dimethylaminopyridine, imidazole or the like at room temperature or under warming within a period of several hours to several days. As a solvent aromatic hydrocarbon (e.g., benzene, toluene), chlorinated hydrocarbon (e.g., chloroform, dichloromethane) or dimethylformamide is exemplified. Alternatively, the reacton may be achieved by treatment with dihydropyran at room temperature in the presence of an acidic cataylst such as p-toluenesulfonic acid, pyridinium p-toluenesulfonate, Amberlyst 15 (Rohm & Hass Co.) or the like. A solvent such as ether (e.g., diethyl ether, tetrahydrofuran), hydrocarbon (e.g., hexane), aromatic hydrocarbon (e.g., benzene, toluene) or chlorinated hydrocarbon (e.g., chloroform, dichloromehane) is used.

Step 16

In this step, the compound 18' is subjected to halogenation involving double bond migration to give the compound 19'.

This step can be carried out in the same manner as described in Tetrahedron Letters, 44, 3909-3912, (1977).

The compound 18' is allowed to react with phenylselenenyl chloride or phenylselenenyl bromide in carbon tetrachloride under cooling for several tens of minutes to give an anti-Markovnikov adduct. The adducts is oxidized with hydrogen peroxide containing pyridine under cooling or at room temperature for several hours to give the compound 19'.

Step 17

In this step, the compound 19' is subjected to substitution using a carboxylate salt to give the compound 20'.

As a carboxylate salt, a sodium or cesium salt of acetic acid, trifluoroacetic acid, chloroacetic acid, methoxyacetic acid, phenoxyacetic acid or benzoic acid is exemplified.

The reaction is carried out in a non-polar solvent such as aromatic hydrocarbon (e.g., benzene, toluene), or a polar solvent such as dimethylformamide, hexamethylphosphoramide, dimethylsulfoxide or the like under heating for a period of several hours to several tens of hours. When a nonpolar solvent is used in order to promote the reaction, a crown ether like phase-transfer catalyst such as 18-crown-6 may be added.

Step 18

In this step, the ester 20' is hydrolyzed to give the alcohol 21'.

The reaction is carried out in a conventional manner of ester hydrolysis. A catalyst such as acid (e.g., hydrochloric acid, sulfuric acid) or base (e.g., sodium hydroxide, potassium hydroxide, barium hydroxide) is used. As a solvent, alcohol (e.g., methanol, ethanol), chlorinated hydrocarbon (e.g., dichloromethane, chloroform) or water is used as a mixture, if necessary.

If the methyl ester is hydrolyzed to the free carboxylic acid during this hydrolysis step, it may be esterified with an esterifing reagent such as diazomethane.

Step 19

In this step, the alcohol 21' is oxidized into the aldehyde II'.

The reaction is achieved by using an oxidizing agent such as chromate (e.g., Collins' reagent, pyridinium chlorochromate, pyridinium dichlorochromate) or dimethylsulfoxide and oxalyl chloride, sulfuryl chloride, or pyridinium sulfur trioxide combined with a base such as triethylamine, 4-dimethylaminopyridine or the like. The reaction is achieved in a solvent such as aromatic hydrocarbon (e.g., benzene), chlorinated hydrocarbon (e.g., chloroform, dichloromethane), ether (e.g., diethyl ether) or acetone under cooling to warming for a period of several tens of minutes to several hours.

Step 20

In this step, the compound 20' is oxidized into the glycol 22'.

As an oxidizing agent, an aqueous solution of alkaline potassium permanganate, osmium tetroxide or the like is exemplified. When an aqueous solution of alkaline potassium permanganate is used, the reaction is preferably carried out by removing the resulting hydroxy anion by magnesium sulfate or the like. When osmium tetroxide is used, an amine such as pyridine is added in order to promote the formation of the cyclic osmium ester, which may be treated with sodium sulfite, sodium hydrogensulfite or the like. As a solvent used in these reactions alcohol (e.g., methanol, ethanol, propanol, tert-butyl alcohol), ether (e.g., diethyl ether, tetrahydrofuran, dioxane), aromatic hydrocarbon (e.g., benzene), chlorinated hydrocarbon (e.g., dichloromethane, chloroform, carbon tetrachloride), acetone or ethyl acetate is used depending on the property of the oxidizing agent. The reaction is carried out at room temperature for a period of several hours to several days.

Step 21

In this step, the glycol 22' is oxidatively cleaved into the aldehyde 23'.

As an oxidizing agent, periodate (e.g., sodium periodate, potassium periodate) or lead tetraacetate is used. When a periodate is used as an oxidizing agent, an aqueous solvent, i.e. an organic solvent such as alcohol (e.g., methanol, ethanol), ether (e.g., diethyl ether, tetrahydrofuran, dioxane) mixed with water, is used. When lead tetraacetate is used as an oxidizing agent, aromatic hydrocarbon (e.g., benzene) is used as a solvent, and if necessary, an acid such as trichloroacetic acid may be added as a catalyst. The reaction is carried out at room temperature for a period of several tens of minutes to several hours.

Step 22

In this step, the aldehyde 23' is allowed to react with an phosphonate to give the unsaturated ketone III.

The reaction is carried out by a general procedure of Horner-Wadsworth-Emmons reaction using a base such as sodium hydride, sodium amide or the like in a solvent such as 1,2-dimethoxyethane, tetrahydrofuran or the like.

As a phosphonate used in this reaction, one having a desired side chain, namely, dimethyl 2-oxoheptylphosphonate, dimethyl 2-oxo-3-methylheptylphosphonate, dimethyl 2-oxo-3,3-dimethylheptylphosphonate, dimethyl 2-oxo-4-methyloctylphosphonate, dimethyl 2-oxo-4,8-dimethyl-7-nonenylphosphonate, dimethyl 2-oxo-3-methyl-5-heptynylphosphonate, dimethyl 2-oxo-5-octynylphosphonate, dimethyl 2-oxo-2-cyclopentylethylphosphonate, dimethyl 2-oxo-2-cyclohexylethylphosphonate, dimethyl 2-oxo-4-phenoxypentylphosphonate, dimethyl (S)-(-)-2-oxo-4-methyl-7-octenylphosphonate, dimethyl 2-oxo-4-(phenoxymethyl)pentylphosphonate, dimethyl 2-oxo-4-(phenylselenylmethyl)octylphosphonate or the like is exemplified.

For example, dimethyl 2-oxo-4-phenoxypentylphosphonate is prepared as follows.

First, 1-O-protected 1,3-butandiol is converted to the corresponding 3-O-phenol ester by reaction using phenol, triphenylphosphine and diethyl azodicarboxylate as described in Step 9. Then, the 1-hydroxy-protecting group is removed and the resulting alcohol is oxidized to the carboxylic acid with a chromate-type oxidizing agent (e.g., Jones reagent) which is followed by esterification. The ester, thus obtained, is treated with anion derived from dimethyl methylphosphonate and base, to give the desired product.

Dimethyl 2-oxo-4-methyl-7-octenylphosphonate is prepared as follows.

Citronellol is oxidized with a chromate-type oxidizing agent (e.g., Jones reagent) to the carboxylic acid which is then esterified to give an ester of citronellic acid. The double bond is converted into an epoxide by a peroxide as described in Step 4. And then, the epoxide is oxidatively cleaved with a periodate to give an aldehyde, which is converted into the olefinic compound by convention Wittig reaction using trimethylphosphonium bromide and a base. The compound thus prepared is condensed with dimethyl methylphosphonate in the presence of base to give the desired compound. When an optically active compound such as (S)-(−)-citronellol is used as a starting material and allowed to react in the same manner, (S)-dimethyl 2-oxo-4-methyl-7-octenylphosphonate is prepared.

Dimethyl 2-oxo-4-(phenoxymethyl)pentylphosphonate can be prepared by condensing methyl 4-phenoxy-3-methylbutanoate with dimethyl methylphosphonate in the presence of base in the same manner as mentioned above.

Dimethyl 2-oxo-4-(phenylselenylmethyl)octylphosphonate is prepared as follows.

2(5H)-furanone is alkylated with lithium di-n-butylcuprate (prepared from copper (I) bromide-dimethyl sulfide complex and n-butyl lithium) in the presence of trimethylsilyl chloride. Then the lactone ring is opened with sodium phenylselenoate, which is prepared by reducing diphenyldiselenide with sodium borohydride in dry dimethylformamide, to give the carboxylic acid, which is then esterified. The resulting ester is condensed with dimethyl methylphosphonate in the presence of a base to prepare the desired compound.

In the reaction scheme, $R_1$, $R_2$, $R_3$, and A are the same as defined above unless limitation is given.

$R_4$ refers to substituted sulfonyl (e.g., methanesulfonyl, p-toluenesulfonyl).

$R_5$ refers to thioacyl (e.g., (methylthio)thiocarbonyl, 1-imidazoylthiocarbonyl, phenoxythiocarbonyl).

$R_6$ refers to alkanoyl (e.g., acetyl, trifluoroacetyl, chloroacetyl, methoxyacetyl, phenoxyacetyl or aroyl (e.g., benzoyl).

Hal refers to halogen (e.g., chlorine, bromine, iodine).

TMS represents trimethylsilyl.

SEM represents (2-trimethylsilyl)ethoxymethyl and Ph represents phenyl.

The following examples are included to explain the present invention in more detail, but these are not intended to limit the scope of the invention.

All the compounds described in the following examples in each step are represented by one enantiomer. The relative or absolute configuration of the racemate is designated by R* and S* or R and S denotations of the compound name, respectively.

The wavy line indicates α or β configuration or their mixture.

PREPARATION OF INTERMEDIATE (1) Preparation of (3R*,4R*)-4-methoxymethoxy-3-phenylthio-1-cyclopentene 2

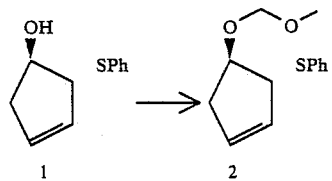

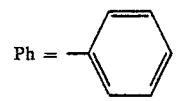

To a solution of 85.0 g (0.443 mol) of alcohol 1 and 109 ml (0.626 mol) of diisopropylamine in 500 ml of dry dichloromethane is added a solution of 38.0 ml (0.500 mol) of methoxymethyl chloride in 100 ml of dichloromethane dropwise under ice-cooling. Then, the temperature is allowed to rise to room temperature and the stirring is continued for 23 hours. The reaction mixture is poured into 150 ml of 1N hydrochloric acid and extracted with dichloromethane twice. The extract is washed once with water, a saturated aqueous solution of sodium hydrogen carbonate, and a saturated aqueous solution of sodium chloride, respectively, dried over anhydrous magnesium sulfate and evaporated under reduced pressure. The residue is distilled under reduced pressure to give 98.6 g of the desired compound 2 as an oil in 94.3% yield.

bp. 98°~100° C. (0.03 mmHg).

$^1$H-NMR: δ (CDCl$_3$) 2.33 (1 H, m), 2.67 (1 H, m), 3.23 (3 H, s), 4.11~4.23 (1 H, m), 4.23~4.40 (1 H, m), 4.50 (1 H, d, J=9 Hz), 4.52 (1 H, d, J=9 Hz), 5.64~5.93 (2 H, m), 7.13~7.51 (5 H, m) ppm.

IR: νmax (CHCl$_3$) 3064, 3004, 2952, 2828, 1585, 1482, 1439, 1148, 1098, 1037, 915 cm$^{-1}$.

MS: m/z M+ 236.

(2) Preparation of (3R*,4R*)-4-methoxymethoxy-3-phenylsulfenyl-1-cyclopentene 3

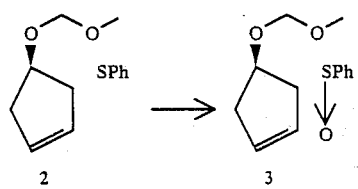

In a nitrogen atmosphere, a solution of 108 g (0.502 mol) of 85% m-chloroperbenzoic acid in 1.4 l of dry dichloromethane is added dropwise to a solution of 98.6 g (0.418 mol) of sulfide 2 (prepared in (1)) in 1 l of dry dichloromethane at −60° C. to −70° C. over 1.5 hours. Then, the mixture is stirred at the same temperature for additional 20 minutes. In order to destroy excess peracid, 9.2 ml (0.125 mol) of dimethylsulfide is added to the mixture. The reaction mixture is filtered and the filtrate is evaporated under reduced pressure. The residue dissolved in 1.2 l of ether is washed with 1N sodium hydroxide, water, and a saturated aqueous solution of ammonium chloride, dried over anhydrous magnesium sulfate, and evaporated under reduced pressure to give 106 g of the crude sulfoxide 3 as an oil, which is employed in the next step without further purification.

(3) Preparation of (1R*,4R*)-4-methoxymethoxy-2-cyclopenten-1-ol 4

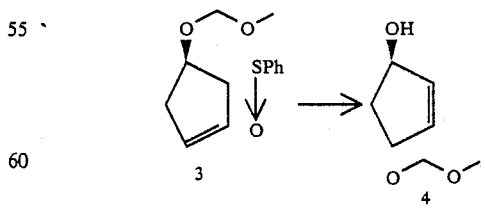

In a nitrogen atmosphere, 106 g of the crude sulfoxide 3 (prepared in (2)) and 165 g (0.623 mol) of triphenylphosphine are dissolved in a mixture of 1 l of toluene and 300 ml of methanol, and the mixture is stirred at 60° C. for 40 hours. The reaction mixture is evaporated under reduced pressure and to the residue dissolved in 300 ml of ether is added 300 ml of n-pentane dropwise under ice cooling. The resulting crystals are collected by filtration and the filtrate is concentrated under reduced pressure. The residue is purified by column chromatography on silica gel (600 g silica gel, ethyl acetate:-benzene=0:1 to 1:0). The eluate is distilled under reduced pressure to give 48.3 g of the desired alcohol 4 as an oil in 80.2% yield over two steps.

bp. 80°~81° C. (1 mmHg).

$^1$H-NMR: δ (CDCl$_3$) 1.70~2.35 (3 H, m), 3.35 (3 H, s), 4.65 (2 H, s), 4.77~5.20 (2 H, m), 5.94~6.13 (2 H, m) ppm.

IR: ν max(CHCl$_3$) 3608, 3004, 2944, 2892, 1360, 1148, 1097, 1033, 914 cm$^{-1}$.

MS: m/z (M−1)+ 143.

(4) Preparation of (1R*,2R*,3S*,4R*)-2,3-epoxy-4-methoxymethoxy-1-cyclopentanol 5

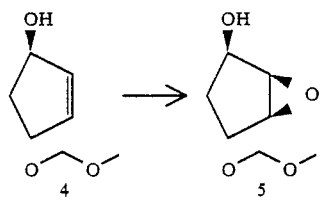

To a solution of 27.0 g (0.188 mol) of the olefin 4 (prepared in (3)) in 400 ml of dry dichloromethane is added 48.5 g (0.225 mol) of 80% m-chloroperbenzoic acid at room temperature and the mixture is stirred overnight. To the reaction mixture cooled on dry ice-acetone bath is added 4.1 ml (0.056 mol) of dimethylsulfide and the mixture is stirred at the same temperature for additional 10 minutes. The reaction mixture is filtered and the filtrate is further filtered through 150 g of alumina (Grade II). The alumina is washed with 1.8 l of ether. The filtrate and the washing are combined and evaporated under reduced pressure. The residue is purified by column chromatography on silica gel (450 g of silica gel, ethyl acetate : n-hexane=1:2 to 1:1) to give 25.9 g of the desired epoxide 5 as an oil in 86.3% yield.

$^1$H-NMR: δ (CDCl$_3$) 1.45 (1 H, ddd, J=6 Hz, 8 Hz, 15 Hz), 2.07 (1 H, dd, J=8 Hz, 15 Hz), 2.27 (1 H, d, j=8 Hz, —OH), 3.37 (3 H, s), 3.49~3.60 (2 H, m), 4.25 (1 H, d, J=6 Hz), 4.37~4.60 (1 H, m), 4.64 (2 H, s) ppm.

IR: ν max(CHCl$_3$) 3588, 3004, 2952, 2896, 1397, 1150, 1102, 1042, 915, 869 cm$^{-1}$.

MS: m/z (M−1)+ 159.

(5) Preparation of 2-methanesulfonyloxy-1,3-dimethoxybenzene

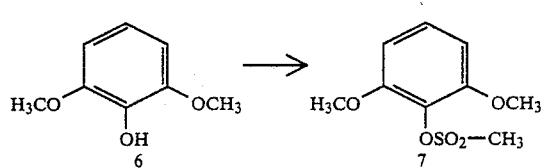

In a nitrogen atmosphere, a solution of 75 g (0.486 mol) of 2,6-dimethoxyphenol 6 (Aldrich) in 130 ml of dimethylformamide (hereinafter abbreviated to DMF) is added dropwise to a suspension of 23.3 g (0.583 mol) of 60% sodium hydride in 400 ml of DMF under ice-cooling over 30 minutes. Then, the mixture is stirred for additional 25 minutes. To this is added dropwise a solution of 54.3 ml (0.680 mol) of methanesulfonyl chloride in 130 ml of DMF and the resulting mixture is stirred at the same temperature for 30 minutes. The reaction mixture is poured into 1.8 l of ice-cold water and extracted with benzene twice. The extract is washed with 1N sodium hydroxide, water, and a saturated aqueous solution of ammonium chloride, dried over anhydrous magnesium sulfate, and evaporated under reduced pressure to give 112 g of the desired sulfonate ester 7 as crude crystals which is employed in the next step without further purification.

(6) Preparation of 2-methanesulfonyloxy-3-methoxyphenol 8

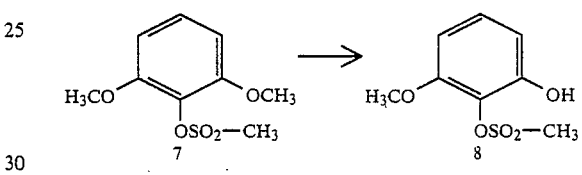

In a nitrogen atmosphere, a solution of 125 g (0.500 mol) of boron tribromide in 500 ml of dichloromethane is added dropwise to a solution of 112 g of the crude crystalline ester 7 (prepared in (5)) in 1 l of dichloromethane at −60° C. to −70° C. Then, the mixture is warmed up to −40° C. and stirred at the same temperature for 40 minutes. The reaction mixture is poured into 1.5 l of water and extracted with dichloromethane twice. The extract is washed with dilute aqueous sodium hydrogencarbonate, dried over anhydrous magnesium sulfate, and evaporated under reduced pressure to give 94 g of the desired phenol 8 as crude crystals, which is recrystallized from benzene to give 80.0 g of the compound 8 in 75.5% yield over two steps.

Mp. 105°~106° C. (benzene).

$^1$H-NMR: δ (CDCl$_3$) 3.26 (3 H, s), 3.64 (3 H, s), 5.95 (1 H, br, s), 6.53 (1 H, dd, J=2 Hz, 8 Hz), 6.64 (1 H, dd, J=2 Hz, 8 Hz), 7.09 (1 H, t, J=8 Hz) ppm.

IR: ν max(CHCl$_3$) 3568, 3472, 1609, 1497, 1483, 1371, 1344, 1146, 1092, 973, 869 cm$^{-1}$.

MS: m/z M+ 218.

(7) Preparation of 2-methanesulfonyloxy-1-methoxy-3-[[(2-trimethylsilyl-)ethoxy]methoxy]benzene 9

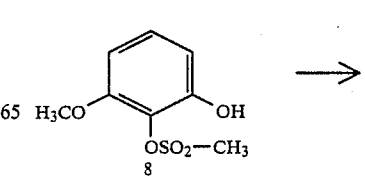

-continued

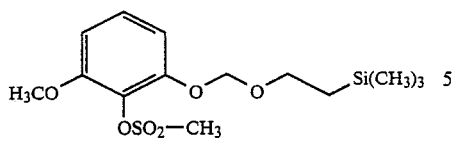

In a nitrogen atmosphere, a solution of 25.0 ml (0.141 mol) of (2-trimethylsilyl)ethoxylmethyl chloride (SEM-Cl) in 125 ml of dichloromethane is added dropwise to a solution of 25.0 g (0.115 mol) of the phenol 8 (prepared in (6)) and 29.3 ml (0.173 mol) of diisopropylethylamine in 400 ml of dichloromethane under ice cooling. After additional stirring for 3 hours, 45 ml (1.11 mol) of dry methanol is added. The resulting mixture is stirred overnight at room temperature. The reaction mixture is washed with 1N hydrochloric acid, water, a saturated aqueous solution of sodium hydrogencarbonate, and a saturated aqueous solution of sodium chloride, dried over anhydrous magnesium sulfate, and evaporated under reduced pressure to give 44 g of the crude desired ether 9 as an oil, which is employed in the next step without further purification.

(8) Preparation of 2-methoxy-6-[[(2-trimethylsilyl)ethoxy]methoxy]-phenol 10

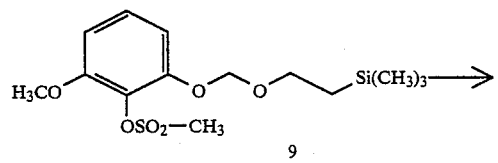

In a nitrogen atmosphere, 130 ml (0.207 mol) of n-butyl-lithium (1.6N in n-hexane) is added dropwise to a solution of 44 g of the crude methanesulfonate 9 (prepared in (7)) in 750 ml of dry ether at −60° C. to −70° C. After additional stirring at the same temperature for 20 minutes, the reaction mixture is poured into 1.5 l of saturated aqueous solution of ammonium chloride. The resulting mixture is extracted with ether twice and the extract is washed with water and a saturated aqueous solution of sodium chloride, dried over anhydrous magnesium sulfate, and evaporated under reduced pressure. The residue is purified by column chromatography on silica gel (700 g of silica gel, ethyl acetate:n-hexane=1:9) to give 29.7 g of the desired phenol 10 as an oil in 95.7% yield over two steps.

$^1$H-NMR: δ (CDCl$_3$) 0.0 (9 H, s), 0.94 (2 H, dd, J=8 Hz, 9 Hz), 3.78 (2 H, dd, J=8 Hz, 9 Hz), 3.74 (3 H, s), 5.21 (2 H, s), 5.83 (1 H, br, s), 6.50~6.80 (3 H, m) ppm.

IR: ν max (CHCl$_3$) 3544, 2960, 1619, 1505, 1481, 1075, 1003, 860, 837 cm$^{-1}$.

MS: m/z M+ 270.

(9) Preparation of 1-[[(1R*,2R*,3R*,4S*)-2,3-epoxy-4-methoxymethoxy-1-cyclopentyl]oxy]-2-methoxy-6-[(2-trimethylsilyle-thoxy)methoxy]benzene 11

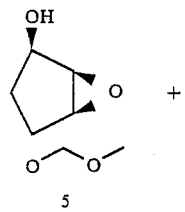

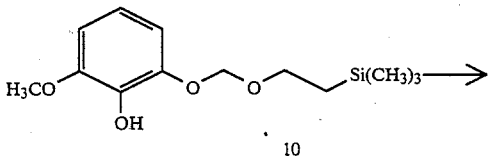

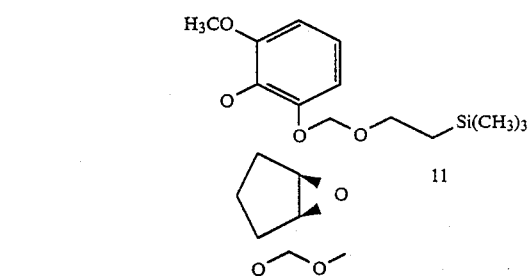

In a nitrogen atmosphere, 25.2 ml (0.160 mol) of diethyl azodicarboxylate is added dropwise to a solution of 39.3 g (0.146 mol) of the phenol 10 (prepared in (8)), 25.8 g (0.161 mol) of the alcohol 5 (prepared in (4)), and 49.6 g (0.189 mol) of triphenylphosphine in 750 ml of dry tetrahydrofuran (hereinafter abbreviated to THF) under ice cooling, and the mixture is stirred at room temperature for three days. Then, additional 11.4 g (0.044 mol) of triphenylphosphine and 6.9 ml (0.044 mol) of diethyl azodicarboxylate is added and the resulting mixture is stirred for additional 2 days. The reaction mixture is evaporated under reduced pressure and the residue dissolved in 500 ml of ether is cooled on dry ice-acetone bath. The precipitated crystals are separated by filtration and the filtrate is concentrated under reduced pressure. The residue is purified by column chromatography on silica gel (1.5 kg of silica gel, ethyl acetate:benzene=1:50 to 1:9) to give 51.8 g of the desired epoxy ether 11 as an oil in 86.2% yield from the compound 10.

$^1$H-NMR: δ (CDCl$_3$) 0.0 (9 H, s), 0.92 (2 H, dd, J=8 Hz, 9 Hz), 1.76~2.33 (2 H, m), 3.41 (3 H, s), 3.80 (3 H, s), 3.65~3.90 (4 H, m), 4.26 (1 H, d, J=6 Hz), 4.50 (1 H, d, J=6 Hz), 4.73 (2 H, s), 5.20 (2 H, s), 6.57 (1 H, dd, J=8 Hz, 8 Hz), 6.76 (1 H, dd, J=2 Hz, 8 Hz), 6.96 (1 H, t, J=8 Hz) ppm.

IR: ν max (CHCl$_3$) 3004, 2960, 2896, 2840, 1598, 1490, 1476, 1249, 1108, 1073, 1012, 859, 847, 837 cm$^{-1}$.

MS: m/z M+ 412.

(10) Preparation of (1R*,2S*,3aR*,9aS*)-5-methoxy-2-methoxymethoxy-2,3,3a,9a-tetrahydro-1H-cyclopenta[b][1,4]benzodioxin-1-ol 12

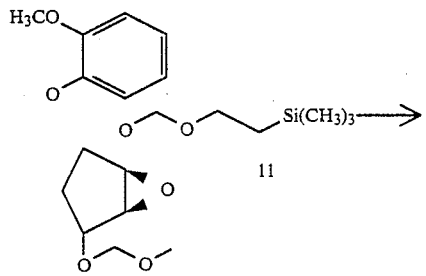

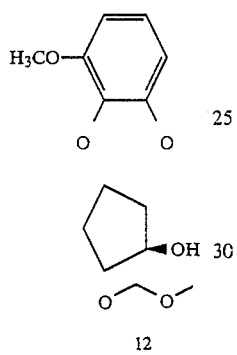

In a nitrogen atmosphere, 251 ml (0.250 mol) of tetra-n-butylammonium fluoride (1M in THF) is added to a solution of 51.8 g (0.125 mol) of the epoxide 11 (prepared in (9)) in 190 ml of dry THF and the mixture is stirred at 55° C. for 3 days. The reaction mixture is poured into water and extracted with ethyl acetate twice. The extract is washed with water and a saturated aqueous solution of ammonium chloride, dried over anhydrous magnesium sulfate, and evaporated under reduced pressure. The residue is purified by column chromatography on silica gel (700 g silica gel, ethyl acetate:n-hexane=1:2 to 1:1) and then crystallized from ether-n-hexane to give 31.7 g of the desired benzodioxine 12 in 89.6% yield.

Mp. 69.0° C. to 70.0° C. (ether-n-hexane)

$^1$H-NMR: δ (CDCl$_3$) 2.13 (1 H, ddd, J=2.5 Hz, 6 Hz, 15 Hz), 2.62 (1 H, ddd, J=6 Hz, 10 Hz, 15 Hz), 3.37 (3 H, s), 3.83 (3 H, s), 3.50~3.95 (2 H, m), 4.05~4.41 (3 H, m), 4.67 (2 H, s), 6.47 (1 H, dd, J=2 Hz, 8 Hz), 6.57 (1 H, dd, J=2 Hz, 8 Hz), 6.80 (1 H, t, J=8 Hz) ppm.

IR: ν max (CHCl$_3$) 3476, 3004, 2952, 2896, 2844, 1603, 1499, 1475, 1280, 1110, 1082 cm$^{-1}$.

MS: m/z M$^+$ 282.

(11) Preparation of (1R*,2S*,3aR*,9aR*)-5-methoxy-2-methoxy-methoxy-1-[[(phenoxy)-thiocarbonyl]oxy]-2,3,3a,9a-tetrahydro-1H-cyclopenta[b][1,4]benzodioxine 13

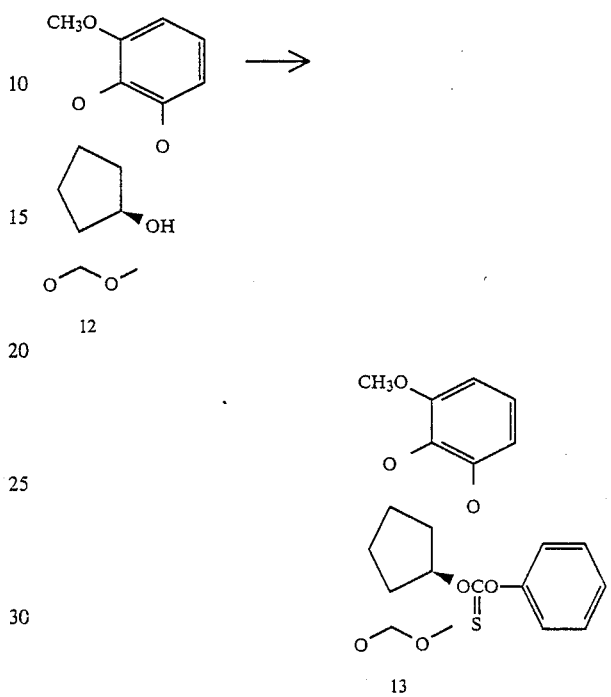

In a nitrogen atmosphere, 36.6 ml (58.6 mmol) of n-butyl-lithium (1.6N in n-hexane) is added dropwise to a solution of 15.0 g (53.2 mmol) of the alcohol 12 (prepared in (10)) in 150 ml of dry THF at −60° C. to −70° C. Then, the mixture is stirred for 20 minutes and 8.82 ml (63.9 mmol) of phenyl chlorothionocarbonate is added. The resulting mixture is further stirred at the same temperature for 20 minutes. The mixture is warmed to 0° C. over 30 minutes and stirred at the same temperature for additional 1 hour. The reaction is quenched by the addition of a saturated aqueous solution of ammonium chloride and then extracted with ethyl acetate twice. The extract is washed with a saturated aqueous solution of sodium hydrogencarbonate, and a saturated aqueous solution of sodium chloride, dried over anhydrous magnesium sulfate, and evaporated under reduced pressure. The residue is purified by column chromatography on silica gel (400 g of silica gel, ethyl acetate:n-hexane=1:5 to 1:2) to give 20.4 g of the desired thionocarbonate 13 as crystals in 91.9% yield.

Mp. 100° C.~102° C. (benzene-n-hexane).

$^1$H-NMR: δ (CDCl$_3$) 2.17 (1 H, dt, J=7 Hz, 15 Hz), 2.66 (1 H, ddd, J=6 Hz, 8 Hz, 15 Hz), 3.33 (3 H, s), 3.85 (3 H, s), 4.14~4.75 (5 H, m), 5.82 (1 H, t, J=4 Hz), 6.43~6.88 (3 H, m), 7.03~7.52 (5 H, m) ppm.

IR: ν max(CHCl$_3$) 3008, 2956, 1603, 1500, 1492, 1477, 1290, 1189, 1111, 1039 cm$^{-1}$.

MS: m/z M$^+$ 418.

(12) Preparation of
(1R*,2S*,3aR*,9aS*)-5-methoxy-2-methoxymethoxy-1-(2-propenyl)-2,3,3a,9a-tetrahydro-1H-cyclopenta[b][1,4]benzodioxine 14

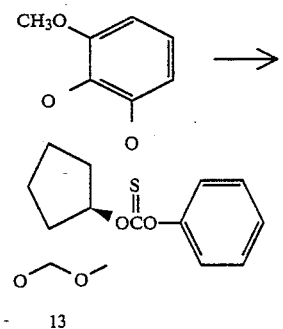
13

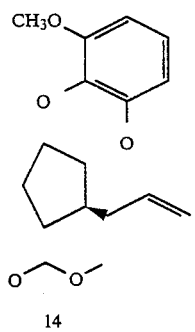
14

A solution of 20.44 g (48.9 mmol) of the thionocarbonate 13 (prepared in (11)) and 48.9 g (148 mmol) of allyl-tri-n-butyl-stannane in 400 ml of dry benzene is thoroughly degassed with argon for 1 hour. In an argon atmosphere, the resulting solution is irradiated with a 450 W high pressure mercury lamp equipped with a pyrex filter for 10 hours. The reaction mixture is concentrated under reduced pressure and the residue is purified by column chromatography on silica gel ( 1 600 g of silica gel, ethyl acetate:n-hexane=1:5 to 1:3, 2 700 g of silica gel, ethyl acetate:dichloromethane=3:97) to give 11.2 g of the desired olefin 14 as crystals in 74.8% yield.

Mp. 48.5° C.~49.5° C. (n-pentane).

$^1$H-NMR: δ (CDCl$_3$) 193~2.57 (5 H, m), 3.33 (3 H, s), 3.85 (3 H, s), 3.72~4.23 (2 H, m), 4.26~4.45 (1 H, m), 4.59 (2 H, m), 4.98~5.30 (2 H, m), 5.60~6.13 (1 H, m), 6.40~6.65 (2 H, m), 6.78 (1 H, t, J=8 Hz) ppm.

IR: ν max(CHCl$_3$) 3008, 2948, 2844, 1642, 1603, 1499, 1477, 1282, 1254, 1107, 1037, 918 cm$^{-1}$.

MS: m/s M$^+$ 306.

(13) Preparation of
(1R*,2S*,3aR*,9aS*)-2-methoxymethoxy-1-(2-propenyl)-2,3,3a,9a-tetrahydro-1H-cyclopenta[b][1,4]benzodioxin-5-ol 15

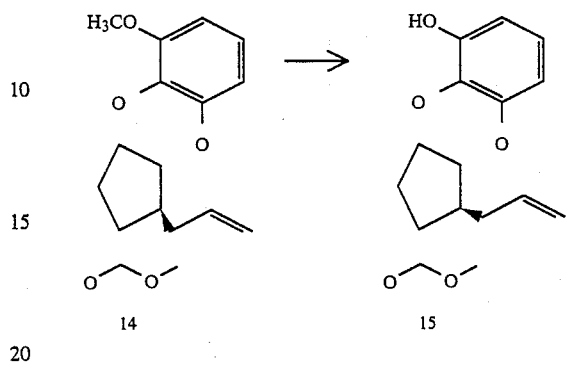

In a nitrogen atmosphere, 30 ml (47 mmol) of n-butyl-lithium (1.58 M in n-hexane) is added dropwise to a solution of 5.25 ml (49 mmol) of n-butyl mercaptane in 30 ml of hexamethylphosphoric triamide (hereinafter abbreviated to HMPA) under ice cooling and then the temperature is allowed to rise to room temperature and n-hexane is evaporated under reduced pressure. To the resulting mixture is added a solution of 6.00 g (19.6 mmol) of the methyl ether 14 (prepared in (12)) in 20 ml of HMPA and the mixture is stirred at 100° C. for 30 minutes. A saturated aqueous solution of ammonium chloride is added to the reaction mixture, which is then extracted with ethyl acetate three times. The extract is washed with water and a saturated aqueous solution of sodium chloride, dried over anhydrous magnesium sulfate, and evaporated under reduced pressure. The residue is purified by column chromatography on silica gel (150 g silica gel, ethyl acetate:n-hexane=1:3) to give 5.64 g of the desired phenol 15 as an oil in 98.5% yield.

$^1$H-NMR: δ (CDCl$_3$) 1.90~2.56 (5 H, m), 3.33 (3 H, s), 3.72~4.36 (3 H, m), 4.57 (2 H, m), 4.96~5.26 (2 H, m), 5.43 (1 H, br, s), 5.62~6.11 (1 H, m), 6.38~6.57 (2 H, m), 6.72 (1 H, t, J=8 Hz) ppm.

IR: ν max(CHCl$_3$) 3552, 3008, 2948, 1642, 1610, 1499, 1487, 1272, 1090, 1040, 917 cm$^{-1}$.

MS: m/z M$^+$ 292.

(14) Preparation of methyl
[(1R*,2S*,3aR*,9aS*)-2-methoxymethoxy-1-(2-propenyl)-2,3,3a,9a-tetrahydro-1H-cyclopenta[b][1,4]benzodioxin-5-yl]oxyacetate 16

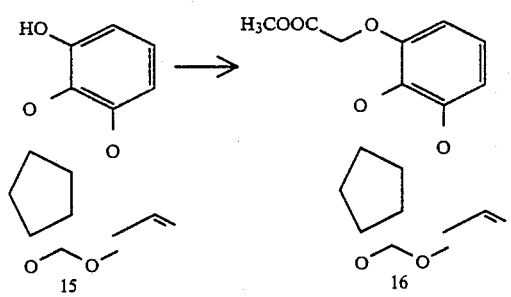

In a nitrogen atmosphere, a solution of 5.64 g (19.3 mmol) of the phenol 15 (prepared in (13)) in 40 ml of dimethoxyethane (hereinafter abbreviated to DME) is added dropwise to a suspension of 850 mg (21.2 mmol) of 60% sodium hydride in 50 ml of dry DME under ice cooling. The temperature is allowed to rise to room temperature and stirred for 20 minutes, and then 3.65 ml (38.6 mmol) of methyl bromoacetate is added. The resulting mixture is stirred overnight. A saturated aqueous solution of ammonium chloride is added to the reaction mixture, which is then extracted with ethyl acetate three times. The extract is washed with water and a saturated aqueous solution of sodium chloride, and evaporated under reduced pressure. The residue is purified by column chromatography on silica gel (150 g of silica gel, ethyl acetate:n-hexane=1:2) to give 6.32 g of the desired methyl ester 16 as crystals in 89.9% yield.

Mp. 65.0° C.~66.0° C. (ether-n-hexane).

$^1$H-NMR: δ (CDCl$_3$) 1.94~2.56 (5 H, m), 3.33 (3 H, s), 3.76 (3 H, s), 3.75~4.46 (3 H, m), 4.58 (2 H, s), 4.67 (2 H, s), 4.98~5.27 (2 H, m), 5.59~6.14 (1 H, m), 6.35~6.85 (3 H, m) ppm.

IR: ν max (CHCl$_3$) 3012, 2960, 1764, 1742, 1643, 1600, 1499, 1476, 1441, 1287, 1125, 1037, 917 cm$^{-1}$.

MS: m/z M+ 364.

(15) Preparation of methyl [(1R*,2S*,3aR*,9aS*)-2-hydroxy-1-(2-propenyl)-2,3,3a,9a-tetrahydro-1H-cyclopenta[b][1,4]benzodioxin-5-yl]oxyacetate 17

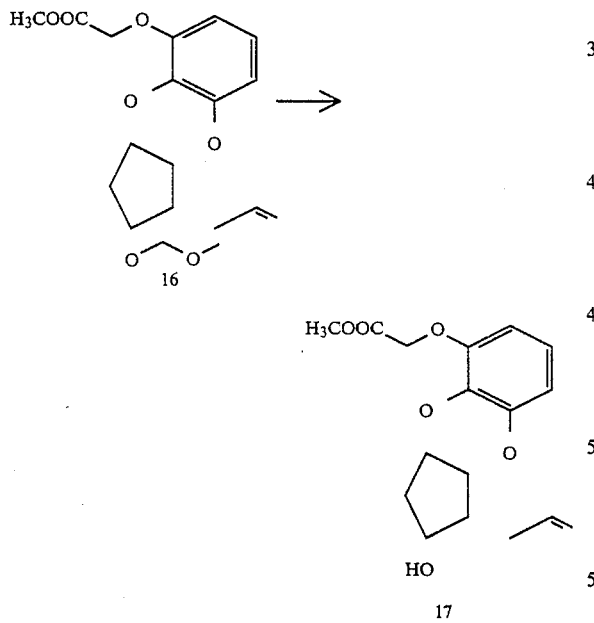

In a nitrogen atmosphere, 10.9 ml (86.8 mmol) of trifluoroboron-diethyl etherate is added dropwise to a solution of 6.32 g (17.4 mmol) of the methoxymethyl ether 16 (prepared in (14)) and 6.38 ml (86.8 mmol) of dimethylsulfide in 95 ml of dichloromethane under ice cooling and the mixture is stirred at the same temperature for 2 hours. To the reaction mixture is added 600 ml of saturated aqueous solution of sodium hydrogen-carbonate and the mixture is vigorously stirred for 30 minutes. The reaction mixture is extracted with dichloromethane three times. The extract is washed with a saturated aqueous solution of sodium hydrogencarbonate, and a saturated aqueous solution of sodium chloride, dried over anhydrous magnesium salfate, and evaporated under reduced pressure. The residue is purified by column chromatography on silica gel (150 g of silica gel, ethyl acetate:n-hexane=1:2 to 1:1) to give 5.20 g of the desired alcohol 17 as crystals in 93.6% yield.

Mp. 101° C.~102° C. (ether).

$^1$H-NMR: δ (CDCl$_3$) 1.91~2.60 (6 H, m), 3.76 (3 H, s), 3.84~4.20 (2 H, m), 4.22~4.43 (1 H, m), 4.67 (2 H, s), 4.99~5.28 (2 H, m), 5.65~6.10 (1 H, m), 6.36~6.86 (3 H, m) ppm.

IR: ν max (CHCl$_3$) 3592, 2012, 2960, 1763, 1744, 1642, 1600, 1498, 1476, 1287, 1271, 1125 cm$^{-1}$.

MS: m/z M+ 320.

(16) Preparation of methyl [(1R*,2R*,3aS*,9aR*)-2-tert-butyldiphenylsilyloxy-1-(2-propenyl)-2,3,3a,9a-tetrahydro-1H-cyclopenta[b][1,4]benzodioxin-5-yl]oxyacetate 18

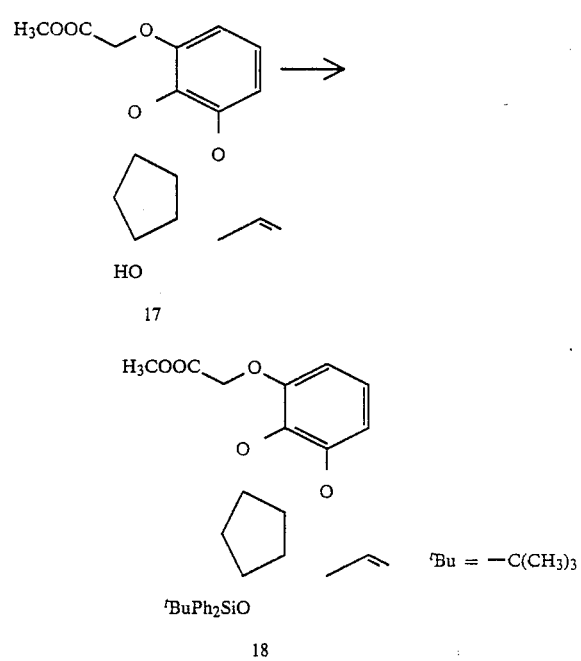

To a solution of the alcohol 17 (prepared in (15)) in 60 ml of N,N-dimethylformamide (hereinafter abbreviated to DMF) is added 3.97 g (32.5 mmol) of N,N-dimethylaminopyridine and 6.34 ml (24.4 mmol) of tert-butyldiphenylsilyl chloride and the mixture is stirred at room temperature for 3 days. The reaction mixture is poured into water and extracted with ethyl acetate three times. The extract is washed with 1N hydrochloric acid, water, a saturated aqueous solution of sodium hydrogencarbonate, and a saturated aqueous solution of sodium chloride, dried over anhydrous magnesium sulfate, and evaporated under reduced pressure. The residue is purified by column chromatography on silica gel (Merck; Lobar column, size C, two columns, ethyl acetate:n-hexane=1:5) to give 8.82 g of the desired silyl ether 18 as an oil in 97.1% yield.

¹H-NMR: δ (CDCl₃) 1.05 (9 H, s), 1.84~2.53 (5 H, m), 3.77 (3 H, s), 3.83~4.03 (2 H, m), 4.13~4.35 (1 H, m), 4.68 (2 H, s), 4.75~5.01 (2 H, m), 5.41~5.88 (1 H, m), 6.40~6.87 (3 H, m), 7.30~7.50 (6 H, m), 7.58~7.78 (4 H, m) ppm.

IR: ν max(CHCl₃) 3076 2960, 2936, 2864, 1764, 1742, 1642, 1600, 1498, 1476, 1429, 1287, 1115, 920, 821, 612 cm⁻¹.

MS: m/z M⁺ 558.

(17) Preparation of methyl [(1R*,2R*,3aS*,9aR*)-2-tert-butyl-diphenylsilyloxy-1-[(E)-3-chloro-1-propenyl]-2,3,3a,9a-tetrahydro-1H-cyclopeta[b][1,4]benzodioxin-5-yl]oxyacetate 19

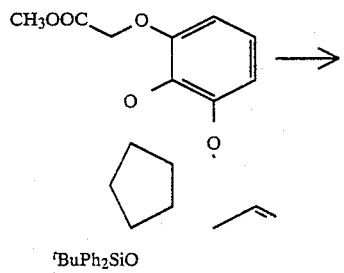

18

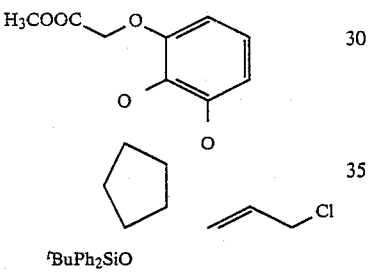

19

In a nitrogen atmosphere, a solution of 3.32 g (17.4 mmol) of phenylselenenyl chloride in 50 ml of carbon tetrachloride is added dropwise to a solution of 8.82 g (15.8 mmol) of the olefin 18 (prepared in (16)) in 70 ml of carbon tetrachloride under ice cooling over 45 minutes. The mixture is stirred for further 15 minutes and 1.66 ml (20.5 mmol) of pyridine and 20 ml of 30% aqueous solution of hydrogen peroxide are added thereto at the same temperature. The resulting mixture is stirred for 20 minutes, then brought to room temperature, and stirred for additional 1 hour and 30 minutes. The reaction mixture is poured into water and extracted with dichloromethane twice. The extract is washed with 1N hydrochloric acid, water, a dilute aqueous solution of sodium hydrogencarbonate, and a saturated aqueous solution of sodium chloride, dried over anhydrous magnesium sulfate, and evaporated under reduced pressure. The residue is purified by column chromatography on silica gel (Merck; Lobar column, size C, two columns: ethyl acetate:n-hexane=1:4) to give 7.20 g of the desired allyl chloride 19 as crystals in 77.0% yield.

Mp.: 127°~130° C. (ether).

¹H-NMR: δ (CDCl₃) 1.03 (9 H, s), 2.04~2.23 (2 H, m), 2.91 (1 H, dt, J=7 Hz, 9 Hz), 3.77 (3 H, s), 3.87~4.28 (5 H, m), 4.70 (2 H, s), 5.46 (1 H, dd, J=7 Hz, 16 Hz), 5.68 (1 H, dd, J=6 Hz, 16 Hz), 6.39~6.86 (3 H, m), 7.30~7.50 (6 H, m), 7.56~7.75 (4 H, m) ppm.

IR: ν max (CHCl₃) 3012, 2960, 2936, 2864, 1764, 1744, 1601, 1498, 1476, 1429, 1289, 1114, 966, 822, 613 cm⁻¹.

MS: m/z M⁺ 594.

(18) Preparation of methyl [(1R*,2R*,3aS*,9aR*)-1-[(E)-3-acetoxy-1-propenyl]-2-tert-butyldiphenylsilyloxy-2,3,3a,9a-tetrahydro-1H-cyclopenta[b][1,4]benzodioxin-5-yl]oxyacetate 20

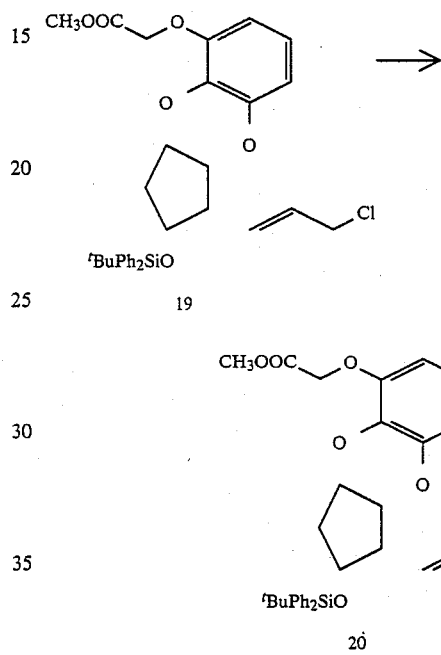

In a nitrogen atmosphere, 4.95 g (25.8 mmol) of cesium acetate and 2.27 g (8.60 mmol) of 18-crown-6 are added to a solution of 5.10 g (8.60 mmol) of the allyl chloride 19 (prepared in (17)) in 150 ml of toluene and the mixture is heated under reflux for 24 hours. After cooling, a saturated aqueous solution of ammonium chloride is added to the reaction mixture and the mixture is extracted with ethyl acetate twice. The extract is washed with water and a saturated aqueous solution of sodium chloride, dried over anhydrous magnesium sulfate, and evaporated under reduced pressure to give the desired acetate 20 as crude crystals. The crude material is recrystallized from ethyl acetate-n-hexane twice to give 4.26 g of the (E)-acetate 20 in 80.4% yield.

Mp.: 132°~134° C. (ethyl acetate-n-hexane).

¹H-NMR: δ (CDCl₃) 1.03 (9 H, s), 2.03 (3 H, s), 2.00~2.25 (2 H, m), 2.77~3.06 (1 H, m), 3.76 (3 H, s), 3.78~4.28 (3 H, m), 4.44 (2 H, d, J=5 Hz), 4.72 (2 H, s), 5.33~5.82 (2 H, m), 6.40~6.87 (3 H, m), 7.30~7.48 (6 H, m), 7.59~7.80 (4 H, m) ppm.

IR: ν max(CHCl₃) 3012, 2960, 2936, 2864, 1763, 1738, 1600, 1498, 1478, 1240, 1114, 968, 822, 695, 612 cm⁻¹.

MS: m/z M⁺ 616.

(19) Preparation of methyl [(1R*,2R*,3aS*,9aR*)-2-tert-butyldiphenylsilyloxy-1-[(E)-3-hydroxy-1-propenyl]-2,3,3a,9a-tetrahydro-1H-cyclopenta[b][1,4]benzodioxin-5-yl]oxyacetate 21

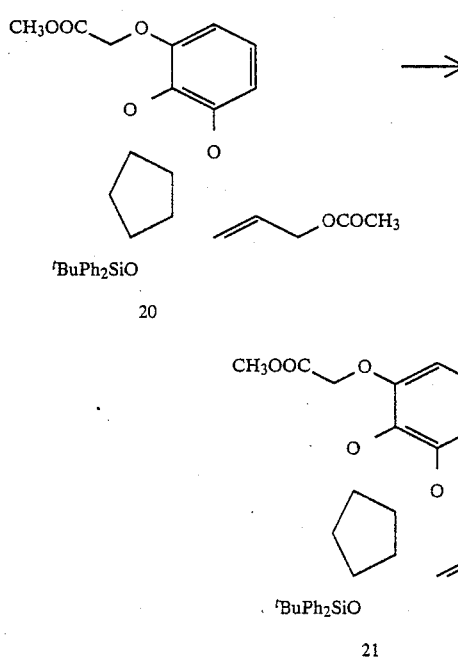

To a solution of 6.12 g (9.92 mmol) of the acetate 20 (prepared in (18)) in 40 ml of dichloromethane and 40 ml of methanol is added 1.65 g (11.9 mmol) of potassium carbonate and the mixture is stirred at room temperature for 2 hours. To the reaction mixture is added 26 ml (26 mmol) of 1N hydrochloric acid and the organic solvent is evaporated under reduced pressure. After addition of a saturated aqueous solution of sodium chloride, the mixture is extracted with ethyl acetate 3 times. The extract is washed with water and a saturated aqueous solution of sodium chloride, dried over anhydrous magnesium sulfate, and evaporated under reduced pressure. The residue containing the carboxylic acid, which is generated by saponification of the methyl ester, is treated with diazomethane as follows to esterify. Namely, the above-mentioned residue is dissolved in 100 ml of methanol and an ethereal solution of diazomethane in ether is added thereto under ice cooling until the yellow color persists. The reaction mixture is evaporated under reduced pressure and the residue is purified by column chromatography on silica gel (Merck; Lobar column, size C, two columns, ethyl acetate:n-hexane=1:1) to give the desired allyl alcohol 21, which is crystallized from ether-n-hexane to give 5.35 g of the crystals in 93.7% yield.

Mp. 102.5°~103.5° C. (ether-n-hexane).

$^1$H-NMR: δ (CDCl$_3$) 1.03 (9 H, s), 1.51 (1 H, s —OH), 2.08~2.27 (2 H, m), 2.75~3.06 (1 H, m), 3.77 (3 H, s), 3.87~4.30 (5 H, m), 4.71 (2 H, s), 5.38 (1 H, dd, J=8 Hz, 16 Hz), 5.66 (1 H, td, J=5 Hz, 16 Hz), 6.39~6.85 (3 H, m), 7.29~7.48 (6 H, m), 7.58~7.80 (4 H, m) ppm.

IR: ν max(CHCl$_3$) 3616, 3012, 2960, 2936, 2864, 1764, 1743, 1600, 1498, 1476, 1429, 1288, 1113, 971, 822, 696, 612 cm$^{-1}$.

MS: m/z M+ 574.

(20) Preparation of methyl [(1R*,2R*,3aS*,9aR*)-2-tert-butyldiphenylsilyloxy-1-[(E)-3-oxo-1-propenyl]-2,3,3a,9a-tetrahydro1H-cyclopenta[b][1,4]benzodioxin-5-yl]oxyacetate II

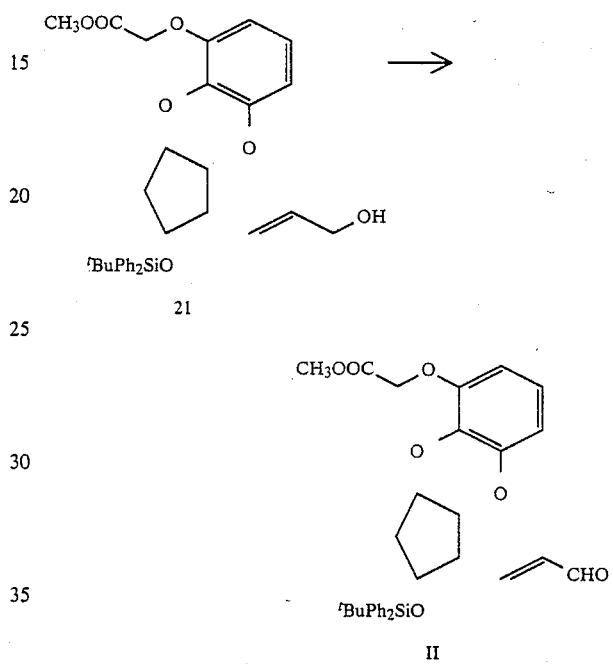

To a solution of 3.35 g (5.83 mmol) of the allyl alcohol 21 (prepared in (19)) in 70 ml of dichloromethane is added 2.51 g (11.6 mmol) of pyridinium chlorochromate (PCC) and the mixture is stirred at room temperature for 3 hours. To the reaction mixture is added 160 ml of ether and the mixture is stirred for 2 minutes and then filtered through 34 g of Florisil (Floridin Company) which is washed with 500 ml of ether. The filtrate and washing are combined and the mixture is evaporated under reduced pressure. The residue is crystallized from ether-n-hexane to give 3.19 g of the desired aldehyde II as crystals in 95.6% yield.

Mp.: 103.5°~104.8° C. (ether-n-hexane).

$^1$H-NMR: δ (CDCl$_3$) 1.03 (9 H, s), 2.20~2.37 (2 H, m), 2.98~3.36 (1 H, m), 3.78 (3 H, s), 4.00~4.30 (3 H, m), 4.71 (2 H, s), 6.15 (1 H, dd, J=7 Hz, 16 Hz), 6.33 (1 H, dd, J=7 Hz, 16 Hz), 6.40~6.85 (3 H, m), 7.28~7.47 (6 H, m), 7.53~7.72 (4 H, m), 9.23 (1 H, d, J=7 Hz) ppm.

IR: ν max (CHCl$_3$) 3012, 2960, 2936, 2864, 1764, 1743, 1692, 1601, 1499, 1476, 1429, 1290, 1113, 974, 823, 697, 612 cm$^{-1}$.

MS: m/z M+ 572.

EXAMPLE 1

Preparation of methyl
[(1R*,2R*,3aS*,9aR*)-2-tert-butyldiphenylsilyloxy-1-
[(3S*,1E)-3-hydroxy-1-octenyl]-2,3,3a,9a-tetrahydro-
1H̲-cyclopenta[b][1,4]benzodioxin-5-yl]oxyacetate
Iaa-a and methyl
[(1R*,2R*,3aS*,9aR*)-2-tert-butyldiphenylsilyloxy-1-
[(3R*,1E)-3-hydroxy-1-octenyl]-2,3,3a,9a-tetrahydro-
1H̲-cyclopenta[b][1,4]benzodioxin-5-yl]oxyacetate
Ica-a

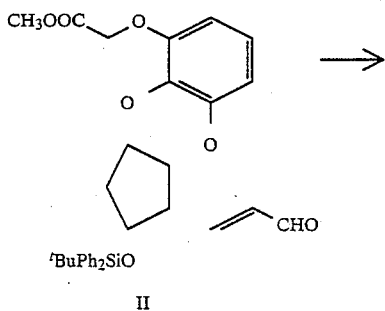

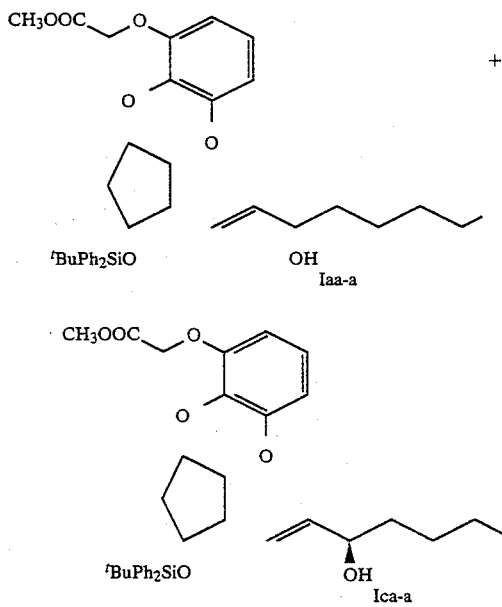

In a nitrogen atmosphere, 1.83 ml (2.01 mmol) of n-pentyl-magnesium bromide (1.1N, in THF) is added dropwise to 962 mg (1.68 mmol) of the aldehyde II (prepared in (20)) in 20 ml of dry THF at −78° C. After stirring for 15 minutes at the same temperature, the reaction is quenched by the addition of a saturated aqueous solution of ammonium chloride. The reaction mixture is extracted with ethyl acetate three times and the extract is washed with water and a saturated aqueous solution of sodium chloride, dried over anhydrous magnesium sulfate, and evaporated under reduced pressure. The residue is purified by the column chromatography on silica gel (Merck, Lobar column, size B, two columns, ethyl acetate:toluene=1:10 to 1:6) to give 517 mg of the less polar isomer Iaa-a as an oil and 252 mg of the more polar isomer Ica-a as crystals in 47.7% and 20.7% yield, respectively.

Compound Iaa-a $^1$H-NMR: δ (CDCl$_3$) 0.87 (3 H, t, J=6 Hz), 1.03 (9 H, s), 1.00~1.90 (9 H, m), 2.05~2.25 (2 H, m), 2.76~3.03 (1 H, m), 3.79 (3 H, s), 3.80~4.30 (4 H, m), 4.72 (2 H, s), 5.22~5.70 (2 H, m), 6.40~6.87 (3 H, m), 7.30~7.50 (6 H, m), 7.60~7.80 (4 H, m) ppm.

IR: ν max (CHCl$_3$) 3608, 3008, 2960, 2936, 2864, 1763, 1743, 1600, 1498, 1475, 1429, 1292, 1114, 970, 821, 697, 612 cm$^{-1}$.

MS: m/z M$^+$ 644.

Compound Ica-a

Mp. 83°~84° C. (ether-n-pentane).

$^1$H-NMR: δ (CDCl$_3$) 0.87 (3 H, t, J=6 Hz), 1.03 (9 H, s), 1.00~1.90 (9 H, m), 2.05~2.25 (2 H, m), 2.76~3.03 (1 H, m), 3.79 (3 H, s), 3.80~4.30 (4 H, m), 4.72 (2 H, s), 5.22~5.70 (2 H, m), 6.40~6.87 (3 H, m), 7.30~7.50 (6 H, m), 7.60~7.80 (4 H, m) ppm.

IR: ν max (CHCl$_3$) 3608, 3008, 2960, 2936, 2864, 1764, 1742, 1600, 1498, 1476, 1429, 1289, 1113, 969, 821, 696, 612 cm$^{-1}$.

MS: m/z M$^+$ 644.

EXAMPLES 2 to 4

According to the same method as described in Example I, the aldehyde II is converted into the allyl alcohol Ia-a and Ic-a, and the results are shown in Table 1. In Example 4, the reaction is carried out using the racemic Grignard reagent to give the four isomers of allyl alcohol Iad-a, Iae-a, Icd-a, and Ice-a.

TABLE 1

$$\text{II} \xrightarrow{R_1-MgBr} \text{Ia-a} + \text{Ic-a}$$

(Structures: II is an aldehyde (CHO) with CH₃O₂C-O-aryl-O-CH₂CO₂CH₃ and cyclopentane with ᵗBuPh₂SiO; Ia-a and Ic-a are the corresponding alcohols with R₁ group and OH, differing in stereochemistry.)

| Ex. No. | R₁ | Compd. No. | Yd. (%) | MS (m/z) | IR νmax (cm⁻¹) | ¹H—NMR δ (ppm) |
|---|---|---|---|---|---|---|
| 2 | cyclohexyl-CH₂ (methylcyclohexyl) | I ab-a | 49.9 | 656 (M⁺) | (CHCl₃) 3608, 3008, 2936, 2860, 1763, 1743, 1600, 1498, 1476, 1429, 1290, 1114, 907, 821, 612. | (CDCl₃) 1.03 (9H,s), 0.70~2.00 (12H,m), 2.00~2.30 (2H,m), 2.76~3.06 (1H,m), 3.77 (3H,s), 3.55~3.80 (1H,s), 3.90~4.31 (3H,m), 4.71 (2H,s), 5.17~5.66 (2H,m), 6.40~6.86 (3H,m), 7.32~7.55 (6H,m), 7.55~7.90 (4H,m). |
| | | I cb-a | 12.1 | 656 (M⁺) | (CHCl₃) 3608, 3008, 2936, 2860, 1764, 1742, 1600, 1498, 1476, 1429, 1290, 1113, 972, 906, 821, 612. | (CDCl₃) 1.03 (9H,s), 0.78~2.00 (12H,m), 2.00~2.30 (2H,m), 2.79~3.06 (1H,m), 3.78 (3H,s), 3.61~3.82 (1H,s), 3.90~4.35 (3H,m), 4.73 (2H,s), 5.23~5.71 (2H,m), 6.41~6.87 (3H,m), 7.25~7.51 (6H,m), 7.60~7.90 (4H,m). |
| 3 | hex-4-ynyl (CH₂C≡CCH₂CH₃) | I ac-a | 37.3 | 654 (M⁺) | (CHCl₃) 3608, 3008, 2940, 2864, 1764, 1743, 1600, 1499, 1476, 1429, 1289, 1114, 970, 906, 821, 612. | (CDCl₃) 1.03 (9H,s), 1.10 (3H,t,J=7Hz), 1.37~2.41 (9H,m), 2.75~3.15 (1H,m), 3.80 (3H,s), 3.85~4.32 (4H,m), 4.73 (2H,s), 5.24~5.70 (2H,m), 6.40~6.87 (3H,m), 7.35~7.50 (6H,m), 7.60~7.80 (4H,m) |
| | | I cc-a | 23.5 | 654 (M⁺) | (CHCl₃) 3608, 3012, 2936, 2864, 1764, 1743, 1600, 1499, 1476, 1429, 1290, 1114, 970, 906, 821, 612 | (CDCl₃) 1.03 (9H,s), 1.13 (3H,t,J=7Hz), 1.40~2.42 (9H,m), 2.78~3.05 (1H,m), 3.80 (3H,s), 3.87~4.35 (4H,m), 4.73 (2H, s), 5.27~5.83 (2H,m), 6.41~6.90 (3H,m), 7.33~7.50 (6H,m), 7.60~7.85 (4H,m) |
| 4 | CH₂CH(*)(C₃H₇)(C₄H₉) (branched alkyl with stereocenter) | I ad-a (Isomer 1) | 23.9 | 672 (M⁺) | (CHCl₃) 3608, 3012, 2936, 2864, 1764, 1743, 1600, 1499, 1476, 1429, 1290, 1114, 970, 906, 821, 612. | (CDCl₃) 0.76~0.92 (6H,m), 1.03 (9H,s), 0.92~1.80 (10H,m), 2.05~2.25 (2H,m), 2.73~3.00 (1H,m), 3.77 (3H,s), 3.87~4.28 (4H,m), 4.70 (2H,s), 5.17~5.67 (2H,m), 6.39~6.86 (3H,m), 7.30~7.48 (6H,m), 7.58~7.75 (4H,m). |
| | | I ac-a (Isomer 2) | 23.5 | 672 (M⁺) | (CHCl₃) 3608, 3012, 2936, 2864, 1764, 1742, 1600, 1499, 1476, 1429, 1288, 1114, 970, 906, 821, 612. | (CDCl₃) 0.77~0.91 (6H,m), 1.03 (9H,s), 0.91~1.80 (10H,m), 1.98~2.26 (2H,m), 2.72~3.00 (1H,m), 3.77 (3H,s), 3.86~4.30 (4H,m), 4.72 (2H,s), 5.17~5.64 (2H,m), 6.39~6.86 (3H,m), 7.30~7.47 (6H,m), 7.57~7.80 (4H,m). |
| | | I cd-a (Isomer 1) | 10.0 | 672 (M⁺) | (CHCl₃) 3608, 3012, 2936, 2864, 1764, 1742, 1601, 1499, 1476, 1429, 1290, 1114, 971, 907, 821, 612. | (CDCl₃) 0.78~0.95 (6H,m), 1.03 (9H,s), 0.95~1.78 (10H,m), 2.05~2.25 (2H,m), 2.73~3.01 (1H,m), 3.77 (3H,s), 3.86~4.27 (4H,m), 4.70 (2H,s), 5.19~5.68 (2H,m), 6.39~6.86 (3H,m), 7.30~7.47 (6H,m), 7.57~7.75 (4H,m). |
| | | I cc-a (Isomer 2) | 11.0 | 672 (M⁺) | (CHCl₃) 3608, 3012, 2936, 2864, 1764, 1743, 1600, 1499, 1476, 1429, 1288, 1114, 970, 906, 821, 612. | (CDCl₃) 0.79~0.93 (6H,m), 1.03 (9H,s), 0.93~1.80 (10H,m), 2.04~2.25 (2H,m), 2.73~3.00 (1H,m), 3.77 (3H,s), 3.86~4.27 (4H,m), 4.70 (2H,s), 5.20~5.67 (2H,m), 6.39~6.87 (3H,m), 7.60~7.80 (4H,m). |

(21) Preparation of methyl [(1RS,2R*,3aS*,9aR*)-1-[(1R*,2RS)-3-acetoxy-1,2-dihydroxypropyl]-2-tert-butyldiphenylsilyloxy-2,3,3a,9a-tetrahydro-1H-cyclopenta[b][1,4]benzodioxin-5-yl]oxyacetate 22

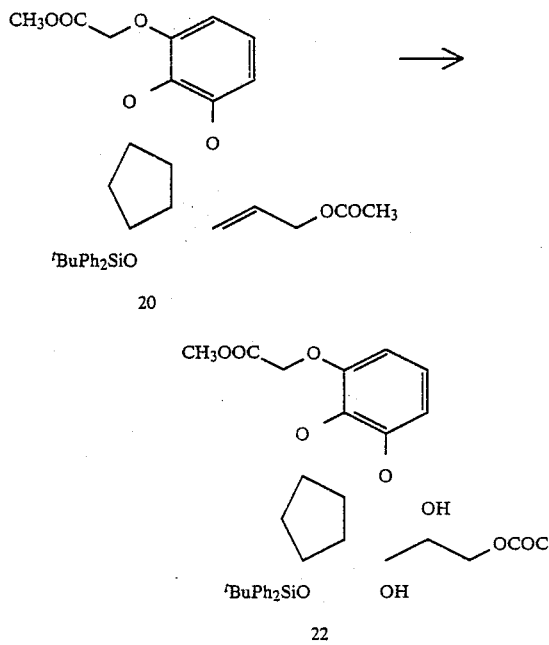

In a nitrogen atmosphere, 19.4 ml (19.4 mmol) of trimethylamine-N-oxide (1N in water) and 4.86 ml (0.97 mmol) of osmium tetraoxide (0.2N in THF) are added to a suspension of 6.00 g (9.72 mmol) of the olefin 20 (prepared in (18)) in 120 ml of acetone and the mixture is stirred for 3 days. To the reaction mixture is added 120 ml of 5% aqueous solution of sodium thiosulfate and acetone is evaporated under reduced pressure. A saturated aqueous solution of sodium chloride is added to the residue which is then extracted with ethyl acetate three times. The extract is washed with water and a saturated aqueous solution of sodium chloride, dried over anhydrous magnesium sulfate, and evaporated under reduced pressure to give 6.60 g of the crude desired diol 22 as a foamy substance, which is employed in the next step without further purification.

(22) Preparation of methyl [(1R*,2R*,3aS*,9aR*)-2-tert-butyldiphenylsilyloxy-1-formyl-2,3,3a,9a-tetrahydro-1H-cyclopenta[b][1,4]benzodioxin-5-yl]oxyacetate 23

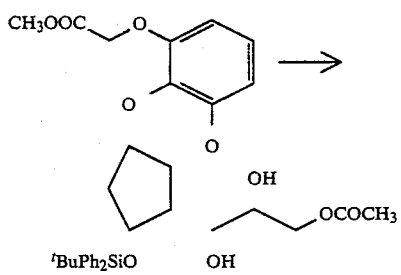

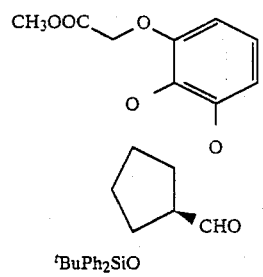

In a nitrogen atmosphere, 4.18 g (19.4 mmol) of sodium periodate is added to a solution of 6.60 g of the crude diol 22 (prepared in (21)) in 180 ml of DME and 60 ml of water at room temperature and the mixture is stirred for 2 days. To the reaction mixture is added 200 ml of 10% aqueous solution of sodium thiosulfate and the mixture is extracted with ethyl acetate three times. The extract is washed with water and a saturated aqueous solution of sodium chloride, dried over anhydrous magnesium sulfate, and evaporated under reduced pressure. The residue is purified by column chromatography on silica gel (Merck, Lobar column, size C, two columns, ethyl acetate:toluene=1:20) to give the desired aldehyde 23, which is crystallized from ether-n-hexane to give 3.38 g of the crystals in 63.6% yield over two steps.

Mp.: 110.3°~111.0° C. (ether-n-hexane).

$^1$H-NMR: δ (CDCl$_3$) 1.04 (9 H, s), 2.20 (2 H, t, J=5 Hz), 3.19~3.44 (1 H, m), 3.76 (3 H, s), 4.12~4.38 (1 H, m), 4.40~4.60 (2 H, m), 4.69 (2 H, s), 6.42~6.90 (3 H, m), 7.32~7.50 (6 H, m), 7.56~7.80 (4 H, m), 9.31 (1 H, d, J=5 Hz) ppm.

IR: ν max (CHCl$_3$) 2960, 2936, 2864, 1763, 1729, 1601, 1499, 1476, 1429, 1295, 1114, 821, 694, 612 cm$^{-1}$.

MS: m/z M+ 546.

(23) Preparation of methyl [(1R*,2R*,3aS*,9aR*)-2-tert-butyldipenylsilyloxy-1-[(E)-3-oxo-1-octenyl]-2,3,3a,9a-tetrahydro-1H-cyclopenta[b][1,4]benzodioxin-5-yl]oxyacetate III a

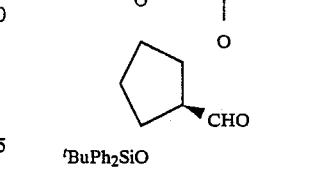

-continued

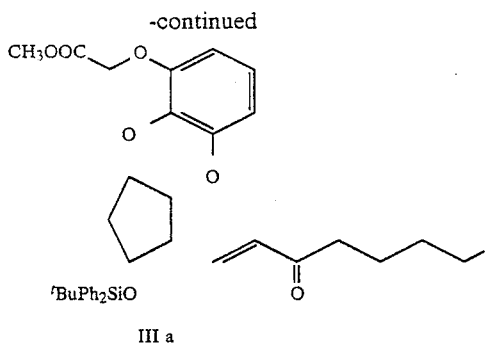

III a

In a nitrogen atmosphere, a solution of 95 mg (0.430 mmol) of dimethyl (2-oxoheptyl)phosphonate in 1.5 ml of dry THF is added to a suspension of 15.2 mg (0.381 mmol) of 60% sodium hydride in 2 ml of dry THF and the mixture is stirred at room temperature for 12 minutes. A solution of the 181 mg (0.331 mmol) of aldehyde 23 (prepared in (22)) in 3 ml of dry THF is added thereto and the resulting mixture is stirred for 30 minutes. The reaction is quenched by the addition of a saturated aqueous solution of ammonium chloride and the mixture is extracted with ethyl acetate twice. The extract is washed with water and a saturated aqueous solution of sodium chloride, dried over anhydrous magnesium sulfate, and evaporated under reduced pressure. The residue is purified by column chromatography on silica gel (Merck, Lobar column, size B, ethyl acetate:-toluene=1:30) to give 199 mg of the desired enone III a as an oil in 93.5% yield.

$^1$H-NMR: δ (CDCl$_3$) 0.89 (3 H, t, J=7 Hz), 1.03 (9 H, s), 1.05~1.80 (6 H, m), 2.10~2.50 (4 H, m), 2.86~3.21 (1 H, m), 3.77 (3 H, s), 4.02~4.26 (3 H, m), 4.71 (2 H, s), 609 (1 H, d, J=16 Hz), 6.39~6.88 (4 H, m), 7.29~7.48 (6 H, m), 7.53~7.73 (4 H, m) ppm.

IR: ν max (CHCl$_3$) 3008, 2960, 2936, 2864, 1763, 1743, 1696, 1672, 1630, 1601, 1498, 1475, 1429, 1114, 977, 822, 695, 612 cm$^{-1}$.

MS: m/z M+ 642.

(24) to (29)

According to the same method as described in (23), the aldehyde is converted into the enone III. The results are shown in Table 2. In (24), (26), and (29), a racemic phosphonate is used.

In (39), an optically active phosphonate [(S)-configuration] is used.

TABLE 2

[Reaction scheme: starting material 23 (CH₃O₂C-substituted phenoxy cyclopentane with CHO and ᵗBuPh₂SiO groups) + (CH₃O)₂PCH₂C(O)-R₁ → product III (with R₁-C(O)-CH=CH- group)]

| No. | Compd. No. | R₁ | Yd. (%) | MS (m/z) | IR νmax (cm⁻¹) | ¹H-NMR δ (ppm) |
|---|---|---|---|---|---|---|
| (24) | IIIf | n-pentyl chain | 99.5 | 656 (M⁺) | (CHCl₃) 3008, 2960, 2936, 2864, 1765, 1742, 1694, 1668, 1629, 1600, 1498, 1475, 1428, 1289, 1113, 983, 821, 612. | (CDCl₃) 0.86 (3H,t,J=7Hz), 1.02 (3H,d,J=7Hz), 1.03 (9H,s), 0.86~1.90 (6H,m), 2.01~2.26 (2H,m), 2.30~2.75 (1H,m), 2.88~3.28 (1H,m), 3.77 (3H,s), 4.02~4.27 (3H,m), 4.71 (2H,s), 6.22 (1H,d,J=16Hz), 6.39~6.87 (4H,m), 7.28~7.48 (6H,m), 7.52~7.80 (4H,m). |
| (25) | IIIg | branched chain | 97.4 | 670 (M⁺) | (CHCl₃) 3008, 2964, 2936, 2864, 1764, 1743, 1690, 1627, 1600, 1498, 1475, 1429, 1288, 1114, 981, 822, 612. | (CDCl₃) 0.84 (3H,t,J=7Hz), 1.02 (9H,s), 1.06 (6H,s), 0.76~1.86 (6H,m), 2.00~2.20 (2H,m), 2.91~3.28 (1H,m), 3.77 (3H,s), 3.96~4.25 (3H,m), 4.71 (2H,s), 6.40~6.93 (5H,m), 7.30~7.49 (6H,m), 7.51~7.80 (4H,m). |
| (26) | IIIh | branched unsaturated chain | 98.7 | 652 (M⁺) | (CHCl₃) 3008, 2960, 2936, 2864, 1764, 1742, 1696, 1669, 1630, 1601, 1498, 1475, 1429, 1288, 1114, 981, 821, 612. | (CDCl₃) 1.02 (9H,s), 1.09 (3H,d,J=7Hz), 1.72 (3H,t,J=2.5Hz), 2.00~2.40 (4H,m), 2.40~3.26 (2H,m), 3.76 (3H,s), 4.01~4.25 (3H,s), 4.70 (2H,s), 6.18 (1H,d,J=16Hz), 6.39~6.87 (4H,m), 7.29~7.47 (6H,m), 7.52~18 7.7 4 (4H,m). |
| (27) | IIIi | cyclopentyl | ~100 | 640 (M⁺) | (CHCl₃) 3008, 2960, 2864, 1764, 1742, 1694, 1666, 1630, 1600, 1498, 1475, 1429, 1290, 1114, 980, 821, 612. | (CDCl₃) 1.02 (9H,s), 1.45~1.90 (8H,m), 2.01~2.28 (2H,m), 2.70~3.23 (2H,m), 3.77 (3H,s), 4.02~4.27 (3H,m), 4.71 (2H,s), 6.17 (1H,d,J=16Hz), 6.40~6.88 (4H,m), 7.27~7.49 (6H,m), 7.52~7.80 (4H,m). |
| (28) | IIIj | cyclohexylmethyl | 97.9 | 668 (M⁺) | (CHCl₃) 3008, 2936, 2860, 1764, 1743, 1693, 1670, 1628, 1601, 1498, 1475, 1429, 1293, 1113, 978, 821, 612. | (CDCl₃) 1.02 (9H,s), 0.60~1.92 (11H,m), 2.06~2.37 (4H,m), 2.82~3.24 (1H,m), 3.77 (3H,s), 3.92~4.28 (3H,m), 4.70 (2H,m), 6.07 (1H,d,J=16Hz), 6.40~6.87 (4H,m), 7.27~7.48 (6H,m), 7.52~7.80 (4H,m). |
| (29) | IIIk | prenyl/unsaturated chain | 98.9 | 696 (M⁺) | (CHCl₃) 3008, 2960, 2864, 1763, 1742, 1694, 1628, 1601, 1498, 1429, 1290, 1114, 979, 821, 612. | (CDCl₃) 0.87 (3H,d,J=6Hz), 1.03 (9H,s), 1.10~1.42 (2H,m), 1.60 (3H,s), 1.67 (3H,s), 1.65~2.60 (7H,m), 2.85~3.29 (1H,m), 3.77 (3H,s), 3.95~4.27 (3H,m), 4.71 (2H,s), 4.93~5.22 (1H,m), 6.13 (1H,d,J=16Hz), 6.40~6.87 (4 H,m), 7.32~7.50 (6H,m), 7.52~7.80(4H,m). |

TABLE 2-continued

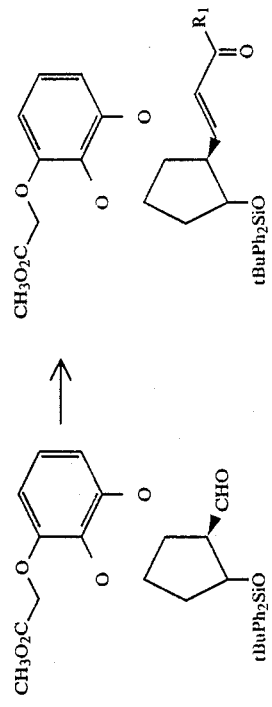

| No. | Compd. No. | R₁ | Yield (%) | MS (m/z) | IR νmax (cm⁻¹) | ¹H—NMR δ (ppm) (200 MHz) |
|---|---|---|---|---|---|---|
| (37) | IIIm | (phenoxypropyl) | 92.7 | 706 (M⁺) | (CHCl₃) 2936, 2864, 1766, 1743, 1698, 1672, 1629, 1600, 1497, 1475, 1428, 1239, 1114, 978, 822, 616. | (CDCl₃) 1.03(9H,s), 1.33(3H,d,J=6Hz), 2.15~2.27(2H,m), 2.58(1H,ddd, J=16Hz, 7Hz, 5Hz), 2.91(1H,ddd,J=16Hz, 6Hz, 1.5Hz), 3.06(1H,q,J=8Hz), 3.80(3H,s), 4.00~4.22(3H,m), 4.74(2H,s), 4.80~4.96(1H,m), 6.13(1H,d, J=16Hz), 6.45~6.64(3H,m), 6.78(1H,t,J=8Hz), 6.86~7.00(3H,m), 7.23~7.48 (8H,m), 7.55~7.70(4H,m). |
| (38) | IIIo | (phenoxybutyl) | 97.8 | 720 (M⁺) 721 (MH⁺) | (CHCl₃) 2936, 2864, 1764, 1743, 1698, 1671, 1631, 1601, 1499, 1475, 1429, 1243, 1113, 822, 612. | (CDCl₃) 1.03(9H,s), 1.04(3H,d,J=6Hz), 2.12~2.22(2H,m), 2.33(1H,dt, J=16Hz, 6Hz), 2.40~2.59(1H,m), 2.69(1H,ddd,J=16Hz, 6Hz, 2Hz), 3.03(1H,q, J=8Hz), 3.80(3H,s), 3.71~3.87(2H,m), 3.97~4.21(3H,m), 4.73(2H,s), 6.12 (1H,d,J=16Hz), 6.45~6.64(3H,m), 6.78(1H,t,J=8Hz), 6.84~6.97(3H,m), 7.20~ 7.46(8H,m), 7.55~7.70(4H,m). |
| (39) | IIIq | (allyl branched chain) | 97.0 | 668 (M⁺) 669 (MH⁺) | (CHCl₃) 2936, 2864, 1764, 1742, 1696, 1667, 1629, 1601, 1499, 1476, 1429, 1289, 1114, 913, 822, 812. | (CDCl₃) 0.88(3H,d,J=7Hz), 1.03(9H,s), 1.14~1.48(2H,m), 1.91~2.46(7H,m), 3.07(1H,q,J=7Hz), 3.80(3H,s), 4.00~4.24(3H,m), 4.74(2H,s), 4.90~5.07 (2H,m), 5.69~5.91(1H,m), 6.14(1H,d,J=16Hz), 6.45~6.64( 3H,m), 6.78(3H,t, J=8Hz), 7.30~7.50(6H,m), 6.55~7.70(4H,m). |
| (40) | IIIs | —SePh (hexyl) | 96.6 | 826 (M⁺) | (CHCl₃) 2936, 2864, 1764, 1743, 1696, 1670, 1636, 1601, 1499, 1476, 1439, 1429, 1291, 1114, 822, 611. | (CDCl₃) 0.87(3H,t,J=7Hz), 1.03(9H,s), 1.10~1.48(6H,m), 2.10~2.44(4H,m), 2.56~2.71(1H,m), 2.87~3.09(3H,m), 3.80(3H,s), 3.98~4.22(3H,m), 4.74(2H, s), 6.05(1H,d,J=16Hz), 6.45~6.63(3H,m), 6.78(3H,t,J=8Hz), 7.14~7.70 (15H,m). |

(30) Preparation of ethyl 3-phenoxybutyrate 28

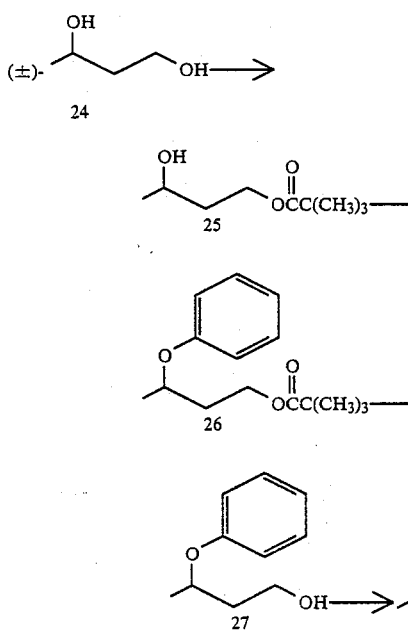

(1) Preparation of 1-tert-butylcarbonyloxy-3-butanol 25

To a mixture of 13.2 ml (0.15 mol) of (±)-1,3-butandiol 24 and 17.8 ml (0.23 mol) of pyridine in 200 ml of dry dichloromethane is added a solution of 22.2 ml (0.18 mol) of pivaloyl chloride in 50 ml of dry dichloromethane dropwise over 20 minutes under ice cooling. Then, the mixture is stirred for additional 30 minutes at room temperature. Ice-cooled water is added and the mixture is stirred for 5 minutes and then 1N hydrochloric acid is added thereto. The mixture is extracted with dichloromethane twice. The extract is washed with water, a saturated aqueous solution of sodium hydrogencarbonate, and a saturated aqueous solution of sodium chloride, dried over anhydrous magnesium sulfate, and evaporated under reduced pressure. The residue is purified by column chromatography on silica gel (250 g of silica gel, ethyl acetate:n-hexane=1:9 to 1:4) to give 20.4 g of the desired monopivaloyl ester 25 as an oil in 78.2% yield.

$^1$H-NMR δ ppm (CDCl$_3$): 1.21 (9 H, s), 1.23 (3 H, d, J=6 Hz), 1.60–1.95 (2 H, m), 2.27 (1 H, br. s., —OH), 3.72–4.47 (3 H, m).

(2) Preparation of 1-tert-butylcarbonyloxy-3-phenoxybutane 26

To a solution of 3.47 g (19.9 mmol) of alcohol 25 (prepared in 30-(1)), 2.81 g (29.9 mmol) of phenol, and 7.88 g (29.9 mmol) of triphenylphosphine in 100 ml of dry THF is added a solution of 4.65 ml of diethyl azodicarboxylate in 40 ml of dry THF dropwise under ice cooling. After additional stirring at the same temperature for 20 minutes, the mixture is stirred for further 2 and half hours. The reaction mixture is concentrated under reduced pressure and the residue is purified by column chromatography on silica gel (200 g of silica gel, ethyl acetate:n-hexane=1:49 to 1:19) to give 4.35 g of the desired phenyl ether 3 as an oil in 87.4% yield.

$^1$H-NMR (200 MHz) δ ppm (CDCl$_3$): 1.10 (9 H, s), 1.34 (3 H, d, J=6 Hz), 1.83–2.16 (2 H, m), 4.11–4.31 (2 H, m), 4.42–4.60 (1 H, m), 6.85–6.98 (3 H, m), 7.21–7.32 (2 H, m),

(3) Preparation of 3-phenoxy-1-butanol 27

To a solution of 4.32 g (17.3 mmol) of pivaloyl ester 26 (prepared in 30-(2)) in 90 ml of dry methanol is added 17.3 ml (17.3 mmol) of 1M sodium methoxide-methanol solution and the mixture is stirred at 55° C. for 9 hours. After cooling, 35 g of ion exchange resin IRC-50 is added and the mixture is stirred for 20 minutes. The ion exchange resin is filtrated off and the filtrate is evaporated under reduced pressure to give 3.15 g of the crude desired alcohol 27 as an oil, which is employed in the next step without further reaction.

(4) Preparation of ethyl 3-phenoxybutyrate 28

To a solution of 3.15 g of the crude alcohol 27 (prepared in 30-(3)) in 80 ml of acetone is added 10 ml of 8N Jones' reagent at 20° C. to 30° C. dropwise. The mixture is stirred for additional 10 minutes, and 3 ml of isopropyl alcohol is added thereto. The resulting mixture is stirred for 10 minutes and acetone is evaporated under reduced pressure. Water is added to the residue, and the residue is extracted with ethyl acetate twice. The organic layer is washed with water and then extracted with 1N aqueous solution of sodium hydroxide. The aqueous layer is acidified to pH 2 with hydrochloric acid and extracted with ethyl acetate again. The ethyl acetate extract is washed with water and a saturated aqueous solution of sodium chloride, dried over anhydrous magnesium sulfate, and evaporated under reduced pressure. The residue is dissolved in 50 ml of ether and an ethereal solution of diazoethane is added at 0° C. until the orange color persists. The reaction mixture is evaporated under reduced pressure and the residue is purified by column chromatography on silica gel (50 of silica gel, ethyl acetate-n-hexane=1:19) to give 2.35 g of the desired ethyl ester 28 as an oil in 67.0% yield from the compound 26.

$^1$H-NMR (200 MHz) δ ppm (CDCl$_3$): 1.24 (3 H, t, J=7 Hz), 1.37 (3 H, d, J=6 Hz), 2.53 (1 H, dd, J=15 Hz, 6.5 Hz), 2.79 (1 H, dd, J=15 Hz, 7 Hz), 4.14 (2 H, q, J=7 Hz), 4.75–4.92 (1 H, m), 6.88–6.98 (3 H, m), 7.22–7.33 (2 H, m).

(31) Preparation of (S)-(−)-methyl 3-methyl-6-heptenoate 32

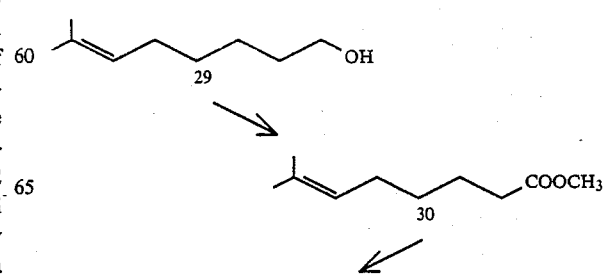

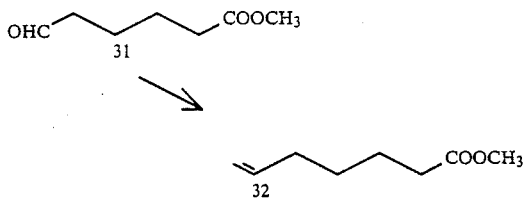

(1) Preparation of (S)-(−)-methyl citronellate 30

To a solution of 10.0 g (64.1 mmol) of (S)-(−)-citronellol 29 (Aldrich, 98% e.e.) in 150 ml of dry DMF is added 84.4 g (224 mmol) of pyridinium dichromate (PDC), and the mixture is stirred overnight. The reaction mixture is poured into 1.5 l of water, and extracted with toluene twice. The extract is washed with water, and then extracted with 1N aqueous solution of sodium hydroxide to separate the carboxylic acid. The aqueous layer is acidified with 5N hydrochloric acid to pH 2, and extracted with ethyl acetate again. The ethyl acetate extract is washed with water, a saturated aqueous solution of sodium chloride, dried over anhydrous magnesium sulfate, and evaporated under reduced pressure. To a solution of residue in 100 ml of ether is added an ethereal solution of diazomethane at 0° C. until the yellow color persists. The reaction mixture is distilled under reduced pressure to give 7.53 g of the desired methyl ester 30 as an oil in 63.9% yield.

Bp. 78° C. to 81° C. (3 mmHg).

$[\alpha]_D$ −7.4±0.1° (24° C., c=5.13, CHCl$_3$).

$^1$H-NMR δ ppm (CDCl$_3$) 0.94 (3 H, d, J=7 Hz), 1.10–1.46 (2 H, m), 1.62 (3 H, s), 1.68 (3 H, s), 1.70–2.50 (5 H, m), 3.66 (3 H, s), 4.93–5.21 (1 H, m).

(2) Preparation of (S)-methyl 3-methyl-6-oxohexanoate 31

To a solution of 7.76 g (36 mmol) of 80% m-chloroperbenzoic acid in 200 ml of dry dichloromethane is added a solution of 6.00 g (32.6 mmol) of (S)-methyl citronellate 30 (prepared in 31-(1)) in 50 ml of dry dichloromethane, and the mixture is stirred at room temperature for one hour. The reaction mixture are added 5% aqueous solution of sodium thiosulfate and a dilute aqueous solution of sodium hydrogencarbonate, and the mixture is extracted with dichloromethane twice. The extract is washed with a saturated aqueous solution of sodium hydrogencarbonate and a saturated aqueous solution of sodium chloride, dried over anhydrous magnesium sulfate, and evaporated under reduced pressure. To a solution of the residue in 80 ml of THF is added a solution of 8.90 g (39 mmol) of periodic acid dihydrate in 80 ml of THF at 0° C. After additional stirring at room temperature for 20 minutes, the reaction mixture is diluted with water, and extracted with ether twice. The extract is washed with water, a saturated aqueous solution of sodium hydrogencarbonate, and a saturated aqueous solution of sodium chloride, dried over anhydrous magnesium sulfate, and evaporated under reduced pressure to give 5.2 g of the crude desired aldehyde 31 as an oil, which is employed in the next step without further purification.

(3) Preparation of (S)-(−)-methyl 3-methyl-6-heptenoate 32

To a suspension of 23.3 g (65.2 mmol) of methyltriphenylphosphonium bromide in 120 ml of dry THF is added 36.9 ml (58.7 mmol) of 1.59 N n-butyllithium-n-hexane solution dropwise under ice cooling in a nitrogen atmosphere. After additional stirring at the same temperature for 10 minutes, the mixture was cooled to −50° C., and a solution of 5.2 g of crude aldehyde 31 (prepared in 31-(2)) in 80 ml of dry THF is added dropwise thereto. Then, the mixture is stirred at the same temperature for 10 minutes, and warmed to room temperature over an hour. To the reaction mixture is added a saturated aqueous solution of ammonium chloride, and the mixture is extracted with ether twice. The extract is washed with water and a saturated aqueous solution of sodium chloride, dried over anhydrous mangeium sulfate, and evaporated at atmospheric pressure. To the residue is added 400 ml of n-pentane and the mixture is stirred under ice cooling for 30 minutes. The precipitated triphenylphosphinoxide is removed by filtration through 100 g of silica gel. The silica gel is washed with 500 ml of mixture of ether:n-pentane=1:9. The filtrate and washing are combined and concentrated at atmospheric pressure. The residue is distilled under reduced pressure to give 2.19 g of the desired olefin 32 as an oil in 43.1% yield from compound 30.

bp. 85° C. to 86° C. (23 mmHg).

$[\alpha]_D$ −6.6±0.2° (23° C., c=2.06, CHCl$_3$).

$^1$H-NMR (200 MHz) δ ppm (CDCl$_3$): 0.95 (3 H, d, J=6 Hz), 0.97–1.52 (2 H, m), 1.88–2.38 (5 H, m), 3.67 (3 H, s), 4.90–5.09 (2 H, m), 5.70–5.91 (1 H, m).

IR: ν max (CHCl$_3$) 2960, 1734, 1642, 1439, 1172, 1006, 916 cm$^{-1}$.

(32) Preparation of methyl 3-(phenylselenylmethyl)heptanoate 35

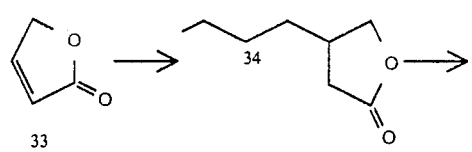

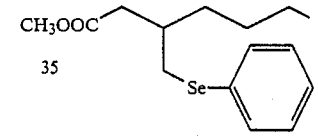

(1) Preparation of 3-n-butyl-γ-butyrolactone 34

To a suspension of 6.17 g (30 mmol) of copper(I) bromide-dimethyl sulfide complex in 100 ml of dry ether is added 38 ml (60 mmol) of 1.59N n-butyllithium-n-hexane solution dropwise at −50° C. under a nitrogen atmosphere over 30 minutes. After additional stirring at the same temperature for 15 minutes, the mixture is cooled to −78° C., and then a solution of 3.8 ml (30 mmol) of chlorotrimethylsilane in 10 ml of dry ether is added, which is followed by addition of a solution of 1.68 g (20 mmol) of 2(5 H)-furanon 33 in 20 ml of dry ether. The mixture is stirred at the same temperature for additional 30 minutes and warmed to −10° C. over 30 minutes. The reaction is quenched by the addition of a saturated aqueous solution of ammonium chloride. Air is blown into the reaction mixture for 30 minutes and it is filtered through Celite. The filtrate is extracted with ether twice and the extract is washed with water, a saturated aqueous solution of sodium chloride, dried over anhydrous magnesium sulfate, and evaporated under reduced pressure. To a solution of the residue in 150 ml of THF is added 20 ml of 2N aqueous solution of sodium hydroxide and the mixture is stirred at room temperature for 40 minutes. The reaction mixture is acidified to pH 2 with 1N hydrochloric acid and extracted with ether twice. The extract is washed with water and a saturated aqueous solution of sodium chloride, dried over anhydrous magnesium sulfate, and evaporated under reduced pressure. To a solution of the residue in 30 ml of dry benzene is added catalytical amount of p-toluenesulfonic acid and the mixture is heated for 15 minutes under reflux. After cooling to room temperature, a dilute aqueous solution of sodium hydrogencarbonate is added, and the mixture is extracted with ethyl acetate twice. The extract is washed with water and a saturated aqueous solution of sodium chloride, dried over anhydrous magnesium sulfate, and evaporated under reduced pressure. The residue is distilled under reduced pressure to give 2.19 g of the desired lacton 34 as an oil in 77.1% yield.

Bp. 94°-95° C. (2 mmHg).

$^1$H-NMR δ ppm (CDCl$_3$): 0.91 (3 H, t, J=7 Hz), 1.12-1.80 (6 H, m), 1.97-2.83 (3 H, m), 3.93 (1 H, dd, J=9 Hz, 6 Hz), 4.43 (1 H, dd, J=9 Hz, 7 Hz).

(2) Preparation of methyl 3-(phenylselenylmethyl)heptanoate 35

To a solution of 2.40 g (7.69 mmol) of diphenyl diselenide in 30 ml of dry DMF is added 655 mg (17.3 mmol) of sodium borohydride in portions under ice cooling in a nitrogen atmosphere. After hydrogen evolution is finished, the reaction mixture is stirred at 100° C. for 20 minutes. At the same temperature, a solution of 1.68 g (11.8 mmol) of lacton 14 (prepared 32-(1)) in 10 ml of DMF is added thereto and the mixture is stirred for two and half hours at 120° C. After cooling with ice, the mixture is acidified to pH 2 by dropwise addition of 10% hydrochloric acid. The reaction mixture is extracted with ether twice and the extract is washed with water and a saturated aqueous solution of sodium chloride, dried over anhydrous magnesium sulfate, and evaporated under reduced pressure. The residue is dissolved in 30 ml of ether and an ethereal solution of diazomethane is added at 0° C. thereto until the yellow color persists. The reaction mixture is evaporated under reduced pressure and the residue is purified by column chromatography on silica gel (Merck, Lobar column, size C, ethyl acetate-n-hexane=1:19) to give 2.64 g of the desired methyl ester 35 as an oil in 71.5% yield.

$^1$H-NMR δ ppm (CDCl$_3$): 0.86 (3 H, t, J=7 Hz), 1.05-1.63 (6 H, m), 2.00-2.70 (3 H, m), 2.98 (2 H, d, J=5 Hz), 3.63 (3 H, m), 7.17-7.33 (3 H, m), 7.32-7.62 (2 H, m).

(33) Preparation of dimethyl 2-oxo-4-(phenylselenylmethyl)octylphosphonate 36

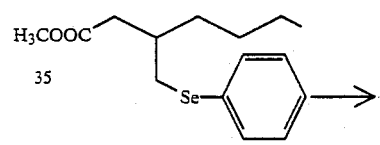

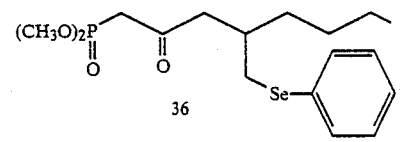

To a solution of 1.35 ml (12.5 mmol) of dimethyl methylphosphonate in 25 ml of dry THF is added 7.0 ml (11.5 mmol) of 1.64N n-butyllithium-n-hexane solution dropwise at −78° C. in a nitrogen atmosphere. After stirring at the same temperature for one hour, 1.57 g (10.0 mmol) of methyl ester (prepared in 32-(2)) in 10 ml of dry THF is added thereto. The resulting mixture is stirred for additional 30 minutes and then the reaction is quenched by the addition of a saturated aqueous solution of ammonium chloride. The reaction mixture is extracted with ethyl acetate twice and the extract is washed with water and a saturated aqueous solution of sodium chloride, dried over anhydrous magnesium sulfate, and evaporated under reduced pressure. The residue is purified by column chromatography on silica gel (Merck, Lobar column, size B, acetone:benzene=1:4) to give 1.42 g of the desired phosphonate 36 as an oil in 70.0% yield.

$^1$H-NMR δ ppm (CDCl$_3$): 0.86 (3 H, t, J=7 Hz), 1.02-1.70 (6 H, m), 1.90-3.05 (5 H, m), 2.95 (2 H, d, J=22 Hz), 3.77 (6 H, d, J=11 Hz), 7.15-7.32 (3 H, m), 7.40-7.62 (2 H, m).

34–36 Preparation of Intermediate

The dimethylphosphonates 37, 38, and 40 can be prepared from the esters 28 (prepared in 30-(4)), 32 (prepared in 31-(3)), and 39 in the same manner as described in 36. In regards to compound 39, the racemate is prepared as described by G. S. Marks et al., J. Chem. Soc., 3851, (1955).

The physical constants of compounds 37, 38, and 40 are shown below.

Compound 37

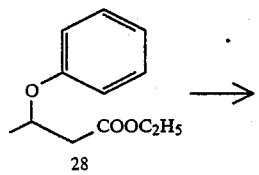

-continued

Compound 37

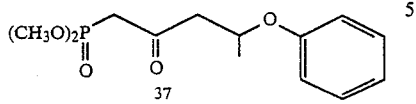

$^1$H-NMR (200 MHz) δ ppm (CDCl$_3$): 1.34 (3 H, d, J=6 Hz), 2.78–3.29 (4 H, m), 3.78 (6 H, d, J=1 Hz), 4.80–4.96 (1 H, m), 6.85–7.00 (3 H, m), 7.22–7.33 (2 H, m).

Compound 38

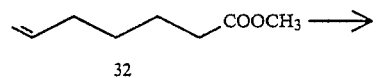

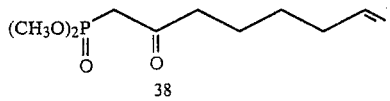

[α]$_D$ −5.5±0.5° (23° C., c=0.98, CHCl$_3$).

$^1$H-NMR (200 MHz) δ ppm (CDCl$_3$): 0.92 (3 H, d, J=7 Hz), 1.16–1.50 (2 H, m), 1.97–2.19 (3 H, m), 2.46 (1 H, dd, J=17 Hz, 7 Hz), 2.59 (1 H, dd, J=17 Hz, 6 Hz), 3.07 (2 H, d, J=22 Hz), 3.79 (6 H, d, J=11 Hz), 4.90–5.08 (2 H, m), 5.69–5.90 (1 H, m).

Compound 40

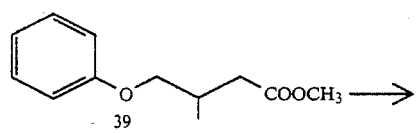

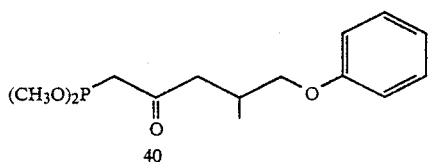

$^1$H-NMR (200 MHz) δ ppm (CDCl$_3$): 1.06 (3 H, d, J=6 Hz), 2.47–2.67 (2 H, m), 2.80–2.96 (1 H, m), 3.12 (2 H, d, J=22 Hz), 3.77 (3 H, d, J=11 Hz), 3.78 (3 H, d, J=11 Hz), 3.75–3.92 (2 H, m), 6.84–6.97 (3 H, m), 7.22–7.33 (2 H, m).

EXAMPLE 5

Preparation of methyl [(1R*,2R*,3aS*,9aR*)-2-tert-butyldiphenylsilyloxy-1-(3S*,1E)-3-hydroxy-1-octenyl]-2,3,3a,9a-tetrahydro-1H-cyclopenta[b][1,4]benzodioxin-5-yl]oxyactate Iaa-a and methyl [(1R*,2R*,3aS*,9aR*)-2-tert-butyldiphenylsilyloxy-1-(3R*,1E)-3-hydroxy-1-octenyl]-2,3,3a,9a-tetrahydro-1H-cyclopenta[b][1,4]benzodioxin-5-yl]oxyacetate Ica-a

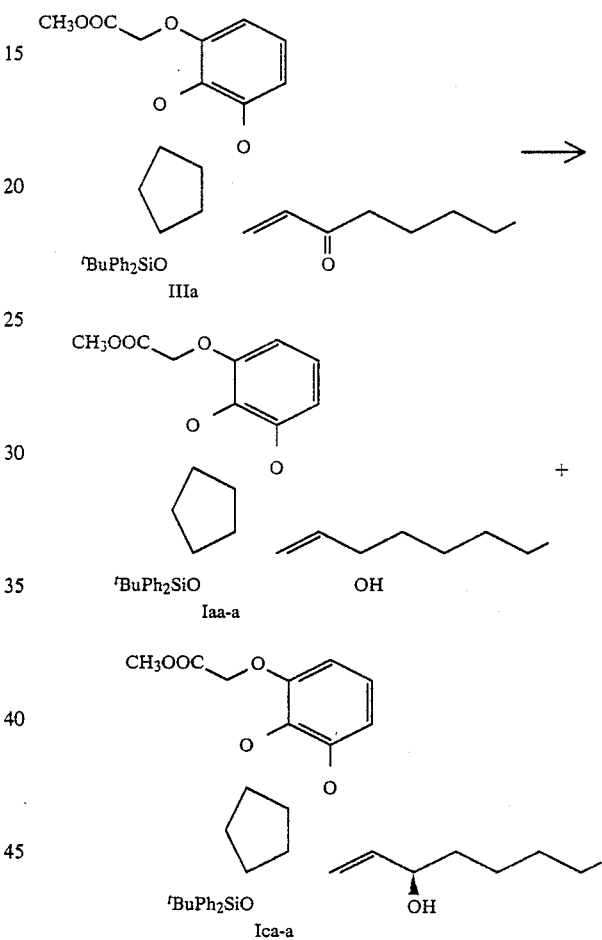

To a solution of 120 mg (0.187 mmol) of the enone IIIa (prepared in (23)) and 70 mg (0.188 mmol) of cerium trichloride heptahydrate in 2 ml of methanol is added a solution of 7.1 mg (0.187 mmol) of sodium borohydride in 0.7 ml of methanol dropwise under ice cooling and then the mixture is stirred at the same temperature for 20 minutes. A saturated aqueous solution of ammonium chloride is added, and the mixture is extracted with ethyl acetate twice. The extract is washed with water and a saturated aqueous solution of sodium chloride, dried over anhydrous magnesium sulfate, and evaporated under reduced pressure. The residue is purified by column chromatography on silica gel (Merck, Lobar column, size A, two columns, ethyl acetate:toluene=1:15) to give the desired allyl alcohol, namely, 84 mg of the less polar isomer Iaa-a and 27 mg of the more polar isomer Ica-a in 70.0% and 22.5% yield, respectively. The physical properties of each compound Iaa-a and Ica-a prepared in Example 5 are identical with those of Iaa-a and Ica-a prepared in Example 1, respectively.

Examples 6 to 13

In the same manner as described in Example 5, the enone III is converted into the allyl alcohol Ia-a and Ic-a. The results are shown in Table 3. In example 11, the four isomers of allyl alcohol Iak-a, Ial-a, Ick-a, and Icl-a are prepared. In Examples 6 and 10, the reaction is carried out at −78° C.

TABLE 3

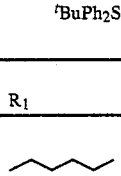

| Ex. No. | R₁ | Compd No. | Yd. (%) | MS (m/z) | IR νmax (cm⁻¹) | ¹H—NMR δ (ppm) |
|---|---|---|---|---|---|---|
| 6 | 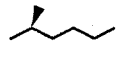 | I af-a | 85.3 | 658 (M⁺) | (CHCl₃) 3612, 3008, 2964, 2936, 2864, 1764, 1743, 1600, 1498, 1475, 1429, 1290, 1114, 970, 821, 612. | (CDCl₃) 0.73~0.97(6H,m), 1.03(9H,s), 1.00~1.70(8H,m), 2.06~2.26(2H,m), 2.75~3.05(1H,m), 3.76(3H,s), 3.65~4.27(4H,m), 4.70(2H,s), 5.16~5.67(2H,m), 6.38~6.86(3H,m), 7.30~7.50(6H,m), 7.59~7.77(4H,m). |
|   |   | I cf-a | 11.8 | 658 (M⁺) | (CHCl₃) 3608, 3008, 2964, 2936, 2864, 1764, 1742, 1600, 1498, 1475, 1429, 1290, 1114, 970, 822, 612. | (CDCl₃) 0.76~1.00(6H,m), 1.03(9H,s), 1.00~1.80(8H,m), 2.06~2.25(2H,m), 2.75~3.06(1H,m), 3.76(3H,s), 3.75~4.30(4H,m), 4.70(2H,s), 5.20~5.71(2H,m), 6.39~6.87(3H,m), 7.29~7.48(6H,m), 7.58~7.80(4H,m). |
| 7 | 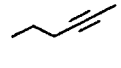 | I ag-a | 70.7 | 672 (M⁺) | (CHCl₃) 3612, 3008, 2964, 2936, 2864, 1764, 1742, 1600, 1498, 1475, 1429, 1293, 1113, 971, 819, 611. | (CDCl₃) 0.76(3H,s), 0.80(3H,s), 0.88(3H,t,J=7Hz), 1.03 (9H,s), 0.78~1.40(7H,m), 2.01~2.26(2H,m), 2.73~3.07(1H,m), 3.61(1H,d,J=7Hz), 3.77(3H,s), 3.86~4.30(3H,m), 4.70(2H,s), 5.13~5.70(2H,m), 6.39~6.87(3H,m), 7.30~7.48(6H,m), 7.59~7.77(4H,m). |
|   |   | I cg-a | 21.9 | 672 (M⁺) | (CHCl₃) 3612, 3008, 2964, 2936, 2864, 1764, 1743, 1600, 1498, 1475, 1429, 1291, 1113, 972, 821, 612. | (CDCl₃) 0.74(3H,s), 0.78(3H,s), 0.87(3H,t,J=7Hz), 1.03 (9H,s), 0.77~1.45(7H,m), 2.02~2.23(2H,m), 2.75~3.06(1H,m), 3.65(1H,d,J=5Hz), 3.76(3H,s), 3.90~4.28(3H,m), 4.70(2H,s), 5.22~5.76(2H,m), 6.39~6.86(3H,m), 7.29~7.46(6H,m), 7.57~7.80(4H,m). |
| 8 | 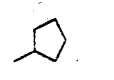 | I ah-a | 65.2 | 654 (M⁺) | (CHCl₃) 3612, 3008, 2964, 2940, 2864, 1765, 1741, 1600, 1498, 1475, 1429, 1291, 1113, 970, 821, 611. | (CDCl₃) 0.81~1.01(3H,m), 1.03(9H,s), 1.78(3H,m), 1.30~ 2.42(6H,m), 2.73~3.10(1H,m), 3.79(3H,s), 3.80~4.40 (3H,m), 4.73(2H,s), 5.20~5.70(2H,m), 6.41~6.89(3H,m), 7.30~7.50(6H,m), 7.60~7.83(4H,m). |
|   |   | I ch-a | 21.0 | 654 (M⁺) | (CHCl₃) 3612, 3008, 2960, 2940, 2864, 1763, 1742, 1600, 1498, 1475, 1429, 1289, 1114, 970, 822, 612. | (CDCl₃) 0.87(3H,d,J=7Hz), 1.03(9H,s), 1.42~1.93(2H,m), 1.77(3H,t,J=2.5Hz), 2.01~2.26(4H,m), 2.76~3.07(1H,m), 3.77(3H,s), 3.75~4.30(4H,m), 4.70 (2H,s), 5.23~5.71(2H,m), 6.40~6.89(3H,m), 7.32~7.50(6H,m), 7.57~7.80(4H,m). |
| 9 |  | I ai-a | 70.1 | 642 (M⁺) | (CHCl₃) 3608, 3008, 2960, 2864, 1764, 1743, 1600, 1498, 1476, 1429, 1290, 1114, 970, 821, 612. | (CDCl₃) 1.03(9H,s), 0.90~1.95(10H,m), 2.06~2.26(2H,m), 2.73~3.03(1H,m), 3.76(3H,s), 3.62~3.82(1H,m), 3.88~4.27(3H,m), 4.69(2H,s), 5.16~5.67(2H,m), 6.39~6.86(3H,m), 7.30~7.47(6H,m), 7.57~7.76(4H,m). |
|   |   | I ci-a | 21.6 | 642 (M⁺) | (CHCl₃) 3608, 3008, 2960, 2864, 1764, 1743, 1600, 1498, 1476, 1428, 1290, 1113, 972, 821, 612. | (CDCl₃) 1.03(9H,s), 0.90~2.05(10H,m), 2.05~2.23(2H,m), 2.75~3.05(1H,m), 3.76(3H,s), 3.63~3.90(1H,m), 3.90~4.30(3H,m), 4.70(2H,s), 5.23~5.72(2H,m), 6.39~6.86(3H,m), 7.30~7.46(6H,m), 7.57~7.76(4H,m). |

TABLE 3-continued

Reaction scheme: Compound III (with CH₃O₂C-O-phenyl-O-cyclopentyl-CH=CH-C(O)-R₁ and tBuPh₂SiO group) → Ia-a (with OH instead of C=O, specific stereochemistry) + Ic-a (with OH, opposite stereochemistry)

| Ex. No. | R₁ | Compound No. | Yd. (%) | MS (m/z) | IR νmax (cm⁻¹) | ¹H—NMR δ ppm (CDCl₃) |
|---|---|---|---|---|---|---|
| 10 | ethyl-cyclohexyl (H) | I aj-a | 77.6 | 670 (M⁺) | (CHCl₃) 3608, 3008, 2932, 2860, 1764, 1742, 1600, 1498, 1475, 1429, 1289, 1113, 971, 821, 611. | (CDCl₃) 1.03(9H,s), 0.60~2.30(15H,m), 2.71~3.03(1H,m), 3.76(3H,s), 3.83~4.29(4H,m), 4.69(2H,s), 5.15~5.66 (2H,m), 6.36~6.86(3H,m), 7.29~7.47(6H,m), 7.52~7.78 (4H,m). |
|  |  | I cj-a | 19.9 | 670 (M⁺) | (CHCl₃) 3608, 3008, 2932, 2860, 2860, 1764, 1742, 1600, 1498, 1475, 1429, 1288, 1113, 971, 822, 612. | (CDCl₃) 1.03(9H,s), 0.60~1.90(13H,m), 2.00~2.23(2H,m), 2.71~3.01(1H,m), 3.76(3H,s), 3.86~4.30(4H,m), 4.69(2H,s), 5.19~5.68(2H,m), 6.37~6.87(3H,m), 7.28~7.47(6H,m), 7.55~7.79(4H,m). |
| 11 | (branched alkenyl chain) | I ak-a (Isomer 1) | 31.8 | 698 (M⁺) | (CHCl₃) 3604, 3008, 2960, 2936, 2864, 1763, 1742, 1600, 1498, 1475, 1429, 1291, 1113, 970, 821, 612. | (CDCl₃) 0.88(3H,d,J=7Hz), 1.03(9H,s), 1.59(3H,s), 1.66(3H,s), 0.95~2.25(10H,m), 2.72~3.04(1H,m), 3.76(3H,s), 3.85~4.27(4H,m), 4.70(2H,s), 4.96~5.68(3H,m), 6.38~6.86(3H,m), 7.29~7.50(6H,m), 7.56~7.80(4H,m). |
|  |  | I al-a (Isomer 2) | 28.9 | 698 (M⁺) | (CHCl₃) 3608, 3008, 2960, 2936, 2864, 1763, 1742, 1600, 1498, 1475, 1429, 1289, 1113, 969, 821, 612. | (CDCl₃) 0.86(3H,d,J=7Hz), 1.03(9H,s), 1.59(3H,s), 1.66(3H,s), 0.95~2.30(10H,m), 2.72~3.03(1H,m), 3.77(3H,s), 3.85~4.30(4H,m), 4.70(2H,s), 4.96~5.65(3H,m), 6.39~6.88(3H,m), 7.30~7.49(6H,m), 7.56~7.80(4H,m). |
|  |  | I ck-a (Isomer 1) | 13.6 | 698 (M⁺) | (CHCl₃) 3604, 3008, 2960, 2936, 2864, 1764, 1743, 1600, 1498, 1475, 1429, 1289, 1114, 969, 821, 612. | (CDCl₃) 0.87(3H,d,J=7Hz), 1.03(9H,s), 1.59(3H,s), 1.66(3H,s), 0.95~2.33(10H,m), 2.72~3.06(1H,m), 3.76(3H,s), 3.85~4.27(4H,m), 4.70(2H,s), 4.95~5.70(3H,m), 6.39~6.86(3H,m), 7.29~7.48(6H,m), 7.59~7.80(4H,m). |
|  |  | I cl-a (Isomer 2) | 11.9 | 698 (M⁺) | (CHCl₃) 3604, 3008, 2960, 2936, 2864, 1764, 1742, 1600, 1498, 1475, 1429, 1289, 1113, 970, 821, 611. | (CDCl₃) 0.87(3H,d,J=7Hz), 1.03(9H,s), 1.58(3H,s), 1.67(3H,s), 0.95~2.26(10H,m), 2.73~3.05(1H,m), 3.76(3H,s), 3.86~4.29(4H,m), 4.69(2H,s), 4.96~5.67(3H,m), 6.39~6.86(3H,m), 7.30~7.47(6H,m), 7.57~7.80(4H,m). |
| 12 | CH(CH₃)CH₂-O-phenyl (*chiral) | I am-a (Isomer-1) | 28.4 | 708 (M⁺) | (CHCl₃) 3612, 2936, 2864, 1764, 1744, 1600, 1497, 1476, 1429, 1238, 1114, 970, 821, 612. | 1.06(9H,s), 1.28(3H,d,J=6Hz), 1.56~1.88(3H,m), 2.04~2.23(2H,m), 2.89(1H,t,J=7Hz), 3.79(3H,s), 3.93~4.05(2H,m), 4.12~4.31(2H,m), 4.52~4.68 (1H,m), 4.73(2H,s), 5.41(1H,dd,J=16Hz, 8Hz), 5.55(1H,dd,J=16Hz, 6Hz), 6.47(1H,dd,J=8Hz, 2Hz), 6.60(1H,dd,J=8Hz, 2Hz), 6.76(1H,t,J=8Hz), 6.86~6.97(3H,m), 7.20~7.50(8H,m), 7.60~7.70(4H,m). |
|  |  | I an-a (Isomer-2) | 29.4 | 708 (M⁺) | (CHCl₃) 3572, 2936, 2864, 1764, 1743, 1600, 1497, 1476, 1429, 1233, 1114, 971, 821, 612. | 1.03(9H,s), 1.29(3H,d,J=6Hz), 1.50~2.25(5H,m), 2.85(1H,q,J=7Hz), 3.79(3H,s), 3.78~4.04(2H,m), 4.10~4.25(2H,m), 4.41~4.58(1H,m), 4.73(2H,s), 5.29(1H,dd,J=16Hz, 8Hz), 5.47(1H,dd,J=16Hz, 6Hz), 6.47(1H,dd,J=8Hz, 2Hz), 6.60(1H,dd,J=8Hz 2Hz), 6.76(1H,t,J=8Hz), 6.86~6.97(3H,m), 7.20~7.50(8H,m), 7.60~7.70(4H,m). |
|  |  | I cm-a (Isomer-1) | 13.5 | 708 (M⁺) | (CHCl₃) 3608, 2936, 2864, 1764, 1743, 1600, 1497, 1476, 1429, 1243, 1114, 970, 821, 612. | 1.04(9H,s), 1.27(3H,d,J=6Hz), 1.55~1.90(3H,m), 2.03~2.23(2H,m), 2.88(1H,q,J=7Hz), 3.79(3H,s), 3.92~4.04(2H,m), 4.12~4.33(2H,m), 4.58~4.73 (1H,m), 4.73(2H,s), 5.40(1H,dd,J=16Hz, 8Hz), 5.56(1H,dd,J=16Hz, 6Hz), 6.47(1H,dd,J=8Hz, 2Hz), 6.60(1H,dd,J=8Hz, 2Hz), 6.76(1H,t,J=8Hz), 6.86~6.97(3H,m), 7.21~7.48(8H,m), 7.60~7.72(4H,m). |
|  |  | I cn-a (Isomer-2) | 16.5 | 708 (M⁺) | (CHCl₃) 3608, 2936, 2864, 1763, 1742, 1600, 1497, 1475, 1429, 1240, 1113, 971, 821, 613. | 1.03(9H,s), 1.29(3H,d,J=6Hz), 1.59(1H,dt,J=14Hz, 5H), 1.88~2.29(4H,m), 2.87(1H,q,J=7Hz), 3.79(3H,s), 3.90~4.05(2H,m), 4.10~4.25(2H,m), 4.72 (2H,s), 5.39(1H,dd,J=16Hz, 8Hz), 5.53(1H,dd,J=16Hz, 6Hz), 6.47(1H,dd,J=8Hz, 2Hz), 6.60(1H,dd,J=8Hz, 2Hz), 6.76(1H,t,J=8Hz), 6.80~6.96(3H,m), 7.17~7.45(8H,m), |

TABLE 3-continued

| | | | | | |
|---|---|---|---|---|---|
| | | | III → | Ia-a + | Ic-a |
| | | | | | 7.60~7.70(4H,m). |
| 13 | (structure: *CH(CH3)CH2-O-C6H5, branched) | I ao-a | 67.3 | 722 (M+) | (CHCl3) 3604, 2936, 2864, 1762, 1742, 1601, 1498, 1475, 1428, 1243, 1113, 970, 821, 612. | 1.04(9H,s), 1.02~1.06(6H,m), 1.23~1.73(3H,m), 2.02~2.29(3H,m), 2.88(1H,q,J=7Hz), 3.79(3H,s), 3.75~3.83(2H,m), 3.94~4.21(4H,m), 4.73(2H,s), 5.30~5.62(2H,m), 6.44~6.80(3H,m), 6.85~6.97(3H,m), 7.20~7.46(8H,m), 7.60~7.70(4H,m). |
| | | I co-a (Isomer-1) | 14.0 | 722 (M+) | (CHCl3) 3608, 2936, 2864, 1763, 1744, 1601, 1499, 1475, 1429, 1245, 1114, 970, 821, 612. | 1.04(9H,s), 1.05(3H,d,J=7Hz), 1.20~1.70(3H,m), 2.03~2.38(3H,m), 2.88(1H,q,J=7Hz), 3.79(3H,s), 3.74~3.83(2H,m), 3.95~4.22(4H,m), 4.73(2H,s), 5.40(1H,dd,J=16Hz, 8Hz), 5.55(1H,dd,J=16Hz, 6Hz), 6.47(1H,dd,J=8Hz, 2Hz), 6.60(1H,dd,J=8Hz, 2Hz), 6.75(1H,t,J=8Hz), 6.58~6.98(3H,m), 7.20~7.48(8H,m), 7.60~7.70(4H,m). |
| | | I cp-a (Isomer-2) | 13.2 | 722 (M+) | (CHCl3) 3604, 2936, 2864, 1763, 1742, 1601, 1499, 1475, 1429, 1244, 1114, 969, 821, 612. | 1.03(9H,s), 1.04(3H,d,J=7Hz), 1.33~1.70(3H,m), 2.20~2.26(3H,m), 2.88(1H,q,J=7Hz), 3.79(3H,s), 3.76~3.83(2H,m), 3.94~4.22(4H,m), 4.73(2H,s), 5.40(1H,dd,J=16Hz, 8Hz), 5.53(1H.dd,J=16Hz, 6Hz), 6.47(1H,dd,J=8Hz, 2Hz), 6.60(1H,dd,J=8Hz, 2Hz), 6.75(1H,t,J=8Hz), 6.85~6.98(3H,m), 7.20~7.47(8H,m), 7.60~7.70(4H,m). |

EXAMPLE 14

Preparation of methyl [(1R*,2R*,3aS*,9aR*)-2-t-butyldiphenylsilyloxy-1-[(3S*,1E)-5-butyl-3-hydroxy-1,5-hexadiene-1-yl]-2,3,3a,9a-tetrahydro-1H-cyclopenta[b][1,4]benzodioxin-5-yl]oxyacetate Iat-a and methyl [(1R*,2R*,3aS*,9aR*)-2-butyldiphenylsilyloxy-1-[(3R*,1E)-5-butyl-3-hydroxy-1,5-hexadiene-1-yl]-2,3,3a,9a-tetrahydro-1H-cyclopenta[b][1,4]benzodioxin-5-yl]oxyacetate Ict-a

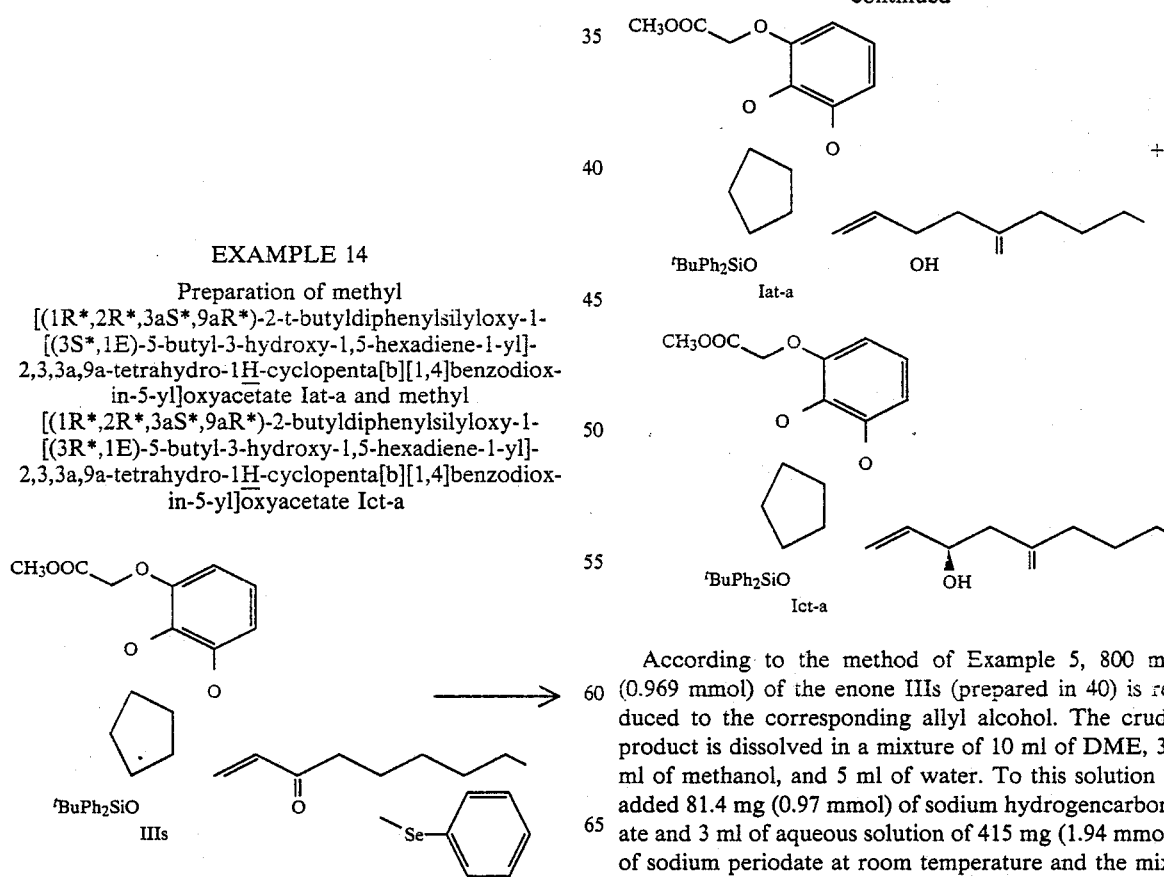

According to the method of Example 5, 800 mg (0.969 mmol) of the enone IIIs (prepared in 40) is reduced to the corresponding allyl alcohol. The crude product is dissolved in a mixture of 10 ml of DME, 30 ml of methanol, and 5 ml of water. To this solution is added 81.4 mg (0.97 mmol) of sodium hydrogencarbonate and 3 ml of aqueous solution of 415 mg (1.94 mmol) of sodium periodate at room temperature and the mixture is stirred overnight. To the reaction mixture is added 5% aqueous solution of sodium thiosulfate and the mixture is extracted with dichloromethane three times. The extract is washed with a saturated aqueous solution of sodium chloride, dried over anhydrous magnesium sulfate, and evaporated under reduced pressure. To a solution of the residue in 40 ml of carbon tetrachloride is added 0.41 ml (2.91 mmol) of diisopropylamine and the mixture is stirred at 60° C. for 1 hour. After cooling to room temperature, ice-water is added, and the mixture is extracted with dichloromethane twice. The extract is washed with 1 N hydrochloric acid, water, a saturated aqueous solution of sodium hydrogencarbonate, and a saturated aqueous solution of sodium chloride, dried over anhydrous magnesium sulfate, and evaporated under reduced pressure. The residue is purified by column chromatography (Merck, Lobar column, size B, two columns; ethyl acetate:-toluene=1:15–1:10) to give the desired dienalcohols, namely, 350 mg of less polar isomer Iat-a as an oil and 155 mg of more polar isomer Ict-a as an oil in 53.7% and 23.8% yield, respectively.

Compound Iat-a $^1$H-NMR (200 MHz) δ ppm (CDCl$_3$): 0.91 (3 H, t, J=7 Hz), 1.04 (9 H, s), 1.22–1.56 (5 H, m), 1.96–2.20 (6 H, m), 2.90 (1 H, q, J=7 Hz), 3.79 (3 H, s), 3.96–4.23 (4 H, m), 4.73 (2 H, s), 4.80 (1 H, s), 4.87 (1 H, s), 5.45 (1 H, dd J=16 Hz, 7 Hz), 5.55 (1 H, dd, J=16 Hz, 5 Hz), 6.47 (1 H, dd, J=8 Hz, 2 Hz), 6.60 (1 H, dd, J=8 Hz, 2 Hz), 6.77 (1 H, t, J=8 Hz), 7.20–7.48 (6 H, m), 7.63–7.73 (4 H, m).

IR ν max (CHCl$_3$) 3604, 2936, 2864, 1763, 1742, 1643, 1600, 1498, 1476, 1429, 1238, 1114, 969, 904, 822, 612 cm$^{-1}$.

MS: m/z 670 (M+).

Compound Ict-a $^1$H-NMR (200 MHz) δ ppm (CDCl$_3$): 0.92 (3 H, t, J=7 Hz), 1.04 (9 H, s), 1.23–1.60 (5 H, m), 1.97–2.20 (6 H, m), 2.90 (1 H, q, J=7 Hz), 3.80 (3 H, s), 3.95–4.24 (4 H, m), 4.73 (2 H, s), 4.81 (1 H, s), 4.87 (1 H, s), 5.46 (1 H, dd J=16 Hz, 7 Hz), 5.54 (1 H, dd, J=16 Hz, 5 Hz), 6.46 (1 H, dd, J=8 Hz, 2 Hz), 6.60 (1 H, dd, J=8 Hz, 2 Hz), 6.76 (1 H, t, J=8 Hz), 7.20–7.47 (6 H, m), 7.60–7.73 (4 H, m).

IR ν max (CHCl$_3$) 3604, 2936, 2864, 1764, 1743, 1642, 1600, 1498, 1476, 1429, 1287, 1114, 969, 906, 821, 613 cm$^{-1}$.

MS: m/z 670 (M+).

EXAMPLE 15

Preparation of methyl [(1R,2R,3aS,9aR)-2-t-butyldiphenylsilyloxy-1-[(3S,5S,1E)-3-hydroxy-5-methyl-1,8-nonadien-1-yl]-2,3,3a,9a-tetrahydro-1H-cyclopenta[b][1,4]benzodioxin-5-yl]oxyacetate Iar-a and its stereoisomers Iaq-a, Icq-a, and Icr-a

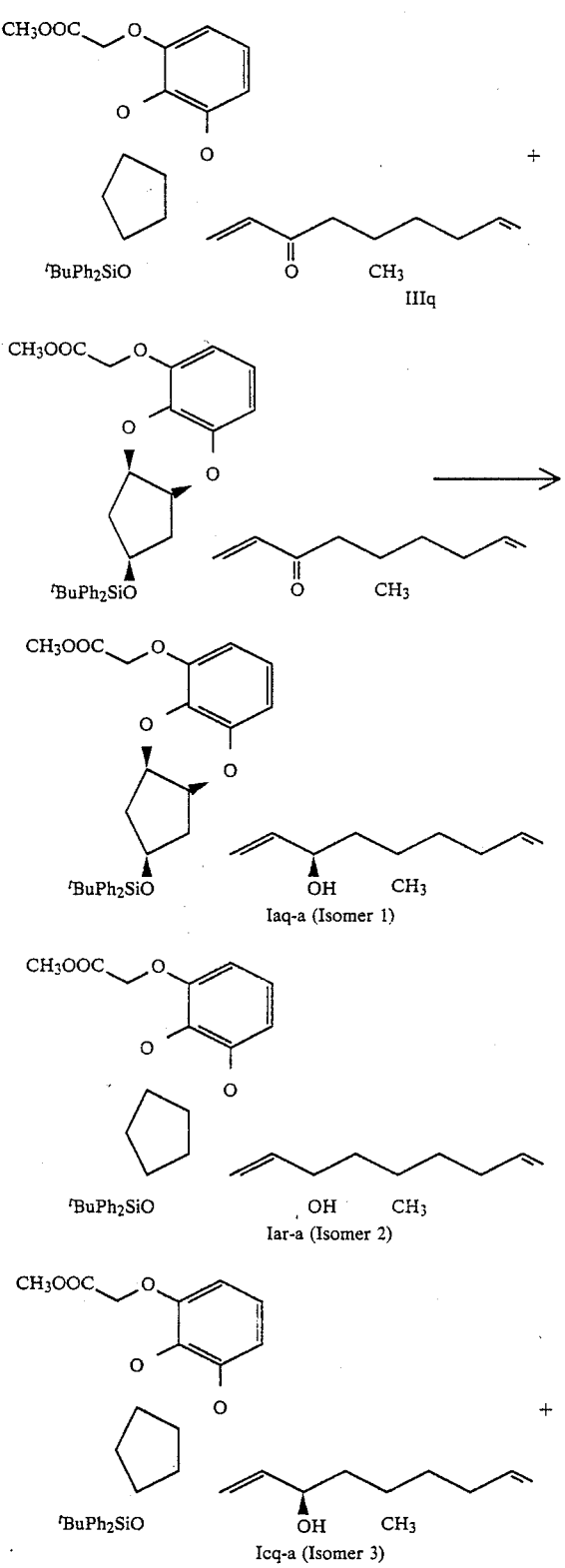

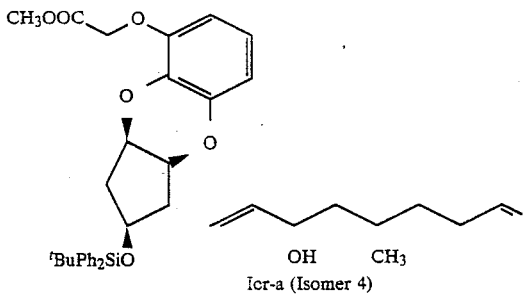

Icr-a (Isomer 4)

According to the method of Example 5, the enone III q (prepared in (39)) is reduced to give four kinds of stereoisomers Iaq-a, Iar-a, Icq-a, and Icr-a.

Compound Iaq-a (Isomer 1)
Yield 32.9%.
Rf: 0.35 (ethyl acetate:toluene=1:6).
$[\alpha]_D$ −43.2±1.6° (24° C., c=0.53, CHCl$_3$).
$^1$H-NMR (200 MHz) δ ppm (CDCl$_3$): 0.90 (3 H, d, J=7 Hz), 1.04 (9 H, s), 1.00–1.72 (6 H, m), 1.94–2.29 (4 H, m), 2.88 (1 H, q, J=7 Hz), 3.80 (3 H, s), 3.95–4.09 (3 H, m), 4.15–4.23 (1 H, m), 4.73 (2 H, s), 4.88–5.03 (2 H, m), 5.35 (1 H, dd, J=16 Hz, 8 Hz), 5.51 (1 H, dd, J=16 Hz, 6 Hz), 5.70–5.91 (1 H, m), 6.47 (1 H, dd, J=8 Hz, 2 Hz), 6.59 (1 H, dd, J=8 Hz, 2 Hz), 6.76 (1 H, t, J=8 Hz), 7.30–7.50 (6 H, m), 7.60–7.70 (4 H, m).
IR ν max (CHCl$_3$) 3604, 2936, 2864, 1763, 1742, 1641, 1600, 1498, 1476, 1429, 1288, 1113, 970, 908, 821, 612 cm$^{-1}$.
MS: m/z 670 (M+).

Compound Iar-a (Isomer 2)
Yield 33.1%.
Rf: 0.32 (ethyl acetate:toluene=1:6).
$[\alpha]_D$ +41.7±1.4° (24° C., c=0.60, CHCl$_3$).
$^1$H-NMR (200 MHz) δ ppm (CDCl$_3$): 0.87 (3 H, d, J=7 Hz), 1.04 (9 H, s), 1.00–1.73 (6 H, m), 1.93–2.30 (4 H, m), 2.88 (1 H, q, J=7 Hz), 3.80 (3 H, s), 3.94–4.09 (3 H, m), 4.15–4.24 (1 H, m), 4.73 (2 H, s), 4.88–5.06 (2 H, m), 5.34 (1 H, dd, J=16 Hz, 8 Hz), 5.46 (1 H, dd, J=16 Hz), 6 Hz), 5.70–5.91 (1 H, m), 6.47 (1 H, dd, J=8 Hz, 2 Hz), 6.58 (1 H, dd, J=8 Hz, 2 Hz), 6.76 (1 H, t, J=8 Hz), 7.30–7.50 (6 H, m), 7.60–7.70 (4 H, m).
IR ν max (CHCl$_3$) 3604, 2936, 2864, 1764, 1744, 1641, 1600, 1499, 1476, 1429, 1290, 1113, 970, 908, 822, 612 cm$^{-1}$.
MS: m/z 670 (M+).

Compound Icq-a (Isomer 3)
Yield 10.4%.
Rf: 0.27 (ethyl acetate:toluene=1:6).
$[\alpha]_D$ +45.0±1.6° (24° C., c=0.52, CHCl$_3$).
$^1$H-NMR (200 MHz) δ ppm (CDCl$_3$): 0.90 (3 H, d, J=7 Hz), 1.04 (9 H, s), 1.00–1.75 (6 H, m), 1.94–2.29 (4 H, m), 2.88 (1 H, q, J=7 Hz), 3.79 (3 H, s), 3.94–4.09 (3 H, m), 4.15–4.23 (1 H, m), 4.73 (2 H, s), 4.88–5.30 (2 H, m), 5.36 (1 H, dd, J=16 Hz, 8 Hz), 5.53 (1 H, dd, J=16 Hz, 6 Hz), 5.70–5.91 (1 H, m), 6.47 (1 H, dd, J=8 Hz, 2 Hz), 6.60 (1 H, dd, J=8 Hz, 2 Hz), 6.76 (1 H, t, J=8 Hz), 7.30–7.50 (6 H, m), 7.60–7.70 (4 H, m).
IR ν max (CHCl$_3$) 3608, 2936, 2864, 1764, 1743, 1641, 1600, 1498, 1476, 1429, 1291, 1114, 970, 908, 821, 612 cm$^{-1}$.
MS: m/z 670 (M+).

Compound Icr-a (Isomer 4)
Yield 8.9%.
Rf: 0.23 (ethyl acetate:toluene=1:6).
$[\alpha]_D$ −42.3±1.8° (24° C., c=0.45, CHCl$_3$).
$^1$H-NMR (200 MHz) δ ppm (CDCl$_3$): 0.88 (3 H, d, J=7 Hz), 1.04 (9 H, s), 1.05–1.74 (6 H, m), 1.95–2.27 (4 H, m), 2.88 (1 H, q, J=7 Hz), 3.80 (3 H, s), 3.95–4.09 (3 H, m), 4.15–4.23 (1 H, m), 5.39 (1 H, dd, J=16 Hz, 7 Hz), 5.50 (1 H, dd, J=16 Hz, 6 Hz), 5.70–5.86 (1 H, m), 6.47 (1 H, dd, J=8 Hz, 2 Hz), 6.60 (1 H, dd, J=8 Hz, 2 Hz), 6.77 (1 H, t, J=8 Hz), 7.30–7.50 (6 H, m), 7.60–7.70 (4 H, m).
IR ν max (CHCl$_3$) 3608, 2936, 2864, 1764, 1744, 1641, 1600, 1499, 1476, 1429, 1293, 1114, 970, 909, 821, 612 cm$^{-1}$.
MS: m/z 670 (M+).

EXAMPLE 16

Preparation of methyl [(1R,2R,3aS,9aR)-2-t-butyldiphenylsilyloxy-1-[(3S,5S,1E)-3-hydroxy-5-methyl-1-nonenyl-2,3,3a,9a-tetrahydro-1H-cyclopenta[b][1,4]benzodioxin-5-yl]oxyacetate Iau-a

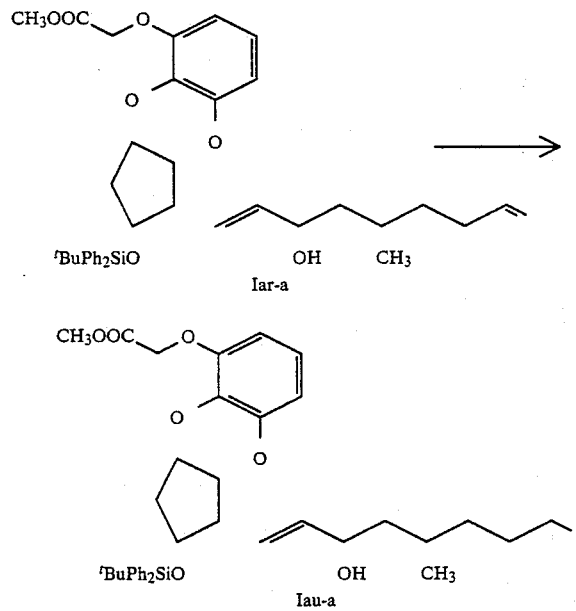

To a solution of 151 mg (0.225 mmol) of diene Iar-a (prepared in Example 15) in 10 ml of dry benzene is added 7.5 mg of 5% palladium-charcoal, and the mixture is stirred at room temperature for 3 hours in a hydrogen atmosphere. The reaction mixture is filtered and the filtrate is evaporated under reduced pressure. The residue is purified by column chromatography on silica gel (Merck, Lobar column, size B, ethyl acetate:toluene=1:15) to give 98 mg of the desired olefin as an oil in 64.9% yield. The $^1$H-NMR, IR, and MS spectra of this optically active compound are completely identical

EXAMPLE 17

Preparation of methyl [(1R*,2S*,3aR*,9aS*)-2-hydroxy-1-[(3R*,1E)-3-hydroxy-1-octenyl]-2,3,3a,9a-tetrahydro-1H-cyclopenta[b][1,4]benzodioxin-5-yl]oxyacetate Iba-a

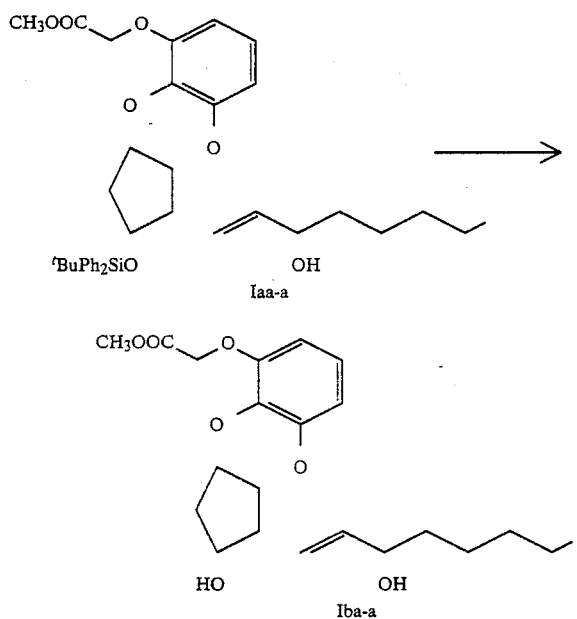

To a solution of 517 mg (0.802 mmol) of the silyl ether Iaa-a (prepared in Examples 1 to 5) in 6 ml of THF is added 1.60 ml (1.60 mmol) of tetra-n-butylammonium fluoride (1M in THF) and the mixture is stirred at room temperature overnight. A saturated aquoues solution of ammonium chloride and 2 ml (2 mmol) of 1N hydrochloric acid is added, and the mixture is extracted with ethyl acetate twice. The extract is washed with water and a saturated aqueous solution of sodium chloride, dried over anhydrous magnesium sulfate. and evaporated under reduced pressure. The residue containing the carboxylic acid generated by saponification of the methyl ester is treated with diazomethane as follows in order to esterify. To this residue dissolved in 6 ml of methanol is added an ethereal solution of diazomethane at 0° C. until the yellow color persists. The reaction mixture is evaporated under reduced pressure and the residue is purified by column chromatography on silica gel (Merck, Lobar column, size B, ethyl acetate:toluene=2:1) to give 282 mg the desired methyl ester Iba-a, which is crystallized from ethyl acetate-n-hexane to give 260 mg of compound Iba-a as crystals in 80.0% yield.

Mp. 121°~123° C. (ethyl acetate-n-hexane).

$^1$H-NMR: δ (CDCl$_3$+CD$_3$OD) 0.88 (3 H, t, J=6 Hz), 1.10~1.80 (8 H, m), 1.90~2.20 (1 H, m), 2.35~2.81 (2 H, m), 3.82 (3 H, s), 3.8~4.4 (4 H, m), 4.70 (2 H, s), 5.43~5.86 (2 H, m), 6.39~6.87 (3 H, m) ppm.

IR: ν max (CHCl$_3$) 3608, 3008, 2960, 2940, 2864, 1762, 1744, 1600, 1498, 1476, 1125, 970 cm$^{-1}$.

EXAMPLES 18 to 34

In the same manner as described in Example 17, desilylation is carried out to give methyl ester Ib-a. The results are shown in Table 4.

TABLE 4

$$\text{CH}_3\text{O}_2\text{C}-\text{O}-\text{C}_6\text{H}_3(\text{O}-\text{cyclopentyl})-\text{O}-\text{Si}^t\text{BuPh}_2 \quad \xrightarrow{\quad} \quad \text{CH}_3\text{O}_2\text{C}-\text{O}-\text{C}_6\text{H}_3(\text{O}-\text{cyclopentyl})-\text{OH}$$

Ia-a → Ib-a

| Ex. No. | Compd. No. | R₁ | Yd. (%) | Mp. (°C.) | [α]D | IR νmax (CHCl₃) (cm⁻¹) | ¹H-NMR δ (CDCl₃ + CD₃OD) (ppm) |
|---|---|---|---|---|---|---|---|
| 18 | I bb-a |  | 73.1 | 124~126 (Ethyl acetate-n-hexane) | | 3608, 3008, 2936, 2860, 1762, 1738, 1600, 1498, 1476, 1243, 1125, 970 | 0.70~2.25 (12H,m), 2.33~2.90 (2H,m), 3.81 (3H,s), 3.70~4.40 (4H,m), 4.70 (2H,s), 5.43~5.83 (2H,m), 6.38~6.90 (3H, m). |
| 19 | I bc-a |  | 68.8 | 111~113 (Ethyl acetate-n-hexane) | | 3604, 3529, 3008, 2944, 1762, 1743, 1600, 1498, 1476, 1439, 1271, 1128, 970. | 1.10 (3H,t,J=7Hz), 1.53~1.86 (2H,m), 1.92~2.85 (7H,m), 3.81 (3H,s), 3.83~4.40 (4H,m), 4.70 (2H,s), 5.45~5.93 (2H, m), 6.38~6.90 (3H,m). |
| 20 | I bd-a | <br>(Isomer 1) | 70.3 | 106~109 (Ethyl acetate-n-hexane) | | 3604, 3008, 2960, 2932, 2876, 1762, 1743, 1600, 1498, 1476, 1271, 1126, 970. | 0.76~1.03 (6H,m), 103~1.80 (9H,m), 1.92~2.22 (1H,m), 2.34~2.68 (2H,m), 3.81 (3H,s), 3.80~4.38 (4H,m), 4.69 (2H,s), 5.46~5.87 (2H,m), 6.38~6.89 (3H,m). |
| 21 | I be-a | <br>(Isomer 2) | 53.4 | Powder | | 3604, 3008, 2960, 2932, 2876, 1762, 1743, 1600, 1498, 1476, 1270, 1125, 970. | 0.75~1.05 (6H,m), 1.05~1.80 (9H,m), 1.90~2.21 (1H,m), 2.32~2.86 (2H,m), 3.81 (3H,s), 3.83~4.42 (4H,m), 4.69 (2H,s), 5.38~5.87 (2H,m), 6.38~6.90 (3H,m). |
| 22 | I bf-a |  | 75.4 | 112~114 (Ethyl acetate-n-hexane) | | 3608, 3008, 2960, 2936, 2876, 1762, 1743, 1601, 1498, 1476, 1271, 1125, 970. | 0.79~1.02 (6H,m), 1.02~1.80 (7H,m), 1.91~2.21 (1H,m), 2.33~2.82 (2H,m), 3.80 (3H,s), 3.74~4.36 (4H,m), 4.67 (2H,s), 5.39~5.84 (2H,m), 6.36~6.90 (3H,m). |
| 23 | I bg-a |  | 59.7 | 77~78 (Ethyl acetate-n-hexane) | | 3612, 3008, 2964, 2976, 1762, 1743, 1600, 1498, 1476, 1271, 1129, 971. | 0.83 (3H,s), 0.87 (3H,s), 0.90 (3H,t,J=7Hz), 1.08~1.47 (6H,m), 1.91~2.21 (1H,m), 2.33~2.86 (2H,m), 3.79 (3H,s), 3.76~4.36 (4H,m), 4.68 (2H,s), 5.45~5.85 (2H,m), 6.36~6.89 (3H,m). |

TABLE 4-continued

| Ex. No. | Compd. No. | R₁ | Yd. (%) | Mp. (°C.) | [α]_D | IR νmax (CHCl₃) (cm⁻¹) | ¹H—NMR δ (CDCl₃ + CD₃OD) (ppm) |
|---|---|---|---|---|---|---|---|
| 24 | I bh-a | (pent-1-ynyl) | 93.9 | Powder | | 3608, 3008, 2960, 2928, 1761, 1744, 1600, 1498, 1476, 1271, 1126, 970. | 0.93 and 0.98 (total 3H, each d,J=7Hz), 1.76 (3H,t, J=2.5Hz), 1.53~2.85 (6H,m), 3.78 (3H,s), 3.73~4.36 (4H,m), 4.67 (2H,s), 5.38~5.87 (2H,m), 6.36~6.87 (3H,m) |
| 25 | I bi-a | (cyclopentylmethyl) | 76.2 | 120~121.5 (Ethyl acetate-n-hexane) | | 3608, 3008, 2960, 2872, 1762, 1742, 1600, 1498, 1476, 1270, 1127, 970. | 1.06~2.21 (10H,m), 2.32~2.80 (2H,m), 3.76~3.79 (3H,s), 4.37 (4H,m), 4.67 (2H,s), 5.41~5.85 (2H,m), 6.35~6.88 (3H,m) |
| 26 | I bj-a | (cyclohexylmethyl) | 79.8 | 109.5~110.5 | | 3600, 3424, 3004, 2928, 2856, 1762, 1743, 1600, 1498, 1475, 1271, 1127, 970. | 0.63~1.90 (13H,m), 1.90~2.21 (1H,m), 2.30~2.86 (2H,m), 3.78 (3H,s), 3.77~4.38 (4H,m), 4.67 (2H,s), 5.38~5.87 (2H,m), 6.35~6.89 (3H,m) |
| 27 | I bk-a | (prenyl chain, Isomer 1) | 80.1 | 100~103 (Ethyl acetate-n-hexane) | | 3604, 3008, 2960, 2932, 2856, 1762, 1744, 1600, 1498, 1476, 1271, 1126, 969. | 0.92 (3H,d,J=6Hz), 1.05~1.65 (5H,m), 1.61 (3H,s), 1.67 (3H,s), 1.84~2.26 (3H,m), 2.33~2.85 (2H,m), 3.79 (3H,s), 3.79~4.40 (4H,m), 4.68 (2H,s), 4.97~5.29 (1H,m), 5.43~5.88 (2H,m), 6.36~6.9 0 (3H,m) |
| 28 | I bl-a | (prenyl chain, Isomer 2) | 81.6 | 86.6~88.0 (Ethyl acetate-n-hexane) | | 3604, 3420, 3008, 2960, 2932, 2856, 1762, 1742, 1600, 1498, 1462, 1272, 1125, 970. | 0.91 (3H,d,J=6Hz), 1.04~1.65 (5H,m), 1.60 (3H,s), 1.67 (3H,s), 1.80~2.23 (3H,m), 2.32~2.81 (2H,m), 3.79 (3H,s), 3.78~4.40 (4H,m), 4.67 (2H,s), 4.97~5.24 (1H,m), 5.38~5.87 (2H,m), 6 .36~6.90 (3H,m) |

TABLE 4-continued $$\text{CH}_3\text{O}_2\text{C}\text{—structure with }{}^t\text{BuPh}_2\text{SiO and }R_1\text{—cyclopentane} \longrightarrow \text{CH}_3\text{O}_2\text{C—structure with OH, }R_1\text{, cyclopentane}$$

Ia-a → Ib-a

| Ex. No. | Compd. No. | $R_1$ | Yd. (%) | Mp. (°C.) | $[\alpha]_D$ | IR $\nu_{max}$ (CHCl$_3$) (cm$^{-1}$) | $^1$H-NMR $\delta$ (CDCl$_3$ + CD$_3$OD) (ppm) |
|---|---|---|---|---|---|---|---|
| 29 | Ibm-a | (phenoxy-CH-ethyl structure) (Isomer-1) | 82.2 | 119~121 Ethyl acetate-n-hexane | | 3604, 3008, 2960, 1762, 1744, 1600, 1496, 1476, 1439, 1238, 1126, 970. | 1.31(3H,d,J=6Hz), 1.68~2.14(3H,m), 2.41~2.73(2H,m), 3.81 (3H,s), 3.87~3.99(1H,m), 4.15~4.40(3H,m), 4.57~4.70(1H,m), 4.70(2H,s), 5.60~5.81(2H,m), 6.45(1H,dd,J=8Hz, 2Hz), 6.59 (1H,d,J=8 Hz), 6.77(1H,t,J=8Hz), 6.88~6.98(3H,m), 7.20~7.32(2H,m). |
| 30 | Ibn-a | (phenoxy-CH-ethyl structure) (Isomer-2) | 69.9 | 90~92 Ethyl acetate-n-hexane | | 3604, 3008, 2960, 1762, 1743, 1600, 1497, 1476, 1440, 1238, 1128, 970. | 1.32(3H,d,J=6Hz), 1.60~1.74(1H,m), 2.00~2.18(2H,m), 2.37~2.69(2H,m), 3.81(3H,s), 3.80~3.93(1H,m), 4.05(1H,dd,J=10Hz,3 Hz), 4.18~4.40(2H,m), 4.46~4.61(1H,m), 4.70(2H,s), 5.49~5.68 (2H,m), 6.45(1H,dd,J=8Hz, 2Hz), 6.60 (1H,dd,J=8Hz,2Hz), 6.78 (1H,t,J=8Hz), 6.88~6.99(3H,m), 7.20~7.32(2H,m). |
| 31 | Ibo-a | (phenoxy-butyl structure) | 79.5 | 99~102 Ethyl acetate-n-hexane | | 3604, 2960, 1762, 1743, 1600, 1498, 1475, 1440, 1243, 1126, 970. | 1.08(3H,t,J=7Hz), 1.34~1.85(2H,m), 2.00~2.25(2H,m), 2.43~2.73(2H,m), 3.81(3H,s), 3.75~4.01(3H,m), 4.14~4.30(3H,m), 4.70(2H,s), 5.55~5.80(2H,m), 6.40~6.82(3H,m), 6.86~6.97(3H,m), 7.20~7.34 (2H,m). |
| 32 | Ibt-a | (heptadienyl structure) | 62.5 | 81~83 Ethyl acetate-n-hexane | | 3600, 2936, 1763, 1742, 1643, 1600, 1498, 1476, 1271, 1127, 969, 900. | 0.91(3H,t,J=7Hz), 1.23~1.52(4H,m), 2.00~2.15(3H,m), 2.25 (2H,d,J=7Hz), 2.43~2.73(2H,m), 3.82(3H,s), 3.92~4.02(1H,m), 4.17~4.31(3H,m), 4.71(2H,s), 4.82(1H,s), 4.86(1H,s), 5.56~5.80(2H,m), 6.45(1H,dd,J=8Hz, 2Hz), 6.60 (1H, dd, J=8Hz, 2Hz), 6.78(1H,t,J=8Hz). |
| 33 | Ibr-a | (heptenyl structure) | 71.3 | Powder | +60.4±2.0° C=0.50 CHCl$_3$ | 3608, 2932, 1762, 1742, 1641, 1600, 1498, 1476, 1271, 1127, 970, 914. | 0.92(3H,t,J=6Hz), 1.14~1.65(5H,m), 1.96~2.19(3H,m), 2.44~2.72(2H,m), 3.82(3H,s), 3.90~4.03(1H,m), 4.10~4.31(3H,m), 4.71(2H,s), 4.88~5.08(2H,m), 5.49~5.93(3H,m), 6.45(1H,d, J=8Hz), 6.59(1H,d,J=8Hz), 6.78 (1H z). |
| 34 | Ibu-a | (branched alkyl structure) | 65.1 | 73~75 | +65.5±2.2° | Identical with the | Identical with the compound Ibe-a (Ex. 16; racemate) |

EXAMPLE 35

Preparation of
[(1R*,2S*,3aR*,9aS*)-2-hydroxy-1-[(3R*,1E)-3-hydroxy-1-octenyl]-2,3,3a,9a-tetrahydro-1H-cyclopenta[b][1,4]benzodioxin-5-yl]oxyacetic acid Iba-b

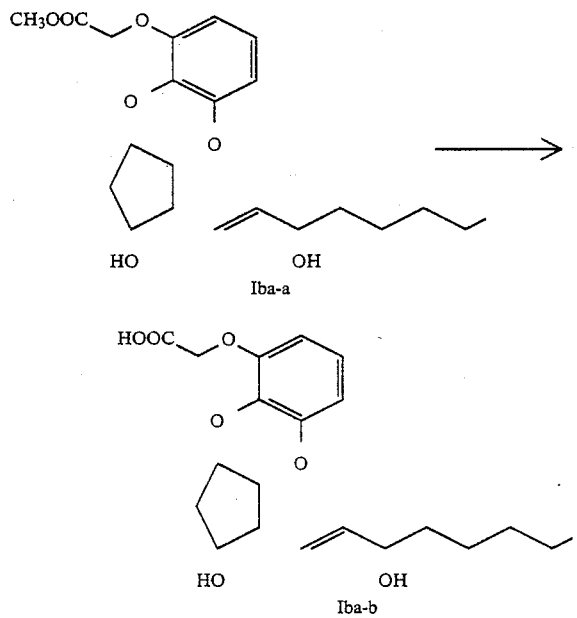

To a solution of 100 mg (0.246 mmol) of the methyl ester Iba-a (prepared in Example 17) in 2 ml of methanol is added 0.50 ml (0.50 mmol) of 1N sodium hydroxide and the mixture is stirred at room temperature for 25 minutes. To the reaction mixture are added 1.0 ml (1.0 mmol) of 1N hydrochloric acid and a saturated aqueous solution of sodium chloride, and the mixture is extracted with chloroform. The extract is washed with a saturated aqueous solution of sodium chloride, dried over anhydrous magnesium sulfate, and evaporated under reduced pressure to give 77 mg of the crude carboxylic acid Iba-b as crystals, which is recrystallized from ethyl acetate-n-hexane to give 68 mg of the crystalline Iba-b in 70.4% yield.

Mp.: 156° C. to 158° C. (ethyl acetate-n-hexane).

$^1$H-NMR: δ (CD$_3$OD) 0.89 (3 H, t, J=6 Hz), 1.10~1.80 (8 H, m), 1.82-2.10 (1 H, m), 2.33~2.75 (2 H, m), 3.86~4.35 (4 H, m), 4.63 (2 H, s), 5.41~5.81 (2 H, m), 6.42~6.83 (3 H, m) ppm.

IR: ν max (KBr) 3404, 2960, 2940, 2864, 1745, 1709, 1615, 1596, 1501, 1477, 1434, 1131, 984, 968, 904, 760, 712 cm$^{-1}$.

EXAMPLES 36 to 46

In the same manner as described in Example 35, the methyl ester is converted into the carboxylic acid Ib-b. The results are shown in Table 5.

TABLE 5

| Ex. No. | Compd. No. | R$_1$ | Yd. (%) | Mp. (°C.) | IR νmax (cm$^{-1}$) | $^1$H—NMR δ (CD$_3$OD) (ppm) |
|---|---|---|---|---|---|---|
| 36 | I bb-b | cyclohexyl-CH | 69.3 | 155~157 (Ethyl acetate-n-hexane) | (KBr) 3420, 2924, 2852, 1762, 1732, 1616, 1598, 1500, 1476, 1284, 1254, 1124, 971, 759, 712. | 0.80~2.15 (12H,m), 2.33~2.79 (2H,m), 3.66~4.39 (4H,m), 4.68 (2H,s), 5.40~5.85 (2H,m), 6.42~6.86 (3H,m). |
| 37 | I bc-b | CH$_3$CH$_2$-C≡C-CH$_2$- | 67.0 | 127~129 (Ether) | (KBr) 3424, 2976, 2920, 1758, 1720, 1599, 1501, 1476, 1255, 1129, 977, 760, 713. | 1.03 (3H,t,J=7Hz), 1.49~1.82 (2H,m), 1.82~2.80 (7H,m), 3.77~4.40 (4H,m), 4.66 (2H,s), 5.43~5.96 (2H,m), 6.43~6.87 (3H,m) |
| 38 | I bd-b | sec-hexyl* (Isomer 1) | 71.4 | 133~135 (Ethyl acetate-n-hexane) | (KBr) 3424, 2972, 2924, 2856, 1757, 1732, 1615, 1597, 1498, 1475, 1120, 971, 758, 710. | 0.76~1.02 (6H,m), 1.02~2.15 (10H,m), 2.30~2.80 (2H,m), 3.82~4.37 (4H,m), 4.63 (2H,s), 5.41~5.93 (2H,m), 6.41~6.85 (3H,m) |
| 39 | I be-b | sec-hexyl* (Isomer 2) | 73.3 | 110~113 (Ethyl acetate-n-hexane) | (KBr) 3360, 2956, 2928, 2872, 1725, 1599, 1500, 1476, 1129, 971, 759, 709. | 0.80~1.05 (6H,m), 1.05~2.16 (10H,m), 2.33~2.80 (2H,m), 3.85~4.39 (4H,m), 4.64 (2H,s), 5.37~5.90 (2H,m), 6.41~6.85 (3H,m) |

TABLE 5-continued

| Ex. No. | Compd. No. | R₁ | Yd. (%) | Mp. (°C.) | IR νmax (cm⁻¹) | ¹H—NMR δ (CD₃OD) (ppm) |
|---|---|---|---|---|---|---|
| 40 | I bf-b | (n-hexyl) | 89.7 | Powder | (KBr) 3388, 2960, 2932, 2876, 1732, 1599, 1506, 1476, 1128, 973, 759, 709. | 0.75~1.05 (6H,m), 1.05~1.80 (7H,m), 1.80~2.13 (1H,m), 2.31~2.78 (2H,m), 3.74~4.34 (4H,m), 4.63 (2H,s), 5.39~5.87 (2H,m), 6.40~6.86 (3H,m) |
| 41 | I bg-b | (2-methylhexyl) | 80.1 | 126~128 (Ethyl acetate-n-hexane) | (KBr) 3464, 2960, 1712, 1597, 1499, 1476, 1264, 1130, 971, 766. | 0.83 (3H,s), 0.86 (3H,s), 0.91 (3H,t,J=6Hz), 1.09~1.50 (6H,m), 1.96 (1H,dd,J=5Hz, 15Hz), 2.33~2.80 (2H,m), 3.69~4.35 (4H,m), 4.63 (2H,s), 5.45~5.87 (2H,m), 6.41~6.86 (3H,m) |
| 42 | I bh-b | (pent-3-ynyl) | 73.6 | Powder | (KBr) 3420, 2916, 1758, 1729, 1598, 1500, 1475, 1126, 977, 761, 713. | 0.93 and 0.97 (total 3H, each d, J=7Hz), 1.46~2.28 (7H,m), 2.30~2.77 (2H,m), 3.80~4.37 (4H,m), 4.63 (2H,s), 5.36~5.82 (2H,m), 6.39~6.86 (3H,m) |
| 43 | I bi-b | (cyclopentyl) | 81.7 | 148~149 (Ethyl acetate-n-hexane) | (KBr) 3380, 2956, 1734, 1599, 1500, 1477, 1131, 971, 758, 709. | 1.10~2.14 (10H,m), 2.33~2.86 (2H,m), 3.72~4.35 (4H,m), 4.63 (2H,s), 5.60~5.90 (2H,m), 6.40~6.85 (3H,m) |
| 44 | I bj-b | (ethylcyclohexyl) | 81.6 | 129~132 (Ethyl acetate-n-hexane) | (KBr) 3600, 3500, 3388, 2928, 1734, 1703, 1599, 1497, 1476, 1129, 975, 759, 711. | 0.60~2.13 (14H,m), 2.33~2.78 (2H,m), 3.83~4.35 (4H,m), 4.63 (2H,s), 5.38~5.91 (2H,m), 6.41~6.85 (3H,m) |
| 45 | I bk-b (Isomer 1) | | 85.3 | 127~129 (Ethyl acetate-n-hexane) | (KBr) 3388, 2980, 2916, 1733, 1599, 1500, 1477, 1128, 973, 761, 711. | 0.92 (3H,d,J=6Hz), 1.03~1.58 (5H,m), 1.60 (3H,s), 1.66 (3H,s), 1.80~2.18 (3H,m), 2.26~2.78 (2H,m), 3.83~4.35 (4H,m), 4.63 (2H,s), 4.95~5.23 (1H,m), 5.41~5.92 (2H,m), 6.40~6.85 (3H,m) |
| 46 | I bl-b (Isomer 2) | | 81.8 | 101~103 (Ethyl acetate-n-hexane) | (KBr) 3524, 3420, 2920, 1719, 1598, 1499, 1475, 1121, 973, 762, 710. | 0.92 (3H,d,J=6Hz), 1.05~1.56 (5H,m), 1.60 (3H,s), 1.65 (3H,s), 1.82~2.17 (3H,m), 2.30~2.80 (2H,m), 3.80~4.36 (4H,m), 4.63 (2H,s), 4.96~5.25 (1H,m), 5.36~5.90 (2H,m), 6.40~6.86 (3H,m) |

EXAMPLE 47

Preparation of methyl [(1R*,2S*,3aR*,9aS*)-2-hydroxy-1-[(3S*,1E)-3-hydroxy-1-octenyl]-2,3,3a,9a-tetrahydro-1H-cyclopenta[b][1,4]benzodioxin-5-yl]oxyacetate Ida-a

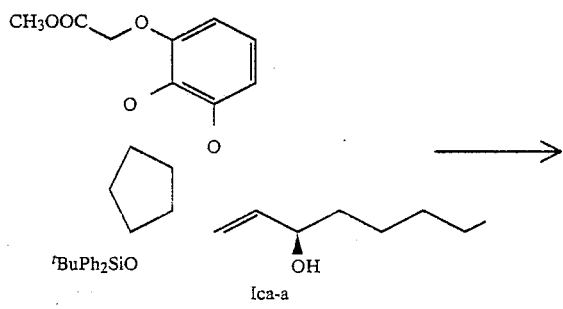

Ica-a

→

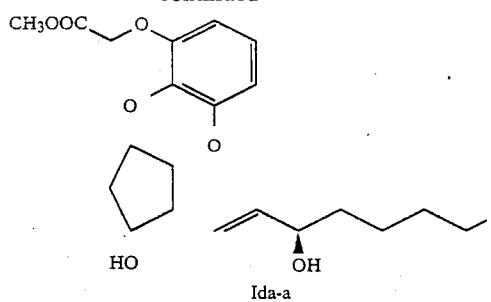

Ida-a

In the same manner as described in Example 17, 252 mg of the silyl ether Ica-a (prepared in Examples 1 and 5) is converted into 110 mg of the desired crystalline methyl ester Ida-a in 69.2% yield.

Mp.: 95°~97° C. (ethyl acetate-n-hexane).

H-NMR: δ ($CDCl_3$+$CD_3OD$) 0.87 (3 H, t, J=6 Hz), 1.10~1.80 (8 H, m), 1.92~2.20 (1 H, m), 2.30~2.80 (2 H, m), 3.80 (3 H, s), 3.8~4.3 (4 H, m), 4.68 (2 H, s), 5.50~5.90 (2 H, m), 6.37~6.87 (3 H, m) ppm.

IR: ν max ($CHCl_3$) 3608, 3008, 2960, 2939, 2864, 1763, 1744, 1600, 1498, 1479, 1127, 970 $cm^{-1}$.

EXAMPLES 48 to 63

In the same manner as described in Example 17, the desilylation is carried out to give the methyl ester Id-a. The results are shown in Table 6.

TABLE 6

| Ex. No. | Compd. No. | R₁ | Yield (%) | Mp (°C.) | IR ν max (CHCl₃) (cm⁻¹) | ¹H-NMR δ (CDCl₃ + CD₃OD) (ppm) |
|---|---|---|---|---|---|---|
| 48 | I db-a | (cyclohexyl) | 71.0 | 121.9~122.2 (Ethyl acetate-n-hexane) | 3608, 3008, 2932, 2860, 1763, 1742, 1600, 1498, 1476, 1270, 1127, 971 | 0.70~2.25 (12H,m), 2.30~2.88 (2H,m), 3.80 (3H,s), 3.80~4.40 (4H,m), 4.69 (2H,s), 5.50~5.90 (2H,m), 6.38~6.88 (3H,m) |
| 49 | I dc-a | | 70.2 | 62~65 (Ethyl acetate-n-hexane) | 3604, 3528, 3008, 1743, 1600, 1498, 1439, 1271, 1124, 971 | 1.10 (3H,t,J=7Hz), 1.50~1.90 (2H,m), 1.93~2.86 (7H,m), 3.82 (3H,s), 3.80~4.43 (4H,m), 4.70 (2H,s), 5.53~5.97 (2H,m), 6.39~6.91 (3H,m) |
| 50 | I dd-a (Isomer 1) | | 53.0 | 60~63 (Ethyl acetate-n-hexane) | 3608, 3008, 2960, 2932, 2876, 1762, 1743, 1600, 1498, 1476, 1270, 1125, 970 | 0.76~1.05 (6H,m), 1.05~1.86 (9H,m), 1.93~2.23 (1H,m), 2.32~2.83 (2H,m), 3.80 (3H,s), 3.80~4.37 (4H,m), 4.69 (2H,s), 5.50~5.93 (2H,m), 6.36~6.89 (3H,m) |
| 51 | I de-a (Isomer 2) | | 73.1 | 65~68 (Ethyl acetate-n-hexane) | 3604, 3008, 2960, 2932, 2876, 1762, 1743, 1600, 1498, 1472, 1271, 1125, 970 | 0.75~1.03 (6H,m), 1.03~1.77 (9H,m), 1.90~2.20 (1H,m), 2.29~2.82 (2H,m), 3.80 (3H,s), 3.80~4.35 (4H,m), 4.68 (2H,s), 5.47~5.93 (2H,m), 6.36~6.88 (3H,m) |
| 52 | I df-a | | 79.6 | Oil | 3608, 3008, 2960, 2936, 2876, 1762, 1744, 1600, 1497, 1475, 1270, 1126, 970. | 0.78~1.03 (6H,m), 1.03~1.90 (7H,m), 1.93~2.23 (1H,m), 2.31~2.84 (2H,m), 3.80 (3H,s), 3.80~4.39 (4H,m), 4.68 (2H,s), 5.46~5.93 (2H,m), 6.36~6.89 (3H,m) |
| 53 | I dg-a | | 86.3 | Oil | 3612, 2964, 2932, 2876, 1762, 1744, 1600, 1497, 1475, 1271, 1127, 972. | 0.83 (3H,s), 0.86 (3H,s), 0.87 (3H,t,J=7Hz), 1.06~1.48 (6H,m), 1.92~2.20 (1H,m), 2.31~2.86 (2H,m), 3.78 (3H,s), 3.75~4.39 (4H,m), 4.67 (2H,s), 5.53~5.92 (2H,m), 6.35~6.86 (3H,m) |
| 54 | I dh-a | | 84.1 | Oil | 3608, 3528, 3008, 2960, 2928, 1762, 1743, 1600, 1497, 1475, 1271, 1126 970. | 0.95 and 0.98 (total 3H, each d,J=7Hz), 1.75 (3H,t,J=2.5hz), 1.56~2.84 (6H,m), 3.78 (3H,s), 3.80~4.40 (3H,m), 4.67 (2H,s), 5.46~5.94 (2H,m), 6.36~6.87 (3H,m) |

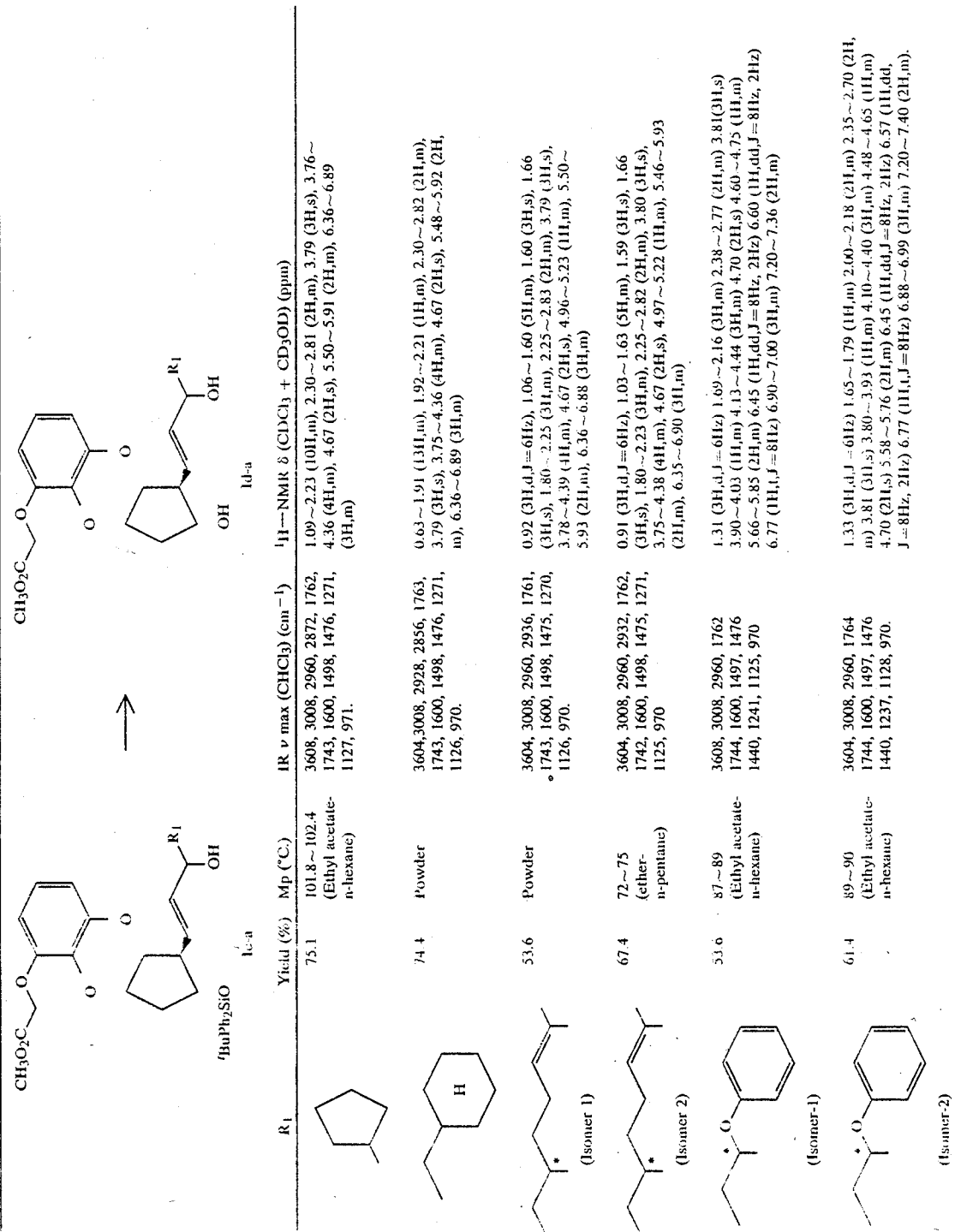

TABLE 6-continued

Structure shown:
CH₃O₂C-O-[phenyl]-O-[cyclopentyl]-CH=CH-CH(R₁)-OH with ᵗBuPh₂SiO group (Ic-a)
→
CH₃O₂C-O-[phenyl]-O-[cyclopentyl]-CH=CH-CH(R₁)-OH with OH group (Id-a)

| Ex. No. | Compd. No. | R₁ | Yield (%) | Mp (°C.) | IR ν max (CHCl₃) (cm⁻¹) | ¹H—NMR δ (CDCl₃ + CD₃OD) (ppm) |
|---|---|---|---|---|---|---|
| 61 | I do-a | *-CH(Et)-CH₂-O-Ph (Isomer-1) | 85.5 | Powder | 3604, 2960, 1762, 1742 1601, 1499, 1476, 1440 1244, 1125, 970. | 1.08 (3H,d,J=7Hz) 1.37~1.53 (1H,m) 1.70~1.84 (1H,m) 2.04~2.29 (2H, m) 2.39~2.73 (2H,m) 3.81 (3H,s) 3.77~4.04 (3H,m) 4.18~4.32 (3H,m) 4.70 (2H,s) 5.65~5.85 (2H,m) 6.44 (1H,dd,J=8Hz, 2Hz) 6.60 (1H, dd,J=8Hz, 2H) 6.76 (1H,t,J=8Hz) 6.86~6.98 (3H,m) 7.21~7.33 (2H,m). |
| 62 | I dp-a | *-CH(Et)-CH₂-O-Ph (Isomer-2) | 70.9 | 100~101 (Ethyl acetate-n-hexane) | 3604, 2960, 1763, 1743 1601, 1499, 1475, 1441 1242, 1125, 971. | 1.08 (3H,d,J=7Hz) 1.47~1.79 (2H,m) 2.04~2.22 (2H,m) 2.38~2.73 (2H, m) 3.81 (3H,s) 3.77~3.88 (2H,m) 3.90~4.07 (1H,m) 4.10~4.33 (3H,m) 4.70 (2H,s) 5.62~5.85 (2H,m) 6.44 (1H,dd,J=8Hz, 2Hz) 6.60 (1H,dd, J=8Hz, 2H) 6.77 (1H,t, J=8Hz) 6.86~6.97 (3H,m) 7.22~7.35 (2H,m). |
| 63 | I dt-a | CH₃CH₂-CH=CH-(CH₂)₃-CH₃ | 51.8 | Powder | 3600, 2940, 1792, 1743 1643, 1601, 1498, 1477 1440, 1127, 969, 902. | 0.91 (3H,t,J=7Hz) 1.22~1.51 (4H,m) 2.00~2.17 (3H,m) 2.26 (2H,d, J=7Hz) 2.39~2.74 (2H,m) 3.81 (3H,s) 3.93~4.05 (1H,m) 4.19~4.34 (3H,m) 4.70 (2H,s) 4.83 (1H,s) 4.86 (1H,s) 5.63~5.87 (2H,m) 6.44 (1H,dd,J=8Hz, 2H) 6.60 (1H,dd,J=8Hz, 2H) 6.78 (1H,t,J=8Hz). |

EXAMPLE 64

Preparation of methyl [(1R*,2R*,3aS*,9aR*)-2-tert-butyldiphenylsilyloxy-1-[(S*)-3-hydroxyoctyl]-2,3,3a,9a-tertahydro-1H-cyclopenta[b][1,4]benzodioxin-5-yl]oxyacetate Ica-a

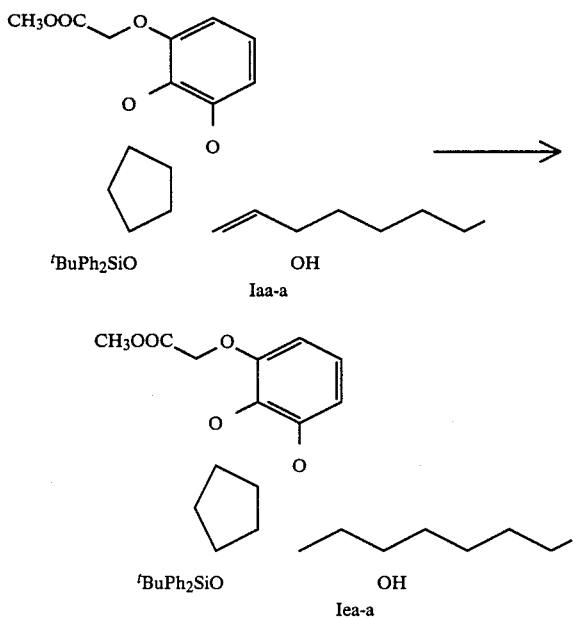

To a solution of 188 mg (0.291 mmol) of the allyl alcohol Iaa-a (prepared in Examples 1 and 5) in 7.5 ml of dry ethanol is added 19 mg of 5% palladium-charcoal and the mixture is stirred at room temperature overnight in a hydrogen atmosphere. The catalyst is removed by filtration and the filtrate is evaporated under reduced pressure. The residue is purified by column chromatography on silica gel (Merck, Lobar column, size A, ethyl acetate:toluene=1:20 to 1:10) to give 156 mg of the desired saturated alcohol Iea-a as an oil in 82.7% yield.

$^1$H-NMR: δ (CDCl$_3$) 0.88 (3 H, t, J=7 Hz), 1.03 (9 H, s), 0.80~1.70 (13 H, m), 1.99~2.40 (3 H, m), 3.30~3.61 (1 H, m), 3.77 (3 H, s), 3.75~4.06 (2 H, m), 4.12~4.37 (1 H, m), 4.70 (2 H, m), 6.40~6.89 (3 H, m), 7.33~7.50 (6 H, m), 7.60~7.80 (4 H, m) ppm.

IR: ν max (CHCl$_3$) 3616, 3008, 2936, 2864, 1763, 1741, 1600, 1498, 1426, 1290, 1110, 822, 611 cm$^{-1}$.

MS: m/z M$^+$ 646.

EXAMPLES 65 to 70

In the same manner as described in Example 64, the reduction is carried out to give a saturated alcohol Ie-a. The results are shown in Table 7.

TABLE 7

| Ex. No. | Compd. No. | R$_1$ | Yd. (%) | MS (m/z) | IR νmax (CHCl$_3$) (cm$^{-1}$) | $^1$H—NMR δ (CDCl$_3$) (ppm) |
|---|---|---|---|---|---|---|
| 65 | I eb-a | cyclohexyl-CH₂ | 70.7 | 658 (M$^+$) | 3608, 3008, 2936, 2860, 1764, 1743, 1600, 1498, 1476, 1292, 1114, 822, 612. | 1.03 (9H,s), 0.73~1.90 (17H,m), 1.99~2.37 (3H,m), 3.00~3.30 (1H,m), 3.74 (3H,s), 3.76~4.01 (2H,m), 4.10~4.32 (1H, m), 4.67 (2H,s), 6.37~6.85 (3H,m), 7.28~7.50 (6H,m), 7.60~7.80 (4H,m) |
| 66 | I ef-a | n-pentyl | 83.0 | 660 (M$^+$) | 3612, 3008, 2960, 2936, 2864, 1763, 7.80 1498, 1475, 1289, 1113, 821, 611. | 1.03 (9H,s), 0.85~1.90 (14H,m), 2.00~2.38 (3H,m), 3.10~3.39 (1H,m), 3.75 (3H,s), 3.75~4.14 (2H,m), 4.10~4.32 (1H, m), 4.67 (2H,s), 6.38~6.86 (3H,m), 7.31~7.47 (6H,m), 7.62~7.80 (4H,m) |
| 67 | I ei-a | cyclopentyl-CH₂ | 56.7 | 644 (M$^+$) | 3620, 3008, 2960, 2864, 1764, 1743, 1600, 1498, 1476, 1291, 1113, 822, 611. | 0.73~1.00 (6H,m), 1.03 (9H,s), 1.00~1.30 (12H,m), 2.00~2.33 (3H,m), 3.10~3.43 (1H,m), 3.76 (3H,s), 3.75~4.03 (2H, m), 4.06~4.34 (1H,m), 4.68 (2H,s), 6.39~6.87 (3H,m), 7.31~7.47 (6H,m), 7.60~7.78 (4H,m) |

TABLE 7-continued

| Ex. No. | Compd. No. | R₁ | Yd. (%) | MS (m/z) | IR νmax (CHCl₃) (cm⁻¹) | ¹H—NMR δ (CDCl₃) (ppm) |
|---|---|---|---|---|---|---|
| 68 | I ej-a | (cyclohexylmethyl) | 87.2 | 672 (M⁺) | 3600, 3008, 2932, 2860, 1761, 1742, 1742, 1600, 1498, 1475, 1289, 1113, 822, 612. | 1.03 (9H,s), 0.60~1.95 (18H,m), 2.00~2.39 (3H,m), 3.38~3.70 (1H,m), 3.74 (3H,s), 3.70~4.03 (2H,m), 4.09~4.33 (1H, m), 4.67 (2H,s), 6.38~6.86 (3H,m), 7.30~7.50 (6H,m), 7.59~7. 80 (4H,m) |
| 69 | I ed-a | (Isomer 1) | 90.7 | 674 (M⁺) | 3608, 2936, 2864, 1763, 1741, 1600, 1498, 1475, 1429, 1289, 1113, 822, 611. | 0.84 (3H,d,J=6Hz) 0.90 (3H,t, J=7Hz) 1.04 (9H,s) 1.10~1.65 (13H,m) 2.05~2.27 (3H,m) 3.40~3.60 (1H,m) 3.79 (3H,s) 3.76~3.98 (2H,m) 4.17~4.28 (1H,m) 4.71 (2H,s) 6.47 (1H,dd,J=8Hz, 2Hz) 6.63 (1H,dd,J=8Hz, 2Hz) 6.76 (1H,t,J=8Hz) 7.30~7.48 (6H,m) 7.64~7.75 (4H,m). |
| 70 | I ee-a | (Isomer 2) | 91.0 | 674 (M⁺) | 3616, 2936, 2864, 1764, 1743, 1600, 1498, 1475, 1428, 1291, 1114, 821, 612. | 0.87 (3H,d,J=7Hz) 0.90 (3H,t, J=7Hz) 1.04 (9H,s) 1.10~1.60 (13H,m) 2.06~2.29 (3H,m) 3.44~3.60 (1H,m) 3.78 (3H,s) 3.80~3.96 (2H,m) 4.18~4.27 (1H,m) 4.71 (2H,s) 6.47 (1H,dd,J=8Hz, 2Hz) 6.63 (1H,dd,J=8Hz, 2Hz) 6.76 (1H,t,J=8Hz) 7.31~7.48 (6H,m) 7.64~7.75 (4H,m). |

EXAMPLE 71

Preparation of methyl[(1R*,2S*,3aR*,9aS*)-2-hydroxy-1-[(R*)-3-hydroxyoctyl]-2,3,3a,9a-tertahydro-1H-cyclopenta[b][1,4]benzodioxin-5-oxyacetate Ifa-a

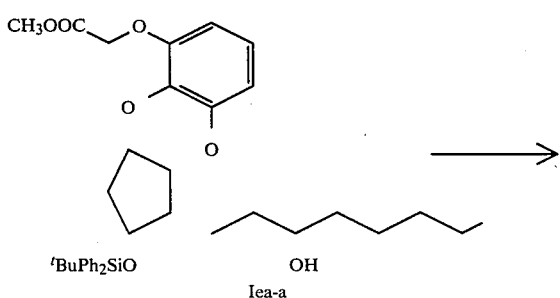

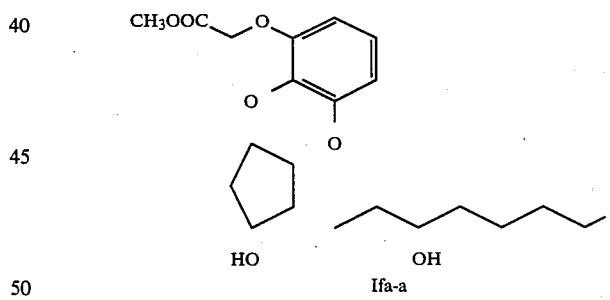

In the same manner as described in Example 17, 186 mg (0.287 mmol) of the silyl ether Iea-a (prepared in Example 64) is converted into 80 mg of the desired crystalline methyl ether Ifa-a in 68.2% yield.

Mp.: 69°~70° C. (ethyl acetate-n-hexane).

¹H-NMR: δ (CDCl₃+CD₃OD) 0.87 (3 H, t, J=7 Hz), 1.10~2.18 (14 H, m), 2.22~2.57 (1 H, m), 3.42~3.69 (1 H, m), 3.79 (3 H, s), 3.73~4.17 (2 H, m), 4.19~4.35 (1 H, m), 4.67 (2 H, s), 6.34~6.87 (3 H, m) ppm.

IR: ν max (CHCl₃) 3616, 3008, 2936, 2864, 1762, 1743, 1600, 1498, 1476, 1286, 1124 cm⁻¹.

EXAMPLES 72 to 77

In the same manner as described in Example 17, the desilylation is carried out to give methyl ester If-a. The results are shown in Table 8.

TABLE 8

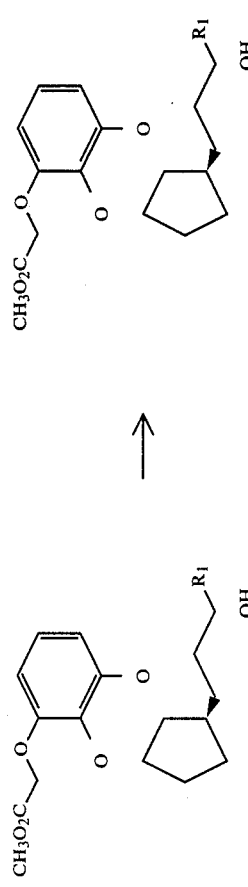

| Ex. No. | Compd. No. | R₁ | Yield (%) | Mp (°C.) | IR ν max (CHCl₃) (cm⁻¹) | ¹H—NMR δ (CDCl₃ + CD₃OD) (ppm) |
|---|---|---|---|---|---|---|
| 72 | I fb-a | cyclohexyl (H) | 80.6 | 84.5~86.5 (ethyl acetate-n-hexane) | 3616, 3008, 2932, 2860, 1763, 1742, 1498, 1476, 1270, 1125 | 0.75~2.62 (18H,m), 3.20~3.50 (1H,m), 3.81 (3H,s), 3.77~4.40 (3H,m), 4.70 (2H,s), 6.39~6.90 (3H,m) |
| 73 | I fi-a | n-pentyl | 92.6 | Powder | 3612, 3008, 2936, 2864, 1764, 1744, 1600, 1497, 1475, 1286, 1126. | 0.75~1.05 (6H,m), 1.05~2.56 (14H,m), 3.28~3.55 (1H,m), 3.78 (3H,s), 3.77~4.36 (3H,m), 4.67 (2H,s), 6.35~6.90 (3H,m) |
| 74 | I fi-a | cyclopentyl | 86.8 | 82~84 (ethyl acetate-n-hexane) | 3621, 3008, 2952, 2872, 1762, 1741, 1599, 1497, 1475, 1271, 1125. | 1.03~2.20 (15H,m), 2.22~2.57 (1H,m), 3.20~3.50 (1H,m), 3.78 (3H,s), 3.75~4.35 (3H,m), 4.67 (2H,s), 6.35~6.87 (3H,m) |
| 75 | I fj-a | cyclohexylmethyl (H) | 77.0 | 56~60 (ethyl acetate-n-hexane) | 3612, 3008, 2928, 2856, 1762, 1742, 1599, 1497, 1475, 1287, 1126. | 0.60~2.60 (20H,m), 3.77 (3H,s), 3.51~4.40 (4H,m), 4.66 (2H,s), 6.35~6.89 (3H,m) |
| 76 | I fd-a | (Isomer 1) branched alkyl | 57.7 | Oil | 3616, 2932, 2864, 1762, 1743, 1600, 1497, 1475, 1286, 1126. | 0.87 (3H,d,J=6Hz) 0.89 (3H,t,J=7Hz) 1.00~1.80 (13H,m) 1.88~2.16 (2H,m) 2.36 (1H,ddd,J=15Hz, 8Hz, 5Hz( 3.60~3.75 (1H,m) 3.81 (3H,s) 3.80~3.94 (1H,m) 4.09 (1H,dd,J=8Hz, 3Hz) 4.23~4.33 (1H,m) 4.70 (2H,s) 6.44 (1H,dd,J=8Hz, 2Hz) 6.61 (1H,dd,J=8Hz, 2Hz) 6.77 (1H,t,J=8Hz). |
| 77 | I fe-a | (Isomer 2) branched alkyl | 64.0 | Oil | 3616, 2932, 2864, 1762, 1744, 1599, 1497, 1475, 1287, 1124. | 0.89 (3H,d,J=6Hz) 0.89 (3H,t,J=7Hz) 1.00~1.80 (13H,m) 1.90~2.14 (2H,m) 2.36 (1H,ddd,J=15Hz, 8Hz, 5Hz) 3.60~3.74 (1H,m) 3.81 (3H,s) 3.80~3.94 (1H,m) 4.09 (1H,dd,J=8Hz, 3Hz) 4.25~4.33 (1H,m) 4.70 (2H,s) 6.44 (1H,dd,J=8Hz, 2Hz) 6.61 (1H,dd,J=8Hz, 2Hz) 6.77 (1H,t,J=8Hz). |

EXAMPLE 78

Preparation of [(1R*,2S*,3aR*,9aS*)-2-hydroxy-1-[(R*)-3-hydroxyoctyl]-2,3,3a,9a-tetrahydro-1H-cyclopenta[b][1,4]benzodioxin-5-yl]oxyacetic acid Ifa-b

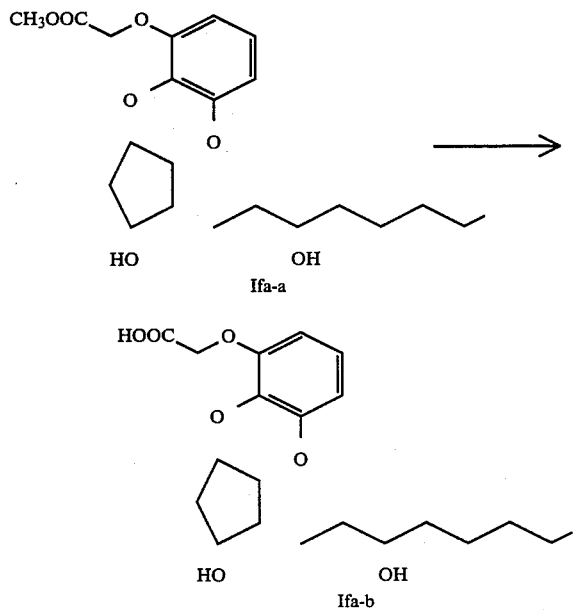

In the same manner as described in Examples 35, 45 mg (0.110 mmol) of the methyl ester Ifa-a is converted into 34 mg of the desired carboxylic acid Ifa-b in 78.2% yield.

Mp.: 111°~113° C. (ethyl acetate-n-hexane).

$^1$H-NMR: δ (CD$_3$OD) 0.89 (3 H, t, J=6 Hz), 1.08~2.16 (14 H, m), 2.23~2.62 (1 H, m), 3.38~3.67 (1 H, m), 3.73~4.00 (1 H, m), 4.00~4.32 (2 H, m), 4.63 (2 H, s), 6.40~6.85 (3 H, m) ppm.

IR: ν max(KBr) 3504, 3368, 2928, 2856, 1716, 1615, 1598, 1500, 1476, 1279, 1134, 759, 713 cm$^{-1}$.

EXAMPLES 79 to 82

In the same manner as described in Example 35, the carboxylic acid If-b is prepared. The results are shown in Table 9.

TABLE 9

| Ex. No. | Compd. No. | R$_1$ | Yd. (%) | Mp. (°C.) | IR νmax (cm$^{-1}$) | $^1$H—NMR δ (CD$_3$OD) (ppm) |
|---|---|---|---|---|---|---|
| 79 | I fb-b | -CH$_3$ | 72.0 | 78~80 (ethyl acetate) | (KBr) 3472, 2944, 2928, 1735, 1598, 1497, 1476, 1436, 1248, 1128, 980, 759, 712 | 1.77~2.13(17H,m), 2.23~2.60(1H,m), 3.25~3.40(1H,m), 3.73~4.30(3H,m), 4.63(2H,s), 6.40~6.84(3H,m) |
| 80 | I ff-b | n-pentyl | 79.2 | Oil | (CHCl$_3$) 3456, 2936, 2864, 1742, 1600, 1497, 1476, 1283, 1123. | 0.76~1.05(6H,m), 1.05~2.17(13H,m), 2.25~2.60(1H,m), 3.30~3.56(1H,m), 3.75~4.34(3H,m), 4.63(2H,s), 6.41~6.86(3H,m) |
| 81 | I fi-b | cyclopentyl | 71.3 | 84~87 (ethyl acetate-n-hexane) | (KBr) 3376, 2952, 1756, 1741, 1700, 1597, 1502, 1475, 1255, 1131, 759, 711. | 1.00~2.13(15H,m), 2.23~2.61(1H,m), 3.25~3.47(1H,m), 3.72~4.30(3H,m), 4.63(2H,s), 6.40~6.83(3H,m) |
| 82 | I fj-b | cyclohexylmethyl | 37.0 | 136.4~137.5 (ethyl acetate-n-hexane) | (KBr) 3468, 2920, 2852, 1747, 1598, 1498, 1476, 1201, 1122, 760, 710. | 0.70~2.62(20H,m), 3.46~4.32(4H,m), 4.63(2H,m), 6.40~6.86(3H,m) |

EXAMPLE 83

Preparation of (9-anthryl)methyl [(1R*,2S*,3aR*,9aS*)-2-hydroxy-1-[(3R*,1E)-3-hydroxy-1-octenyl]-2,3,3a,9a-tetrahydro-1H-cyclopenta[b][1,4]benzodioxin-5-yl]oxyacetate Iba-a'

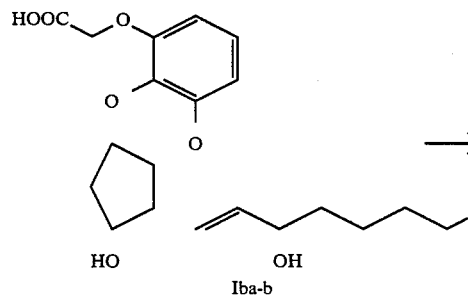
Iba-b

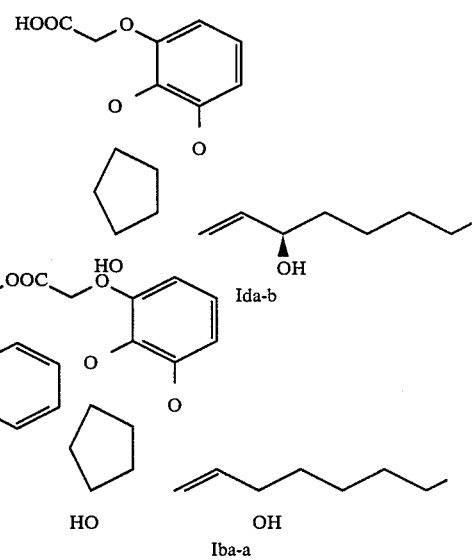
Ida-b

To a solution of 25 mg (0.064 mmol) of the carboxylic acid Iba-a (prepared in Example 35) in 0.5 ml of methanol is added dropwise 1.5 ml (0.138 mmol) of (9-anthryl)diazomethane (2% in ethyl acetate) at room temperature. Then, the mixture is stirred for 45 minutes and the precipitated crystals are collected by filtration to give 27 mg of the crude (9-anthryl)methyl ester Iba-a'. The crude crystals are dissolved in pyridine and insoluble material is removed by filtration. The filtrate is concentrated and the residue is recrystallized from ethyl acetate to give 19 mg of the crystalline Iba-a' in 51.2% yield.

Mp.: 185°~188° C. (ethyl acetate).

$^1$H-NMR: δ (pyridine-d$_5$) 0.83 (3 H, t, J=6 Hz), 1.02~1.93 (8 H, m), 2.12~2.70 (2 H, m), 2.97~3.31 (1 H, m), 4.10~4.50 (4 H, m), 4.95 (2 H, s), 5.86~6.30 (2 H, m), 6.41 (2 H, s), 6.65~6.83 (3 H, m), 7.38~7.70 (4 H, m), 8.00~8.17 (2 H, m), 8.35~8.66 (3 H, m) ppm.

IR: ν max (KBr) 3592, 3428, 2928, 2856, 1741, 1596, 1499, 1475, 1207, 1124, 973, 723 cm$^{-1}$.

EXAMPLE 84

Preparation of [(1R*,2S*,3aR*,9aS*)-2-hydroxy-1-[(3S*,1E)-3-hydroxy-1-octenyl]-2,3,3a,9a-tetrahydro-1H-cyclopenta[b][1,4]benzodioxin-5-yl]oxyacetic acid Ida-b

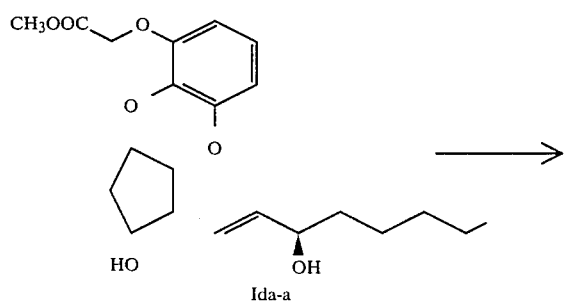
Ida-a

In the same manner as described in Example 35, 110 mg of the methyl ester Ida-a (prepared in Example 47) is converted into 80 mg of the desired carboxylic acid Ida-b in 75.5% yield.

Mp.: 109.5°~111.5° C. (ethyl acetate - h-hexane).

$^1$H-NMR: δ (CD$_3$OD) 0.89 (3 H, t, J=6 Hz), 1.10~1.70 (8 H, m), 1.82~2.12 (1 H, m), 2.30~2.77 (2 H, m), 3.85~4.43 (4 H, m), 4.65 (2 H, s), 5.47~5.93 (2 H, m), 6.43~6.85 (3 H, m) ppm.

IR: ν max (KBr) 3496, 3241, 2932, 2852, 1708, 1617, 1596, 1502, 1476, 1129, 978, 758, 702 cm$^{-1}$.

EXAMPLES 85 to 86

In the same manner as described in Example 35, the carboxylic acid Id-b is prepared. The results are shown in Table 10.

TABLE 10

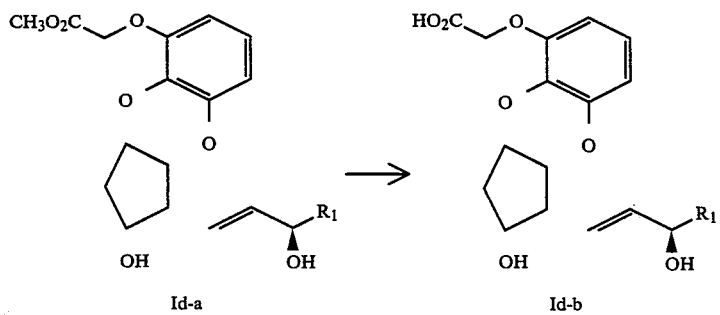

| Ex. No. | Compd. No. | R₁ | Yd. (%) | Mp. (°C.) | IR $\nu$ max (KBr) (cm$^{-1}$) | $^1$H—NMR $\delta$ (CD$_3$OD) (ppm) |
|---|---|---|---|---|---|---|
| 85 | I db-b | cyclohexyl-H | 45.4 | 119.5~121.5 (ethyl acetate-n-hexane) | 3532, 3244, 2928, 2852, 1761, 1745, 1597, 1495, 1475, 1125, 972, 759, 711 | 0.70~2.12 (12H,m), 2.30~2.78 (2H,m), 3.69~4.40 (4H,m), 4.63 (2H,s), 5.43~5.87 (2H,m), 6.42~6.82 (3H,m). |
| 86 | I dc-b | propargyl chain | 82.9 | Powder | 3488, 2924, 1615, 1596, 1500, 1476, 1129, 972, 760, 713 | 1.07 (3H,t,J=7Hz), 1.50~1.82 (2H,m), 1.82~2.76 (7H,m), 3.75~4.38 (4H,m), (2H,s), 5.44~5.95 (2H,m), 6.41~6.86 (3H,m). |

EFFECT OF THE INVENTION

The compounds of the present invention are benzodioxane PGI$_2$ analogues which are long acting and chemically stable.

The compounds of the present invention, as well as PGI$_2$, have cytoprotective effect and/or platelet aggregation inhibitory activity. Especially, the compounds of the present invention have a potent cytoprotective effect and are expected to be used as drugs for treating peptic ulcer. The antiulcer activity of the representative compounds of the present invention against hydrochloric acid ethanol-induced gastric ulcer is examined in the following test.

The Effect Against Hydrochloric Acid Ethanol-Induced Gastric Ulcer

To male JCL-SD rats or CRJ-SD rats (weight: 220 g to 260 g) which have been fasted for 24 hours is administered orally 1 ml of 150 mM hydrochloric acid-60% ethanol. After an hour, the stomachs are excised. The ulcer size is determined by measuring the length of each lesion using a stereoscopic microscope and the sum of individual lesion length is expressed as lesion index. The vehicle (1% to 10% ethanol) and the test compounds are administered orally 30 minutes before the hydrochloric acid-ethanol administration. The percent suppression is calculated from the lesion indexes of treated versus non-treated animals. The results are shown in Table 11.

TABLE II

| Compd. No.* | Dose μg/kg | P.S. (%) | Compd. No.* | Dose μg/kg | P.S. (%) |
|---|---|---|---|---|---|
| (No. 1) (JCL-SD rats) | | | | | |
| Iba-a | 30 | 36 | Ibe-b | 30 | 80 |
| Ibb-a | 30 | 63 | Ibf-b | 30 | 18 |
| Ibc-a | 30 | 29 | Ibh-b | 30 | 58 |
| Ibd-a | 30 | 91 | Ibk-b | 30 | 70 |
| Ibe-a | 30 | 96 | Ibl-b | 30 | 83 |
| Ibf-a | 30 | 50 | Ida-a | 30 | 37 |

TABLE II-continued

| Compd. No.* | Dose μg/kg | P.S. (%) | Compd. No.* | Dose μg/kg | P.S. (%) |
|---|---|---|---|---|---|
| Ibg-a | 30 | 15 | Idd-a | 30 | 32 |
| Ibh-a | 30 | 61 | Ide-a | 30 | 37 |
| Ibi-a | 30 | 41 | Ida-b | 100 | 19 |
| Ibk-a | 30 | 81 | Idb-b | 30 | 25 |
| Ibl-a | 30 | 64 | Ifa-a | 30 | 27 |
| Ibm-a | 30 | 58 | Ifb-a | 30 | 78 |
| Ibo-a | 30 | 63 | Ifd-a | 30 | 66 |
| Iba-b | 100 | 30 | Ife-a | 30 | 91 |
| Ibb-b | 30 | 25 | Iff-a | 30 | 57 |
| Ibc-b | 30 | 14 | Ifi-a | 30 | 52 |
| Ibd-b | 30 | 74 | Ifj-a | 30 | 25 |
| | | | Ifb-b | 30 | 75 |
| (No. 2) (CRJ-SD rats) | | | | | |
| Ibe-a | 30 | 99 | Ibr-a | 30 | 96 |
| Ibu-a | 30 | 98 | | | |

*Each compound number corresponds to the number used in the example.
P.S. means Percent Suppression.
Reference Compound Hoe-892
Dose 300 μg/Kg, Percent Suppression (P.S.) 28%

The compounds of the present invention potently inhibit hydrochloric acid ethanol-induced gastric ulcer.

It is expected that the pharmacological effect of the compounds of the present invention can be applied as useful curative medicine. For example, they have a cytoprotective effect, as well as PG I$_2$, and are expected to be used as curative medicine for ulcerous lesions in esophagus, stomach, duodenum, or anastomosed parts of the stomach.

The compounds of the present invention can be administered orally or parenterally. For oral administration, the compounds are prepared in dosage forms such as tablets, capsules, pills, granules, subtilized granule, solution, or emulsions and for parenteral administration, in forms such as suppositories or injections, e.g., intravenous, intramuscular or subcutaneous injection. In preparing the pharmaceutical preparation of the compounds adequate carriers and fillers are selected from conventionally used carriers and fillers.

The compounds of the present invention may be administered in a dose of about 0.1 to 100 mg per day for an adult.

What we claim is:

1. A compound of the formula:

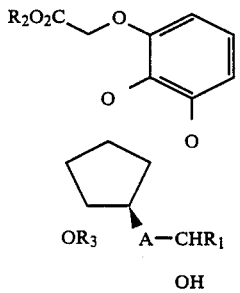

wherein $R_1$ is alkyl, alkenyl, alkynyl, cycloalkyl, cycloalkylalkyl, or phenoxyalkyl; $R_2$ is hydrogen, lower alkyl, or lower alkyl substituted by (1) or more phenyl which may have one or more substituents selected from the group consisting of methyl, methoxy, bromo and nitro or (2) anthryl; $R_3$ is hydrogen or a hydroxy-protecting group; A is ethylene or vinylene; and the wavy line indicates α or β configuration or their mixture; or a pharmaceutically acceptable salt thereof.

2. A compound claimed in claim 1, wherein $R_2$ is hydrogen or lower alkyl; and $R_3$ is hydrogen.

3. A compound claimed in claim 1, wherein $R_1$ is alkyl, alkenyl or cycloalkyl; $R_2$ is hydrogen or lower alkyl; and $R_3$ is hydrogen.

4. A compound claimed in claim 1, namely, methyl [2-hydroxy-1-(3-hydroxy-5-methyl-1-nonenyl)-2,3,3a,-9a-tetrahydro-1H-cyclopenta[b][1,4]benzodioxin-5-yl]oxyacetate.

5. A compound claimed in claim 1, namely, methyl [2-hydroxy-1-(3-hydroxy-5-methyl-1,8-nonadienyl)-2,3,3a,9a-tetrahydro-1H-cyclopenta[b][1,4]benzodioxin-5-yl]oxyacetate.

6. A compound claimed in claim 1, namely, methyl [2-hydroxy-1-(3-hydroxy-5,9-dimethyl-1,8-decadienyl)-2,3,3a,9a-tetrahydro-1H-cyclopenta[b][1,4]benzodioxin-5-yl]oxyacetate.

7. A compound claimed in claim 1, namely, methyl [2-hydroxy-1-(3-cyclohexy-3-hydroxypropyl)-2,3,3a,-9a-tetrahydro-1H-cyclopenta[b][1,4]benzodioxin-5-yl]oxyacetate.

8. A compound claimed in claim 1, namely, [2-hydroxy-1-(3-hydroxy-5-methyl-1-nonenyl)-2,3,3a,9a-tetrahydro-1H-cyclopenta[b][1,4]benzodioxin-5-yl]oxyacetic acid.

9. A compound claimed in claim 1, namely, [2-hydroxy-1-(3-hydroxy-5,9-dimethyl-1,8-decadienyl)-2,3,3a,9a-tetrahydro-1H-cyclopenta[b][1,4]benzodioxin-5-yl]oxyacetic acid.

* * * * *

UNITED STATES PATENT AND TRADEMARK OFFICE
CERTIFICATE OF CORRECTION

PATENT NO. : 4,902,811

DATED : Feb. 20, 1990

INVENTOR(S) : Sachio Mori, et al.

It is certified that error appears in the above-identified patent and that said Letters Patent is hereby corrected as shown below:

Columns 1 - 96 should be deleted to appear as per attached columns 1 - 96.

Signed and Sealed this

Twenty-third Day of February, 1993

*Attest:*

STEPHEN G. KUNIN

*Attesting Officer*     Acting Commissioner of Patents and Trademarks

BENZODIOXANE PROSTACYCLIN ANALOGS

Background of the Invention

(1) Field of the Invention

The compounds of the present invention are related to novel benzodioxane prostacyclin analogues and intermediates thereof. In more detail, this invention relates to the compounds represented by the general formula (I) or the salts thereof, which have prostacyclin (prostaglandin $I_2$; prostaglandin is abbreviated to PG hereinafter) like antiulcer activity and platelet aggregation inhibitory activity, and the intermediate thereof.

General formula:

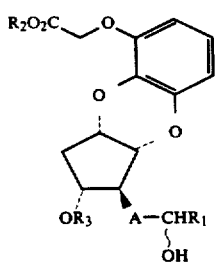

(wherein $R_1$ is alkyl, alkenyl, alkynyl, cycloalkyl, cycloalkylalkyl, or phenoxyalkyl; $R_2$ is hydrogen, lower alkyl or aralkyl; $R_3$ is hydrogen or a protecting group; A is ethylene or vinylene; the wavy line indicates α or β configuration or their mixture)

(2) Prior Art

It is said that a peptic ulcer is formed by the action of gastric juice on the weak part of gastric mucosa which is generated by local nutrition disorder. Though the origin of peptic ulcers is uncertain, it is thought that various factors such as local factor (e.g., mechanical stimulation, chemical stimulation, gastric juice digestion, gastritis, gastric mucous parasecretion) and systemic factor (e.g., stress, neurovegetative disease, cryptorrhea, systemic cacotrophy, allergy, anomalous constitution) are responsible. Such idea is summarized in the Shay's theory, concerning balance between aggressive and defensive factors, that postulates ulceration is induced by the imbalance between mucous aggressive factor (e.g., supersecretion of hydrochloric acid, pepsin, or gastrin, vagotonia, increasing of number of gastric parietal cells, or Zollinger-Ellison syndrome) and mucous defensive factor (e.g., gastric mucosal barrier, mucosal resistance, hyposecretion of duodenal gastric juice). Therefore, a ulcer is treated by such a method that the mucous defensive factor is activated and the mucosa is protected from aggressive factor. In the pharmacotherapy of ulcers the medication has been by the administration of, for example, (1) tranquilizer, (2) parasympatholytic, (3) antacid, (4) antipepsin, (5) antigastrin, (6) gastric mucosa protectant (e.g., mucin preparation) or (7) gastric anagenetic accelerator.

Since Robert et al., found that PG $E_2$, PG $I_2$ and the like inhibited acid secretion and/or had cytoprotection effect, these PGs or their derivatives have been noted because they may be useful for the medication of peptic ulcers.

As PG $I_2$ analogues having antiulcer activity, such compounds as nileprost (U.S. Pat. No. 4,219,479), Hoe-892 (S. J. Konturek et al., Prostaglandins, 28, 443, (1984)), U-68215 (A. Robert et al., Prostaglandins, 30, 619, (1985)) and compounds disclosed in JP Kokai 83-164585 are cited.

After being discovered as a new arachidonic acid metabolite, PG $I_2$ has caught considerable attention because of its various interesting biological activity, e.g., gastric mucosa protective activity (gastric antisecretory and cytoprotective effect), platelet aggregation inhibition, vasodilation or broncosmooth muscle relaxation or the like.

It is thought that the acid hyposecretive or cytoprotective action of PG $I_2$ (mucous secretion, supersecretion, stabilization of membrane, maintenance of sodium pomp, bicarbonate ion secretion, increasing of gastric mucosal blood flow or the like) protects the gastric mucosa from various aggressive factors.

However, the naturally occurring PG $I_2$ has some problems, that is, (1) inactiveness in oral administration and a short duration of action when administered parenterally because of rapid metabolism (2) incidence of numerous side effects and (3) chemical instability. PG $I_2$ analogues which are fully satisfactory as antiulcer agent have not been developed yet.

SUMMARY

The invention provides benzodioxane prostacyclin analogues represented by the formula (I):

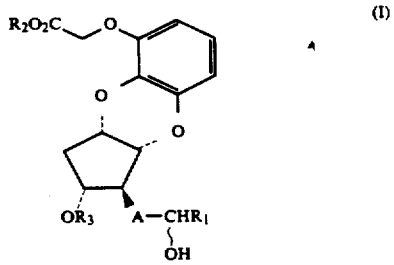

wherein $R_1$ is alkyl, alkenyl, alkynyl, cycloalkyl, cycloalkylalkyl or phenoxyalkyl; $R_2$ is hydrogen, lower alkyl or aralkyl; $R_3$ is hydrogen or a protecting group; A is ethylene or vinylene; the wavy line indicates α or β configuration or their mixture; or a salt thereof. Said compounds have antiulcer and platelet aggregation inhibitory activities.

DESCRIPTION OF THE PREFERRED EMBODIMENTS

The present invention conducted an investigation to resolve these problems and prepared the benzodioxane prostacyclin analogues represented by the formula (I). They found that the novel compounds had potent protective effect for gastric mucosa and were chemically stable and long acting, and completed the invention.

The following definitions are given for various terms used throughout this specification.

The term "lower alkyl" refers to straight or branched $C_1$ to $C_6$ alkyl, e.g., methyl, ethyl, propyl, isopropyl, butyl, isobutyl, tert-butyl, pentyl, and hexyl.

The term "alkyl" refers to straight or branched $C_1$ to $C_{10}$ alkyl, e.g., methyl, ethyl, propyl, isopropyl, butyl, isobutyl, tert-butyl, pentyl, 1-methylpentyl, 1,1-dimethylpentyl, 2-methylpentyl, hexyl, 1-methylhexyl, 1,1-dimethylhexyl, 2-methylhexyl, heptyl, octyl, nonyl, and decyl.

The term "alkenyl" refers to straight or branched $C_2$ to $C_{10}$ alkenyl, e.g., vinyl, 1-propenyl, 2-propenyl, 2-butyl-2-propenyl, 1-butenyl, 2-butenyl, 2-pentenyl, 1-methyl-3-pentenyl, 3-hexenyl, 2-methyl-5-hexenyl, 2,6-dimethyl-5-heptenyl, 3-octenyl, and 3-nonyl.

The term "alkynyl" refers to straight or branched $C_2$ to $C_{10}$ alkynyl, e.g., ethynyl, 1-propynyl, 2-propynyl, 1-butynyl, 2-butynyl, 2-pentynyl, 2-methyl-3-pentynyl, 3-hexynyl, 2-methyl-5-heptynyl, 3-octynyl, and 3-nonynyl.

The term "cycloalkyl" refers to $C_3$ to $C_8$ cycloalkyl, e.g., cyclopropyl, cyclobutyl, cyclopentyl, cyclohexyl, cycloheptyl, and cyclooctyl.

The term "cycloalkylalkyl" refers to lower alkyl substituted by $C_3$ to $C_8$ cycloalkyl, e.g., cyclopropylmethyl, cyclobutylmethyl, cyclopentylmethyl, cyclopentylethyl, cyclohexylmethyl, cyclohexylethyl, cycloheptylmethyl, and cyclooctylmethyl.

The term "phenoxyalkyl" refers to lower alkyl substituted by phenoxy, e.g., phenoxymethyl, phenoxyethyl, 1-phenoxypropyl, 2-phenoxypropyl, 1-phenoxy-2-methylpropyl, 1-phenoxybutyl, 2-phenoxybutyl, 1-phenoxypentyl, 1-phenoxyhexyl, 1-phenoxyheptyl, and 1-phenoxyoctyl.

The term "aralkyl" refers to lower alkyl substituted by aryl, e.g., benzyl, substituted benzyl (2,4,6-trimethylbenzyl, 4-bromobenzyl, 4-methoxybenzyl or the like), diphenylmethyl, triphenylmethyl, bis(2-nitrophenyl)methyl or 9-anthrylmethyl.

In the general formula (I), especially preferably $R_1$ is alkyl (e.g., pentyl, 1-methylpentyl, 1,1-dimethylpentyl, 2-methylhexyl), alkenyl (e.g., 2,6-dimethyl-5-heptenyl, 2-methyl-5-hexenyl, 2-butyl-2-propenyl), alkynyl (e.g., 1-methyl-3-pentynyl, 3-hexynyl), cycloalkyl (e.g., cyclopentyl, cyclohexyl) or cycloalkylalkyl (e.g., cyclohexylmethyl), phenoxyalkyl (e.g., phenoxy-2-propyl, phenoxy-2-methylpropyl). Especially preferable $R_2$ is hydrogen, lower alkyl (e.g., methyl) or aralkyl (e.g., 9-anthrylmethyl). Especially preferable $R_3$ is hydrogen or ordinarily used protecting group (e.g., trimethylsilyl, tert-butyldimethylsilyl or tert-butyldiphenylsilyl). Especially preferable A is ethylene or vinylene (trans).

The salts which may be formed when $R_2$ is hydrogen in the general formula (I) include, for example, salts with alkali metal (e.g., lithium, sodium, potassium), salts with alkaline earth metal (e.g., calcium), ammonium salts, salts with organic base (e.g., triethylamine, N-methylmorpholine, dicyclohexylamine, pyridine, trimethylamine), or amino acid (e.g., glycine, valine, alanine).

Illustrative compounds (I) of the present invention are as follows:

[2-hydroxy-1-(3-hydroxy-1-octenyl)-2,3,3a,9a-tetrahydro-1H-cyclopenta[b][1,4]benzodioxin-5-yl]oxyacetic acid,

[2-hydroxy-1-(3-cyclohexyl-3-hydroxy-1-propenyl)-2,3,3a,9a-tetrahydro-1H-cyclopenta[b][1,4]benzodioxin-5-yl]oxyacetic acid,

[2-hydroxy-1-(3-hydroxy-1-nonen-6-ynyl)-2,3,3a,9a-tetrahydro-1-H-cyclopenta[b][1,4]benzodioxin-5-yl]oxyacetic acid,

[2-hydroxy-1-(3-hydroxy-5-methyl-1-nonenyl)-2,3,3a,9a-tetrahydro-1H-cyclopenta[b][1,4]benzodioxin-5-yl]oxyacetic acid,

[2-hydroxy-1-(3-hydroxy-4-methyl-1-octenyl)-2,3,3a,9a-tetrahydro-1H-cyclopenta[b][1,4]benzodioxin-5-yl]oxyacetic acid,

[2-hydroxy-1-(3-hydroxy-4,4-dimethyl-1-octenyl)-2,3,3a,9a-tetrahydro-1H-cyclopenta[b][1,4]benzodioxin-5-yl]oxyacetic acid,

[2-hydroxy-1-(3-hydroxy-4-methyl-1-octen-6-ynyl)-2,3,3a,9a-tetrahydro-1H-cyclopenta[b][1,4]benzodioxin-5-yl]oxyacetic acid,

[2-hydroxy-1-(3-cyclopentyl-3-hydroxy-1-propenyl)-2,3,3a,9a-tetrahydro-1H-cyclopenta[b][1,4]benzodioxin-5-yl]oxyacetic acid,

[2-hydroxy-1-(4-cyclohexyl-3-hydroxy-1-butenyl)-2,3,3a,9a-tetrahydro-1H-cyclopenta[b][1,4]benzodioxin-5-yl]oxyacetic acid,

[2-hydroxy-1-(3-hydroxy-5,9-dimethyl-1,8-decadienyl)-2,3,3a,9a-tetrahydro-1H-cyclopenta[b][1,4]benzodioxin-5-yl]oxyacetic acid,

[2-hydroxy-1-(3-hydroxy-5-phenoxy-1-hexenyl)-2,3,3a,9a-tetrahydro-1H-cyclopenta[b][1,4]benzodioxin-5-yl]oxyacetic acid,

[2-hydroxy-1-(3-hydroxy-5-phenoxymethyl-1-hexenyl)-2,3,3a,9a-tetrahydro-1H-cyclopenta[b][1,4]benzodioxin-5-yl]oxyacetic acid,

[2-hydroxy-1-(3-hydroxy-5-methyl-1,8-nonadienyl)-2,3,3a,9a-tetrahydro-1H-cyclopenta[b][1,4]benzodioxin-5-yl]oxyacetic acid,

[2-hydroxy-1-(5-butyl-3-hydroxy-1,5-hexadienyl)-2,3,3a,9a-tetrahydro-1H-cyclopenta[b][1,4]benzodioxin-5-yl]oxyacetic acid,

[2-hydroxy-1-(3-hydroxyoctyl)-2,3,3a,9a-tetrahydro-1H-cyclopenta[b][1,4]benzodioxin-5-yl]oxyacetic acid,

[2-hydroxy-1-(3-cyclohexyl-3-hydroxypropyl)-2,3,3a,9a-tetrahydro-1H-cyclopenta[b][1,4]benzodioxin-5-yl]oxyacetic acid,

[2-hydroxy-1-(3-hydroxy-4-methyloctyl)-2,3,3a,9a-tetrahydro-1H-cyclopenta[b][1,4]benzodioxin-5-yl]oxyacetic acid,

[2-hydroxy-1-(3-cyclopentyl-3-hydroxypropyl)-2,3,3a,9a-tetrahydro-1H-cyclopenta[b][1,4]benzodioxin-5-yl]oxyacetic acid, and

[2-hydroxy-1-(4-cyclohexyl-3-hydroxybutyl)-2,3,3a,9a-tetrahydro-1H-cyclopenta[b][1,4]benzodioxin-5-yl]oxyacetic acid.

The above compounds can be converted into the desired esters or their salts.

The compounds of the present invention are racemates or optically active compounds whose one enantiomer is represented by the general formula (I). Therefore, the present invention includes all of the stereoisomers or their mixture shown by the general formula (I).

The compounds of the present invention can be prepared according to the following scheme.

Process

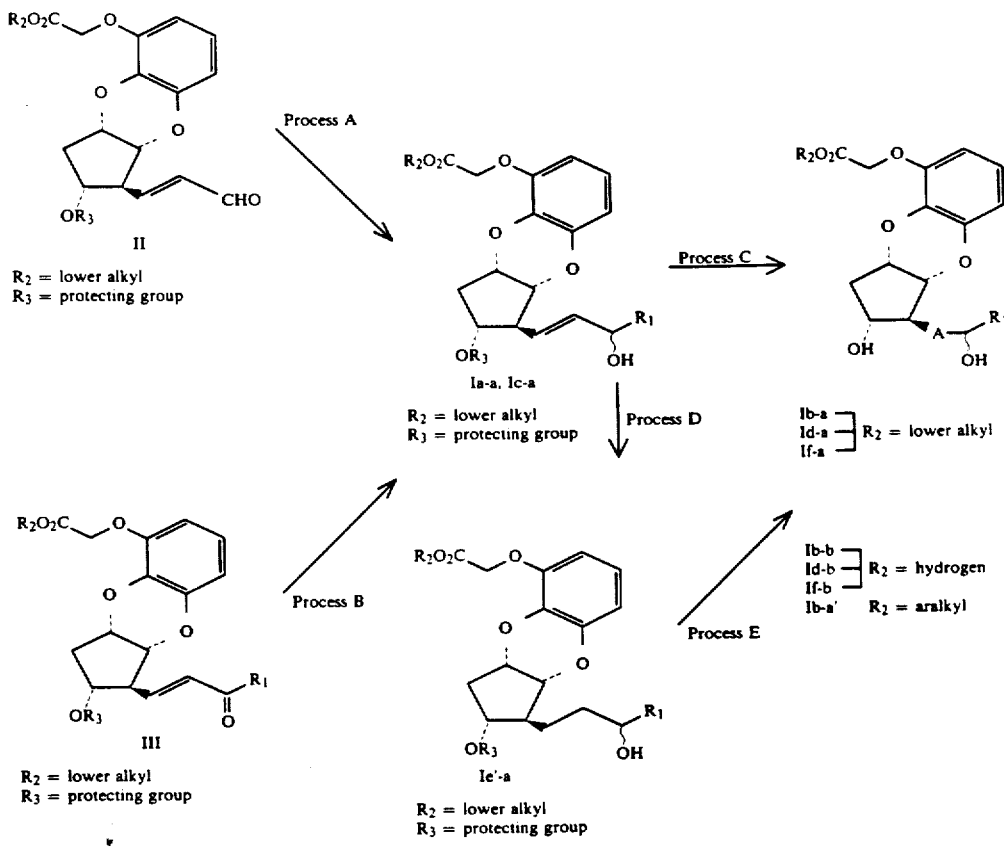

PROCESS A

In this process, the aldehyde II is treated with a Grignard reagent to give the compounds of the present invention Ia-a and Ic-a.

The reaction is carried out in a usual manner of Grignard reaction in an etherial solvent (e.g., diethyl ether, tetrahydrofuran) for a period of several tens of minutes to several hours under cooling. The Grignard reagent used in the reaction is exemplified by a magnesium halide having a desired side chain, such as alkylmagnesium halide (e.g., n-pentyl-magnesium bromide, 1-methylpentylmagnesium bromide, 1,1-dimethylpentylmagnesium chloride, n-hexylmagnesium bromide, 2-methylhexylmagnesium bromide), alkenylmagnesium halide (e.g., 2, 6-dimethyl-5-heptenylmagnesium bromide), alkynylmagnesium halide (e.g., 3-hexynylmagnesium bromide, 1-methyl-3-pentynylmagnesium bromide), cycloalkylmagnesium halide (e.g., cyclopentylmagnesium bromide, cyclohexylmagnesium bromide) or cycloalkylalkylmagnesium halide (e.g., cyclohexylmethylmagnesium bromide).

PROCESS B

In this process, the enone III is reduced to give the unsaturated alcohol Ia-a and Ic-a.

A reducing agent such as aluminium isopropoxide, diisobornyl aluminium isopropoxide, sodium cyanoborohydride, potassium tri-sec-butylborohydride, zinc borohydride, sodium borohydride, a combination of sodium borohydride and cerium (III) chloride, 2,6-di-tert-butyl-4-methylphenoxidodiisobutyl aluminium, lithium hexyllimonylborohydride or BINAL-H [prepared from binaphthol, lithium aluminium hydride and ethanol (J. Am. Chem. Soc., 106,6709, (1984))]can be used.

As a solvent ether (e.g., diethyl ether, tetrahydrofuran), alcohol (e.g., methanol, ethanol), aromatic hydrocarbon (e.g., benzene, toluene) or chlorinated hydrocarbon (e.g., dichloromethane, chloroform) is used alone or as a mixture depending on the reagent used. The reaction is carried out at room temperature or under cooling for several tens of minutes.

When the allyl alcohol thus prepared contains a phenylselenyl moiety, it is subjected to oxidative elimination to give a dienyl alcohol.

The phenylselenyl allyl alcohol is oxidized with ozone, sodium periodate, peroxide (e.g., hydrogen peroxide, peracetic acid, m-chloroperbenzoice acid) or the like to give the selenoxide which is then refluxed in chlorinated hydrocarbon (e.g., carbon tetrachloride, chloroform, dichloromethane), if necessary, in the presence of an amine such as diisopropylamine to give the dienyl alcohol.

The alcohol prepared in this process is a mixture of the epimers.

In this process the compounds Ia-a and Ic-a, the hydroxy protected compounds of the present invention, are prepared.

PROCESS C

In this process, the hydroxy-protecting groups of the compounds Ia—a and Ic-a are removed to give the compound Ib-a and Id-a, respectively.

The reaction can be achieved using a reagent such as acetic acid, hydrochloric acid, p-toluenesulfonic acid, hydrogen fluoride and pyridine, tetrabutylammonium fluoride or the like in a solvent such as alcohol (e.g., methanol, ethanol), ether (e.g., diethyl ether, tetrahydrofuran), acetonitrile or water at room temperature or under heating within a period of several tens of minutes to several hours. In this reaction, the methyl ester of carboxylic acid is sometimes hydrolyzed; in such a case, the resulting carboxylic acid may be esterified, for example, with diazomethane, if necessary.

In this process the compound Ib-a and Id-a, the hydroxy-deprotected compounds of the present invention, are prepared.

PROCESS D

In this process the compound Ia-a is catalytically hydrogenated to give the compound Ie-a.

The hydrogenation is performed at atmospheric pressure or higher pressure in the presence of metal catalyst itself (e.g., palladium, platinum, nickel) or metal catalyst absorbed on a carrier (e.g., active carbon, alumina, barium sulfate, calcium carbonate, strontium carbonate), or nickel boride or rhodium chlorotris(triphenylphosphine).

A solvent such as alcohol (e.g., methanol, ethanol), ether (e.g., diethyl ether, tetrahydrofuran, dioxane) or ester (e.g., ethyl acetate) is used alone or as a mixture. The reaction is carried out at room temperature for a period of several hours to several tens of hours.

PROCESS E

In this process the hydroxy-protecting group of the compound Ie-a is removed to give the compound If-a.

The reaction can be carried out in the same manner as in Process C.

In this process, the compound If-a, the hydroxy-deprotected compound of the present invention, is prepared.

PROCESS F

In this process, the esters of the carboxylic acids Ib-a, Id-a and If-a are hydrolyzed to give the free carboxylic acids Ib-b, Id-b and If-b, respectively.

The hydrolysis may be carried out in the conventional manner.

In this process, the free carboxylic acids Ib-b, Id-b and If-b, compounds of the present invention, are prepared.

PROCESS G

In this process, the free carboxylic acid Ib-b is esterified to give the compound Ib-a', aralkyl ester of the carboxylic acid.

The esterification is carried out by the following conventional methods, (1) the reaction of a carboxylic acid with an alcohol, (2) the reaction of an acid chloride with an alcohol, (3) the reaction of a carboxylate salt with a halide, (4) the reaction of a carboxylic acid with a diazo compound or the like.

The aralkyl moiety constituting a part of the alcohol, halide or diazo-compound which is used for ester formation includes, for example, benzyl, substituted benzyl (e.g., 2,4,6-trimethylbenzyl, 4-bromobenzyl, 4-methoxybenzyl), diphenylmethyl, triphenylmethyl, bis(2-nitrophenyl)methyl, 9-anthrylmethyl or the like.

The definitions of $R_1$, $R_2$, $R_3$ and A are the same as mentioned above unless special limitation is given.

The wavy line indicates $\alpha$ or $\beta$ configuration or their mixture.

The starting compound (II) and (III) can be prepared by the methods shown in the following figures.

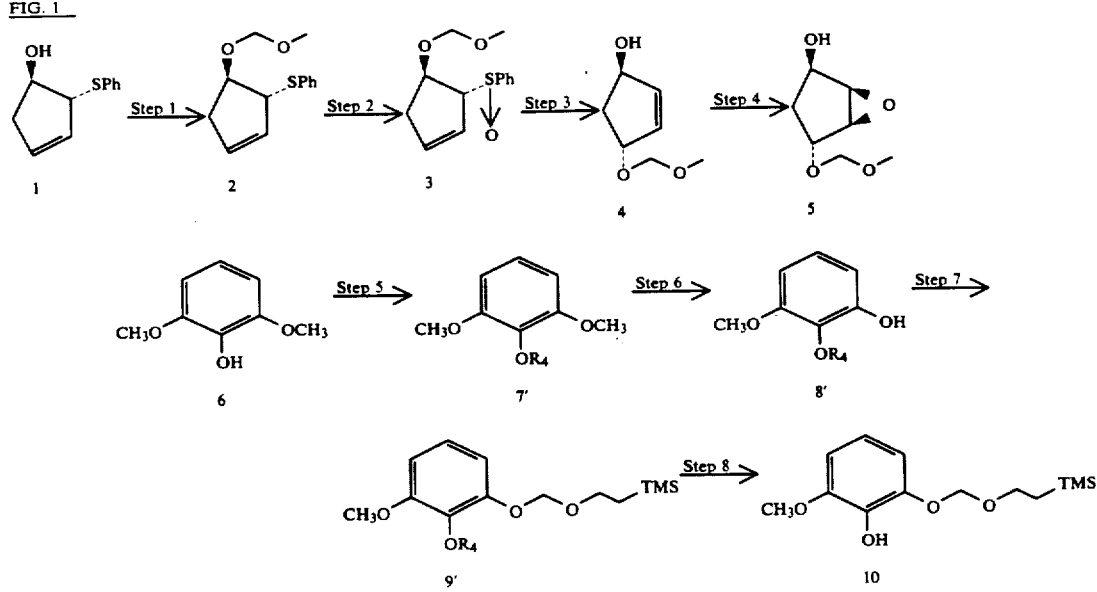

FIG. 1

FIG. 2

-continued
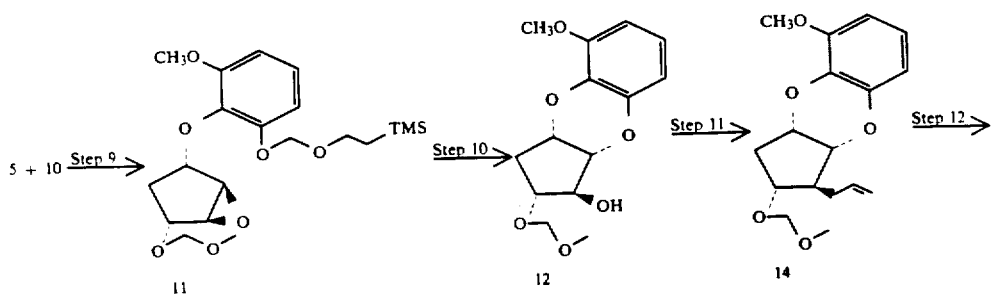
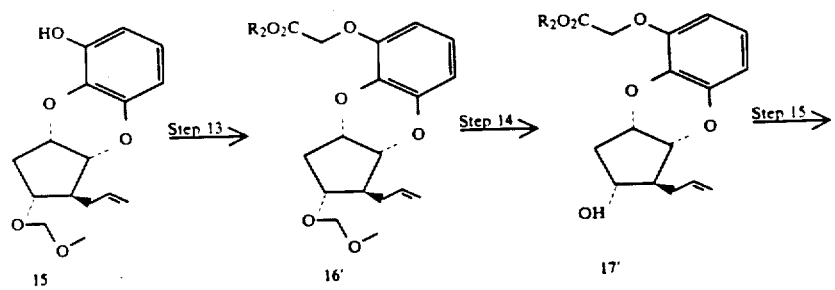
FIG. 3
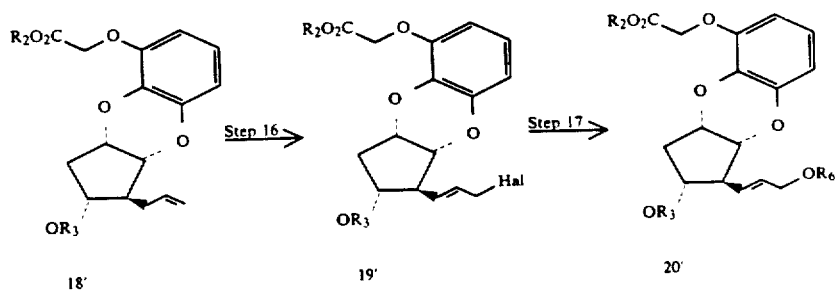
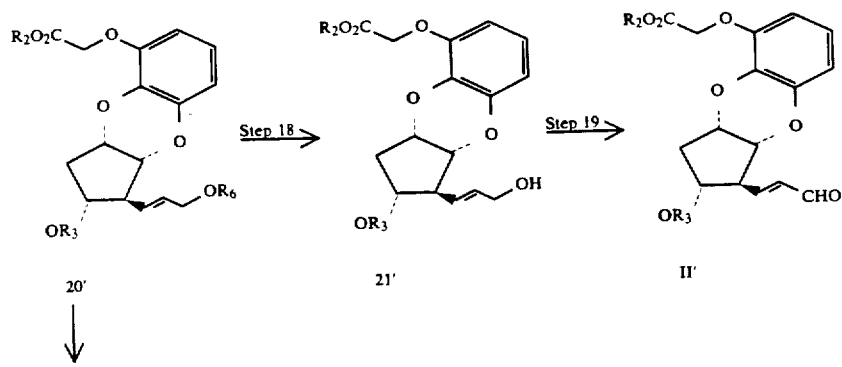

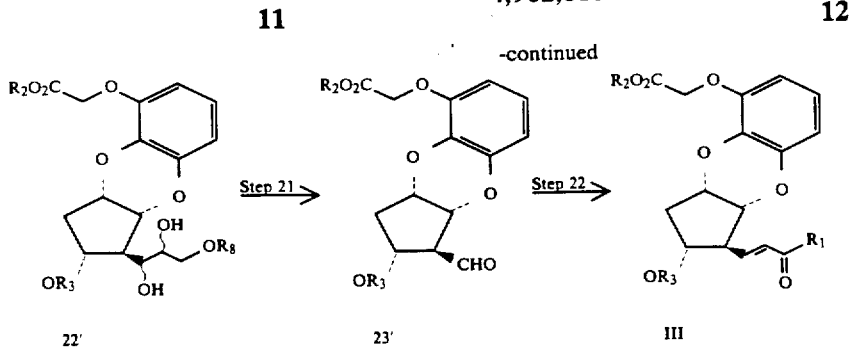

REACTION STEPS

Step 1

In this step, the hydroxy of the compound 1 is alkylated for protection with an alkyl halide in the presence of a base to give the ether 2.

The reaction is carried out using an alkyl halide such as methoxymethyl chloride, methoxymethyl bromide or the like in a solvent such as ether (e.g., dimethyl ether, tetrahydrofuran), chlorinated hydrocarbon (e.g., dichloromethane, chloroform), dimethylsulfoxide or dimethylformamide under cooling or at room temperature for a period of several hours to several tens of hours. As a base, sodium amide, potassium carbonate, triethylamine, diisopropylethylamine, sodium hydroxide, barium oxide, silver oxide, sodium hydride or the like is exemplified.

Step 2

In this step, the sulfide 2 is oxidized to the sulfoxide 3.

The reaction is carried out using an oxidizing agent such as hydrogen peroxide, tert-butyl hydroperoxide, performic acid, peracetic acid, perbenzoic acid, m-chloroperbenzoic acid, p-nitroperbenzoic acid or the like in a solvent such as alcohol (e.g., methanol, ethanol), ether (e.g., diethyl ether, tetrahydrofuran) or chlorinated hydrocarbon (e.g., dichloromethane, chloroform) under cooling for a period of several tens of minutes to several hours.

Step 3

In this step, the sulfoxide 3 is rearranged to the sulfenate ester which is further converted to the alcohol 4 by ester exchange.

In order to facilitate the rearrangement of the sulfoxide 3 into the sulfenate ester, a reagent such as phosphine (e.g., triphenylphosphine) or phosphite (e.g., trimethylphosphite, triethylphosphite) is used.

The reaction is carried out in a mixed solvent such as aromatic hydrocarbon (e.g., benzene, toluene) and alcohol (e.g., methanol, ethanol) under heating for several tens of hours.

Step 4

In this step, the double bond of the compound 4 is oxidized to give the compound 5.

The reaction is carried out using an oxidizing agent such as peroxide (e.g., hydrogen peroxide, tert-butyl hydroperoxide, performic acid, peracetic acid, perbenzoic acid, m-chloroperbenzoic acid, p-nitroperbenzoic acid) in a solvent such as alcohol (e.g., methanol, ethanol), ether (e.g., diethyl ether, tetrahydrofuran) or chlorinated hydrocarbon (e.g., dichloromethane, chloroform) under cooling for a period of several tens of minutes to several hours.

Step 5

In this step, the hydroxy group of the compound 6 is protected.

As a compound which is used for protection, methanesulfonyl chloride, p-toluenesulfonyl chloride or the like is exemplified. The reaction is carried out in the presence of a base such as sodium hydroxide, triethylamine, pyridine or the like in a solvent such as ether (e.g., diethyl ether, tetrahydrofuran), chlorinated hydrocarbon (e.g., dichloromethane, chloroform), dimethylsulfoxide or dimethylformamide under cooling for a period of several tens of minutes to several hours.

Step 6

In this step, the methyl group of the compound 7' is removed to give the compound 8'.

The reaction is carried out using a boron trichloride or boron tribromide in a solvent such as chlorinated hydrocarbon (e.g., dichloromethane, chloroform) under cooling for a period of several tens of minutes to several hours.

There are some other methods, for example, oxidation of the methyl ether with chromium trioxide-acetic acid to the formate ester, which is followed by hydrolysis to give the phenol; or a method by of heating with hydroiodic acid or hydrobromic acid.

Step 7

In this step, the hydroxy group of the compound 8' is alkylated for protection with an alkyl halide in the presence of a base to give the ether 9'.

As an alkyl halide, (2-trimethylsilyl)ethoxymethyl chloride or (2-trimethylsilyl)ethoxymethyl bromide is used. The reaction is carried out in the same manner as in Step 1.

Step 8

In this step, the sulfonate ester 9' is converted into the phenol 10.

The reaction is carried out by, first, preparing a metal adduct using a nucleophilic reagent such as alkyllithium (e.g., methyllithium, ethyllithium, isopropyllithium, n-butyllithium), alkylmagnesium halide (Grignard reagent) (e.g., methylmagnesium bromide, ethylmagensium bromide, isopropylmagensium bromide, n-butylmagnesium bromide) or the like in an ether solvent such as diethyl ether, or tertrahydrofuran under cooling for a period of several tens of minutes to several hours and then decomposing the resulting metal adduct with water.

Step 9

In this step, the compound 5 and the compound 10 are condensed.

The reaction is carried out by reacting the compound 5 with the acidic compound 10 in the presence of triphenylphosphine and diethyl azodicarboxylate under cooling or at room temperature for a period of several tens of minutes to several days. A dry solvent such as aromatic hydrocarbon (e.g., benzene), chlorinated hydrocarbon (e.g., dichloromethane, chloroform) or ether (e.g., diethyl ether, tetrahydrofuran) is used.

Step 10

In this step, the hydroxy-protecting group of the compound 11 is removed to give the compound 12.

The reaction is carried out in a conventional manner for removing the hydroxy-protecting group, for example, using a reagent such as hydrogen fluoride-pyridine or tetrabutylammonium fluoride in a solvent such as ether (e.g., diethyl ether, tetrahydrofuran) at room temperature or under heating for a period of several hours to several days. When the hydroxy-protecting group of the compound 11 is removed, cyclization to the compound 12 occurs spontaneously.

Step 11

In this step, the hydroxy group of the compound 12 is allylated to give the compound 14.

This step can be carried out by the method as described in Tetrahedron, 41, 4079–4094 (1985). First, the compound 12 is converted into the precursor of a carbon radical such as thioacyl derivative, and then, the precursor is irradiated in the presence of allyl stannane such as allyl-tri-n-butyl stannane.

The acylation is carried out using phenyl chlorothionocarbonate, diimidazole thionocarbonate or carbon disulfide-methyl iodide in a solvent such as ether (e.g., diethyl ether, tetrahydrofuran) in the presence of a base such as methyl lithium, n-butyl lithium or the like.

The photo-reaction is carried out by irradiation in an argon atmosphere using a 450 W high pressure mercury lamp equipped with a pyrex filter for a period of several hours to several tens of hours. A solvent such as aromatic hydrocarbon (e.g., benzene, toluene) or ester (e.g., ethyl acetate) is used alone or as a mixture.

Step 12

In this step, the methyl ether 14 is demethylated to give the compound 15.

As a reagent, a metal salt (e.g., lithium, sodium) of thiol such as lithium methylthiolate, sodium ethylthiolate, lithium n-propylthiolate, lithium n-butylthiolate or the like is exemplified. The reaction is carried out in an aprotic polar solvent such as dimethylformamide, hexamethylphosphoric triamide, dimethylsulfoxide for a period of several tens of minutes to several hours.

Step 13

In this step, the compound 15 is alkylated with an alkyl halide in the presence of a base to give the compound 16'.

An alkyl halide such as methyl bromoacetate or methyl iodoacetate is used for the reaction.

This step can be carried out in the same manner as in Step 1.

Step 14

In this step, the hydroxy-protecting group of the compound 16' is removed to give the compound 17'.

As a reagent, a combination of a Lewis acid and sulfide, or thiol is used. As the Lewis acid, boron trifluoride diethyl etherate, aluminium chloride, aluminium bromide or the like is exemplified. As the sulfide, dimethylsulfide, diethylsulfide diphenylsulfide or the like, and as the thiol, methanethiol, ethanethiol, benzenethiol or the like are respectively exemplified. The reaction is carried out at −10° C. or at room temperature in a chlorinated hydrocarbon such as dichloromethane or chloroform.

This step can also be achieved by hydrolysis with an acidic catalyst (e.g., hydrochloric acid, acetic acid).

Step 15

In this step, the hydroxy group of the compound 17' is protected from the subsequent reactions.

The reaction is achieved using a tert-butyldimethylsilyl chloride, tert-butyldiphenylsilyl chloride, trimethylsilyl chloride or the like in the presence of a base such as triethylamine, pyridine, 4-dimethylaminopyridine, imidazole or the like at room temperature or under warming within a period of several hours to several days. As a solvent aromatic hydrocarbon (e.g., benzene, toluene), chlorinated hydrocarbon (e.g., chloroform, dichloromethane) or dimethylformamide is exemplified. Alternatively, the reacton may be achieved by treatment with dihydropyran at room temperature in the presence of an acidic cataylst such as p-toluenesulfonic acid, pyridinium p-toluenesulfonate, Amberlyst 15 (Rohm & Hass Co.) or the like. A solvent such as ether (e.g., diethyl ether, tetrahydrofuran), hydrocarbon (e.g., hexane), aromatic hydrocarbon (e.g., benzene, toluene) or chlorinated hydrocarbon (e.g., chloroform, dichloromehane) is used.

Step 16

In this step, the compound 18' is subjected to halogenation involving double bond migration to give the compound 19'.

This step can be carried out in the same manner as described in Tetrahedron Letters, 44, 3909–3912, (1977).

The compound 18' is allowed to react with phenylselenenyl chloride or phenylselenenyl bromide in carbon tetrachloride under cooling for several tens of minutes to give an anti-Markovnikov adduct. The adducts is oxidized with hydrogen peroxide containing pyridine under cooling or at room temperature for several hours to give the compound 19'.

Step 17

In this step, the compound 19' is subjected to substitution using a carboxylate salt to give the compound 20'.

As a carboxylate salt, a sodium or cesium salt of acetic acid, trifluoroacetic acid, chloroacetic acid, methoxyacetic acid, phenoxyacetic acid or benzoic acid is exemplified.

The reaction is carried out in a non-polar solvent such as aromatic hydrocarbon (e.g., benzene, toluene), or a polar solvent such as dimethylformamide, hexamethylphosphoramide, dimethylsulfoxide or the like under heating for a period of several hours to several tens of hours. When a nonpolar solvent is used in order to promote the reaction, a crown ether like phase-transfer catalyst such as 18-crown-6 may be added.

Step 18

In this step, the ester 20' is hydrolyzed to give the alcohol 21'.

The reaction is carried out in a conventional manner of ester hydrolysis. A catalyst such as acid (e.g., hydrochloric acid, sulfuric acid) or base (e.g., sodium hydroxide, potassium hydroxide, barium hydroxide) is used. As a solvent, alcohol (e.g., methanol, ethanol), chlorinated hydrocarbon (e.g., dichloromethane, chloroform) or water is used as a mixture, if necessary.

If the methyl ester is hydrolyzed to the free carboxylic acid during this hydrolysis step, it may be esterified with an esterifing reagent such as diazomethane.

Step 19

In this step, the alcohol 21' is oxidized into the aldehyde II'.

The reaction is achieved by using an oxidizing agent such as chromate (e.g., Collins' reagent, pyridinium chlorochromate, pyridinium dichlorochromate) or dimethylsulfoxide and oxalyl chloride, sulfuryl chloride, or pyridinium sulfur trioxide combined with a base such as triethylamine, 4-dimethylaminopyridine or the like. The reaction is achieved in a solvent such as aromatic hydrocarbon (e.g., benzene), chlorinated hydrocarbon (e.g., chloroform, dichloromethane), ether (e.g., diethyl ether) or acetone under cooling to warming for a period of several tens of minutes to several hours.

Step 20

In this step, the compound 20' is oxidized into the glycol 22'.

As an oxidizing agent, an aqueous solution of alkaline potassium permanganate, osmium tetroxide or the like is exemplified. When an aqueous solution of alkaline potassium permanganate is used, the reaction is preferably carried out by removing the resulting hydroxy anion by magnesium sulfate or the like. When osmium tetroxide is used, an amine such as pyridine is added in order to promote the formation of the cyclic osmium ester, which may be treated with sodium sulfite, sodium hydrogensulfite or the like. As a solvent used in these reactions alcohol (e.g., methanol, ethanol, propanol, tert-butyl alcohol), ether (e.g., diethyl ether, tetrahydrofuran, dioxane), aromatic hydrocarbon (e.g., benzene), chlorinated hydrocarbon (e.g., dichloromethane, chloroform, carbon tetrachloride), acetone or ethyl acetate is used depending on the property of the oxidizing agent. The reaction is carried out at room temperature for a period of several hours to several days.

Step 21

In this step, the glycol 22' is oxidatively cleaved into the aldehyde 23'.

As an oxidizing agent, periodate (e.g., sodium periodate, potassium periodate) or lead tetraacetate is used. When a periodate is used as an oxidizing agent, an aqueous solvent, i.e. an organic solvent such as alcohol (e.g., methanol, ethanol), ether (e.g., diethyl ether, tetrahydrofuran, dioxane) mixed with water, is used. When lead tetraacetate is used as an oxidizing agent, aromatic hydrocarbon (e.g., benzene) is used as a solvent, and if necessary, an acid such as trichloroacetic acid may be added as a catalyst. The reaction is carried out at room temperature for a period of several tens of minutes to several hours.

Step 22

In this step, the aldehyde 23' is allowed to react with an phosphonate to give the unsaturated ketone III.

The reaction is carried out by a general procedure of Horner-Wadsworth-Emmons reaction using a base such as sodium hydride, sodium amide or the like in a solvent such as 1,2-dimethoxyethane, tetrahydrofuran or the like.

As a phosphonate used in this reaction, one having a desired side chain, namely, dimethyl 2-oxoheptylphosphonate, dimethyl 2-oxo-3-methylheptylphosphonate, dimethyl 2-oxo-3,3-dimethylheptylphosphonate, dimethyl 2-oxo-4-methyloctylphosphonate, dimethyl 2-oxo-4,8-dimethyl-7-nonenylphosphonate, dimethyl 2-oxo-3-methyl-5-heptynylphosphonate, dimethyl 2-oxo-5-octynylphosphonate, dimethyl 2-oxo-2-cyclopentylethylphosphonate, dimethyl 2-oxo-2-cyclohexylethylphosphonate, dimethyl 2-oxo-4-phenoxypentylphosphonate, dimethyl (S)-(-)-2-oxo-4-methyl-7-octenylphosphonate, dimethyl 2-oxo-4-(phenoxymethyl)pentylphosphonate, dimethyl 2-oxo-4-(phenylselenylmethyl)octylphosphonate or the like is exemplified.

For example, dimethyl 2-oxo-4-phenoxypentylphosphonate is prepared as follows.

First, 1-O-protected 1,3-butandiol is converted to the corresponding 3-O-phenol ester by reaction using phenol, triphenylphosphine and diethyl azodicarboxylate as described in Step 9. Then, the 1-hydroxy-protecting group is removed and the resulting alcohol is oxidized to the carboxylic acid with a chromate-type oxidizing agent (e.g., Jones reagent) which is followed by esterification. The ester, thus obtained, is treated with anion derived from dimethyl methylphosphonate and base, to give the desired product.

Dimethyl 2-oxo-4-methyl-7-octenylphosphonate is prepared as follows.

Citronellol is oxidized with a chromate-type oxidizing agent (e.g., Jones reagent) to the carboxylic acid which is then esterified to give an ester of citronellic acid. The double bond is converted into an epoxide by a peroxide as described in Step 4. And then, the epoxide is oxidatively cleaved with a periodate to give an aldehyde, which is converted into the olefinic compound by conventional Wittig reaction using trimethylphosphonium bromide and a base. The compound thus prepared is condensed with dimethyl methylphosphonate in the presence of base to give the desired compound. When an optically active compound such as (S)-(-)-citronellol is used as a starting material and allowed to react in the same manner, (S)-dimethyl 2-oxo-4-methyl-7-octenylphosphonate is prepared.

Dimethyl 2-oxo-4-(phenoxymethyl)pentylphosphonate can be prepared by condensing methyl 4-phenoxy-3-methylbutanoate with dimethyl methylphosphonate in the presence of base in the same manner as mentioned above.

Dimethyl 2-oxo-4-(phenylselenylmethyl)octylphosphonate is prepared as follows.

2(5H)-furanone is alkylated with lithium di-n-butylcuprate (prepared from copper (I) bromide-dimethyl sulfide complex and n-butyl lithium) in the presence of trimethylsilyl chloride. Then the lactone ring is opened with sodium phenylselenoate, which is prepared by reducing diphenyldiselenide with sodium borohydride in dry dimethylformamide, to give the carboxylic acid, which is then esterified. The resulting ester is condensed with dimethyl methylphosphonate in the presence of a base to prepare the desired compound.

In the reaction scheme, $R_1$, $R_2$, $R_3$, and A are the same as defined above unless limitation is given.

$R_4$ refers to substituted sulfonyl (e.g., methanesulfonyl, p-toluenesulfonyl).

$R_5$ refers to thioacyl (e.g., (methylthio)thiocarbonyl, 1-imidazoylthiocarbonyl, phenoxythiocarbonyl).

$R_6$ refers to alkanoyl (e.g., acetyl, trifluoroacetyl, chloroacetyl, methoxyacetyl, phenoxyacetyl or aroyl (e.g., benzoyl).

Hal refers to halogen (e.g., chlorine, bromine, iodine).

TMS represents trimethylsilyl.

SEM represents (2-trimethylsilyl)ethoxymethyl and Ph represents phenyl.

The following examples are included to explain the present invention in more detail, but these are not intended to limit the scope of the invention.

All the compounds described in the following examples in each step are represented by one enantiomer. The relative or absolute configuration of the racemate is

PREPARATION OF INTERMEDIATE

(1) Preparation of (3R*,4R*)-4-methoxymethoxy-3-phenylthio-1-cyclopentene 2

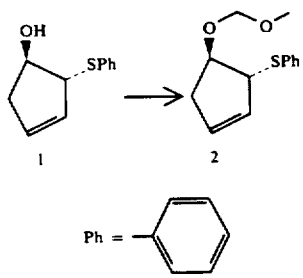

To a solution of 85.0 g (0.443 mol) of alcohol 1 and 109 ml (0.626 mol) of diisopropylamine in 500 ml of dry dichloromethane is added a solution of 38.0 ml (0.500 mol) of methoxymethyl chloride in 100 ml of dichloromethane dropwise under ice-cooling. Then, the temperature is allowed to rise to room temperature and the stirring is continued for 23 hours. The reaction mixture is poured into 150 ml of 1N hydrochloric acid and extracted with dichloromethane twice. The extract is washed once with water, a saturated aqueous solution of sodium hydrogen carbonate, and a saturated aqueous solution of sodium chloride, respectively, dried over anhydrous magnesium sulfate and evaporated under reduced pressure. The residue is distilled under reduced pressure to give 98.6 g of the desired compound 2 as an oil in 94.3% yield.

bp. 98°~100° C. (0.03 mmHg).

$^1$H-NMR: δ (CDCl$_3$) 2.33 (1 H, m), 2.67 (1 H, m), 3.23 (3 H, s), 4.11~4.23 (1 H, m), 4.23~4.40 (1 H, m), 4.50 (1 H, d, J=9 Hz), 4.52 (1 H, d, J=9 Hz), 5.64~5.93 (2 H, m), 7.13~7.51 (5 H, m) ppm.

IR: νmax (CHCl$_3$) 3064, 3004, 2952, 2828, 1585, 1482, 1439, 1148, 1098, 1037, 915 cm$^{-1}$.

MS: m/z M+ 236.

(2) Preparation of (3R*,4R*)-4-methoxymethoxy-3-phenylsulfenyl-1-cyclopentene 3

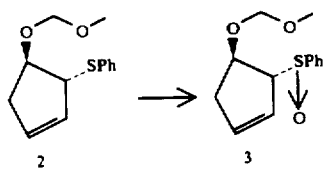

In a nitrogen atmosphere, a solution of 108 g (0.502 mol) of 85% m-chloroperbenzoic acid in 1.4 l of dry dichloromethane is added dropwise to a solution of 98.6 g (0.418 mol) of sulfide 2 (prepared in (1)) in 1 l of dry dichloromethane at −60° C. to −70° C. over 1.5 hours. Then, the mixture is stirred at the same temperature for additional 20 minutes. In order to destroy excess peracid, 9.2 ml (0.125 mol) of dimethylsulfide is added to the mixture. The reaction mixture is filtered and the filtrate is evaporated under reduced pressure. The residue dissolved in 1.2 l of ether is washed with 1N sodium hydroxide, water, and a saturated aqueous solution of ammonium chloride, dried over anhydrous magnesium sulfate, and evaporated under reduced pressure to give 106 g of the crude sulfoxide 3 as an oil, which is employed in the next step without further purification.

(3) Preparation of (1R*,4R*)-4-methoxymethoxy-2-cyclopenten-1-ol 4

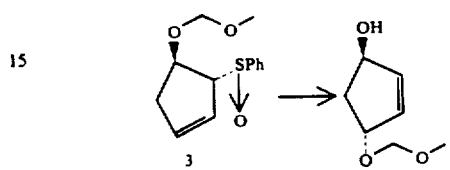

In a nitrogen atmosphere, 106 g of the crude sulfoxide 3 (prepared in (2)) and 165 g (0.623 mol) of triphenylphosphine are dissolved in a mixture of 1 l of toluene and 300 ml of methanol, and the mixture is stirred at 60° C. for 40 hours. The reaction mixture is evaporated under reduced pressure and to the residue dissolved in 300 ml of ether is added 300 ml of n-pentane dropwise under ice cooling. The resulting crystals are collected by filtration and the filtrate is concentrated under reduced pressure. The residue is purified by column chromatography on silica gel (600 g silica gel, ethyl acetate:-benzene=0:1 to 1:0). The eluate is distilled under reduced pressure to give 48.3 g of the desired alcohol 4 as an oil in 80.2% yield over two steps.

bp. 80°~81° C. (1 mmHg).

$^1$H-NMR: δ (CDCl$_3$) 1.70~2.35 (3 H, m), 3.35 (3 H, s), 4.65 (2 H, s), 4.77~5.20 (2 H, m), 5.94~6.13 (2 H, m) ppm.

IR: ν max(CHCl$_3$) 3608, 3004, 2944, 2892, 1360, 1148, 1097, 1033, 914 cm$^{-1}$.

MS: m/z (M−1)+ 143.

(4) Preparation of (1R*,2R*,3S*,4R*)-2,3-epoxy-4-methoxymethoxy-1-cyclopentanol 5

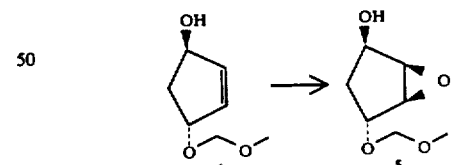

To a solution of 27.0 g (0.188 mol) of the olefin 4 (prepared in (3)) in 400 ml of dry dichloromethane is added 48.5 g (0.225 mol) of 80% m-chloroperbenzoic acid at room temperature and the mixture is stirred overnight. To the reaction mixture cooled on dry ice-acetone bath is added 4.1 ml (0.056 mol) of dimethylsulfide and the mixture is stirred at the same temperature for additional 10 minutes. The reaction mixture is filtered and the filtrate is further filtered through 150 g of alumina (Grade II). The alumina is washed with 1.8 l of ether. The filtrate and the washing are combined and evaporated under reduced pressure. The residue is purified by column chromatography on silica gel (450 g of silica gel, ethyl acetate : n-hexane=1:2 to 1:1) to give 25.9 g of the desired epoxide 5 as an oil in 86.3% yield.

¹H-NMR: δ (CDCl₃) 1.45 (1 H, ddd, J=6 Hz, 8 Hz, 15 Hz), 2.07 (1 H, dd, J=8 Hz, 15 Hz), 2.27 (1 H, d, j=8 Hz, —OH), 3.37 (3 H, s), 3.49~3.60 (2 H, m), 4.25 (1 H, d, J=6 Hz), 4.37~4.60 (1 H, m), 4.64 (2 H, s) ppm.

IR: ν max(CHCl₃) 3588, 3004, 2952, 2896, 1397, 1150, 1102, 1042, 915, 869 cm⁻¹.

MS: m/z (M−1)⁺ 159.

(5) Preparation of 2-methanesulfonyloxy-1,3-dimethoxybenzene

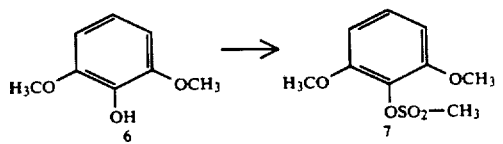

In a nitrogen atmosphere, a solution of 75 g (0.486 mol) of 2,6-dimethoxyphenol 6 (Aldrich) in 130 ml of dimethylformamide (hereinafter abbreviated to DMF) is added dropwise to a suspension of 23.3 g (0.583 mol) of 60% sodium hydride in 400 ml of DMF under ice-cooling over 30 minutes. Then, the mixture is stirred for additional 25 minutes. To this is added dropwise a solution of 54.3 ml (0.680 mol) of methanesulfonyl chloride in 130 ml of DMF and the resulting mixture is stirred at the same temperature for 30 minutes. The reaction mixture is poured into 1.8 l of ice-cold water and extracted with benzene twice. The extract is washed with 1N sodium hydroxide, water, and a saturated aqueous solution of ammonium chloride, dried over anhydrous magnesium sulfate, and evaporated under reduced pressure to give 112 g of the desired sulfonate ester 7 as crude crystals which is employed in the next step without further purification.

(6) Preparation of 2-methanesulfonyloxy-3-methoxyphenol 8

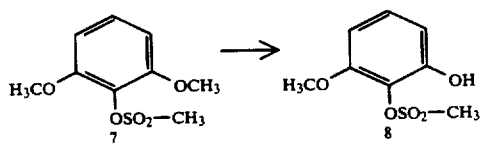

In a nitrogen atmosphere, a solution of 125 g (0.500 mol) of boron tribromide in 500 ml of dichloromethane is added dropwise to a solution of 112 g of the crude crystalline ester 7 (prepared in (5)) in 1 l of dichloromethane at −60° C. to −70° C. Then, the mixture is warmed up to −40° C. and stirred at the same temperature for 40 minutes. The reaction mixture is poured into 1.5 l of water and extracted with dichloromethane twice. The extract is washed with dilute aqueous sodium hydrogencarbonate, dried over anhydrous magnesium sulfate, and evaporated under reduced pressure to give 94 g of the desired phenol 8 as crude crystals, which is recrystallized from benzene to give 80.0 g of the compound 8 in 75.5% yield over two steps.

Mp. 105°~106° C. (benzene).

¹H-NMR: δ (CDCl₃) 3.26 (3 H, s), 3.64 (3 H, s), 5.95 (1 H, br, s), 6.53 (1 H, dd, J=2 Hz, 8 Hz), 6.64 (1 H, dd, J=2 Hz, 8 Hz), 7.09 (1 H, t, J=8 Hz) ppm.

IR: ν max(CHCl₃) 3568, 3472, 1609, 1497, 1483, 1371, 1344, 1146, 1092, 973, 869 cm⁻¹.

MS: m/z M⁺ 218.

(7) Preparation of 2-methanesulfonyloxy-1-methoxy-3-[[(2-trimethylsilyl)ethoxy]methoxy]benzene 9

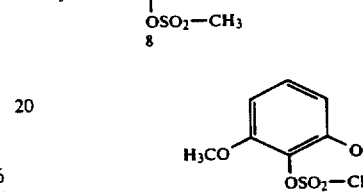

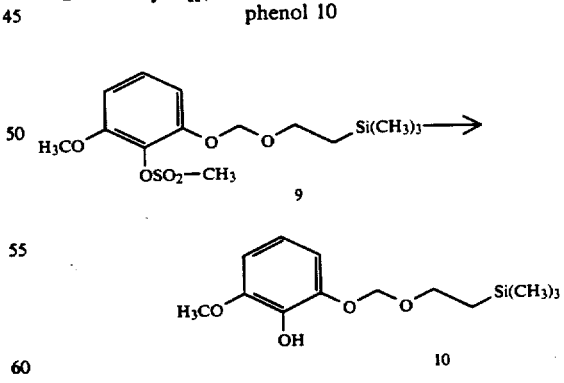

In a nitrogen atmosphere, a solution of 25.0 ml (0.141 mol) of (2-trimethylsilyl)ethoxylmethyl chloride (SEM-Cl) in 125 ml of dichloromethane is added dropwise to a solution of 25.0 g (0.115 mol) of the phenol 8 (prepared in (6)) and 29.3 ml (0.173 mol) of diisopropylethylamine in 400 ml of dichloromethane under ice cooling. After additional stirring for 3 hours, 45 ml (1.11 mol) of dry methanol is added. The resulting mixture is stirred overnight at room temperature. The reaction mixture is washed with 1N hydrochloric acid, water, a saturated aqueous solution of sodium hydrogencarbonate, and a saturated aqueous solution of sodium chloride, dried over anhydrous magnesium sulfate, and evaporated under reduced pressure to give 44 g of the crude desired ether 9 as an oil, which is employed in the next step without further purification.

(8) Preparation of 2-methoxy-6-[[(2-trimethylsilyl)ethoxy]methoxy]phenol 10

In a nitrogen atmosphere, 130 ml (0.207 mol) of n-butyl-lithium (1.6N in n-hexane) is added dropwise to a solution of 44 g of the crude methanesulfonate 9 (prepared in (7)) in 750 ml of dry ether at −60° C. to −70° C. After additional stirring at the same temperature for 20 minutes, the reaction mixture is poured into 1.5 l of saturated aqueous solution of ammonium chloride. The resulting mixture is extracted with ether twice and the extract is washed with water and a saturated aqueous solution of sodium chloride, dried over anhydrous magnesium sulfate, and evaporated under reduced pressure. The residue is purified by column chromatography on silica gel (700 g of silica gel, ethyl acetate:n-hexane=1:9) to give 29.7 g of the desired phenol 10 as an oil in 95.7% yield over two steps.

¹H-NMR: δ (CDCl₃) 0.0 (9 H, s), 0.94 (2 H, dd, J=8 Hz, 9 Hz), 3.78 (2 H, dd, J=8 Hz, 9 Hz), 3.74 (3 H, s), 5.21 (2 H, s), 5.83 (1 H, br, s), 6.50~6.80 (3 H, m) ppm.

IR: ν max (CHCl₃) 3544, 2960, 1619, 1505, 1481, 1075, 1003, 860, 837 cm⁻¹.

MS: m/z M⁺ 270.

(9) Preparation of 1-[[(1R*,2R*,3R*,4S*)-2,3-epoxy-4-methoxymethoxy-1-cyclopentyl]oxy]-2-methoxy-6-[(2-trimethylsilylethoxy)methoxy]benzene 11

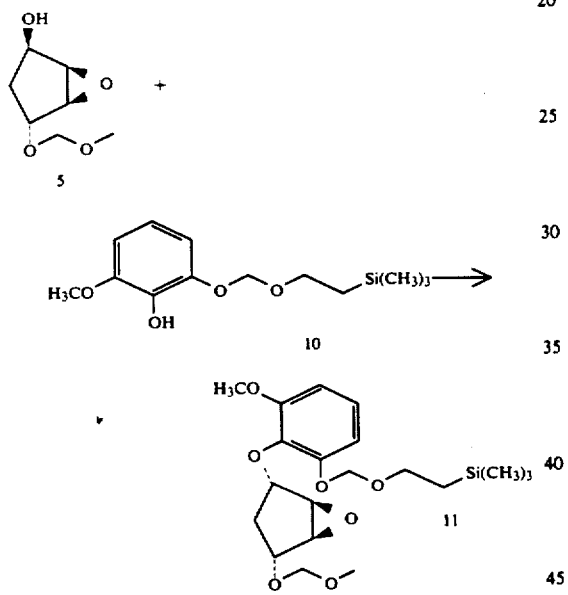

In a nitrogen atmosphere, 25.2 ml (0.160 mol) of diethyl azodicarboxylate is added dropwise to a solution of 39.3 g (0.146 mol) of the phenol 10 (prepared in (8)), 25.8 g (0.161 mol) of the alcohol 5 (prepared in (4)), and 49.6 g (0.189 mol) of triphenylphosphine in 750 ml of dry tetrahydrofuran (hereinafter abbreviated to THF) under ice cooling, and the mixture is stirred at room temperature for three days. Then, additional 11.4 g (0.044 mol) of triphenylphosphine and 6.9 ml (0.044 mol) of diethyl azodicarboxylate is added and the resulting mixture is stirred for additional 2 days. The reaction mixture is evaporated under reduced pressure and the residue dissolved in 500 ml of ether is cooled on dry ice-acetone bath. The precipitated crystals are separated by filtration and the filtrate is concentrated under reduced pressure. The residue is purified by column chromatography on silica gel (1.5 kg of silica gel, ethyl acetate:benzene=1:50 to 1:9) to give 51.8 g of the desired epoxy ether 11 as an oil in 86.2% yield from the compound 10.

¹H-NMR: δ (CDCl₃) 0.0 (9 H, s), 0.92 (2 H, dd, J=8 Hz, 9 Hz), 1.76~2.33 (2 H, m), 3.41 (3 H, s), 3.80 (3 H, s), 3.65~3.90 (4 H, m), 4.26 (1 H, d, J=6 Hz), 4.50 (1 H, d, J=6 Hz), 4.73 (2 H, s), 5.20 (2 H, s), 6.57 (1 H, dd, J=8 Hz, 8 Hz), 6.76 (1 H, dd, J=2 Hz, 8 Hz), 6.96 (1 H, t, J=8 Hz) ppm.

IR: ν max (CHCl₃) 3004, 2960, 2896, 2840, 1598, 1490, 1476, 1249, 1108, 1073, 1012, 859, 847, 837 cm⁻¹.

MS: m/z M⁺ 412.

(10) Preparation of (1R*,2S*,3aR*,9aS*)-5-methoxy-2-methoxymethoxy-2,3,3a,9a-tetrahydro-1H-cyclopenta[b][1,4]benzodioxin-1-ol 12

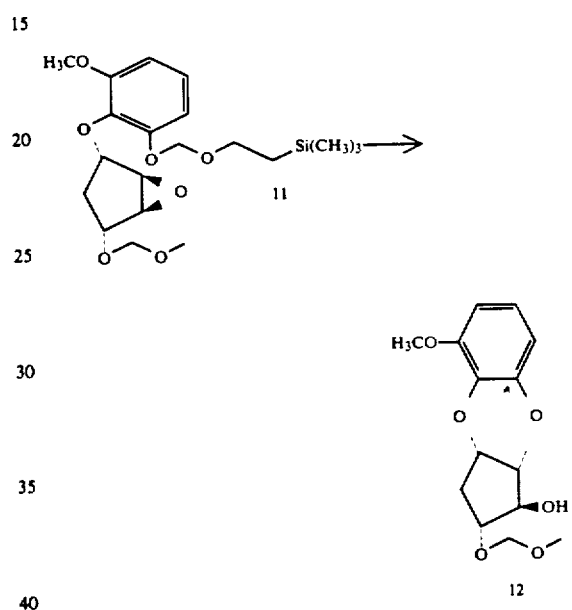

In a nitrogen atmosphere, 251 ml (0.250 mol) of tetra-n-butylammonium fluoride (1M in THF) is added to a solution of 51.8 g (0.125 mol) of the epoxide 11 (prepared in (9)) in 190 ml of dry THF and the mixture is stirred at 55° C. for 3 days. The reaction mixture is poured into water and extracted with ethyl acetate twice. The extract is washed with water and a saturated aqueous solution of ammonium chloride, dried over anhydrous magnesium sulfate, and evaporated under reduced pressure. The residue is purified by column chromatography on silica gel (700 g silica gel, ethyl acetate:n-hexane=1:2 to 1:1) and then crystallized from ether-n-hexane to give 31.7 g of the desired benzodioxine 12 in 89.6% yield.

Mp. 69.0° C. to 70.0° C. (ether-n-hexane)

¹H-NMR: δ (CDCl₃) 2.13 (1 H, ddd, J=2.5 Hz, 6 Hz, 15 Hz), 2.62 (1 H, ddd, J=6 Hz, 10 Hz, 15 Hz), 3.37 (3 H, s), 3.83 (3 H, s), 3.50~3.95 (2 H, m), 4.05~4.41 (3 H, m), 4.67 (2 H, s), 6.47 (1 H, dd, J=2 Hz, 8 Hz), 6.57 (1 H, dd, J=2 Hz, 8 Hz), 6.80 (1 H, t, J=8 Hz) ppm.

IR: ν max (CHCl₃) 3476, 3004, 2952, 2896, 2844, 1603, 1499, 1475, 1280, 1110, 1082 cm⁻¹.

MS: m/z M⁺ 282.

(11) Preparation of (1R*,2S*,3aR*,9aR*)-5-methoxy-2-methoxy-methoxy-1-[[(phenoxy)-thiocarbonyl]oxy]-2,3,3a,9a-tetrahydro-1H-cyclopenta[b][1,4]benzodioxine 13

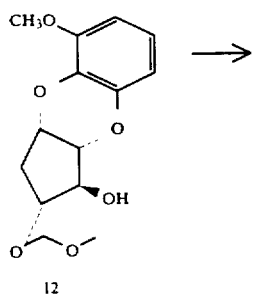

12

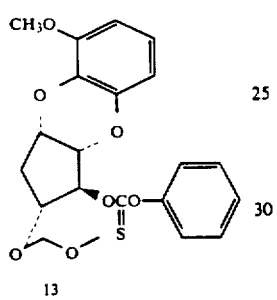

13

In a nitrogen atmosphere, 36.6 ml (58.6 mmol) of n-butyl-lithium (1.6N in n-hexane) is added dropwise to a solution of 15.0 g (53.2 mmol) of the alcohol 12 (prepared in (10)) in 150 ml of dry THF at −60° C. to −70° C. Then, the mixture is stirred for 20 minutes and 8.82 ml (63.9 mmol) of phenyl chlorothionocarbonate is added. The resulting mixture is further stirred at the same temperature for 20 minutes. The mixture is warmed to 0° C. over 30 minutes and stirred at the same temperature for additional 1 hour. The reaction is quenched by the addition of a saturated aqueous solution of ammonium chloride and then extracted with ethyl acetate twice. The extract is washed with a saturated aqueous solution of sodium hydrogencarbonate, and a saturated aqueous solution of sodium chloride, dried over anhydrous magnesium sulfate, and evaporated under reduced pressure. The residue is purified by column chromatography on silica gel (400 g of silica gel, ethyl acetate:n-hexane = 1:5 to 1:2) to give 20.4 g of the desired thionocarbonate 13 as crystals in 91.9% yield.

Mp. 100° C. ~ 102° C. (benzene-n-hexane).

$^1$H-NMR: δ (CDCl$_3$) 2.17 (1 H, dt, J=7 Hz, 15 Hz), 2.66 (1 H, ddd, J=6 Hz, 8 Hz, 15 Hz), 3.33 (3 H, s), 3.85 (3 H, s), 4.14~4.75 (5 H, m), 5.82 (1 H, t, J=4 Hz), 6.43~6.88 (3 H, m), 7.03~7.52 (5 H, m) ppm.

IR: ν max(CHCl$_3$) 3008, 2956, 1603, 1500, 1492, 1477, 1290, 1189, 1111, 1039 cm$^{-1}$.

MS: m/z M$^+$ 418.

(12) Preparation of (1R*,2S*,3aR*,9aS*)-5-methoxy-2-methoxymethoxy-1-(2-propenyl)-2,3,3a,9a-tetrahydro-1H-cyclopenta[b][1,4]benzodioxine 14

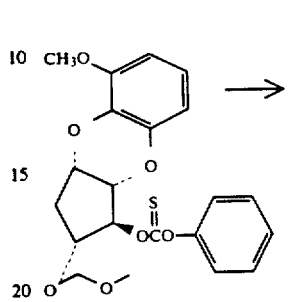

13

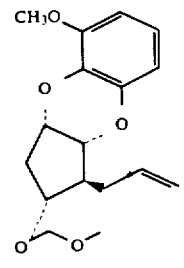

14

A solution of 20.44 g (48.9 mmol) of the thionocarbonate 13 (prepared in (11)) and 48.9 g (148 mmol) of allyl-tri-n-butyl-stannane in 400 ml of dry benzene is thoroughly degassed with argon for 1 hour. In an argon atmosphere, the resulting solution is irradiated with a 450 W high pressure mercury lamp equipped with a pyrex filter for 10 hours. The reaction mixture is concentrated under reduced pressure and the residue is purified by column chromatography on silica gel ( 1 600 g of silica gel, ethyl acetate:n-hexane = 1:5 to 1:3, 2 700 g of silica gel, ethyl acetate:dichloromethane = 3:97) to give 11.2 g of the desired olefin 14 as crystals in 74.8% yield.

Mp. 48.5° C. ~49.5° C. (n-pentane).

$^1$H-NMR: δ (CDCl$_3$) 193~2.57 (5 H, m), 3.33 (3 H, s), 3.85 (3 H, s), 3.72~4.23 (2 H, m), 4.26~4.45 (1 H, m), 4.59 (2 H, m), 4.98~5.30 (2 H, m), 5.60~6.13 (1 H, m), 6.40~6.65 (2 H, m), 6.78 (1 H, t, J=8 Hz) ppm.

IR: ν max(CHCl$_3$) 3008, 2948, 2844, 1642, 1603, 1499, 1477, 1282, 1254, 1107, 1037, 918 cm$^{-1}$.

MS: m/s M$^+$ 306.

(13) Preparation of (1R*,2S*,3aR*,9aS*)-2-methoxymethoxy-1-(2-propenyl)-2,3,3a,9a-tetrahydro-1H-cyclopenta[b][1,4-]benzodioxin-5-ol 15

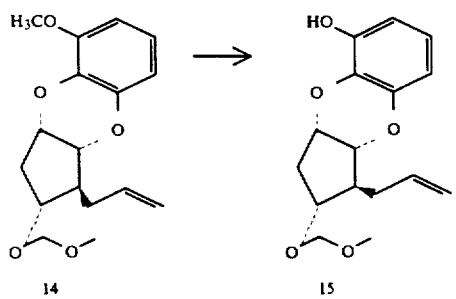

In a nitrogen atmosphere, 30 ml (47 mmol) of n-butyllithium (1.58 M in n-hexane) is added dropwise to a solution of 5.25 ml (49 mmol) of n-butyl mercaptane in 30 ml of hexamethylphosphoric triamide (hereinafter abbreviated to HMPA) under ice cooling and then the temperature is allowed to rise to room temperature and n-hexane is evaporated under reduced pressure. To the resulting mixture is added a solution of 6.00 g (19.6 mmol) of the methyl ether 14 (prepared in (12)) in 20 ml of HMPA and the mixture is stirred at 100° C. for 30 minutes. A saturated aqueous solution of ammonium chloride is added to the reaction mixture, which is then extracted with ethyl acetate three times. The extract is washed with water and a saturated aqueous solution of sodium chloride, dried over anhydrous magnesium sulfate, and evaporated under reduced pressure. The residue is purified by column chromatography on silica gel (150 g silica gel, ethyl acetate:n-hexane=1:3) to give 5.64 g of the desired phenol 15 as an oil in 98.5% yield.

1H-NMR: δ (CDCl3) 1.90~2.56 (5 H, m), 3.33 (3 H, s), 3.72~4.36 (3 H, m), 4.57 (2 H, m), 4.96~5.26 (2 H, m), 5.43 (1 H, br, s), 5.62~6.11 (1 H, m), 6.38~6.57 (2 H, m), 6.72 (1 H, t, J=8 Hz) ppm.

IR: ν max(CHCl3) 3552, 3008, 2948, 1642, 1610, 1499, 1487, 1272, 1090, 1040, 917 cm$^{-1}$.

MS: m/z M+ 292.

(14) Preparation of methyl [(1R*,2S*,3aR*,9aS*)-2-methoxymethoxy-1-(2-propenyl)-2,3,3a,9a-tetrahydro-1H-cyclopenta[b][1,4-]benzodioxin-5-yl]oxyacetate 16

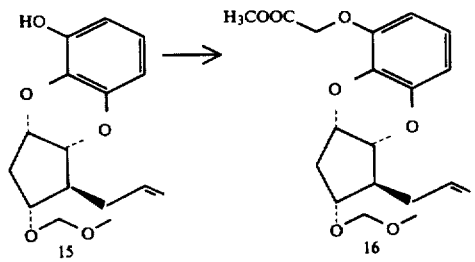

In a nitrogen atmosphere, a solution of 5.64 g (19.3 mmol) of the phenol 15 (prepared in (13)) in 40 ml of dimethoxyethane (hereinafter abbreviated to DME) is added dropwise to a suspension of 850 mg (21.2 mmol) of 60% sodium hydride in 50 ml of dry DME under ice cooling. The temperature is allowed to rise to room temperature and stirred for 20 minutes, and then 3.65 ml (38.6 mmol) of methyl bromoacetate is added. The resulting mixture is stirred overnight. A saturated aqueous solution of ammonium chloride is added to the reaction mixture, which is then extracted with ethyl acetate three times. The extract is washed with water and a saturated aqueous solution of sodium chloride, and evaporated under reduced pressure. The residue is purified by column chromatography on silica gel (150 g of silica gel, ethyl acetate:n-hexane=1:2) to give 6.32 g of the desired methyl ester 16 as crystals in 89.9% yield.

Mp. 65.0° C.~66.0° C. (ether-n-hexane).

1H-NMR: δ (CDCl3) 1.94~2.56 (5 H, m), 3.33 (3 H, s), 3.76 (3 H, s), 3.75~4.46 (3 H, m), 4.58 (2 H, s), 4.67 (2 H, s), 4.98~5.27 (2 H, m), 5.59~6.14 (1 H, m), 6.35~6.85 (3 H, m) ppm.

IR: ν max (CHCl3) 3012, 2960, 1764, 1742, 1643, 1600, 1499, 1476, 1441, 1287, 1125, 1037, 917 cm$^{-1}$.

MS: m/z M+ 364.

(15) Preparation of methyl [(1R*,2S*,3aR*,9aS*)-2-hydroxy-1-(2-propenyl)-2,3,3a,9a-tetrahydro-1H-cyclopenta[b][1,4]benzodioxin-5-yl]oxyacetate 17

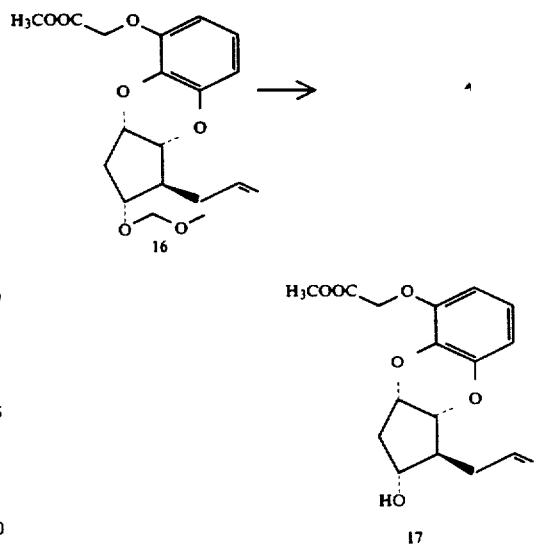

In a nitrogen atmosphere, 10.9 ml (86.8 mmol) of trifluoroboron-diethyl etherate is added dropwise to a solution of 6.32 g (17.4 mmol) of the methoxymethyl ether 16 (prepared in (14)) and 6.38 ml (86.8 mmol) of dimethylsulfide in 95 ml of dichloromethane under ice cooling and the mixture is stirred at the same temperature for 2 hours. To the reaction mixture is added 600 ml of saturated aqueous solution of sodium hydrogen-carbonate and the mixture is vigorously stirred for 30 minutes. The reaction mixture is extracted with dichloromethane three times. The extract is washed with a saturated aqueous solution of sodium hydrogencarbonate, and a saturated aqueous solution of sodium chloride, dried over anhydrous magnesium salfate, and evaporated under reduced pressure. The residue is purified by column chromatography on silica gel (150 g of silica gel, ethyl acetate:n-hexane=1:2 to 1:1) to give 5.20 g of the desired alcohol 17 as crystals in 93.6% yield.

Mp. 101° C.~102° C. (ether).

¹H-NMR: δ (CDCl₃) 1.91~2.60 (6 H, m), 3.76 (3 H, s), 3.84~4.20 (2 H, m), 4.22~4.43 (1 H, m), 4.67 (2 H, s), 4.99~5.28 (2 H, m), 5.65~6.10 (1 H, m), 6.36~6.86 (3 H, m) ppm.

IR: ν max (CHCl₃) 3592, 2012, 2960, 1763, 1744, 1642, 1600, 1498, 1476, 1287, 1271, 1125 cm⁻¹.

MS: m/z M⁺ 320.

(16) Preparation of methyl [(1R*,2R*,3aS*,9aR*)-2-tert-butyldiphenylsilyloxy-1-(2-propenyl)-2,3,3a,9a-tetrahydro-1H-cyclopenta[b][1,4]benzodioxin-5-yl]oxyacetate 18

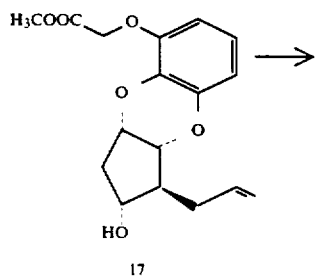

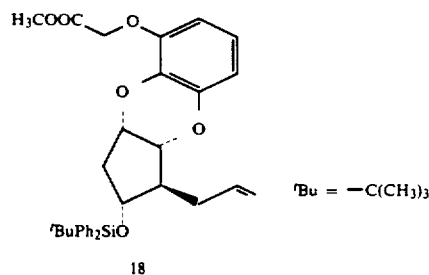

'Bu = —C(CH₃)₃

To a solution of the alcohol 17 (prepared in (15)) in 60 ml of N,N-dimethylformamide (hereinafter abbreviated to DMF) is added 3.97 g (32.5 mmol) of N,N-dimethylaminopyridine and 6.34 ml (24.4 mmol) of tert-butyldiphenylsilyl chloride and the mixture is stirred at room temperature for 3 days. The reaction mixture is poured into water and extracted with ethyl acetate three times. The extract is washed with 1N hydrochloric acid, water, a saturated aqueous solution of sodium hydrogencarbonate, and a saturated aqueous solution of sodium chloride, dried over anhydrous magnesium sulfate, and evaporated under reduced pressure. The residue is purified by column chromatography on silica gel (Merck; Lobar column, size C, two columns, ethyl acetate:n-hexane=1:5) to give 8.82 g of the desired silyl ether 18 as an oil in 97.1% yield.

¹H-NMR: δ (CDCl₃) 1.05 (9 H, s), 1.84~2.53 (5 H, m), 3.77 (3 H, s), 3.83~4.03 (2 H, m), 4.13~4.35 (1 H, m), 4.68 (2 H, s), 4.75~5.01 (2 H, m), 5.41~5.88 (1 H, m), 6.40~6.87 (3 H, m), 7.30~7.50 (6 H, m), 7.58~7.78 (4 H, m) ppm.

IR: ν max(CHCl₃) 3076 2960, 2936, 2864, 1764, 1742, 1642, 1600, 1498, 1476, 1429, 1287, 1115, 920, 821, 612 cm⁻¹.

MS: m/z M⁺ 558.

(17) Preparation of methyl [(1R*,2R*,3aS*,9aR*)-2-tert-butyl-diphenylsilyloxy-1-[(E)-3-chloro-1-propenyl]-2,3,3a,9a-tetrahydro-1H-cyclopeta[b][1,4]benzodioxin-5-yl]oxyacetate 19

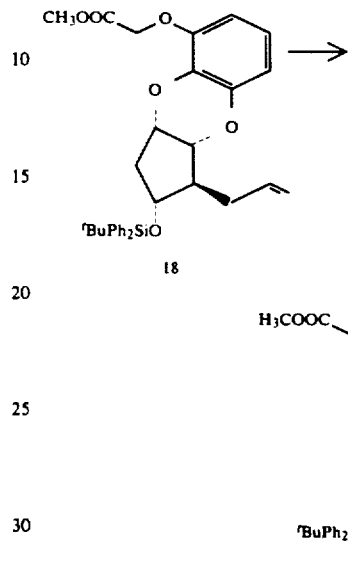

In a nitrogen atmosphere, a solution of 3.32 g (17.4 mmol) of phenylselenenyl chloride in 50 ml of carbon tetrachloride is added dropwise to a solution of 8.82 g (15.8 mmol) of the olefin 18 (prepared in (16)) in 70 ml of carbon tetrachloride under ice cooling over 45 minutes. The mixture is stirred for further 15 minutes and 1.66 ml (20.5 mmol) of pyridine and 20 ml of 30% aqueous solution of hydrogen peroxide are added thereto at the same temperature. The resulting mixture is stirred for 20 minutes, then brought to room temperature, and stirred for additional 1 hour and 30 minutes. The reaction mixture is poured into water and extracted with dichloromethane twice. The extract is washed with 1N hydrochloric acid, water, a dilute aqueous solution of sodium hydrogencarbonate, and a saturated aqueous solution of sodium chloride, dried over anhydrous magnesium sulfate, and evaporated under reduced pressure. The residue is purified by column chromatography on silica gel (Merck; Lobar column, size C, two columns: ethyl acetate:n-hexane=1:4) to give 7.20 g of the desired allyl chloride 19 as crystals in 77.0% yield.

Mp.: 127°~130° C. (ether).

¹H-NMR: δ (CDCl₃) 1.03 (9 H, s), 2.04~2.23 (2 H, m), 2.91 (1 H, dt, J=7 Hz, 9 Hz), 3.77 (3 H, s), 3.87~4.28 (5 H, m), 4.70 (2 H, s), 5.46 (1 H, dd, J=7 Hz, 16 Hz), 5.68 (1 H, dd, J=6 Hz, 16 Hz), 6.39~6.86 (3 H, m), 7.30~7.50 (6 H, m), 7.56~7.75 (4 H, m) ppm.

IR: ν max (CHCl₃) 3012, 2960, 2936, 2864, 1764, 1744, 1601, 1498, 1476, 1429, 1289, 1114, 966, 822, 613 cm⁻¹.

MS: m/z M⁺ 594.

(18) Preparation of methyl [(1R*,2R*,3aS*,9aR*)-1-[(E)-3-acetoxy-1-propenyl]-2-tert-butyldiphenylsilyloxy-2,3,3a,9a-tetrahydro-1H-cyclopenta[b][1,4]benzodioxin-5-yl]oxyacetate 20

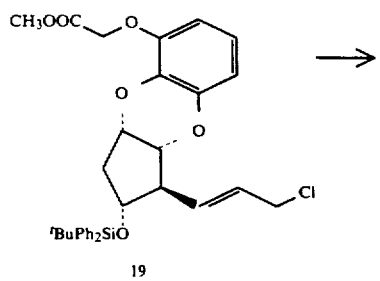

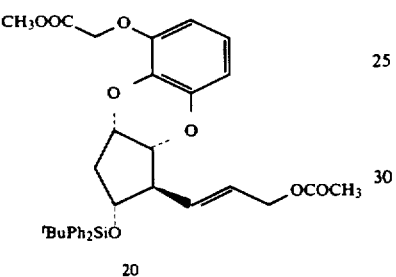

In a nitrogen atmosphere, 4.95 g (25.8 mmol) of cesium acetate and 2.27 g (8.60 mmol) of 18-crown-6 are added to a solution of 5.10 g (8.60 mmol) of the allyl chloride 19 (prepared in (17)) in 150 ml of toluene and the mixture is heated under reflux for 24 hours. After cooling, a saturated aqueous solution of ammonium chloride is added to the reaction mixture and the mixture is extracted with ethyl acetate twice. The extract is washed with water and a saturated aqueous solution of sodium chloride, dried over anhydrous magnesium sulfate, and evaporated under reduced pressure to give the desired acetate 20 as crude crystals. The crude material is recrystallized from ethyl acetate-n-hexane twice to give 4.26 g of the (E)-acetate 20 in 80.4% yield.

Mp.: 132° ~ 134° C. (ethyl acetate-n-hexane).

¹H-NMR: δ (CDCl₃) 1.03 (9 H, s), 2.03 (3 H, s), 2.00~2.25 (2 H, m), 2.77~3.06 (1 H, m), 3.76 (3 H, s), 3.78~4.28 (3 H, m), 4.44 (2 H, d, J=5 Hz), 4.72 (2 H, s), 5.33~5.82 (2 H, m), 6.40~6.87 (3 H, m), 7.30~7.48 (6 H, m), 7.59~7.80 (4 H, m) ppm.

IR: ν max(CHCl₃) 3012, 2960, 2936, 2864, 1763, 1738, 1600, 1498, 1478, 1240, 1114, 968, 822, 695, 612 cm⁻¹.

MS: m/z M⁺ 616.

(19) Preparation of methyl [(1R*,2R*,3aS*,9aR*)-2-tert-butyldiphenylsilyloxy-1-[(E)-3-hydroxy-1-propenyl]-2,3,3a,9a-tetrahydro-1H-cyclopenta[b][1,4]benzodioxin-5-yl]oxyacetate 21

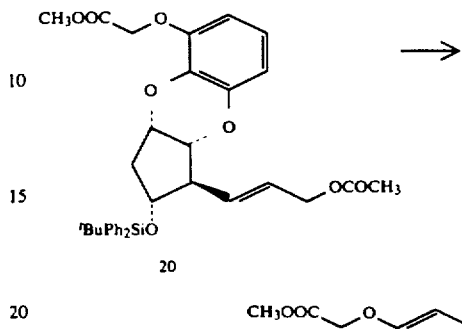

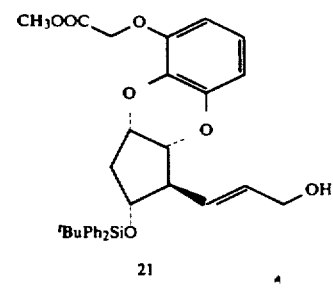

To a solution of 6.12 g (9.92 mmol) of the acetate 20 (prepared in (18)) in 40 ml of dichloromethane and 40 ml of methanol is added 1.65 g (11.9 mmol) of potassium carbonate and the mixture is stirred at room temperature for 2 hours. To the reaction mixture is added 26 ml (26 mmol) of 1N hydrochloric acid and the organic solvent is evaporated under reduced pressure. After addition of a saturated aqueous solution of sodium chloride, the mixture is extracted with ethyl acetate 3 times. The extract is washed with water and a saturated aqueous solution of sodium chloride, dried over anhydrous magnesium sulfate, and evaporated under reduced pressure. The residue containing the carboxylic acid, which is generated by saponification of the methyl ester, is treated with diazomethane as follows to esterify. Namely, the above-mentioned residue is dissolved in 100 ml of methanol and an ethereal solution of diazomethane in ether is added thereto under ice cooling until the yellow color persists. The reaction mixture is evaporated under reduced pressure and the residue is purified by column chromatography on silica gel (Merck; Lobar column, size C, two columns, ethyl acetate:n-hexane=1:1) to give the desired allyl alcohol 21, which is crystallized from ether-n-hexane to give 5.35 g of the crystals in 93.7% yield.

Mp. 102.5° ~ 103.5° C. (ether-n-hexane).

¹H-NMR: δ (CDCl₃) 1.03 (9 H, s), 1.51 (1 H, s —OH), 2.08~2.27 (2 H, m), 2.75~3.06 (1 H, m), 3.77 (3 H, s), 3.87~4.30 (5 H, m), 4.71 (2 H, s), 5.38 (1 H, dd, J=8 Hz, 16 Hz), 5.66 (1 H, td, J=5 Hz, 16 Hz), 6.39~6.85 (3 H, m), 7.29~7.48 (6 H, m), 7.58~7.80 (4 H, m) ppm.

IR: ν max(CHCl₃) 3616, 3012, 2960, 2936, 2864, 1764, 1743, 1600, 1498, 1476, 1429, 1288, 1113, 971, 822, 696, 612 cm⁻¹.

MS: m/z M⁺ 574.

(20) Preparation of methyl [(1R*,2R*,3aS*,9aR*)-2-tert-butyldiphenylsilyloxy-1-[(E)-3-oxo-1-propenyl]-2,3,3a,9a-tetrahydro1H-cyclopenta[b][1,4]benzodioxin-5-yl]oxyacetate II

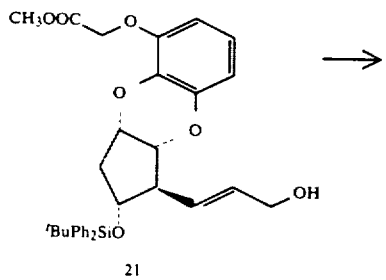

21

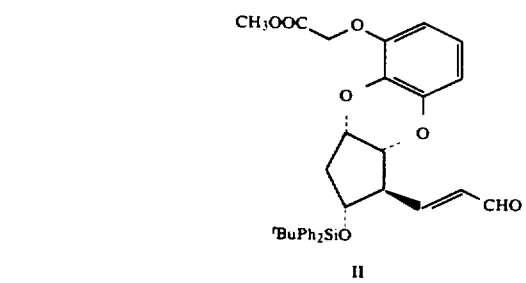

II

To a solution of 3.35 g (5.83 mmol) of the allyl alcohol 21 (prepared in (19)) in 70 ml of dichloromethane is added 2.51 g (11.6 mmol) of pyridinium chlorochromate (PCC) and the mixture is stirred at room temperature for 3 hours. To the reaction mixture is added 160 ml of ether and the mixture is stirred for 2 minutes and then filtered through 34 g of Florisil (Floridin Company) which is washed with 500 ml of ether. The filtrate and washing are combined and the mixture is evaporated under reduced pressure. The residue is crystallized from ether-n-hexane to give 3.19 g of the desired aldehyde II as crystals in 95.6% yield.

Mp.: 103.5°~104.8° C. (ether-n-hexane).

$^1$H-NMR: δ (CDCl$_3$) 1.03 (9 H, s), 2.20~2.37 (2 H, m), 2.98~3.36 (1 H, m), 3.78 (3 H, s), 4.00~4.30 (3 H, m), 4.71 (2 H, s), 6.15 (1 H, dd, J=7 Hz, 16 Hz), 6.33 (1 H, dd, J=7 Hz, 16 Hz), 6.40~6.85 (3 H, m), 7.28~7.47 (6 H, m), 7.53~7.72 (4 H, m), 9.23 (1 H, d, J=7 Hz) ppm.

IR: ν max (CHCl$_3$) 3012, 2960, 2936, 2864, 1764, 1743, 1692, 1601, 1499, 1476, 1429, 1290, 1113, 974, 823, 697, 612 cm$^{-1}$.

MS: m/z M+ 572.

EXAMPLE 1

Preparation of methyl [(1R*,2R*,3aS*,9aR*)-2-tert-butyldiphenylsilyloxy-1-[(3S*,1E)-3-hydroxy-1-octenyl]-2,3,3a,9a-tetrahydro-1H-cyclopenta[b][1,4]benzodioxin-5-yl]oxyacetate Iaa-a and methyl [(1R*,2R*,3aS*,9aR*)-2-tert-butyldiphenylsilyloxy-1-[(3R*,1E)-3-hydroxy-1-octenyl]-2,3,3a,9a-tetrahydro-1H-cyclopenta[b][1,4]benzodioxin-5-yl]oxyacetate Ica-a

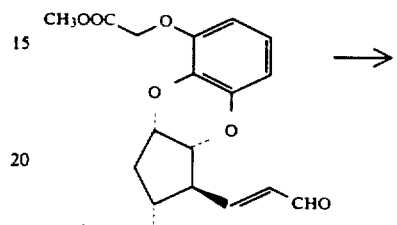

II

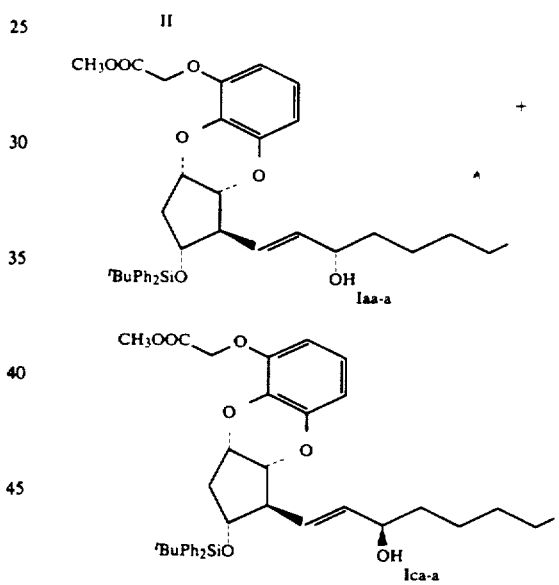

In a nitrogen atmosphere, 1.83 ml (2.01 mmol) of n-pentyl-magnesium bromide (1.1N, in THF) is added dropwise to 962 mg (1.68 mmol) of the aldehyde II (prepared in (20)) in 20 ml of dry THF at −78° C. After stirring for 15 minutes at the same temperature, the reaction is quenched by the addition of a saturated aqueous solution of ammonium chloride. The reaction mixture is extracted with ethyl acetate three times and the extract is washed with water and a saturated aqueous solution of sodium chloride, dried over anhydrous magnesium sulfate, and evaporated under reduced pressure. The residue is purified by the column chromatography on silica gel (Merck, Lobar column, size B, two columns, ethyl acetate:toluene=1:10 to 1:6) to give 517 mg of the less polar isomer Iaa-a as an oil and 252 mg of the more polar isomer Ica-a as crystals in 47.7% and 20.7% yield, respectively.

Compound Iaa-a $^1$H-NMR: δ (CDCl$_3$) 0.87 (3 H, t, J=6 Hz), 1.03 (9 H, s), 1.00~1.90 (9 H, m), 2.05~2.25 (2 H, m), 2.76~3.03 (1 H, m), 3.79 (3 H, s), 3.80~4.30 (4 H, m), 4.72 (2 H, s), 5.22~5.70 (2 H, m), 6.40~6.87 (3 H, m), 7.30~7.50 (6 H, m), 7.60~7.80 (4 H, m) ppm.

IR: ν max (CHCl$_3$) 3608, 3008, 2960, 2936, 2864, 1763, 1743, 1600, 1498, 1475, 1429, 1292, 1114, 970, 821, 697, 612 cm$^{-1}$.

MS: m/z M$^+$ 644.

Compound Ica-a

Mp. 83°~84° C. (ether-n-pentane).

$^1$H-NMR: δ (CDCl$_3$) 0.87 (3 H, t, J=6 Hz), 1.03 (9 H, s), 1.00~1.90 (9 H, m), 2.05~2.25 (2 H, m), 2.76~3.03 (1 H, m), 3.79 (3 H, s), 3.80~4.30 (4 H, m), 4.72 (2 H, s), 5.22~5.70 (2 H, m), 6.40~6.87 (3 H, m), 7.30~7.50 (6 H, m), 7.60~7.80 (4 H, m) ppm.

IR: ν max (CHCl$_3$) 3608, 3008, 2960, 2936, 2864, 1764, 1742, 1600, 1498, 1476, 1429, 1289, 1113, 969, 821, 696, 612 cm$^{-1}$.

MS: m/z M$^+$ 644.

EXAMPLES 2 to 4

According to the same method as described in Example 1, the aldehyde II is converted into the allyl alcohol Ia-a and Ic-a, and the results are shown in Table 1. In Example 4, the reaction is carried out using the racemic Grignard reagent to give the four isomers of allyl alcohol Iad-a, Iae-a, Icd-a, and Ice-a.

TABLE 1

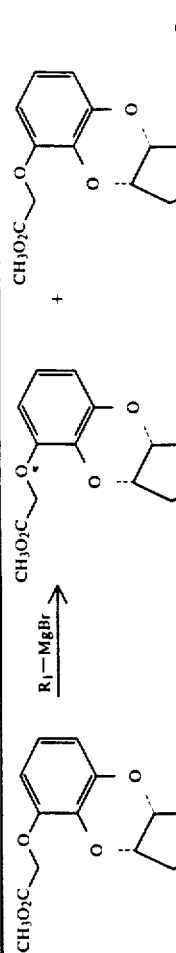

| Ex. No. | R₁ | Compd. No. | Yd. (%) | MS (m/z) | IR νmax (cm⁻¹) | ¹H—NMR δ (ppm) |
|---|---|---|---|---|---|---|
| 2 | H | Iab-a | 49.9 | 656 (M⁺) | (CHCl₃) 3608, 3008, 2936, 2860, 1763, 1743, 1600, 1498, 1476, 1429, 1290, 1114, 970, 907, 821, 612. | (CDCl₃) 1.03 (9H,s), 0.70~2.00 (12H,m), 2.00~2.30 (2H,m), 2.76~3.06 (1H,m), 3.77 (3H,s), 3.55~3.80 (1H,s), 3.90~4.31 (3H,m), 4.71 (2H,s), 5.17~5.66 (2H,m), 6.40~6.86 (3H,m), 7.32~7.55 (6H,m), 7.55~7.90 (4H,m) |
| | | Icb-a | 12.1 | 656 (M⁺) | (CHCl₃) 3608, 3008, 2936, 2860, 1764, 1742, 1600, 1498, 1476, 1429, 1290, 1114, 1113, 972, 906, 821, 612. | (CDCl₃) 1.03 (9H,s), 0.78~2.00 (12H,m), 2.00~2.30 (2H,m), 2.79~3.06 (1H,m), 3.78 (3H,s), 3.61~3.82 (1H,s), 3.90~4.35 (3H,m), 4.73 (2H,s), 5.23~5.71 (2H,m), 6.41~6.87 (3H,m), 7.25~7.51 (6H,m), 7.60~7.90 (4H,m) |
| 3 | | Iac-a | 37.3 | 654 (M⁺) | (CHCl₃) 3608, 3008, 2940, 2936, 1476, 1764, 1743, 1600, 1499, 1476, 1429, 1289, 1288, 1114, 970, 906, 821, 612. | (CDCl₃) 1.03 (9H,s), 1.10 (3H,t,J=7Hz), 1.37~2.41 (9H,m), 2.75~3.15 (1H,m), 3.80 (3H,s), 3.85~4.32 (4H,m), 4.73 (2H,s), 5.24~5.70 (2H,m), 6.40~6.87 (3H,m), 7.35~7.50 (6H,m), 7.60~7.80 (4H,m) |
| | | Icc-a | 23.5 | 654 (M⁺) | (CHCl₃) 3608, 3012, 2936, 2864, 1476, 1764, 1743, 1600, 1499, 1476, 1429, 1290, 1114, 970, 906, 821, 612. | (CDCl₃) 1.03 (9H,s), 1.13 (3H,t,J=7Hz), 1.40~2.42 (9H,m), 2.78~3.05 (1H,m), 3.80 (3H,s), 3.87~4.35 (4H,m), 4.73 (2H,s), 5.27~5.83 (2H,m), 6.41~6.90 (3H,m), 7.33~7.50 (6H,m), 7.60~7.85 (4H,m) |
| 4 | | Iad-a (Isomer 1) | 23.9 | 672 (M⁺) | (CHCl₃) 3608, 3008, 2936, 2864, 1764, 1743, 1600, 1499, 1476, 1429, 1290, 1114, 970, 906, 821, 612. | (CDCl₃) 0.76~0.92 (6H,m), 1.03 (9H,s), 0.92~1.80 (10H,m), 2.05~2.25 (2H,m), 2.73~3.00 (1H,m), 3.77 (3H,s), 3.87~4.28 (4H,m), 4.70 (2H,s), 5.17~5.67 (2H,m), 6.39~6.86 (3H,m), 7.30~7.48 (6H,m), 7.58~7.75 (4H,m). |
| | | Iac-a (Isomer 2) | 23.5 | 672 (M⁺) | (CHCl₃) 3608, 3012, 2936, 2864, 1764, 1743, 1600, 1499, 1476, 1429, 1288, 1114, 970, 906, 821, 612. | (CDCl₃) 0.77~0.91 (6H,m), 1.03 (9H,s), 0.91~1.80 (10H,m), 1.98~2.26 (2H,m), 2.72~3.00 (1H,m), 3.77 (3H,s), 3.86~4.30 (4H,m), 4.72 (2H,s), 5.17~5.64 (2H,m), 6.39~6.86 (3H,m), 7.30~7.47 (6H,m), 7.57~7.80 (4H,m). |
| | | Icd-a (Isomer 1) | 10.0 | 672 (M⁺) | (CHCl₃) 3608, 3012, 2936, 2864, 1764, 1742, 1601, 1499, 1476, 1429, 1290, 1114, 971, 907, 821, 612. | (CDCl₃) 0.78~0.95 (6H,m), 1.03 (9H,s), 0.95~1.78 (10H,m), 2.05~2.25 (2H,m), 2.73~3.01 (1H,m), 3.77 (3H,s), 3.86~4.27 (4H,m), 4.70 (2H,s), 5.19~5.68 (2H,m), 6.39~6.86 (3H,m), 7.30~7.47 (6H,m), 7.57~7.75 (4H,m). |
| | | Icc-a (Isomer 2) | 11.0 | 672 (M⁺) | (CHCl₃) 3608, 3012, 2936, 2864, 1764, 1743, 1600, 1499, 1476, 1429, 1288, 1114, 970, 906, 821, 612. | (CDCl₃) 0.79~0.91 (6H,m), 1.03 (9H,s), 0.93~1.80 (10H,m), 2.04~2.25 (2H,m), 2.73~3.00 (1H,m), 3.77 (3H,s), 3.86~4.27 (4H,m), 4.70 (2H,s), 5.20~5.67 (2H,m), 6.39~6.87 (3H,m), 7.30~7.47 (6H,m), 7.60~7.80 (4H,m). |

(21) Preparation of methyl [(1R*,2R*,3aS*,9aR*)-1-[(1RS,2RS)-3-acetoxy-1,2-dihydroxypropyl]-2-tert-butyldiphenylsilyloxy-2,3,3a,9a-tetrahydro-1H-cyclopenta[b][1,4]benzodioxin-5-yl]oxyacetate 22

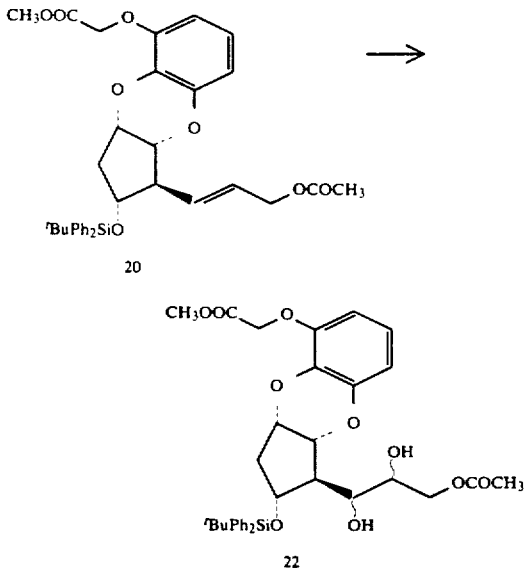

In a nitrogen atmosphere, 19.4 ml (19.4 mmol) of trimethylamine-N-oxide (1N in water) and 4.86 ml (0.97 mmol) of osmium tetraoxide (0.2N in THF) are added to a suspension of 6.00 g (9.72 mmol) of the olefin 20 (prepared in (18)) in 120 ml of acetone and the mixture is stirred for 3 days. To the reaction mixture is added 120 ml of 5% aqueous solution of sodium thiosulfate and acetone is evaporated under reduced pressure. A saturated aqueous solution of sodium chloride is added to the residue which is then extracted with ethyl acetate three times. The extract is washed with water and a saturated aqueous solution of sodium chloride, dried over anhydrous magnesium sulfate, and evaporated under reduced pressure to give 6.60 g of the crude desired diol 22 as a foamy substance, which is employed in the next step without further purification.

(22) Preparation of methyl [(1R*,2R*,3aS*,9aR*)-2-tert-butyldiphenylsilyloxy-1-formyl-2,3,3a,9a-tetrahydro-1H-cyclopenta[b][1,4]benzodioxin-5-yl]oxyacetate 23

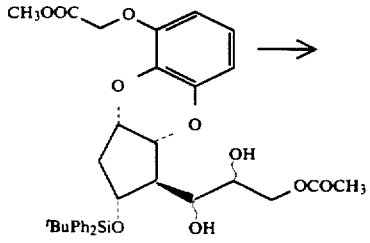

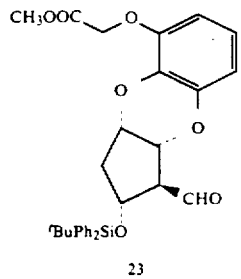

In a nitrogen atmosphere, 4.18 g (19.4 mmol) of sodium periodate is added to a solution of 6.60 g of the crude diol 22 (prepared in (21)) in 180 ml of DME and 60 ml of water at room temperature and the mixture is stirred for 2 days. To the reaction mixture is added 200 ml of 10% aqueous solution of sodium thiosulfate and the mixture is extracted with ethyl acetate three times. The extract is washed with water and a saturated aqueous solution of sodium chloride, dried over anhydrous magnesium sulfate, and evaporated under reduced pressure. The residue is purified by column chromatography on silica gel (Merck, Lobar column, size C, two columns, ethyl acetate:toluene=1:20) to give the desired aldehyde 23, which is crystallized from ether-n-hexane to give 3.38 g of the crystals in 63.6% yield over two steps.

Mp.: 110.3°~111.0° C. (ether-n-hexane).

$^1$H-NMR: δ (CDCl$_3$) 1.04 (9 H, s), 2.20 (2 H, t, J=5 Hz), 3.19~3.44 (1 H, m), 3.76 (3 H, s), 4.12~4.38 (1 H, m), 4.40~4.60 (2 H, m), 4.69 (2 H, s), 6.42~6.90 (3 H, m), 7.32~7.50 (6 H, m), 7.56~7.80 (4 H, m), 9.31 (1 H, d, J=5 Hz) ppm.

IR: ν max (CHCl$_3$) 2960, 2936, 2864, 1763, 1729, 1601, 1499, 1476, 1429, 1295, 1114, 821, 694, 612 cm$^{-1}$.

MS: m/z M+ 546.

(23) Preparation of methyl [(1R*,2R*,3aS*,9aR*)-2-tert-butyldipenylsilyloxy-1-[(E)-3-oxo-1-octenyl]-2,3,3a,9a-tetrahydro-1H-cyclopenta[b][1,4]benzodioxin-5-yl]oxyacetate III a

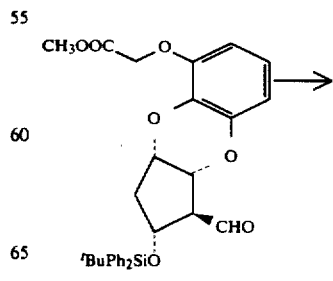

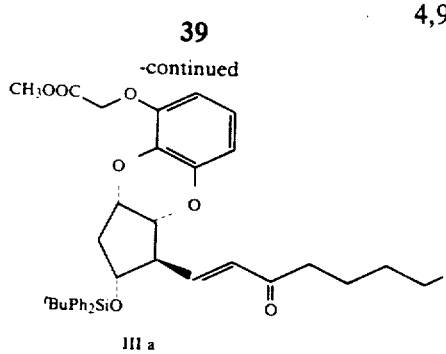

III a

In a nitrogen atmosphere, a solution of 95 mg (0.430 mmol) of dimethyl (2-oxoheptyl)phosphonate in 1.5 ml of dry THF is added to a suspension of 15.2 mg (0.381 mmol) of 60% sodium hydride in 2 ml of dry THF and the mixture is stirred at room temperature for 12 minutes. A solution of the 181 mg (0.331 mmol) of aldehyde 23 (prepared in (22)) in 3 ml of dry THF is added thereto and the resulting mixture is stirred for 30 minutes. The reaction is quenched by the addition of a saturated aqueous solution of ammonium chloride and the mixture is extracted with ethyl acetate twice. The extract is washed with water and a saturated aqueous solution of sodium chloride, dried over anhydrous magnesium sulfate, and evaporated under reduced pressure. The residue is purified by column chromatography on silica gel (Merck, Lobar column, size B, ethyl acetate:-toluene=1:30) to give 199 mg of the desired enone III a as an oil in 93.5% yield.

$^1$H-NMR: δ (CDCl$_3$) 0.89 (3 H, t, J=7 Hz), 1.03 (9 H, s), 1.05~1.80 (6 H, m), 2.10~2.50 (4 H, m), 2.86~3.21 (1 H, m), 3.77 (3 H, s), 4.02~4.26 (3 H, m), 4.71 (2 H, s), 6.09 (1 H, d, J=16 Hz), 6.39~6.88 (4 H, m), 7.29~7.48 (6 H, m), 7.53~7.73 (4 H, m) ppm.

IR: ν max (CHCl$_3$) 3008, 2960, 2936, 2864, 1763, 1743, 1696, 1672, 1630, 1601, 1498, 1475, 1429, 1114, 977, 822, 695, 612 cm$^{-1}$.

MS: m/z M+ 642.

(24) to (29)

According to the same method as described in (23), the aldehyde is converted into the enone III. The results are shown in Table 2. In (24), (26), and (29), a racemic phosphonate is used.

In (39), an optically active phosphonate [(S)-configuration] is used.

TABLE 2

Reaction scheme: Compound 23 (with CHO group) + $(CH_3O)_2\overset{O}{\overset{\|}{P}}CH_2\overset{O}{\overset{\|}{C}}-R_1$ → Compound III Structure of 23: cyclopentane with CH₃O₂C-O-phenyl-O substituent and ᵗBuPh₂SiO group, bearing CHO Structure of III: cyclopentane with CH₃O₂C-O-phenyl-O substituent and ᵗBuPh₂SiO group, bearing -CH=CH-C(=O)-R₁

| No. | Compd. No. | R₁ | Yd (%) | MS (m/z) | IR νmax (cm⁻¹) | ¹H-NMR δ (ppm) |
|---|---|---|---|---|---|---|
| (24) | IIIf | isohexyl (iPr-CH₂CH₂CH₂-) | 99.5 | 656 (M⁺) | (CHCl₃) 3008, 2960, 2936, 2864, 1765, 1742, 1694, 1668, 1629, 1600, 1498, 1475, 1428, 1289, 1113, 983, 821, 612. | (CDCl₃) 0.86 (3H,t,J=7Hz), 1.02 (9H,s), 1.03 (9H,s), 0.86~1.90 (6H,m), 2.01~2.26 (2H,m), 2.30~2.75 (1H,m), 2.88~3.28 (1H,m), 3.77 (3H,s), 4.02~4.27 (3H,m), 4.71 (2H,s), 6.22 (1H,d,J=16Hz), 6.39~6.87 (4H,m), 7.28~7.48 (6H,m), 7.52~7.80 (4H,m). |
| (25) | IIIg | 2,2-dimethylpentyl | 97.4 | 670 (M⁺) | (CHCl₃) 3008, 2964, 2936, 2864, 1764, 1743, 1690, 1627, 1600, 1498, 1475, 1429, 1288, 1114, 981, 822, 612. | (CDCl₃) 0.84 (3H,t,J=7Hz), 1.02 (9H,s), 1.06 (6H,s), 0.76~1.86 (6H,m), 2.00~2.20 (2H,m), 2.91~3.28 (1H,m), 3.77 (3H, s), 3.96~4.25 (3H,m), 4.71 (2H,s), 6.40~6.93 (5H,m), 7.30~7.49 (6H,m), 7.51~7.80 (4H,m). |
| (26) | IIIh | propargyl isopropyl | 98.7 | 652 (M⁺) | (CHCl₃) 3008, 2960, 2936, 2864, 1764, 1742, 1696, 1669, 1630, 1601, 1498, 1475, 1429, 1288, 1114, 981, 821, 611. | (CDCl₃) 1.02 (9H,s), 1.09 (3H,d,J=7Hz), 1.72 (3H,t, J=2.5Hz), 2.00~2.40 (4H,m), 2.40~3.26 (2H,m), 3.76 (3H,s), 4.01~4.25 (3H,m), 4.70 (2H,s), 6.18 (1H,d,J=16Hz), 6.39~6.87 (4H,m), 7.29~7.47 (6H,m), 7.52~7.74 (4H,m). |
| (27) | IIIi | cyclopentyl | ~100 | 640 (M⁺) | (CHCl₃) 3008, 2960, 2864, 1764, 1742, 1694, 1666, 1630, 1600, 1498, 1475, 1429, 1290, 1114, 980, 821, 611. | (CDCl₃) 1.02 (9H,s), 1.45~1.90 (8H,m), 2.01~2.28 (2H,m), 2.70~3.23 (2H,m), 3.77 (3H,s), 4.02~4.27 (3H,m), 4.71 (2H, s), 6.17 (1H,d,J=16Hz), 6.40~6.88 (4H,m), 7.27~7.49 (6H, m), 7.52~7.80 (4H,m). |
| (28) | IIIj | benzyl | 97.9 | 668 (M⁺) | (CHCl₃) 3008, 2936, 2860, 1764, 1743, 1693, 1670, 1628, 1601, 1498, 1475, 1429, 1293, 1113, 978, 821, 612. | (CDCl₃) 1.02 (9H,s), 0.60~1.92 (11H,m), 2.06~2.37 (4H,m), 2.82~3.24 (1H,m), 3.77 (3H,s), 3.92~4.28 (3H,m), 4.70 (2H, m), 4.70 (2H,s), 6.07 (1H,d,J=16Hz), 6.40~6.87 (4H,m), 7.27~7.48 (6H,m), 7.52~7.80 (4H,m). |
| (29) | IIIk | 6-methyl-5-hepten-2-yl | 98.9 | 696 (M⁺) | (CHCl₃) 3008, 2960, 2936, 2864, 1763, 1742, 1694, 1670, 1628, 1601, 1498, 1429, 1290, 1114, 979, 821, 612. | (CDCl₃) 0.87 (1H,d,J=6Hz), 1.03 (9H,s), 1.10~1.42 (2H,m), 1.60 (3H,s), 1.67 (3H,s), 1.65~2.60 (7H,m), 2.85~3.29 (1H, m), 3.77 (3H,s), 3.95~4.27 (3H,m), 4.71 (2H,s), 4.93~5.22 (1H,m), 6.13 (1H,d,J=16Hz), 6.40~6.87 (4H,m), 7.32~7.50 (6H,m), 7.53~7.80 (4H,m). |

TABLE 2-continued

| No. | Compd. No. | R₁ | Yield (%) | MS (m/z) | IR νmax (cm⁻¹) | ¹H—NMR δ (ppm) (200 MHz) |
|---|---|---|---|---|---|---|
| (37) | IIIm | (phenoxy-sec-butyl) | 92.7 | 706 (M⁺) | (CHCl₃) 2936, 2864, 1766, 1743, 1698, 1672, 1629, 1600, 1497, 1475, 1428, 1239, 1114, 978, 822, 616. | (CDCl₃) 1.03(9H,s), 1.33(3H,d,J=6Hz), 2.15~2.27(2H,m), 2.58(1H,ddd, J=16Hz, 7Hz, 5Hz), 2.91(1H,ddd,J=16Hz, 6Hz, 1.5Hz), 3.06(1H,q,J=8Hz), 3.80(3H,s), 4.00~4.22(1H,m), 4.74(2H,s), 4.80~4.96(1H,m), 6.13(1H,d, J=16Hz), 6.45~6.64(3H,m), 6.78(1H,t,J=8Hz), 6.86~7.00(3H,m), 7.23~7.48 (8H,m), 7.55~7.70(4H,m). |
| (38) | IIIo | (phenoxymethyl-butyl) | 97.8 | 720 (M⁺) 721 (MH⁺) | (CHCl₃) 2936, 2864, 1764, 1743, 1698, 1671, 1631, 1601, 1499, 1475, 1429, 1243, 1113, 822, 612. | (CDCl₃) 1.03(9H,s), 1.04(3H,d,J=6Hz), 2.12~2.22(2H,m), 2.33(1H,dt, J=16Hz, 6Hz), 2.40~2.59(1H,m), 2.69(1H,ddd,J=16Hz, 6Hz, 2Hz), 3.03(1H,q, J=8Hz), 3.80(3H,s), 3.71~3.87(2H,m), 3.97~4.21(3H,m), 4.73(2H,s), 6.12 (1H,d,J=16Hz), 6.45~6.64(3H,m), 6.78(1H,t,J=8Hz), 6.84~6.97(3H,m), 7.20~ 7.46(8H,m), 7.55~7.70(4H,m). |
| (39) | IIIq | (pentenyl) | 97.0 | 668 (M⁺) 669 (MH⁺) | (CHCl₃) 2936, 2864, 1764, 1742, 1696, 1667, 1629, 1601, 1499, 1476, 1429, 1289, 1114, 913, 822, 812. | (CDCl₃) 0.88(3H,d,J=7Hz), 1.03(9H,s), 1.14~1.48(2H,m), 1.91~2.46(7H,m), 3.07(1H,q,J=7Hz), 3.80(3H,s), 4.00~4.24(3H,m), 4.74(2H,s), 4.90~5.07 (2H,m), 5.69~5.91(1H,m), 6.14(1H,d,J=16Hz), 6.45~6.64(3H,m), 6.78(3H,t, J=8Hz), 7.30~7.50(6H,m), 6.55~7.70(4H,m). |
| (40) | IIIs | (SePh-alkyl) | 96.6 | 826 (M⁺) | (CHCl₃) 2936, 2864, 1764, 1743, 1696, 1670, 1636, 1601, 1499, 1476, 1439, 1429, 1291, 1114, 822, 611. | (CDCl₃) 0.87(6H,t,J=7Hz), 1.03(9H,s), 1.10~1.48(6H,m), 2.10~2.44(4H,m), 2.56~2.71(1H,m), 2.87~3.09(3H,m), 3.80(3H,s), 3.98~4.22(3H,m), 4.74(2H, s), 6.05(1H,d,J=16Hz), 6.45~6.63(3H,m), 6.78(3H,t,J=8Hz), 7.14~7.70 (15H,m). |

(30) Preparation of ethyl 3-phenoxybutyrate 28

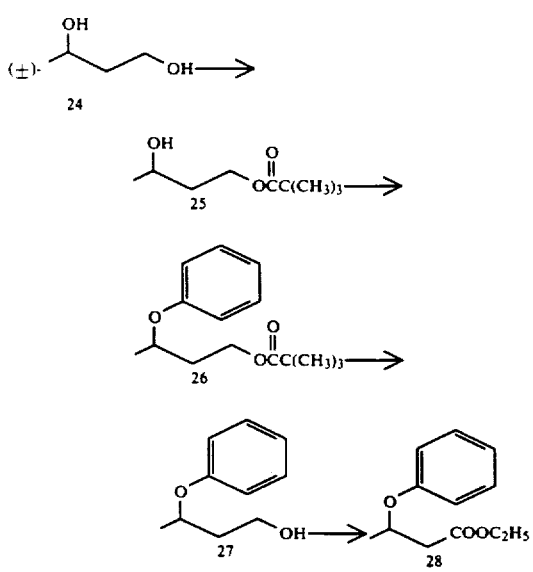

(1) Preparation of 1-tert-butylcarbonyloxy-3-butanol 25

To a mixture of 13.2 ml (0.15 mol) of (±)-1,3-butandiol 24 and 17.8 ml (0.23 mol) of pyridine in 200 ml of dry dichloromethane is added a solution of 22.2 ml (0.18 mol) of pivaloyl chloride in 50 ml of dry dichloromethane dropwise over 20 minutes under ice cooling. Then, the mixture is stirred for additional 30 minutes at room temperature. Ice-cooled water is added and the mixture is stirred for 5 minutes and then 1N hydrochloric acid is added thereto. The mixture is extracted with dichloromethane twice. The extract is washed with water, a saturated aqueous solution of sodium hydrogencarbonate, and a saturated aqueous solution of sodium chloride, dried over anhydrous magnesium sulfate, and evaporated under reduced pressure. The residue is purified by column chromatography on silica gel (250 g of silica gel, ethyl acetate:n-hexane=1:9 to 1:4) to give 20.4 g of the desired monopivaloyl ester 25 as an oil in 78.2% yield.

$^1$H-NMR δ ppm (CDCl$_3$): 1.21 (9 H, s), 1.23 (3 H, d, J=6 Hz), 1.60–1.95 (2 H, m), 2.27 (1 H, br. s., —OH), 3.72–4.47 (3 H, m).

(2) Preparation of 1-tert-butylcarbonyloxy-3-phenoxybutane 26

To a solution of 3.47 g (19.9 mmol) of alcohol 25 (prepared in 30-(1)), 2.81 g (29.9 mmol) of phenol, and 7.88 g (29.9 mmol) of triphenylphosphine in 100 ml of dry THF is added a solution of 4.65 ml of diethyl azodicarboxylate in 40 ml of dry THF dropwise under ice cooling. After additional stirring at the same temperature for 20 minutes, the mixture is stirred for further 2 and half hours. The reaction mixture is concentrated under reduced pressure and the residue is purified by column chromatography on silica gel (200 g of silica gel, ethyl acetate:n-hexane=1:49 to 1:19) to give 4.35 g of the desired phenyl ether 3 as an oil in 87.4% yield.

$^1$H-NMR (200 MHz) δ ppm (CDCl$_3$): 1.10 (9 H, s), 1.34 (3 H, d, J=6 Hz), 1.83–2.16 (2 H, m), 4.11–4.31 (2 H, m), 4.42–4.60 (1 H, m), 6.85–6.98 (3 H, m), 7.21–7.32 (2 H, m),

(3) Preparation of 3-phenoxy-1-butanol 27

To a solution of 4.32 g (17.3 mmol) of pivaloyl ester 26 (prepared in 30-(2)) in 90 ml of dry methanol is added 17.3 ml (17.3 mmol) of 1M sodium methoxide-methanol solution and the mixture is stirred at 55° C. for 9 hours. After cooling, 35 g of ion exchange resin IRC-50 is added and the mixture is stirred for 20 minutes. The ion exchange resin is filtrated off and the filtrate is evaporated under reduced pressure to give 3.15 g of the crude desired alcohol 27 as an oil, which is employed in the next step without further reaction.

(4) Preparation of ethyl 3-phenoxybutyrate 28

To a solution of 3.15 g of the crude alcohol 27 (prepared in 30-(3)) in 80 ml of acetone is added 10 ml of 8N Jones' reagent at 20° C. to 30° C. dropwise. The mixture is stirred for additional 10 minutes, and 3 ml of isopropyl alcohol is added thereto. The resulting mixture is stirred for 10 minutes and acetone is evaporated under reduced pressure. Water is added to the residue, and the residue is extracted with ethyl acetate twice. The organic layer is washed with water and then extracted with 1N aqueous solution of sodium hydroxide. The aqueous layer is acidified to pH 2 with hydrochloric acid and extracted with ethyl acetate again. The ethyl acetate extract is washed with water and a saturated aqueous solution of sodium chloride, dried over anhydrous magnesium sulfate, and evaporated under reduced pressure. The residue is dissolved in 50 ml of ether and an ethereal solution of diazoethane is added at 0° C. until the orange color persists. The reaction mixture is evaporated under reduced pressure and the residue is purified by column chromatography on silica gel (50 of silica gel, ethyl acetate-n-hexane=1:19) to give 2.35 g of the desired ethyl ester 28 as an oil in 67.0% yield from the compound 26.

$^1$H-NMR (200 MHz) δ ppm (CDCl$_3$): 1.24 (3 H, t, J=7 Hz), 1.37 (3 H, d, J=6 Hz), 2.53 (1 H, dd, J=15 Hz, 6.5 Hz), 2.79 (1 H, dd, J=15 Hz, 7 Hz), 4.14 (2 H, q, J=7 Hz), 4.75–4.92 (1 H, m), 6.88–6.98 (3 H, m), 7.22–7.33 (2 H, m).

(31) Preparation of (S)-(−)-methyl 3-methyl-6-heptenoate 32

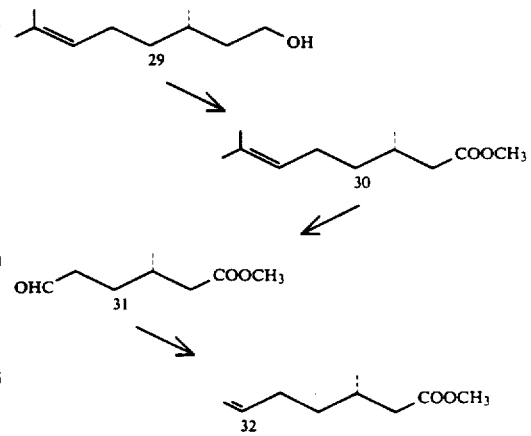

(1) Preparation of (S)-(−)-methyl citronellate 30

To a solution of 10.0 g (64.1 mmol) of (S)-(−)-citronellol 29 (Aldrich, 98% e.e.) in 150 ml of dry DMF is added 84.4 g (224 mmol) of pyridinium dichromate (PDC), and the mixture is stirred overnight. The reaction mixture is poured into 1.5 l of water, and extracted with toluene twice. The extract is washed with water, and then extracted with 1N aqueous solution of sodium hydroxide to separate the carboxylic acid. The aqueous layer is acidified with 5N hydrochloric acid to pH 2, and extracted with ethyl acetate again. The ethyl acetate extract is washed with water, a saturated aqueous solution of sodium chloride, dried over anhydrous magnesium sulfate, and evaporated under reduced pressure. To a solution of residue in 100 ml of ether is added an ethereal solution of diazomethane at 0° C. until the yellow color persists. The reaction mixture is distilled under reduced pressure to give 7.53 g of the desired methyl ester 30 as an oil in 63.9% yield.

Bp. 78° C. to 81° C. (3 mmHg).

$[\alpha]_D$ −7.4±0.1° (24° C., c=5.13, CHCl$_3$).

$^1$H-NMR δ ppm (CDCl$_3$) 0.94 (3 H, d, J=7 Hz), 1.10–1.46 (2 H, m), 1.62 (3 H, s), 1.68 (3 H, s), 1.70–2.50 (5 H, m), 3.66 (3 H, s), 4.93–5.21 (1 H, m).

(2) Preparation of (S)-methyl 3-methyl-6-oxohexanoate 31

To a solution of 7.76 g (36 mmol) of 80% m-chloroperbenzoic acid in 200 ml of dry dichloromethane is added a solution of 6.00 g (32.6 mmol) of (S)-methyl citronellate 30 (prepared in 31-(1)) in 50 ml of dry dichloromethane, and the mixture is stirred at room temperature for one hour. To the reaction mixture are added 5% aqueous solution of sodium thiosulfate and a dilute aqueous solution of sodium hydrogencarbonate, and the mixture is extracted with dichloromethane twice. The extract is washed with a saturated aqueous solution of sodium hydrogencarbonate and a saturated aqueous solution of sodium chloride, dried over anhydrous magnesium sulfate, and evaporated under reduced pressure. To a solution of the residue in 80 ml of THF is added a solution of 8.90 g (39 mmol) of periodic acid dihydrate in 80 ml of THF at 0° C. After additional stirring at room temperature for 20 minutes, the reaction mixture is diluted with water, and extracted with ether twice. The extract is washed with water, a saturated aqueous solution of sodium hydrogencarbonate, and a saturated aqueous solution of sodium chloride, dried over anhydrous magnesium sulfate, and evaporated under reduced pressure to give 5.2 g of the crude desired aldehyde 31 as an oil, which is employed in the next step without further purification.

(3) Preparation of (S)-(−)-methyl 3-methyl-6-heptenoate 32

To a suspension of 23.3 g (65.2 mmol) of methyltriphenylphosphonium bromide in 120 ml of dry THF is added 36.9 ml (58.7 mmol) of 1.59 N n-butyllithium-n-hexane solution dropwise under ice cooling in a nitrogen atmosphere. After additional stirring at the same temperature for 10 minutes, the mixture was cooled to −50° C., and a solution of 5.2 g of crude aldehyde 31 (prepared in 31-(2)) in 80 ml of dry THF is added dropwise thereto. Then, the mixture is stirred at the same temperature for 10 minutes, and warmed to room temperature over an hour. To the reaction mixture is added a saturated aqueous solution of ammonium chloride, and the mixture is extracted with ether twice. The extract is washed with water and a saturated aqueous solution of sodium chloride, dried over anhydrous mangeium sulfate, and evaporated at atmospheric pressure. To the residue is added 400 ml of n-pentane and the mixture is stirred under ice cooling for 30 minutes. The precipitated triphenylphosphineoxide is removed by filtration through 100 g of silica gel. The silica gel is washed with 500 ml of mixture of ether:n-pentane=1:9. The filtrate and washing are combined and concentrated at atmospheric pressure. The residue is distilled under reduced pressure to give 2.19 g of the desired olefin 32 as an oil in 43.1% yield from compound 30.

bp. 85° C. to 86° C. (23 mmHg).

$[\alpha]_D$ −6.6±0.2° (23° C., c=2.06, CHCl$_3$).

$^1$H-NMR (200 MHz) δ ppm (CDCl$_3$): 0.95 (3 H, d, J=6 Hz), 0.97–1.52 (2 H, m), 1.88–2.38 (5 H, m), 3.67 (3 H, s), 4.90–5.09 (2 H, m), 5.70–5.91 (1 H, m).

IR: ν max (CHCl$_3$) 2960, 1734, 1642, 1439, 1172, 1006, 916 cm$^{-1}$.

(32) Preparation of methyl 3-(phenylselenylmethyl)heptanoate 35

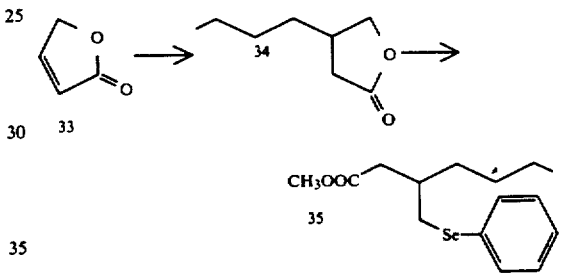

(1) Preparation of 3-n-butyl-τ-butyrolactone 34

To a suspension of 6.17 g (30 mmol) of copper(I) bromide-dimethyl sulfide complex in 100 ml of dry ether is added 38 ml (60 mmol) of 1.59N n-butyllithium-n-hexane solution dropwise at −50° C. under a nitrogen atmosphere over 30 minutes. After additional stirring at the same temperature for 15 minutes, the mixture is cooled to −78° C., and then a solution of 3.8 ml (30 mmol) of chlorotrimethylsilane in 10 ml of dry ether is added, which is followed by addition of a solution of 1.68 g (20 mmol) of 2(5 H)-furanon 33 in 20 ml of dry ether. The mixture is stirred at the same temperature for additional 30 minutes and warmed to −10° C. over 30 minutes. The reaction is quenched by the addition of a saturated aqueous solution of ammonium chloride. Air is blown into the reaction mixture for 30 minutes and it is filtered through Celite. The filtrate is extracted with ether twice and the extract is washed with water, a saturated aqueous solution of sodium chloride, dried over anhydrous magnesium sulfate, and evaporated under reduced pressure. To a solution of the residue in 150 ml of THF is added 20 ml of 2N aqueous solution of sodium hydroxide and the mixture is stirred at room temperature for 40 minutes. The reaction mixture is acidified to pH 2 with 1N hydrochloric acid and extracted with ether twice. The extract is washed with water and a saturated aqueous solution of sodium chloride, dried over anhydrous magnesium sulfate, and evaporated under reduced pressure. To a solution of the residue in 30 ml of dry benzene is added a catalytic amount of p-toluenesulfonic acid and the mixture is heated for 15 minutes under reflux. After cooling to room temperature, a dilute aqueous solution of sodium hydrogencarbonate is added, and the mixture is extracted with ethyl acetate twice. The extract is washed with water and a saturated aqueous solution of sodium chloride, dried over anhydrous magnesium sulfate, and evaporated under reduced pressure. The residue is distilled under reduced pressure to give 2.19 g of the desired lacton 34 as an oil in 77.1% yield.

Bp. 94°-95° C. (2 mmHg).

$^1$H-NMR δ ppm (CDCl$_3$): 0.91 (3 H, t, J=7 Hz), 1.12–1.80 (6 H, m), 1.97–2.83 (3 H, m), 3.93 (1 H, dd, J=9 Hz, 6 Hz), 4.43 (1 H, dd, J=9 Hz, 7 Hz).

(2) Preparation of methyl 3-(phenylselenylmethyl)heptanoate 35

To a solution of 2.40 g (7.69 mmol) of diphenyl diselenide in 30 ml of dry DMF is added 655 mg (17.3 mmol) of sodium borohydride in portions under ice cooling in a nitrogen atmosphere. After hydrogen evolution is finished, the reaction mixture is stirred at 100° C. for 20 minutes. At the same temperature, a solution of 1.68 g (11.8 mmol) of lacton 14 (prepared 32-(1)) in 10 ml of DMF is added thereto and the mixture is stirred for two and half hours at 120° C. After cooling with ice, the mixture is acidified to pH 2 by dropwise addition of 10% hydrochloric acid. The reaction mixture is extracted with ether twice and the extract is washed with water and a saturated aqueous solution of sodium chloride, dried over anhydrous magnesium sulfate, and evaporated under reduced pressure. The residue is dissolved in 30 ml of ether and an ethereal solution of diazomethane is added at 0° C. thereto until the yellow color persists. The reaction mixture is evaporated under reduced pressure and the residue is purified by column chromatography on silica gel (Merck, Lobar column, size C, ethyl acetate-n-hexane=1:19) to give 2.64 g of the desired methyl ester 35 as an oil in 71.5% yield.

$^1$H-NMR δ ppm (CDCl$_3$): 0.86 (3 H, t, J=7 Hz), 1.05–1.63 (6 H, m), 2.00–2.70 (3 H, m), 2.98 (2 H, d, J=5 Hz), 3.63 (3 H, m), 7.17–7.33 (3 H, m), 7.32–7.62 (2 H, m).

(33) Preparation of dimethyl 2-oxo-4-(phenylselenylmethyl)octylphosphonate 36

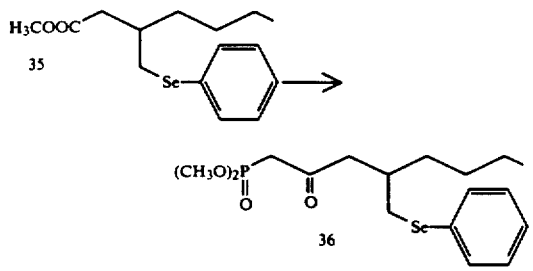

To a solution of 1.35 ml (12.5 mmol) of dimethyl methylphosphonate in 25 ml of dry THF is added 7.0 ml (11.5 mmol) of 1.64N n-butyllithium-n-hexane solution dropwise at −78° C. in a nitrogen atmosphere. After stirring at the same temperature for one hour, 1.57 g (10.0 mmol) of methyl ester (prepared in 32-(2)) in 10 ml of dry THF is added thereto. The resulting mixture is stirred for additional 30 minutes and then the reaction is quenched by the addition of a saturated aqueous solution of ammonium chloride. The reaction mixture is extracted with ethyl acetate twice and the extract is washed with water and a saturated aqueous solution of sodium chloride, dried over anhydrous magnesium sulfate, and evaporated under reduced pressure. The residue is purified by column chromatography on silica gel (Merck, Lobar column, size B, acetone:benzene=1:4) to give 1.42 g of the desired phosphonate 36 as an oil in 70.0% yield.

$^1$H-NMR δ ppm (CDCl$_3$): 0.86 (3 H, t, J=7 Hz), 1.02–1.70 (6 H, m), 1.90–3.05 (5 H, m), 2.95 (2 H, d, J=22 Hz), 3.77 (6 H, d, J=11 Hz), 7.15–7.32 (3 H, m), 7.40–7.62 (2 H, m).

34–36 Preparation of Intermediate

The dimethylphosphonates 37, 38, and 40 can be prepared from the esters 28 (prepared in 30-(4)), 32 (prepared in 31-(3)), and 39 in the same manner as described in 36. In regards to compound 39, the racemate is prepared as described by G. S. Marks et al., J. Chem. Soc., 3851, (1955).

The physical constants of compounds 37, 38, and 40 are shown below.

Compound 37

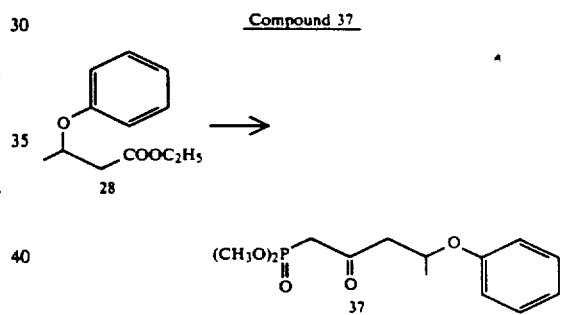

$^1$H-NMR (200 MHz) δ ppm (CDCl$_3$): 1.34 (3 H, d, J=6 Hz), 2.78–3.29 (4 H, m), 3.78 (6 H, d, J=1 Hz), 4.80–4.96 (1 H, m), 6.85–7.00 (3 H, m), 7.22–7.33 (2 H, m).

Compound 38

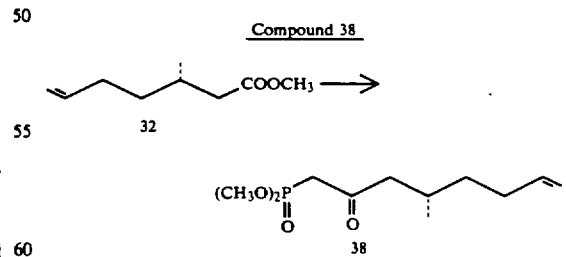

[α]$_D$ −5.5±0.5° (23° C., c=0.98, CHCl$_3$).

$^1$H-NMR (200 MHz) δ ppm (CDCl$_3$): 0.92 (3 H, d, J=7 Hz), 1.16–1.50 (2 H, m), 1.97–2.19 (3 H, m), 2.46 (1 H, dd, J=17 Hz, 7 Hz), 2.59 (1 H, dd, J=17 Hz, 6 Hz), 3.07 (2 H, d, J=22 Hz), 3.79 (6 H, d, J=11 Hz), 4.90–5.08 (2 H, m), 5.69–5.90 (1 H, m).

Compound 40

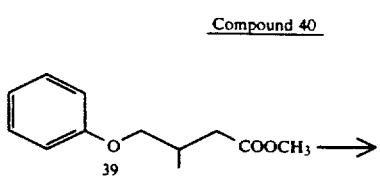

$^1$H-NMR (200 MHz) δ ppm (CDCl$_3$): 1.06 (3 H, d, J=6 Hz), 2.47–2.67 (2 H, m), 2.80–2.96 (1 H, m), 3.12 (2 H, d, J=22 Hz), 3.77 (3 H, d, J=11 Hz), 3.78 (3 H, d, J=11 Hz), 3.75–3.92 (2 H, m), 6.84–6.97 (3 H, m), 7.22–7.33 (2 H, m).

EXAMPLE 5

Preparation of methyl [(1R*,2R*,3aS*,9aR*)-2-tert-butyldiphenylsilyloxy-1[(3S*,1E)-3-hydroxy-1-octenyl]-2,3,3a,9a-tetrahydro-1H-cyclopenta[b][1,4]benzodioxin-5-yl]oxyacetate Iaa-a and methyl [(1R*,2R*,3aS*,9aR*)-2-tert-butyldiphenylsilyloxy-1[(3R*,1E)-3-hydroxy-1-octenyl]-2,3,3a,9a-tetrahydro-1H-cyclopenta[b][1,4]benzodioxin-5-yl]oxyacetate Ica-a

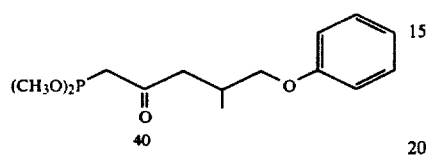

To a solution of 120 mg (0.187 mmol) of the enone III a (prepared in (23)) and 70 mg (0.188 mmol) of cerium trichloride heptahydrate in 2 ml of methanol is added a solution of 7.1 mg (0.187 mmol) of sodium borohydride in 0.7 ml of methanol dropwise under ice cooling and then the mixture is stirred at the same temperature for 20 minutes. A saturated aqueous solution of ammonium chloride is added, and the mixture is extracted with ethyl acetate twice. The extract is washed with water and a saturated aqueous solution of sodium chloride, dried over anhydrous magnesium sulfate, and evaporated under reduced pressure. The residue is purified by column chromatography on silica gel (Merck, Lobar column, size A, two columns, ethyl acetate:-toluene=1:15) to give the desired allyl alcohol, namely, 84 mg of the less polar isomer Iaa-a and 27 mg of the more polar isomer Ica-a in 70.0% and 22.5% yield, respectively. The physical properties of each compound Iaa-a and Ica-a prepared in Example 5 are identical with those of Iaa-a and Ica-a prepared in Example 1, respectively.

Examples 6 to 13

In the same manner as described in Example 5, the enone III is converted into the allyl alcohol Ia-a and Ic-a. The results are shown in Table 3. In example 11, the four isomers of allyl alcohol Iak-a, Ial-a, Ick-a, and Icl-a are prepared. In Examples 6 and 10, the reaction is carried out at −78° C.

TABLE 3

| Ex. No. | R₁ | Compd No. | Yd. (%) | MS (m/z) | IR νmax (cm⁻¹) | ¹H—NMR δ (ppm) |
|---|---|---|---|---|---|---|
| 6 | (n-pentyl) | I af-a | 85.3 | 658 (M⁺) | (CHCl₃) 3612, 3008, 2964, 2936, 2864, 1764, 1743, 1600, 1498, 1475, 1429, 1290, 1114, 970, 821, 612. | (CDCl₃) 0.73~0.97(6H,m), 1.03(9H,s), 1.00~1.70(8H,m), 2.06~2.26(2H,m), 2.75~3.05(1H,m), 3.76(3H,s), 3.65~4.27(4H,m), 4.70(2H,s), 5.16~5.67(2H,m), 6.38~6.86(3H,m), 7.30~7.50(6H,m), 7.59~7.77(4H,m). |
| | | I cf-a | 11.8 | 658 (M⁺) | (CHCl₃) 3608, 3008, 2964, 2936, 2864, 1764, 1742, 1600, 1498, 1475, 1429, 1290, 1114, 970, 822, 612. | (CDCl₃) 0.76~1.00(6H,m), 1.03(9H,s), 1.00~1.80(8H,m), 2.06~2.25(2H,m), 2.75~3.06(1H,m), 3.76(3H,s), 3.75~4.30(4H,m), 4.70(2H,s), 5.20~5.71(2H,m), 6.39~6.87(3H,m), 7.29~7.48(6H,m), 7.58~7.80(4H,m). |
| 7 | (branched alkyl) | I ag-a | 70.7 | 672 (M⁺) | (CHCl₃) 3612, 3008, 2964, 2936, 2864, 1764, 1742, 1600, 1498, 1475, 1429, 1293, 1113, 971, 819, 611. | (CDCl₃) 0.76(3H,s), 0.80(3H,s), 0.88(3H,t,J=7Hz), 1.03 (9H,s), 0.78~1.40(7H,m), 2.01~2.26(2H,m), 2.73~3.07(1H,m), 3.61(1H,d,J=7Hz), 3.77(3H,s), 3.86~4.30(3H,m), 4.70(2H,s), 5.13~5.70(2H,m), 6.39~6.87(3H,m), 7.30~7.48(6H,m), 7.59~7.77(4H,m). |
| | | I cg-a | 21.9 | 672 (M⁺) | (CHCl₃) 3612, 3008, 2964, 2936, 2864, 1764, 1743, 1600, 1498, 1475, 1429, 1291, 1113, 972, 821, 612. | (CDCl₃) 0.74(3H,s), 0.78(3H,s), 0.87(3H,t,J=7Hz), 1.03 (9H,s), 0.77~1.45(7H,m), 2.02~2.23(2H,m), 2.75~3.06(1H,m), 3.65(1H,d,J=5Hz), 3.76(3H,s), 3.90~4.28(3H,m), 4.70(2H,s), 5.22~5.76(2H,m), 6.39~6.86(3H,m), 7.29~7.46(6H,m), 7.57~7.80(4H,m). |
| 8 | (pentynyl) | I ah-a | 65.2 | 654 (M⁺) | (CHCl₃) 3612, 3008, 2964, 2940, 2864, 1764, 1765, 1741, 1600, 1498, 1475, 1429, 1291, 1113, 970, 821, 611. | (CDCl₃) 0.81~1.01(3H,m), 1.03(9H,s), 1.78(3H,m), 1.30~ 2.42(6H,m), 2.73~3.10(1H,m), 3.79(3H,s), 3.80~4.40 (3H,m), 4.73(2H,s), 5.20~5.70(2H,m), 6.41~6.89(3H,m), 7.30~7.50(6H,m), 7.60~7.83(4H,m). |
| | | I ch-a | 21.0 | 654 (M⁺) | (CHCl₃) 3612, 3008, 2960, 2940, 2864, 1763, 1742, 1600, 1498, 1475, 1429, 1289, 1114, 970, 822, 612. | (CDCl₃) 0.87(3H,d,J=7Hz), 1.03(9H,s), 1.42~1.93(2H,m), 1.77(3H,t,J=2.5Hz), 2.01~2.26(4H,m), 2.76~3.07(1H,m), 3.77(3H,s), 3.75~4.30(4H,m), 4.70 (2H,s), 5.23~5.71(2H,m), 6.40~6.89(3H,m), 7.32~7.50(6H,m), 7.57~7.80(4H,m). |
| 9 | (cyclopentylmethyl) | I ai-a | 70.1 | 642 (M⁺) | (CHCl₃) 3608, 3008, 2960, 2864, 1764, 1743, 1600, 1498, 1476, 1429, 1290, 1114, 970, 821, 612. | (CDCl₃) 1.03(9H,s), 0.90~1.95(10H,m), 2.06~2.26(2H,m), 2.73~3.03(1H,m), 3.76(3H,s), 3.62~3.82(1H,m), 3.88~4.27(3H,m), 4.69(2H,s), 5.16~5.67(2H,m), 6.39~6.86(3H,m), 7.30~7.47(6H,m), 7.57~7.76(4H,m). |
| | | I ci-a | 21.6 | 642 (M⁺) | (CHCl₃) 3608, 3008, 2960, 2864, 1764, 1743, 1600, 1498, 1476, 1428, 1290, 1113, 972, 821, 612. | (CDCl₃) 1.03(9H,s), 0.90~2.05(10H,m), 2.05~2.23(2H,m), 2.75~3.05(1H,m), 3.76(3H,s), 3.63~3.90(1H,m), 3.90~4.30(3H,m), 4.70(2H,s), 5.23~5.72(2H,m), 6.39~6.86(3H,m), 7.30~7.46(6H,m), 7.57~7.76(4H,m). |
| 10 | (cyclohexylmethyl, H) | I aj-a | 77.6 | 670 (M⁺) | (CHCl₃) 3608, 3008, 2932, 2860, 1764, 1742, 1600, 1498, 1475, 1429, 1289, 1113, 971, 821, 611. | (CDCl₃) 1.03(9H,s), 0.60~2.30(15H,m), 2.71~3.03(1H,m), 3.76(3H,s), 3.83~4.29(4H,m), 4.69(2H,s), 5.15~5.66 (2H,m), 6.36~6.86(3H,m), 7.29~7.47(6H,m), 7.52~7.78 (4H,m). |
| | | I cj-a | 19.9 | 670 (M⁺) | (CHCl₃) 3608, 3008, 2932, 2860, 2860, 1764, 1742, 1600, 1498, 1475, 1429, 1288, 1113, 971, 822, 612. | (CDCl₃) 1.03(9H,s), 0.60~1.90(13H,m), 2.00~2.23(2H,m), 2.71~3.01(1H,m), 3.76(3H,s), 3.86~4.30(4H,m), 4.69(2H,s), 5.19~5.68(2H,m), 6.37~6.87(3H,m), 7.28~7.47(6H,m), 7.55~7.79(4H,m). |

TABLE 3-continued

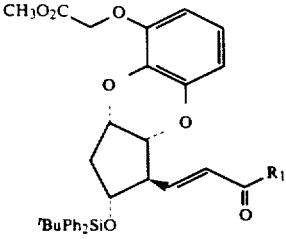

| Ex. No. | R₁ | Compound No. | Yd. (%) | MS (m/z) | IR νmax (cm⁻¹) | ¹H—NMR δ ppm (CDCl₃) |
|---|---|---|---|---|---|---|
| 11 | (structure) | I ak-a (Isomer 1) | 31.8 | 698 (M⁺) | (CHCl₃) 3604, 3008, 2960, 2936, 2864, 1763, 1742, 1600, 1498, 1475, 1429, 1291, 1113, 970, 821, 612. | (CDCl₃) 0.88(3H,d,J=7Hz), 1.03(9H,s), 1.59(3H,s), 1.66(3H,s), 0.95~2.25(10H,m), 2.72~3.04(1H,m), 3.76(3H,s), 3.85~4.27(4H,m), 4.70(2H,m), 4.96~5.68(3H,m), 6.38~6.86(3H,m), 7.29~7.50(6H,m), 7.56~7.80(4H,m). |
| | | I al-a (Isomer 2) | 28.9 | 698 (M⁺) | (CHCl₃) 3608, 3008, 2960, 2936, 2864, 1763, 1742, 1600, 1498, 1475, 1429, 1289, 1113, 969, 821, 612. | (CDCl₃) 0.86(3H,d,J=7Hz), 1.03(9H,s), 1.59(3H,s), 1.66(3H,s), 0.95~2.30(10H,m), 2.72~3.03(1H,m), 3.77(3H,s), 3.85~4.30(4H,m), 4.70(2H,m), 4.96~5.65(3H,m), 6.39~6.88(3H,m), 7.30~7.49(6H,m), 7.56~7.80(4H,m). |
| | | I ck-a (Isomer 1) | 13.6 | 698 (M⁺) | (CHCl₃) 3604, 3008, 2960, 2936, 2864, 1764, 1743, 1600, 1498, 1475, 1429, 1289, 1114, 969, 821, 612. | (CDCl₃) 0.87(3H,d,J=7Hz), 1.03(9H,s), 1.59(3H,s), 1.66(3H,s), 0.95~2.33(10H,m), 2.72~3.06(1H,m), 3.76(3H,s), 3.85~4.27(4H,m), 4.70(2H,m), 4.95~5.70(3H,m), 6.39~6.86(3H,m), 7.29~7.48(6H,m), 7.59~7.80(4H,m). |
| | | I cl-a (Isomer 2) | 11.9 | 698 (M⁺) | (CHCl₃) 3604, 3008, 2960, 2936, 2864, 1764, 1742, 1600, 1498, 1475, 1429, 1289, 1113, 970, 821, 611. | (CDCl₃) 0.87(3H,d,J=7Hz), 1.03(9H,s), 1.58(3H,s), 1.67(3H,s), 0.95~2.26(10H,m), 2.73~3.05(1H,m), 3.76(3H,s), 3.86~4.29(4H,m), 4.69(2H,m), 4.96~5.67(3H,m), 6.39~6.86(3H,m), 7.30~7.47(6H,m), 7.57~7.80(4H,m). |
| 12 | 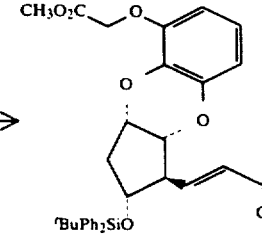 | I am-a (Isomer-1) | 28.4 | 708 (M⁺) | (CHCl₃) 3612, 2936, 2864, 1764, 1744, 1600, 1497, 1476, 1429, 1238, 1114, 970, 821, 612. | 1.06(9H,s), 1.28(3H,d,J=6Hz), 1.56~1.88(3H,m), 2.04~2.23(2H,m), 2.89(1H,t,J=7Hz), 3.79(3H,s), 3.93~4.05(2H,m), 4.12~4.31(2H,m), 4.52~4.68 (1H,m), 4.73(2H,s), 5.41(1H,dd,J=16Hz, 8Hz), 5.55(1H,dd,J=16Hz, 6Hz), 6.47(1H,dd,J=8Hz, 2Hz), 6.60(1H,dd,J=8Hz, 2Hz), 6.76(1H,t,J=8Hz), 6.86~6.97(3H,m), 7.20~7.50(8H,m), 7.60~7.70(4H,m). |
| | | I an-a (Isomer-2) | 29.4 | 708 (M⁺) | (CHCl₃) 3572, 2936, 2864, 1764, 1743, 1600, 1497, 1476, 1429, 1233, 1114, 971, 821, 612. | 1.03(9H,s), 1.29(3H,d,J=6Hz), 1.50~2.25(5H,m), 2.85(1H,q,J=7Hz), 3.79(3H,s), 3.78~4.04(2H,m), 4.10~4.25(2H,m), 4.41~4.58(1H,m), 4.73(2H,s), 5.29(1H,dd,J=16Hz, 8Hz), 5.47(1H,dd,J=16Hz, 6Hz), 6.47(1H,dd,J=8Hz, 2Hz), 6.60(1H,dd,J=8Hz 2Hz), 6.76(1H,t,J=8Hz), 6.86~6.97(3H,m), 7.20~7.50(8H,m), 7.60~7.70(4H,m). |
| | | I cm-a (Isomer-1) | 13.5 | 708 (M⁺) | (CHCl₃) 3608, 2936, 2864, 1764, 1743, 1600, 1497, 1476, 1429, 1243, 1114, 970, 821, 612. | 1.04(9H,s), 1.27(3H,d,J=6Hz), 1.55~1.90(3H,m), 2.03~2.23(2H,m), 2.88(1H,q,J=7Hz), 3.79(3H,s), 3.92~4.04(2H,m), 4.12~4.33(2H,m), 4.58~4.73 (1H,m), 4.73(2H,s), 5.40(1H,dd,J=16Hz, 8Hz), 5.56(1H,dd,J=16Hz, 6Hz), 6.47(1H,dd,J=8Hz, 2Hz), 6.60(1H,dd,J=8Hz, 2Hz), 6.76(1H,t,J=8Hz), 6.86~6.97(3H,m), 7.21~7.48(8H,m), 7.60~7.72(4H,m). |
| | | I cn-a (Isomer-2) | 16.5 | 708 (M⁺) | (CHCl₃) 3608, 2936, 2864, 1763, 1742, 1600, 1497, 1475, 1429, 1240, 1113, 971, 821, 613. | 1.03(9H,s), 1.29(3H,d,J=6Hz), 1.59(1H,dt,J=14Hz, 5Hz), 1.88~2.29(4H,m), 2.87(1H,q,J=7Hz), 3.79(3H,s), 3.90~4.05(2H,m), 4.10~4.25(2H,m), 4.72 (2H,s), 5.39(1H,dd,J=16Hz, 8Hz), 5.53(1H,dd,J=16Hz, 6Hz), 6.47(1H,dd,J=8Hz, 2Hz), 6.60(1H,dd,J=8Hz, 2Hz), 6.76(1H,t,J=8Hz), 6.80~6.96(3H,m), 7.17~7.45(8H,m), 7.60~7.70(4H,m). |
| 13 |  | I ao-a | 67.3 | 722 (M⁺) | (CHCl₃) 3604, 2936, 2864, 1762, 1742, 1601, 1498, 1475, 1428, 1243, 1113, 970, 821, 612. | 1.04(9H,s), 1.02~1.06(6H,m), 1.23~1.73(3H,m), 2.02~2.29(3H,m), 2.88(1H,q,J=7Hz), 3.79(3H,s), 3.75~3.83(2H,m), 3.94~4.21(4H,m), 4.73(2H,s), 5.30~5.62(2H,m), 6.44~6.80(3H,m), 6.85~6.97(3H,m), 7.20~7.46(8H,m), 7.60~7.70(4H,m). |
| | | I co-a (Isomer-1) | 14.0 | 722 (M⁺) | (CHCl₃) 3608, 2936, 2864, 1763, 1744, 1601, 1499, 1475, 1429, 1245, 1114, | 1.04(9H,s), 1.05(3H,d,J=7Hz), 1.20~1.70(3H,m), 2.03~2.38(3H,m), 2.88(1H,q,J=7Hz), 3.79(3H,s), 3.74~3.83(2H,m), 3.95~4.22(4H,m), 4.73(2H,s), |

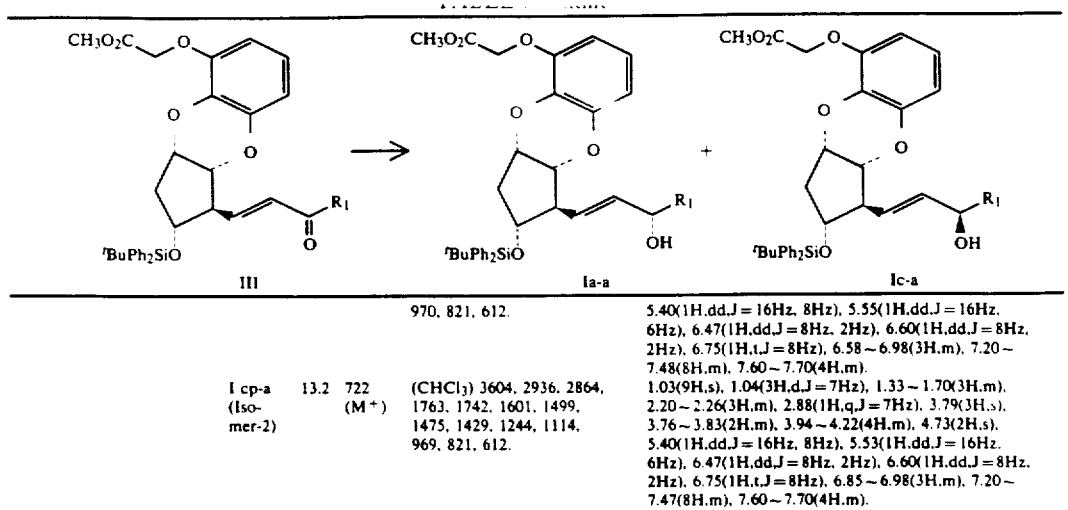

| | | | | |
|---|---|---|---|---|
| | | | 970, 821, 612. | 5.40(1H,dd,J = 16Hz, 8Hz), 5.55(1H,dd,J = 16Hz, 6Hz), 6.47(1H,dd,J = 8Hz, 2Hz), 6.60(1H,dd,J = 8Hz, 2Hz), 6.75(1H,t,J = 8Hz), 6.58~6.98(3H,m), 7.20~7.48(8H,m), 7.60~7.70(4H,m). |
| I cp-a (Iso-mer-2) | 13.2 | 722 (M+) | (CHCl₃) 3604, 2936, 2864, 1763, 1742, 1601, 1499, 1475, 1429, 1244, 1114, 969, 821, 612. | 1.03(9H,s), 1.04(3H,d,J = 7Hz), 1.33~1.70(3H,m), 2.20~2.26(3H,m), 2.88(1H,q,J = 7Hz), 3.79(3H,s), 3.76~3.83(2H,m), 3.94~4.22(4H,m), 4.73(2H,s), 5.40(1H,dd,J = 16Hz, 8Hz), 5.53(1H,dd,J = 16Hz, 6Hz), 6.47(1H,dd,J = 8Hz, 2Hz), 6.60(1H,dd,J = 8Hz, 2Hz), 6.75(1H,t,J = 8Hz), 6.85~6.98(3H,m), 7.20~7.47(8H,m), 7.60~7.70(4H,m). |

EXAMPLE 14

Preparation of methyl [(1R*,2R*,3aS*,9aR*)-2-t-butyldiphenylsilyloxy-1-[(3S*,1E)-5-butyl-3-hydroxy-1,5-hexadiene-1-yl]-2,3,3a,9a-tetrahydro-1H-cyclopenta[b][1,4]benzodioxin-5-yl]oxyacetate Iat-a and methyl [(1R*,2R*,3aS*,9aR*)-2-butyldiphenylsilyloxy-1-[(3R*,1E)-5-butyl-3-hydroxy-1,5-hexadiene-1-yl]-2,3,3a,9a-tetrahydro-1H-cyclopenta[b][1,4]benzodioxin-5-yl]oxyacetate Ict-a

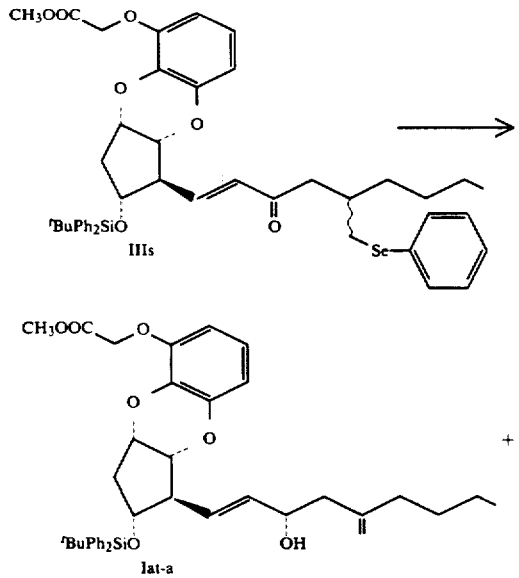

According to the method of Example 5, 800 mg (0.969 mmol) of the enone IIIs (prepared in 40) is reduced to the corresponding allyl alcohol. The crude product is dissolved in a mixture of 10 ml of DME, 30 ml of methanol, and 5 ml of water. To this solution is added 81.4 mg (0.97 mmol) of sodium hydrogencarbonate and 3 ml of aqueous solution of 415 mg (1.94 mmol) of sodium periodate at room temperature and the mixture is stirred overnight. To the reaction mixture is added 5% aqueous solution of sodium thiosulfate and the mixture is extracted with dichloromethane three times. The extract is washed with a saturated aqueous solution of sodium chloride, dried over anhydrous magnesium sulfate, and evaporated under reduced pressure. To a solution of the residue in 40 ml of carbon tetrachloride is added 0.41 ml (2.91 mmol) of diisopropylamine and the mixture is stirred at 60° C. for 1 hour. After cooling to room temperature, ice-water is added, and the mixture is extracted with dichloromethane twice. The extract is washed with 1 N hydrochloric acid, water, a saturated aqueous solution of sodium hydrogencarbonate, and a saturated aqueous solution of sodium chloride, dried over anhydrous magnesium sulfate, and evaporated under reduced pressure. The residue is purified by column chromatography (Merck, Lobar column, size B, two columns; ethyl acetate:-toluene=1:15-1:10) to give the desired dienalcohols, namely, 350 mg of less polar isomer Iat-a as an oil and 155 mg of more polar isomer Ict-a as an oil in 53.7% and 23.8% yield, respectively.

Compound Iat-a

¹H-NMR (200 MHz) δ ppm (CDCl₃): 0.91 (3 H, t, J=7 Hz), 1.04 (9 H, s), 1.22–1.56 (5 H, m), 1.96–2.20 (6 H, m), 2.90 (1 H, q, J=7 Hz), 3.79 (3 H, s), 3.96–4.23 (4 H, m), 4.73 (2 H, s), 4.80 (1 H, s), 4.87 (1 H, s), 5.45 (1 H, dd J=16 Hz, 7 Hz), 5.55 (1 H, dd, J=16 Hz, 5 Hz), 6.47 (1 H, dd, J=8 Hz, 2 Hz), 6.60 (1 H, dd, J=8 Hz, 2 Hz), 6.77 (1 H, t, J=8 Hz), 7.20–7.48 (6 H, m), 7.63–7.73 (4 H, m).

IR ν max (CHCl₃) 3604, 2936, 2864, 1763, 1742, 1643, 1600, 1498, 1476, 1429, 1288, 1114, 969, 904, 822, 612 cm⁻¹.

MS: m/z 670 (M⁺).

Compound Ict-a

¹H-NMR (200 MHz) δ ppm (CDCl₃): 0.92 (3 H, t, J=7 Hz), 1.04 (9 H, s), 1.23–1.60 (5 H, m), 1.97–2.20 (6 H, m), 2.90 (1 H, q, J=7 Hz), 3.80 (3 H, s), 3.95–4.24 (4 H, m), 4.73 (2 H, s), 4.81 (1 H, s), 4.87 (1 H, s), 5.46 (1 H, dd J=16 Hz, 7 Hz), 5.54 (1 H, dd, J=16 Hz, 5 Hz), 6.46 (1 H, dd, J=8 Hz, 2 Hz), 6.60 (1 H, dd, J=8 Hz, 2 Hz), 6.76 (1 H, t, J=8 Hz), 7.20–7.47 (6 H, m), 7.60–7.73 (4 H, m).

IR ν max (CHCl₃) 3604, 2936, 2864, 1764, 1743, 1642, 1600, 1498, 1476, 1429, 1287, 1114, 969, 906, 821, 613 cm⁻¹.

MS: m/z 670 (M⁺).

EXAMPLE 15

Preparation of methyl [(1R,2R,3aS,9aR)-2-t-butyldiphenylsilyloxy-1-[(3S,5S,1E)-3-hydroxy-5-methyl-1,8-nonadien-1-yl]-2,3,3a,9a-tetrahydro-1H-cyclopenta[b][1,4]benzodioxin-5-yl]oxyacetate Iar-a and its stereoisomers Iaq-a, Icq-a, and Icr-a

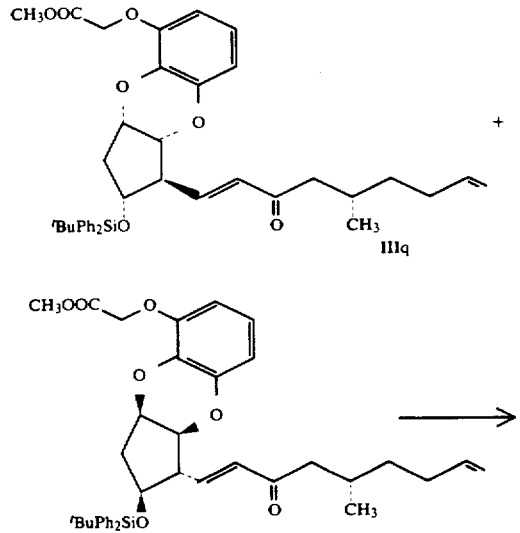

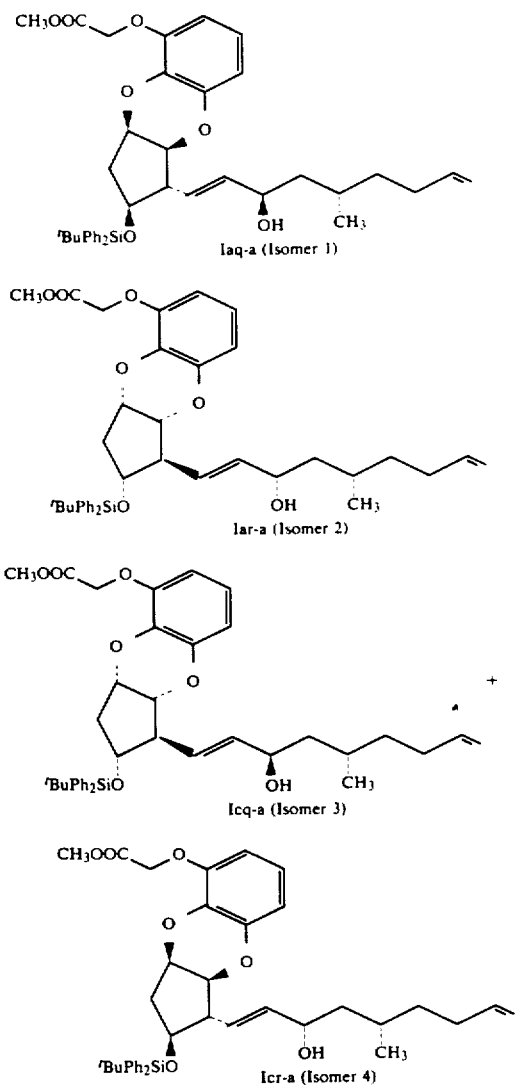

According to the method of Example 5, the enone III q (prepared in (39)) is reduced to give four kinds of stereoisomers Iaq-a, Iar-a, Icq-a, and Icr-a.

Compound Iaq-a (Isomer 1)

Yield 32.9%.

Rf: 0.35 (ethyl acetate:toluene=1:6).

[α]_D −43.2±1.6° (24° C., c=0.53, CHCl₃).

¹H-NMR (200 MHz) δ ppm (CDCl₃): 0.90 (3 H, d, J=7 Hz), 1.04 (9 H, s), 1.00–1.72 (6 H, m), 1.94–2.29 (4 H, m), 2.88 (1 H, q, J=7 Hz), 3.80 (3 H, s), 3.95–4.09 (3 H, m), 4.15–4.23 (1 H, m), 4.73 (2 H, s), 4.88–5.03 (2 H, m), 5.35 (1 H, dd, J=16 Hz, 8 Hz), 5.51 (1 H. dd, J=16 Hz, 6 Hz), 5.70–5.91 (1 H, m), 6.47 (1 H, dd, J=8 Hz, 2 Hz), 6.59 (1 H, dd, J=8 Hz, 2 Hz), 6.76 (1 H, t, J=8 Hz), 7.30–7.50 (6 H, m), 7.60–7.70 (4 H, m).

IR ν max (CHCl₃) 3604, 2936, 2864, 1763, 1742, 1641, 1600, 1498, 1476, 1429, 1288, 1113, 970, 908, 821, 612 cm⁻¹.

MS: m/z 670 (M⁺).

Compound Iar-a (Isomer 2)
Yield 33.1%.
Rf: 0.32 (ethyl acetate:toluene=1:6).
$[\alpha]_D$ +41.7±1.4° (24° C., c=0.60, CHCl$_3$).
$^1$H-NMR (200 MHz) δ ppm (CDCl$_3$): 0.87 (3 H, d, J=7 Hz), 1.04 (9 H, s), 1.00–1.73 (6 H, m), 1.93–2.30 (4 H, m), 2.88 (1 H, q, J=7 Hz), 3.80 (3 H, s), 3.94–4.09 (3 H, m), 4.15–4.24 (1 H, m), 4.73 (2 H, s), 4.88–5.06 (2 H, m), 5.34 (1 H, dd, J=16 Hz, 8 Hz), 5.46 (1 H, dd, J=16 Hz), 6 Hz), 5.70–5.91 (1 H, m), 6.47 (1 H, dd, J=8 Hz, 2 Hz), 6.58 (1 H, dd, J=8 Hz, 2 Hz), 6.76 (1 H, t, J=8 Hz), 7.30–7.50 (6 H, m), 7.60–7.70 (4 H, m).
IR ν max (CHCl$_3$) 3604, 2936, 2864, 1764, 1744, 1641, 1600, 1499, 1476, 1429, 1290, 1113, 970, 908, 822, 612 cm$^{-1}$.
MS: m/z 670 (M+).

Compound Icq-a (Isomer 3)
Yield 10.4%.
Rf: 0.27 (ethyl acetate:toluene=1:6).
$[\alpha]_D$ +45.0±1.6° (24° C., c=0.52, CHCl$_3$).
$^1$H-NMR (200 MHz) δ ppm (CDCl$_3$): 0.90 (3 H, d, J=7 Hz), 1.04 (9 H, s), 1.00–1.75 (6 H, m), 1.94–2.29 (4 H, m), 2.88 (1 H, q, J=7 Hz), 3.79 (3 H, s), 3.94–4.09 (3 H, m), 4.15–4.23 (1 H, m), 4.73 (2 H, s), 4.88–5.30 (2 H, m), 5.36 (1 H, dd, J=16 Hz, 8 Hz), 5.53 (1 H, dd, J=16 Hz, 6 Hz), 5.70–5.91 (1 H, m), 6.47 (1 H, dd, J=8 Hz, 2 Hz), 6.60 (1 H, dd, J=8 Hz, 2 Hz), 6.76 (1 H, t, J=8 Hz), 7.30–7.50 (6 H, m), 7.60–7.70 (4 H, m).
IR ν max (CHCl$_3$) 3608, 2936, 2864, 1764, 1743, 1641, 1600, 1498, 1476, 1429, 1291, 1114, 970, 908, 821, 612 cm$^{-1}$.
MS: m/z 670 (M+).

Compound Icr-a (Isomer 4)
Yield 8.9%.
Rf: 0.23 (ethyl acetate:toluene=1:6).
$[\alpha]_D$ −42.3±1.8° (24° C., c=0.45, CHCl$_3$).
$^1$H-NMR (200 MHz) δ ppm (CDCl$_3$): 0.88 (3 H, d, J=7 Hz), 1.04 (9 H, s), 1.05–1.74 (6 H, m), 1.95–2.27 (4 H, m), 2.88 (1 H, q, J=7 Hz), 3.80 (3 H), s), 3.95–4.09 (3 H, m), 4.15–4.23 (1 H, m), 5.39 (1 H, dd, J=16 Hz, 7 Hz), 5.50 (1 H, dd, J=16 Hz, 6 Hz), 5.70–5.86 (1 H, m), 6.47 (1 H, dd, J=8 Hz, 2 Hz), 6.60 (1 H, dd, J=8 Hz, 2 Hz), 6.77 (1 H, t, J=8 Hz), 7.30–7.50 (6 H, m), 7.60–7.70 (4 H, m).
IR ν max (CHCl$_3$) 3608, 2936, 2864, 1764, 1744, 1641, 1600, 1499, 1476, 1429, 1293, 1114, 970, 909, 821, 612 cm$^{-1}$.
MS: m/z 670 (M+).

EXAMPLE 16

Preparation of methyl [(1R,2R,3aS,9aR)-2-t-butyldiphenylsilyloxy-1-[(3S,5S,1E)-3-hydroxy-5-methyl-1-nonenyl-2,3,3a,9a-tetrahydro-1H-cyclopenta[b][1,4]benzodioxin-5-yl]oxyacetate Iau-a

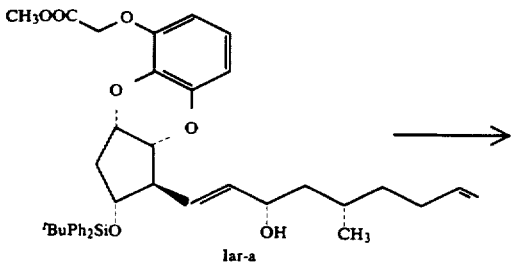
Iar-a

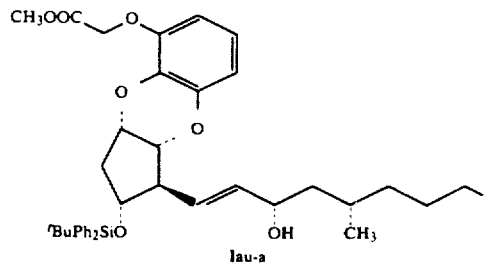
Iau-a

To a solution of 151 mg (0.225 mmol) of diene Iar-a (prepared in Example 15) in 10 ml of dry benzene is added 7.5 mg of 5% palladium-charcoal, and the mixture is stirred at room temperature for 3 hours in a hydrogen atmosphere. The reaction mixture is filtered and the filtrate is evaporated under reduced pressure. The residue is purified by column chromatography on silica gel (Merck, Lobar column, size B, ethyl acetate:toluene=1:15) to give 98 mg of the desired olefin as an oil in 64.9% yield. The $^1$H-NMR, IR, and MS spectra of this optically active compound are completely identical with those of its racemate Iae-a (prepared in Example 4).
$[\alpha]_D$ +40.4±0.8° (24° C., c=1.04, CHCl$_3$).

EXAMPLE 17

Preparation of methyl [(1R*,2S*,3aR*,9aS*)-2-hydroxy-1-[(3R*,1E)-3-hydroxy-1-octenyl]-2,3,3a,9a-tetrahydro-1H-cyclopenta[b][1,4]benzodioxin-5-yl]oxyacetate Iba-a

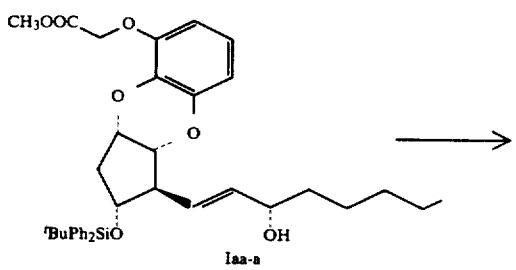
Iaa-a

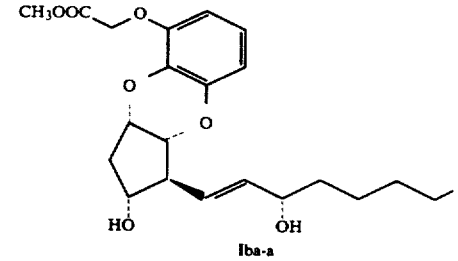
Iba-a

To a solution of 517 mg (0.802 mmol) of the silyl ether Iaa-a (prepared in Examples 1 to 5) in 6 ml of THF is added 1.60 ml (1.60 mmol) of tetra-n-butylammonium fluoride (1M in THF) and the mixture is stirred at room temperature overnight. A saturated aquoues solution of ammonium chloride and 2 ml (2 mmol) of 1N hydrochloric acid is added, and the mixture is extracted with ethyl acetate twice. The extract is washed with water and a saturated aqueous solution of sodium chloride, dried over anhydrous magnesium sulfate, and evaporated under reduced pressure. The residue containing the carboxylic acid generated by saponification of the methyl ester is treated with diazomethane as follows in order to esterify. To this residue dissolved in 6 ml of methanol is added an ethereal solution of diazomethane at 0° C. until the yellow color persists. The reaction mixture is evaporated under reduced pressure and the residue is purified by column chromatography on silica gel (Merck, Lobar column, size B, ethyl acetate:-toluene=2:1) to give 282 mg the desired methyl ester Iba-a, which is crystallized from ethyl acetate-n-hexane to give 260 mg of compound Iba-a as crystals in 80.0% yield.

Mp. 121°~123° C. (ethyl acetate-n-hexane).

$^1$H-NMR: δ (CDCl$_3$+CD$_3$OD) 0.88 (3 H, t, J=6 Hz), 1.10~1.80 (8 H, m), 1.90~2.20 (1 H, m), 2.35~2.81 (2 H, m), 3.82 (3 H, s), 3.8~4.4 (4 H, m), 4.70 (2 H, s), 5.43~5.86 (2 H, m), 6.39~6.87 (3 H, m) ppm.

IR: ν max (CHCl$_3$) 3608, 3008, 2960, 2940, 2864, 1762, 1744, 1600, 1498, 1476, 1125, 970 cm$^{-1}$.

EXAMPLES 18 to 34

In the same manner as described in Example 17, desilylation is carried out to give methyl ester Ib-a. The results are shown in Table 4.

TABLE 4

Ia-a → Ib-a

| Ex. No. | Compd. No. | R₁ | Yd. (%) | Mp. (°C.) | [α]$_D$ | IR νmax(CHCl₃) (cm⁻¹) | ¹H—NMR δ (CDCl₃ + CD₃OD) (ppm) |
|---|---|---|---|---|---|---|---|
| 18 | I bb-a | (cyclohexyl with H) | 73.1 | 124~126 (Ethyl acetate-n-hexane) | | 3608, 3008, 2936, 2860, 1762, 1738, 1600, 1498, 1476, 1243, 1125, 970 | 0.70~2.25 (12H,m), 2.33~2.90 (2H,m), 3.81 (3H,s), 3.70~4.40 (4H,m), 4.70 (2H,s), 5.43~5.83 (2H,m), 6.38~6.90 (3H, m). |
| 19 | I bc-a | (alkynyl chain) | 68.8 | 111~113 (Ethyl acetate-n-hexane) | | 3604, 3529, 3008, 2944, 1762, 1743, 1600, 1498, 1476, 1439, 1271, 1128, 970 | 1.10 (3H,t,J=7Hz), 1.53~1.86 (2H,m), 1.92~2.85 (7H,m), 3.81 (3H,s), 3.83~4.40 (4H,m), 4.70 (2H,s), 5.45~5.93 (2H, m), 6.38~6.90 (3H,m). |
| 20 | I bd-a | (branched chain, Isomer 1) | 70.3 | 106~109 (Ethyl acetate-n-hexane) | | 3604, 3008, 2960, 2932, 2876, 1762, 1743, 1600, 1498, 1476, 1271, 1126, 970 | 0.76~1.03 (6H,m), 1.03~1.80 (9H,m), 1.92~2.22 (1H,m), 2.34~2.68 (2H,m), 3.81 (3H,s), 3.80~4.38 (4H,m), 4.69 (2H,s), 5.46~5.87 (2H,m), 6.38~6.89 (3H,m). |
| 21 | I be-a | (branched chain, Isomer 2) | 53.4 | Powder | | 3604, 3008, 2960, 2932, 2876, 1762, 1743, 1600, 1498, 1476, 1270, 1125, 970 | 0.75~1.05 (6H,m), 1.05~1.80 (9H,m), 1.90~2.21 (1H,m), 2.32~2.86 (2H,m), 3.81 (3H,s), 3.83~4.42 (4H,m), 4.69 (2H,s), 5.38~5.87 (2H,m), 6.38~6.90 (3H,m). |
| 22 | I bf-a | (branched chain) | 75.4 | 112~114 (Ethyl acetate-n-hexane) | | 3608, 3008, 2960, 2936, 2876, 1762, 1743, 1601, 1498, 1476, 1271, 1125, 970 | 0.79~1.02 (6H,m), 1.02~1.80 (7H,m), 1.91~2.21 (1H,m), 2.33~2.82 (2H,m), 3.80 (3H,s), 3.74~4.36 (4H,m), 4.67 (2H,s), 5.39~5.84 (2H,m), 6.36~6.90 (3H,m). |
| 23 | I bg-a | (branched chain) | 59.7 | 77~78 (Ethyl acetate-n-hexane) | | 3612, 3008, 2964, 2976, 1762, 1743, 1600, 1498, 1476, 1271, 1129, 971. | 0.83 (3H,s), 0.87 (3H,s), 0.90 (3H,t,J=7Hz), 1.08~1.47 (6H,m), 1.91~2.21 (1H,m), 2.33~2.86 (2H,m), 3.79 (3H,s), 3.76~4.36 (4H,m), 4.68 (2H,s), 5.45~5.85 (2H,m), 6.36~6.89 (3H,m) |

TABLE 4-continued

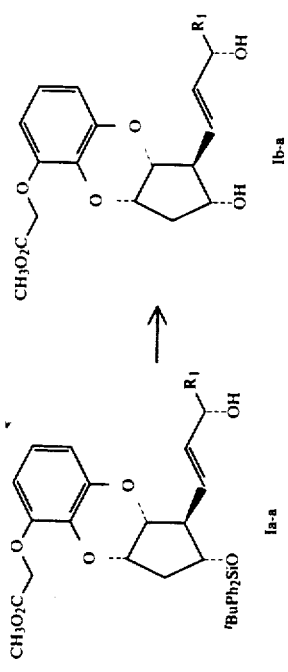

| Ex. No. | Compd. No. | R₁ | Yd. (%) | Mp. (°C.) | [a]_D | IR νmax (CHCl₃) (cm⁻¹) | ¹H—NMR δ (CDCl₃ + CD₃OD) (ppm) |
|---|---|---|---|---|---|---|---|
| 24 | I bh-a | (isopropyl-alkyne) | 93.9 | Powder | | 3608, 3008, 2960, 2928, 1761, 1744, 1600, 1498, 1476, 1271, 1126, 970. | 0.93 and 0.98 (total 3H, each d, J=7Hz), 1.76 (3H, t, J=2.5Hz), 1.53~2.85 (6H, m), 3.78 (3H, s), 3.73~4.36 (4H, m), 4.67 (2H, s), 5.38~5.87 (2H, m), 6.36~6.87 (3H, m) |
| 25 | I bi-a | (cyclopentyl) | 76.2 | 120~121.5 (Ethyl acetate-n-hexane) | | 3608, 3008, 2960, 2872, 1762, 1742, 1600, 1498, 1476, 1270, 1127, 970. | 1.06~2.21 (10H, m), 2.32~2.80 (2H, m), 3.79 (3H, s), 3.76~4.37 (4H, m), 4.67 (2H, s), 5.41~5.85 (2H, m), 6.35~6.88 (3H, m) |
| 26 | I bj-a | (cyclohexyl-H) | 79.8 | 109.5~110.5 (Ethyl acetate-n-hexane) | | 3600, 3424, 3004, 2928, 2856, 1762, 1743, 1600, 1498, 1475, 1271, 1127, 970. | 0.63~1.90 (13H, m), 1.90~2.21 (1H, m), 2.30~2.86 (2H, m), 3.78 (3H, s), 3.77~4.38 (4H, m), 4.67 (2H, s), 5.38~5.87 (2H, m), 6.35~6.89 (3H, m) |
| 27 | I bk-a | (alkenyl, Isomer 1) | 80.1 | 100~103 (Ethyl acetate-n-hexane) | | 3604, 3008, 2960, 2932, 2856, 1762, 1744, 1600, 1498, 1476, 1271, 1126, 969. | 0.92 (3H, d, J=6Hz), 1.05~1.65 (5H, m), 1.61 (3H, s), 1.67 (3H, s), 1.84~2.26 (3H, m), 2.33~2.85 (2H, m), 3.79 (3H, s), 3.79~4.40 (4H, m), 4.68 (2H, s), 4.97~5.29 (1H, m), 5.43~5.88 (2H, m), 6.36~6.90 (3H, m) |
| 28 | I bl-a | (alkenyl, Isomer 2) | 81.6 | 86.6~88.0 (Ethyl acetate-n-hexane) | | 3604, 3420, 3008, 2960, 2932, 2856, 1762, 1742, 1600, 1498, 1462, 1272, 1125, 970. | 0.91 (3H, d, J=6Hz), 1.04~1.65 (5H, m), 1.60 (3H, s), 1.67 (3H, s), 1.80~2.23 (3H, m), 2.32~2.81 (2H, m), 1.79 (3H, s), 3.78~4.40 (4H, m), 4.67 (2H, s), 4.97~5.24 (1H, m), 5.38~5.87 (2H, m), 6.36~6.90 (3H, m) |

TABLE 4-continued

| Ex. No. | Compd. No. | $R_1$ | Yd. (%) | Mp. (°C) | $[\alpha]_D$ | IR $\nu$max (CHCl$_3$) (cm$^{-1}$) | $^1$H—NMR $\delta$ (CDCl$_3$ + CD$_3$OD) (ppm) |
|---|---|---|---|---|---|---|---|
| 29 | Ibm-a | (Isomer-1) phenoxy-sec-butyl | 82.2 | 119–121 Ethyl acetate- n-hexane | | 3604, 3008, 2960, 1762, 1744, 1600, 1496, 1476, 1439, 1238, 1126, 970. | 1.31(3H,d,J=6Hz), 1.68~2.14(3H,m), 2.41~2.73(2H,m), 3.81 (3H,s), 3.87-3.99(1H,m), 4.15~4.40(3H,m), 4.57~4.70(1H,m), 4.70(2H,s), 5.60~5.81(2H,m), 6.45(1H,d,J=8Hz, 2Hz), 6.59 (1H,dd,J=8 Hz), 6.77(1H,t,J=8Hz), 6.88~6.98(3H,m), 7.20~ 7.32(2H,m). |
| 30 | Ibn-a | (Isomer-2) phenoxy-sec-butyl | 69.9 | 90–92 Ethyl acetate- n-hexane | | 3604, 3008, 2960, 1762, 1743, 1600, 1497, 1476, 1440, 1238, 1128, 970. | 1.32(3H,d,J=6Hz), 1.60~1.74(1H,m), 2.00~2.18(2H,m), 2.37~ 2.69(2H,m), 3.81(3H,s), 3.80~3.93(1H,m), 4.05(1H,dd,J=10Hz,3 Hz), 4.18~4.40(2H,m), 4.46~4.61(1H,m), 4.70(2H,s), 5.49~5.68 (2H,m), 6.45(1H,dd,J=8Hz, 2Hz), 6.60 (1H,dd,J=8Hz,2Hz), 6.78 (1H,t,J=8Hz), 6.88~6.99(3H,m), 7.20~7.32(2H,m). |
| 31 | Ibo-a | phenoxymethyl | 79.5 | 99–102 Ethyl acetate- n-hexane | | 3604, 2960, 1762, 1743, 1600, 1498, 1475, 1440, 1243, 1126, 970. | 1.08(3H,d,J=7Hz), 1.34~1.85(2H,m), 2.00~2.25(2H,m), 2.43~ 2.73(2H,m), 3.81(3H,s), 3.75~4.01(3H,m), 4.14~4.30(3H,m), 4.70(2H,s), 5.55~5.80(2H,m), 6.40~6.82(3H,m), 6.86~6.97(3H,m), 7.20~7.34 (2H,m). |
| 32 | Ibt-a | n-hexyl | 62.5 | 81–83 Ethyl acetate- n-hexane | | 3600, 2936, 1763, 1742, 1643, 1600, 1498, 1476, 1271, 1127, 969, 900. | 0.91(3H,t,J=7Hz), 1.23~1.52(4H,m), 2.00~2.15(3H,m), 2.25 (2H,d,J=7Hz), 2.43~2.73(2H,m), 3.82(3H,s), 3.92~4.02(1H,m), 4.17~4.31(3H,m), 4.71(2H,s), 4.82(1H,s), 4.86(1H,s), 5.56~ 5.80(2H,m), 6.45(1H,dd,J=8Hz, 2Hz), 6.60(1H, dd,J=8Hz, 2Hz), 6.78(1H,J=8Hz). |
| 33 | Ibr-a | n-pentenyl | 71.3 | Powder | +60.4±2.0° C=0.50 CHCl$_3$ | 3608, 2932, 1762, 1741, 1600, 1498, 1476, 1271, 1127, 970, 914. | 0.92(3H,J=6Hz), 1.14~1.65(5H,m), 1.96~2.19(3H,m), 2.44~ 2.72(2H,m), 3.82(3H,s), 3.90~4.03(1H,m), 4.10~4.31(3H,m), 4.71(2H,s), 4.88~5.08(2H,m), 5.49~5.93(3H,m), 6.45(1H,d, J=8Hz), 6.59(1H,d,J=8Hz),6.78 (1H,t,J=8H z). |
| 34 | Ibu-a | | 65.1 | 73–75 Ether n-pentane | +65.5±2.2° C=0.49 CHCl$_3$ | Identical with the compound Ibe-a (Ex. 16; racemate) | Identical with the compound Ibe-a (Ex. 16; racemate) |

EXAMPLE 35

Preparation of
[(1R*,2S*,3aR*,9aS*)-2-hydroxy-1-[(3R*,1E)-3-hydroxy-1-octenyl]-2,3,3a,9a-tetrahydro-1H-cyclopenta[b][1,4]benzodioxin-5-yl]oxyacetic acid Iba-b

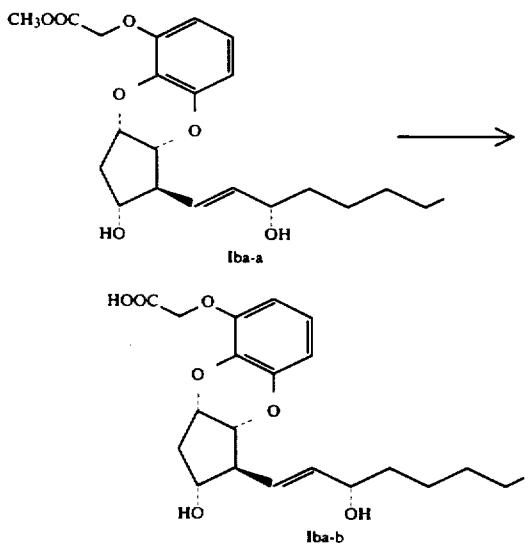

To a solution of 100 mg (0.246 mmol) of the methyl ester Iba-a (prepared in Example 17) in 2 ml of methanol is added 0.50 ml (0.50 mmol) of 1N sodium hydroxide and the mixture is stirred at room temperature for 25 minutes. To the reaction mixture are added 1.0 ml (1.0 mmol) of 1N hydrochloric acid and a saturated aqueous solution of sodium chloride, and the mixture is extracted with chloroform. The extract is washed with a saturated aqueous solution of sodium chloride, dried over anhydrous magnesium sulfate, and evaporated under reduced pressure to give 77 mg of the crude carboxylic acid Iba-b as crystals, which is recrystallized from ethyl acetate-n-hexane to give 68 mg of the crystalline Iba-b in 70.4% yield.

Mp.: 156° C. to 158° C. (ethyl acetate-n-hexane).
$^1$H-NMR: δ (CD$_3$OD) 0.89 (3 H, t, J=6 Hz), 1.10~1.80 (8 H, m), 1.82–2.10 (1 H, m), 2.33~2.75 (2 H, m), 3.86~4.35 (4 H, m), 4.63 (2 H, s), 5.41~5.81 (2 H, m), 6.42~6.83 (3 H, m) ppm.
IR: ν max (KBr) 3404, 2960, 2940, 2864, 1745, 1709, 1615, 1596, 1501, 1477, 1434, 1131, 984, 968, 904, 760, 712 cm$^{-1}$.

EXAMPLES 36 to 46

In the same manner as described in Example 35, the methyl ester is converted into the carboxylic acid Ib-b. The results are shown in Table 5.

TABLE 5

| Ex. No. | Compd. No. | R$_1$ | Yd. (%) | Mp. (°C.) | IR νmax (cm$^{-1}$) | $^1$H—NMR δ (CD$_3$OD) (ppm) |
|---|---|---|---|---|---|---|
| 36 | I bb-b | cyclohexyl-CH$_2$– | 69.3 | 155–157 (Ethyl acetate-n-hexane) | (KBr) 3420, 2924, 2852, 1762, 1732, 1616, 1598, 1500, 1476, 1284, 1254, 1124, 971, 759, 712. | 0.80~2.15 (12H,m), 2.33~2.79 (2H,m), 3.66~4.39 (4H,m), 4.68 (2H,s), 5.40~5.85 (2H,m), 6.42~6.86 (3H,m). |
| 37 | I bc-b | –CH$_2$–C≡C–CH$_2$–CH$_3$ | 67.0 | 127–129 (Ether) | (KBr) 3424, 2976, 2920, 1758, 1720, 1599, 1501, 1476, 1255, 1129, 977, 760, 713. | 1.03 (3H,t,J=7Hz), 1.49~1.82 (2H,m), 1.82~2.80 (7H,m), 3.77~4.40 (4H,m), 4.66 (2H,s), 5.43~5.96 (2H,m), 6.43~6.87 (3H,m) |
| 38 | I bd-b | –CH$_2$–CH(CH$_3$)–CH$_2$–CH$_2$–CH$_2$–CH$_3$ (Isomer 1) | 71.4 | 133–135 (Ethyl acetate-n-hexane) | (KBr) 3424, 2972, 2924, 2856, 1757, 1732, 1615, 1597, 1498, 1475, 1120, 971, 758, 710. | 0.76~1.02 (6H,m), 1.02~2.15 (10H,m), 2.30~2.80 (2H,m), 3.82~4.37 (4H,m), 4.63 (2H,s), 5.41~5.93 (2H,m), 6.41~6.85 (3H,m) |
| 39 | I be-b | –CH$_2$–CH(CH$_3$)–CH$_2$–CH$_2$–CH$_2$–CH$_3$ (Isomer 2) | 73.3 | 110–113 (Ethyl acetate-n-hexane) | (KBr) 3360, 2956, 2928, 2872, 1725, 1599, 1500, 1476, 1129, 971, 759, 709. | 0.80~1.05 (6H,m), 1.05~2.16 (10H,m), 2.33~2.80 (2H,m), 3.85~4.39 (4H,m), 4.64 (2H,s), 5.37~5.90 (2H,m), 6.41~6.85 (3H,m) |

TABLE 5-continued

Ib-a → Ib-b

| Ex. No. | Compd. No. | R₁ | Yd. (%) | Mp. (°C.) | IR νmax (cm⁻¹) | ¹H—NMR δ (CD₃OD) (ppm) |
|---|---|---|---|---|---|---|
| 40 | I bf-b | (isohexyl) | 89.7 | Powder | (KBr) 3388, 2960, 2932, 2876, 1732, 1599, 1506, 1476, 1128, 973, 759, 709. | 0.75~1.05 (6H,m), 1.05~1.80 (7H,m), 1.80~2.13 (1H,m), 2.31 ~2.78 (2H,m), 3.74~4.34 (4H,m), 4.63 (2H,s), 5.39~5.87 (2H,m), 6.40~6.86 (3H,m) |
| 41 | I bg-b | (branched pentyl) | 80.1 | 126~128 (Ethyl acetate-n-hexane) | (KBr) 3464, 2960, 1712, 1597, 1499, 1476, 1264, 1130, 971, 766. | 0.83 (3H,s), 0.86 (3H,s), 0.91 (3H,t,J=6Hz), 1.09~1.50 (6H,m), 1.96 (1H,dd,J=5Hz, 15Hz), 2.33~2.80 (2H,m), 3.69~4.35 (4H,m), 4.63 (2H,s), 5.45~5.87 (2H,m), 6.41~6.86 (3H,m) |
| 42 | I bh-b | (methylpentynyl) | 73.6 | Powder | (KBr) 3420, 2916, 1758, 1729, 1598, 1500, 1475, 1126, 977, 761, 713. | 0.93 and 0.97 (total 3H, each d, J=7Hz), 1.46~2.28 (7H,m), 2.30~2.77 (2H,m), 3.80~4.37 (4H,m), 4.63 (2H,s), 5.36~5.82 (2H,m), 6.39~6.86 (3H,m) |
| 43 | I bi-b | (cyclopentyl) | 81.7 | 148~149 (Ethyl acetate-n-hexane) | (KBr) 3380, 2956, 1734, 1599, 1500, 1477, 1131, 971, 758, 709. | 1.10~2.14 (10H,m), 2.33~2.86 (2H,m), 3.72~4.35 (4H,m), 4.63 (2H,s), 5.60~5.90 (2H,m), 6.40~6.85 (3H,m) |
| 44 | I bj-b | (ethylcyclohexyl) | 81.6 | 129~132 (Ethyl acetate-n-hexane) | (KBr) 3600, 3500, 3388, 2928, 1734, 1703, 1599, 1497, 1476, 1129, 975, 759, 711. | 0.60~2.13 (14H,m), 2.33~2.78 (2H,m), 3.83~4.35 (4H,m), 4.63 (2H,s), 5.38~5.91 (2H,m), 6.41~6.85 (3H,m) |
| 45 | I bk-b | (Isomer 1) | 85.3 | 127~129 (Ethyl acetate-n-hexane) | (KBr) 3388, 2980, 2916, 1733, 1599, 1500, 1477, 1128, 973, 761, 711. | 0.92 (3H,d,J=6Hz), 1.03~1.58 (5H,m), 1.60 (3H,s), 1.66 (3H,s), 1.80~2.18 (3H,m), 2.26~2.78 (2H,m), 3.83~4.35 (4H,m), 4.63 (2H,s), 4.95~5.23 (1H,m), 5.41~5.92 (2H,m), 6.40~6.85 (3H,m) |
| 46 | I bl-b | (Isomer 2) | 81.8 | 101~103 (Ethyl acetate-n-hexane) | (KBr) 3524, 3420, 2920, 1719, 1598, 1499, 1475, 1121, 973, 762, 710. | 0.92 (3H,d,J=6Hz), 1.05~1.56 (5H,m), 1.60 (3H,s), 1.65 (3H,s), 1.82~2.17 (3H,m), 2.30~2.80 (2H,m), 3.80~4.36 (4H,m), 4.63 (2H,s), 4.96~5.25 (1H,m), 5.36~5.90 (2H,m), 6.40~6.86 (3H,m) |

EXAMPLE 47

Preparation of methyl [(1R*,2S*,3aR*,9aS*)-2-hydroxy-1-[(3S*,1E)-3-hydroxy-1-octenyl]-2,3,3a,9a-tetrahydro-1H-cyclopenta[b][1,4]benzodioxin-5-yl]oxyacetate Id-a-a

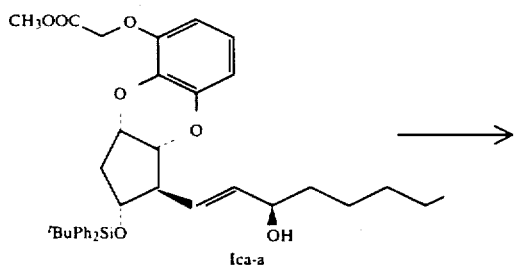
Ica-a

→

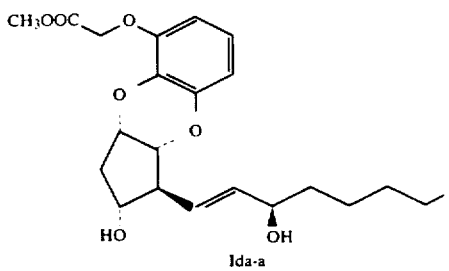
Ida-a

In the same manner as described in Example 17, 252 mg of the silyl ether Ica-a (prepared in Examples 1 and 5) is converted into 110 mg of the desired crystalline methyl ester Ida-a in 69.2% yield.

Mp.: 95°~97° C. (ethyl acetate-n-hexane).

$H$-NMR: δ ($CDCl_3$+$CD_3OD$) 0.87 (3 H, t, J=6 Hz), 1.10~1.80 (8 H, m), 1.92~2.20 (1 H, m), 2.30~2.80 (2 H, m), 3.80 (3 H, s), 3.8~4.3 (4 H, m), 4.68 (2 H, s), 5.50~5.90 (2 H, m), 6.37~6.87 (3 H, m) ppm.

IR: ν max ($CHCl_3$) 3608, 3008, 2960, 2939, 2864, 1763, 1744, 1600, 1498, 1479, 1127, 970 cm$^{-1}$.

EXAMPLES 48 to 63

In the same manner as described in Example 17, the desilylation is carried out to give the methyl ester Id-a. The results are shown in Table 6.

TABLE 6

| Ex. No. | Compd. No. | R₁ | Yield (%) | Mp (°C.) | IR ν max (CHCl₃) (cm⁻¹) | ¹H—NMR δ (CDCl₃ + CD₃OD) (ppm) |
|---|---|---|---|---|---|---|
| 48 | I db-a | H | 71.0 | 121.9~122.2 (Ethyl acetate-n-hexane) | 3608, 3008, 2932, 2860, 1763, 1742, 1600, 1498, 1476, 1270, 1127, 971 | 0.70~2.25 (12H,m), 2.30~2.88 (2H,m), 3.80 (3H,s), 3.80~4.40 (4H,m), 4.69 (2H,s), 5.50~5.90 (2H,m), 6.38~6.88 (3H, m) |
| 49 | I dc-a |  | 70.2 | 62~65 (Ethyl acetate-n-hexane) | 3604, 3528, 3008, 2944, 1762, 1743, 1600, 1498, 1476, 1439, 1271, 1124, 971 | 1.10 (3H,t,J=7Hz), 1.50~1.90 (2H,m), 1.93~2.86 (7H,m), 3.82 (3H,s), 3.80~4.43 (4H,m), 4.70 (2H,s), 5.53~5.97 (2H, m), 6.39~6.91 (3H,m) |
| 50 | I dd-a |  (Isomer 1) | 53.0 | 60~63 (Ethyl acetate-n-hexane) | 3608, 3008, 2960, 2932, 2876, 1762, 1743, 1600, 1498, 1476, 1270, 1125, 970 | 0.76~1.05 (6H,m), 1.05~1.86 (9H,m), 1.93~2.23 (1H,m), 2.32~2.83 (2H,m), 3.80 (3H,s), 3.80~4.37 (4H,m), 4.69 (2H,s), 5.50~5.93 (2H,m), 6.36~6.89 (3H,m) |
| 51 | I de-a |  (Isomer 2) | 73.1 | 65~68 (Ethyl acetate-n-hexane) | 3604, 3008, 2960, 2932, 2876, 1762, 1743, 1600, 1498, 1472, 1271, 1125, 970 | 0.75~1.03 (6H,m), 1.03~1.77 (9H,m), 1.90~2.20 (1H,m), 2.29~2.82 (2H,m), 3.80 (3H,s), 3.80~4.35 (4H,m), 4.68 (2H,s), 5.47~5.93 (2H,m), 6.36~6.88 (3H,m) |
| 52 | I df-a |  | 79.6 | Oil | 3608, 3008, 2960, 2936, 2876, 1762, 1744, 1600, 1497, 1475, 1270, 1126, 970 | 0.78~1.03 (6H,m), 1.03~1.90 (7H,m), 1.93~2.23 (1H,m), 2.31~2.84 (2H,m), 3.80 (3H,s), 3.80~4.39 (4H,m), 4.68 (2H, s), 5.46~5.93 (2H,m), 6.36~6.89 (3H,m) |
| 53 | I dg-a |  | 88.3 | Oil | 3612, 2964, 2932, 2876, 1762, 1744, 1600, 1497, 1475, 1271, 1127, 972 | 0.83 (3H,s), 0.86 (3H,s), 0.87 (3H,t,J=7Hz), 1.06~1.48 (6H,m), 1.92~2.20 (1H,m), 2.31~2.86 (2H,m), 3.78 (3H,s), 3.75~4.39 (4H,m), 4.67 (2H,s), 5.53~5.92 (2H,m), 6.35~6.86 (3H,m) |
| 54 | I dh-a |  | 84.1 | Oil | 3608, 3528, 3008, 2960, 2928, 1762, 1743, 1600, 1497, 1475, 1271, 1126, 970 | 0.95 and 0.98 (total 3H, each d,J=7Hz), 1.75 (3H,t, J=2.5hz), 1.56~2.84 (6H,m), 3.78 (3H,s), 3.80~4.40 (3H, m), 4.67 (2H,s), 5.46~5.94 (2H,m), 6.36~6.87 (3H,m) |

TABLE 6-continued

| Ex. No. | Compd. No. | R₁ | Yield (%) | Mp (°C.) | IR ν max (CHCl₃) (cm⁻¹) | ¹H—NMR δ (CDCl₃ + CD₃OD) (ppm) |
|---|---|---|---|---|---|---|
| 55 | I di-a | cyclopentyl | 75.1 | 101.8~102.4 (Ethyl acetate-n-hexane) | 3608, 3008, 2960, 2872, 1762, 1743, 1600, 1498, 1476, 1271, 1127, 971 | 1.09~2.23 (10H,m), 2.30~2.81 (2H,m), 3.79 (3H,s), 3.76~4.36 (4H,m), 4.67 (2H,s), 5.50~5.91 (2H,m), 6.36~6.89 (3H,m) |
| 56 | I dj-a | cyclohexylmethyl | 74.4 | Powder | 3604, 3008, 2928, 2856, 1763, 1743, 1600, 1498, 1476, 1271, 1126, 970 | 0.63~1.91 (13H,m), 1.92~2.21 (1H,m), 2.30~2.82 (2H,m), 3.79 (3H,s), 3.75~4.36 (4H,m), 4.67 (2H,s), 5.48~5.92 (2H,m), 6.36~6.89 (3H,m) |
| 57 | I dk-a | (Isomer 1) | 53.6 | Powder | 3604, 3008, 2960, 2936, 1761, 1743, 1600, 1498, 1475, 1270, 1126, 970 | 0.92 (3H,d,J=6Hz), 1.06~1.60 (5H,m), 1.66 (3H,s), 1.80~2.25 (3H,m), 2.25~2.83 (2H,m), 3.79 (3H,s), 3.78~4.39 (4H,m), 4.67 (2H,s), 4.96~5.23 (1H,m), 5.50~5.93 (2H,m), 6.36~6.88 (3H,m) |
| 58 | I dl-a | (Isomer 2) | 67.4 | 72~75 (ether-n-pentane) | 3604, 3008, 2960, 2932, 1762, 1742, 1600, 1498, 1475, 1271, 1125, 970 | 0.91 (3H,d,J=6Hz), 1.03~1.63 (5H,m), 1.66 (3H,s), 1.80~2.23 (3H,m), 2.25~2.82 (2H,m), 3.80 (3H,s), 3.75~4.38 (4H,m), 4.67 (2H,s), 4.97~5.22 (1H,m), 5.46~5.93 (2H,m), 6.35~6.90 (3H,m) |
| 59 | I dm-a | (Isomer-1) | 53.6 | 87~89 (Ethyl acetate-n-hexane) | 3608, 3008, 2960, 1762, 1744, 1600, 1497, 1476, 1440, 1241, 1125, 970 | 1.31 (3H,d,J=6Hz), 1.69~2.16 (3H,m), 2.38~2.77 (2H,m), 3.81(3H,s) 3.90~4.03 (1H,m) 4.13~4.44 (3H,m), 4.10~4.40 (3H,m) 4.48~4.65 (1H,m) 5.66~5.85 (2H,m) 6.45 (1H,dd,J=8Hz, 2Hz) 6.60 (1H,dd,J=8Hz, 2Hz) 6.77 (1H,J=8Hz) 6.90~7.00 (3H,m) 7.20~7.36 (2H,m) |
| 60 | I dn-a | (Isomer-2) | 61.4 | 89~90 (Ethyl acetate-n-hexane) | 3604, 3008, 2960, 1764, 1744, 1600, 1497, 1476, 1440, 1237, 1128, 970 | 1.33 (3H,d,J=6Hz) 1.65~1.79 (1H,m) 2.00~2.18 (2H,m) 2.35~2.70 (2H, m) 3.81 (3H,s) 3.80~3.93 (1H,m) 4.10~4.40 (3H,m) 4.48~4.65 (1H,m) 4.70 (2H,s) 5.58~5.76 (2H,m) 6.45 (1H,dd,J=8Hz, 2Hz) 6.57 (1H,dd, J=8Hz, 2Hz) 6.77 (1H,J=8Hz) 6.88~6.99 (3H,m) 7.20~7.40 (2H,m) |

TABLE 6-continued

| Ex. No. | Compd. No. | R₁ | Yield (%) | Mp (°C.) | IR ν max (CHCl₃) (cm⁻¹) | ¹H—NMR δ (CDCl₃ + CD₃OD) (ppm) |
|---|---|---|---|---|---|---|
| 61 | I do-a | (phenoxy-sec-butyl) (Isomer-1) | 85.5 | Powder | 3604, 2960, 1762, 1742 1601, 1499, 1476, 1440 1244, 1125, 970. | 1.08 (3H,d,J=7Hz) 1.37~1.53 (1H,m) 1.70~1.84 (1H,m) 2.04~2.29 (2H, m) 2.39~2.73 (2H,m) 3.81 (3H,s) 3.77~4.04 (3H,m) 4.18~4.32 (3H,m) 4.70 (2H,s) 5.65~5.85 (2H,m) 6.44 (1H,dd,J=8Hz, 2Hz) 6.60 (1H, dd,J=8Hz, 2Hz) 6.76 (1H,t,J=8Hz) 6.86~6.98 (3H,m) 7.21~7.33 (2H,m). |
| 62 | I dp-a | (phenoxy-sec-butyl) (Isomer-2) | 70.9 | 100~101 (Ethyl acetate-n-hexane) | 3604, 2960, 1763, 1743 1601, 1499, 1475, 1441 1242, 1125, 971. | 1.08 (3H,d,J=7Hz) 1.47~1.79 (2H,m) 2.04~2.22 (2H,m) 2.38~2.73 (2H, m) 3.81 (3H,s) 3.77~3.88 (2H,m) 3.90~4.07 (1H,m) (1H,m) 4.10~4.33 (3H,m) 4.70 (2H,s) 5.62~5.85 (2H,m) 6.44 (1H,dd,J=8Hz, 2Hz) 6.60 (1H,dd, J=8Hz, J=8Hz) 6.77 (1H,t, J=8Hz) 6.86~6.97 (3H,m) 7.22~7.35 (2H,m). |
| 63 | I dt-a | (heptenyl) | 51.8 | Powder | 3600, 2940, 1792, 1743 1643, 1601, 1498, 1477 1440, 1127, 969, 902. | 0.91 (3H,t,J=7Hz) 1.22~1.51 (4H,m) 2.00~2.17 (3H,m) 2.26 (2H,d, J=7Hz) 2.39~2.74 (2H,m) 3.81 (3H,s) 3.93~4.05 (1H,m) 4.19~4.34 (3H,m) 4.70 (2H,s) 4.83 (1H,s) 4.86 (1H,s) 5.63~5.87 (2H,m) 6.44 (1H,dd, J=8Hz, 2Hz) 6.60 (1H,dd,J=8Hz, 2Hz) 6.78 (1H,t,J=8Hz) |

EXAMPLE 64

Preparation of methyl
[(1R*,2R*,3aS*,9aR*)-2-tert-butyldiphenylsilyloxy-1-
[(S*)-3-hydroxyoctyl]-2,3,3a,9a-tertahydro-1H-
cyclopenta[b][1,4]benzodioxin-5-yl]oxyacetate Ica-a

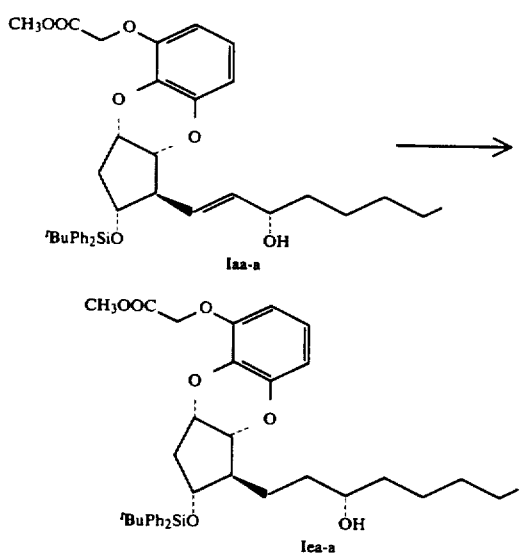

To a solution of 188 mg (0.291 mmol) of the allyl alcohol Iaa-a (prepared in Examples 1 and 5) in 7.5 ml of dry ethanol is added 19 mg of 5% palladium-charcoal and the mixture is stirred at room temperature overnight in a hydrogen atmosphere. The catalyst is removed by filtration and the filtrate is evaporated under reduced pressure. The residue is purified by column chromatography on silica gel (Merck, Lobar column, size A, ethyl acetate:toluene=1:20 to 1:10) to give 156 mg of the desired saturated alcohol Iea-a as an oil in 82.7% yield.

$^1$H-NMR: δ (CDCl$_3$) 0.88 (3 H, t, J=7 Hz), 1.03 (9 H, s), 0.80~1.70 (13 H, m), 1.99~2.40 (3 H, m), 3.30~3.61 (1 H, m), 3.77 (3 H, s), 3.75~4.06 (2 H, m), 4.12~4.37 (1 H, m), 4.70 (2 H, m), 6.40~6.89 (3 H, m), 7.33~7.50 (6 H, m), 7.60~7.80 (4 H, m) ppm.

IR: ν max (CHCl$_3$) 3616, 3008, 2936, 2864, 1763, 1741, 1600, 1498, 1426, 1290, 1110, 822, 611 cm$^{-1}$.

MS: m/z M+ 646.

EXAMPLES 65 to 70

In the same manner as described in Example 64, the reduction is carried out to give a saturated alcohol Ie-a. The results are shown in Table 7.

TABLE 7

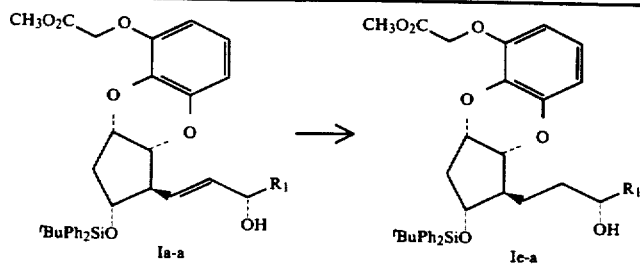

| Ex. No. | Compd. No. | R$_1$ | Yd. (%) | MS (m/z) | IR νmax (CHCl$_3$) (cm$^{-1}$) | $^1$H—NMR δ (CDCl$_3$) (ppm) |
|---|---|---|---|---|---|---|
| 65 | I eb-a | cyclohexyl-H | 70.7 | 658 (M+) | 3608, 3008, 2936, 2860, 1764, 1743, 1600, 1498, 1476, 1292, 1114, 822, 612. | 1.03 (9H,s), 0.73~1.90 (17H,m), 1.99~2.37 (3H,m), 3.00~3.30 (1H,m), 3.74 (3H,s), 3.76~4.01 (2H,m), 4.10~4.32 (1H, m), 4.67 (2H,s), 6.37~6.85 (3H,m), 7.28~7.50 (6H,m), 7.60~7.80 (4H,m) |
| 66 | I ef-a | isohexyl | 83.0 | 660 (M+) | 3612, 3008, 2960, 2936, 2864, 1763, 7.80 1498, 1475, 1289, 1113, 821, 611. | 1.03 (9H,s), 0.85~1.90 (14H,m), 2.00~2.38 (3H,m), 3.10~3.39 (1H,m), 3.75 (3H,s), 3.75~4.14 (2H,m), 4.10~4.32 (1H, m), 4.67 (2H,s), 6.38~6.86 (3H,m), 7.31~7.47 (6H,m), 7.62~7.80 (4H,m) |
| 67 | I ei-a | cyclopentyl | 56.7 | 644 (M+) | 3620, 3008, 2960, 2864, 1764, 1743, 1600, 1498, 1476, 1291, 1113, 822, 611. | 0.73~1.00 (6H,m), 1.03 (9H,s), 1.00~1.30 (12H,m), 2.00~2.33 (3H,m), 3.10~3.43 (1H,m), 3.76 (3H,s), 3.75~4.03 (2H, m), 4.06~4.34 (1H,m), 4.68 (2H,s), 6.39~6.87 (3H,m), 7.31~7.47 (6H,m), 7.60~7.78 (4H,m) |

TABLE 7-continued

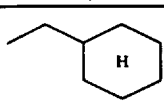

| Ex. No. | Compd. No. | R₁ | Yd. (%) | MS (m/z) | IR νmax (CHCl₃) (cm⁻¹) | ¹H—NMR δ (CDCl₃) (ppm) |
|---|---|---|---|---|---|---|
| 68 | I ej-a | 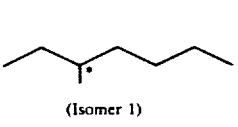 H | 87.2 | 672 (M⁺) | 3600, 3008, 2932, 2860, 1761, 1742, 1742, 1600, 1498, 1475, 1289, 1113, 822, 612. | 1.03 (9H,s), 0.60~1.95 (18H,m), 2.00~2.39 (3H,m), 3.38~3.70 (1H,m), 3.74 (3H,s), 3.70~4.03 (2H,m), 4.09~4.33 (1H, m), 4.67 (2H,s), 6.38~6.86 (3H,m), 7.30~7.50 (6H,m), 7.59~7.80 (4H,m) |
| 69 | I ed-a | 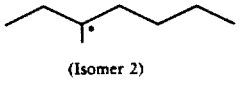 (Isomer 1) | 90.7 | 674 (M⁺) | 3608, 2936, 2864, 1763, 1741, 1600, 1498, 1475, 1429, 1289, 1113, 822, 611. | 0.84 (3H,d,J=6Hz) 0.90 (3H,t, J=7Hz) 1.04 (9H,s) 1.10~1.65 (13H,m) 2.05~2.27 (3H,m) 3.40~3.60 (1H,m) 3.79 (3H,s) 3.76~3.98 (2H,m) 4.17~4.28 (1H,m) 4.71 (2H,s) 6.47 (1H,dd,J=8Hz, 2Hz) 6.63 (1H,dd,J=8Hz, 2Hz) 6.76 (1H,t,J=8Hz) 7.30~7.48 (6H,m) 7.64~7.75 (4H,m). |
| 70 | I ee-a | (Isomer 2) | 91.0 | 674 (M⁺) | 3616, 2936, 2864, 1764, 1743, 1600, 1498, 1475, 1428, 1291, 1114, 821, 612. | 0.87 (3H,d,J=7Hz) 0.90 (3H,t, J=7Hz) 1.04 (9H,s) 1.10~1.60 (13H,m) 2.06~2.29 (3H,m) 3.44~3.60 (1H,m) 3.78 (3H,s) 3.80~3.96 (2H,m) 4.18~4.27 (1H,m) 4.71 (2H,s) 6.47 (1H,dd,J=8Hz, 2Hz) 6.63 (1H,dd,J=8Hz, 2Hz) 6.76 (1H,t,J=8Hz) 7.31~7.48 (6H,m) 7.64~7.75 (4H,m). |

EXAMPLE 71

Preparation of methyl[(1R*,2S*,3aR*,9aS*)-2-hydroxy-1-[(R*)-3-hydroxyoctyl]-2,3,3a,9a-tertahydro-1H-cyclopenta[b][1,4]benzodioxin-5-oxyacetate Ifa-a

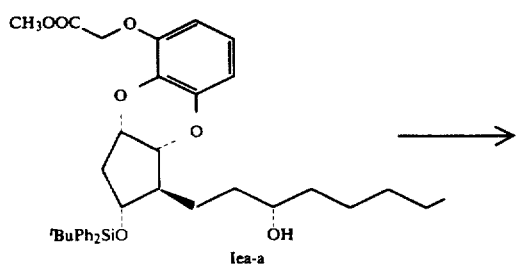

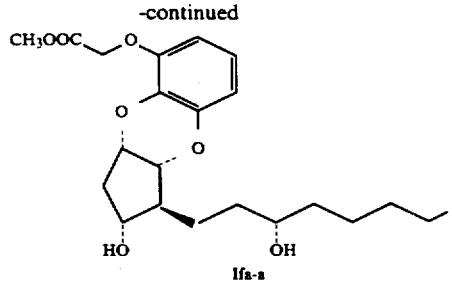

In the same manner as described in Example 17, 186 mg (0.287 mmol) of the silyl ether Iea-a (prepared in Example 64) is converted into 80 mg of the desired crystalline methyl ether Ifa-a in 68.2% yield.

Mp.: 69°~70° C. (ethyl acetate-n-hexane).

¹H-NMR: δ (CDCl₃+CD₃OD) 0.87 (3 H, t, J=7 Hz), 1.10~2.18 (14 H, m), 2.22~2.57 (1 H, m), 3.42~3.69 (1 H, m), 3.79 (3 H, s), 3.73~4.17 (2 H, m), 4.19~4.35 (1 H, m), 4.67 (2 H, s), 6.34~6.87 (3 H, m) ppm.

IR: ν max (CHCl₃) 3616, 3008, 2936, 2864, 1762, 1743, 1600, 1498, 1476, 1286, 1124 cm⁻¹.

EXAMPLES 72 to 77

In the same manner as described in Example 17, the desilylation is carried out to give methyl ester If-a. The results are shown in Table 8.

TABLE 8

Ie-a → If-a (Structures shown: Ie-a has CH₃O₂C-substituted diphenyl ether linked to cyclopentane ring bearing 'BuPh₂SiO and a side chain with R₁ and OH; If-a is the corresponding compound with OH replacing the silyl ether)

| Ex. No. | Compd. No. | R₁ | Yield (%) | Mp (°C) | IR ν max (CHCl₃) (cm⁻¹) | ¹H—NMR δ (CDCl₃ + CD₃OD) (ppm) |
|---|---|---|---|---|---|---|
| 72 | Ifb-a | (cyclohexyl) | 80.6 | 84.5–86.5 (ethyl acetate-n-hexane) | 3616, 3008, 2932, 2860, 1763, 1742, 1498, 1476, 1270, 1125 | 0.75–2.62 (18H,m), 3.20–3.50 (1H,m), 3.81 (3H,s), 3.77–4.40 (3H,m), 4.70 (2H,s), 6.39–6.90 (3H,m) |
| 73 | Iff-a | (isobutyl/isopentyl branched chain) | 92.6 | Powder | 3612, 3008, 2936, 2864, 1764, 1744, 1600, 1497, 1475, 1286, 1126 | 0.75–1.05 (6H,m), 1.05–2.56 (14H,m), 3.28–3.55 (1H,m), 3.78 (3H,s), 3.77–4.36 (3H,m), 4.67 (2H,s), 6.35–6.90 (3H,m) |
| 74 | Ifi-a | (cyclopentyl) | 86.8 | 82–84 (ethyl acetate-n-hexane) | 3621, 3008, 2952, 2872, 1762, 1741, 1599, 1497, 1475, 1271, 1125. | 1.03–2.20 (15H,m), 2.22–2.57 (1H,m), 3.20–3.50 (1H,m), 3.78 (3H,s), 3.75–4.35 (3H,m), 4.67 (2H,s), 6.35–6.87 (3H,m) |
| 75 | Ifj-a | (cyclohexyl) | 77.0 | 56–60 (ethyl acetate-n-hexane) | 3612, 3008, 2928, 2856, 1762, 1742, 1599, 1497, 1475, 1287, 1126. | 0.60–2.60 (20H,m), 3.77 (3H,s), 3.51–4.40 (4H,m), 4.66 (2H,s), 6.35–6.89 (3H,m) |
| 76 | Ifd-a | (branched alkyl, Isomer 1) | 57.7 | Oil | 3616, 2932, 2864, 1762, 1743, 1600, 1497, 1475, 1286, 1124. | 0.87 (3H,t,J=6Hz) 0.89 (3H,d,J=7Hz) 1.08–1.80 (13H,m) 1.88–2.16 (2H,m) 2.36 (1H,ddd,J=15Hz, 8Hz, 5Hz( 3.60–3.75 (1H,m) 3.81 (3H,s) 3.80–3.94 (1H,m) 4.09 (1H,dd,J=8Hz, 3Hz) 4.23–4.33 (1H,m) 4.70 (2H,s) 6.44 (1H,dd,J=8Hz, 2Hz) 6.61 (1H,dd,J=8Hz, 2Hz) 6.77 (1H,t,J=8Hz). |
| 77 | Ife-a | (branched alkyl, Isomer 2) | 64.0 | Oil | 3616, 2932, 2864, 1762, 1744, 1599, 1497, 1475, 1287, 1124. | 0.89 (3H,d,J=6Hz) 0.89 (3H,t,J=7Hz) 1.00–1.80 (13H,m) 1.90–2.14 (2H,m) 2.36 (1H,ddd,J=15Hz, 8Hz, 5Hz) 3.60–3.74 (1H,m) 3.81 (3H,s) 3.80–3.94 (1H,m) 4.09 (1H,dd,J=8Hz, 3Hz) 4.25–4.33 (1H,m) 4.70 (2H,s) 6.44 (1H,dd,J=8Hz, 2Hz) 6.61 (1H,dd,J=8Hz, 2Hz) 6.77 (1H,t, J=8Hz). |

EXAMPLE 78

Preparation of
[(1R*,2S*,3aR*,9aS*)-2-hydroxy-1-[(R*)-3-hydroxyoctyl]-2,3,3a,9a-tetrahydro-1H-cyclopenta[b][1,4]benzodioxin-5-yl]oxyacetic acid Ifa-b

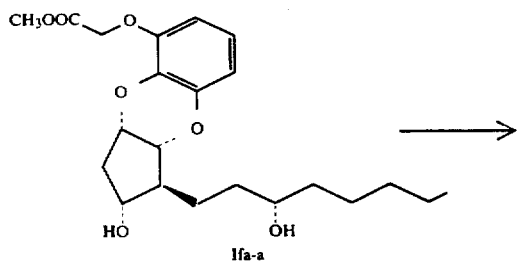

In the same manner as described in Examples 35, 45 mg (0.110 mmol) of the methyl ester Ifa-a is converted into 34 mg of the desired carboxylic acid Ifa-b in 78.2% yield.

Mp.: 111°~113° C. (ethyl acetate-n-hexane).

$^1$H-NMR: δ (CD$_3$OD) 0.89 (3 H, t, J=6 Hz), 1.08~2.16 (14 H, m), 2.23~2.62 (1 H, m), 3.38~3.67 (1 H, m), 3.73~4.00 (1 H, m), 4.00~4.32 (2 H, m), 4.63 (2 H, s), 6.40~6.85 (3 H, m) ppm.

IR: ν max(KBr) 3504, 3368, 2928, 2856, 1716, 1615, 1598, 1500, 1476, 1279, 1134, 759, 713 cm$^{-1}$.

EXAMPLES 79 to 82

In the same manner as described in Example 35, the carboxylic acid If-b is prepared. The results are shown in Table 9.

TABLE 9

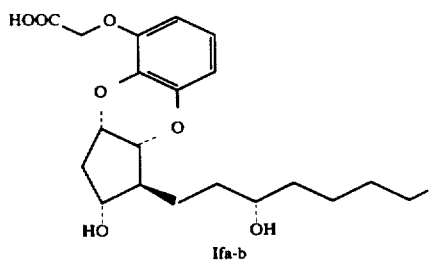

| Ex. No. | Compd. No. | R$_1$ | Yd. (%) | Mp. (°C.) | IR νmax (cm$^{-1}$) | $^1$H—NMR δ (CD$_3$OD) (ppm) |
|---|---|---|---|---|---|---|
| 79 | I fb-b | cyclohexylmethyl | 72.0 | 78~80 (ethyl acetate) | (KBr) 3472, 2944, 2928, 1735, 1598, 1497, 1476, 1436, 1248, 1128, 980, 759, 712 | 1.77~2.13(17H,m), 2.23~2.60(1H,m), 3.25~3.40(1H,m), 3.73~4.30(3H,m), 4.63(2H,s), 6.40~6.84(3H,m) |
| 80 | I ff-b | isohexyl | 79.2 | Oil | (CHCl$_3$) 3456, 2936, 2864, 1742, 1600, 1497, 1476, 1283, 1123 | 0.76~1.05(6H,m), 1.05~2.17(13H,m), 2.25~2.60(1H,m), 3.30~3.56(1H,m), 3.75~4.34(3H,m), 4.63(2H,s), 6.41~6.86(3H,m) |
| 81 | I fi-b | cyclopentylmethyl | 71.3 | 84~87 (ethyl acetate-n-hexane) | (KBr) 3376, 2952, 1756, 1741, 1700, 1597, 1502, 1475, 1255, 1131, 759, 711. | 1.00~2.13(15H,m), 2.23~2.61(1H,m), 3.25~3.47(1H,m), 3.72~4.30(3H,m), 4.63(2H,s), 6.40~6.83(3H,m) |
| 82 | I fj-b | cyclohexylethyl | 37.0 | 136.4~137.5 (ethyl acetate-n-hexane) | (KBr) 3468, 2920, 2852, 1747, 1598, 1498, 1476, 1201, 1122, 760, 710. | 0.70~2.62(20H,m), 3.46~4.32(4H,m), 4.63(2H,m), 6.40~6.86(3H,m) |

EXAMPLE 83

Preparation of (9-anthryl)methyl [(1R*,2S*,3aR*,9aS*)-2-hydroxy-1-[(3R*,1E)-3-hydroxy-1-octenyl]-2,3,3a,9a-tetrahydro-1H-cyclopenta[b][1,4]benzodioxin-5-yl]oxyacetate Iba-a'

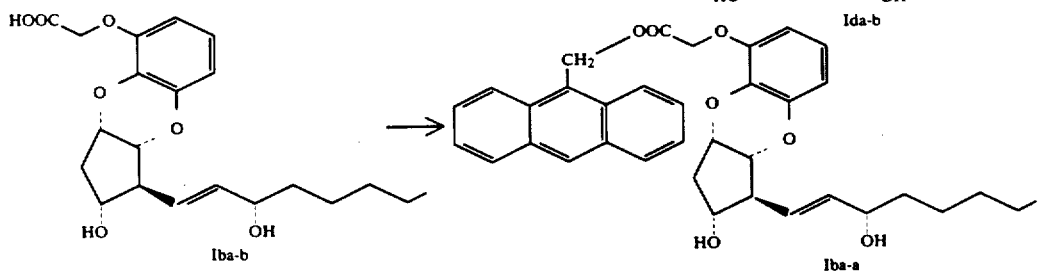

To a solution of 25 mg (0.064 mmol) of the carboxylic acid Iba-a (prepared in Example 35) in 0.5 ml of methanol is added dropwise 1.5 ml (0.138 mmol) of (9-anthryl)diazomethane (2% in ethyl acetate) at room temperature. Then, the mixture is stirred for 45 minutes and the precipitated crystals are collected by filtration to give 27 mg of the crude (9-anthryl)methyl ester Iba-a'. The crude crystals are dissolved in pyridine and insoluble material is removed by filtration. The filtrate is concentrated and the residue is recrystallized from ethyl acetate to give 19 mg of the crystalline Iba-a' in 51.2% yield.

Mp.: 185°~188° C. (ethyl acetate).

$^1$H-NMR: δ (pyridine-d$_5$) 0.83 (3 H, t, J=6 Hz), 1.02~1.93 (8 H, m), 2.12~2.70 (2 H, m), 2.97~3.31 (1 H, m), 4.10~4.50 (4 H, m), 4.95 (2 H, s), 5.86~6.30 (2 H, m), 6.41 (2 H, s), 6.65~6.83 (3 H, m), 7.38~7.70 (4 H, m), 8.00~8.17 (2 H, m), 8.35~8.66 (3 H, m) ppm.

IR: ν max (KBr) 3592, 3428, 2928, 2856, 1741, 1596, 1499, 1475, 1207, 1124, 973, 723 cm$^{-1}$.

EXAMPLE 84

Preparation of [(1R*,2S*,3aR*,9aS*)-2-hydroxy-1-[(3S*,1E)-3-hydroxy-1-octenyl]-2,3,3a,9a-tetrahydro-1H-cyclopenta[b][1,4]benzodioxin-5-yl]oxyacetic acid Ida-b

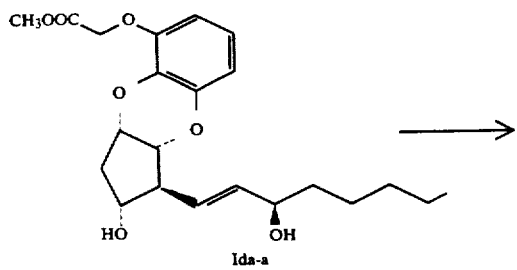

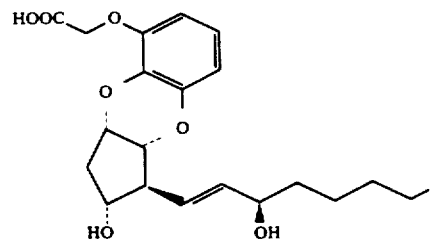

In the same manner as described in Example 35, 110 mg of the methyl ester Ida-a (prepared in Example 47) is converted into 80 mg of the desired carboxylic acid Ida-b in 75.5% yield.

Mp.: 109.5°~111.5° C. (ethyl acetate - h-hexane).

$^1$H-NMR: δ (CD$_3$OD) 0.89 (3 H, t, J=6 Hz), 1.10~1.70 (8 H, m), 1.82~2.12 (1 H, m), 2.30~2.77 (2 H, m), 3.85~4.43 (4 H, m), 4.65 (2 H, s), 5.47~5.93 (2 H, m), 6.43~6.85 (3 H, m) ppm.

IR: ν max (KBr) 3496, 3241, 2932, 2852, 1708, 1617, 1596, 1502, 1476, 1129, 978, 758, 702 cm$^{-1}$.

EXAMPLES 85 to 86

In the same manner as described in Example 35, the carboxylic acid Id-b is prepared. The results are shown in Table 10.

TABLE 10

| Ex. No. | Compd. No. | R₁ | Yd. (%) | Mp. (°C.) | IR ν max (KBr) (cm$^{-1}$) | $^1$H—NMR δ (CD$_3$OD) (ppm) |
|---|---|---|---|---|---|---|
| 85 | I db-b | (cyclohexylmethyl) | 45.4 | 119.5–121.5 (ethyl acetate-n-hexane) | 3532, 3244, 2928, 2852, 1761, 1745, 1597, 1495, 1475, 1125, 972, 759, 711 | 0.70–2.12 (12H,m), 2.30–2.78 (2H,m), 3.69–4.40 (4H,m), 4.63 (2H,s), 5.43–5.87 (2H,m), 6.42–6.82 (3H,m). |
| 86 | I dc-b | (pent-2-ynyl) | 82.9 | Powder | 3488, 2924, 1615, 1596, 1500, 1476, 1129, 972, 760, 713 | 1.07 (3H,t,J=7Hz), 1.50–1.82 (2H,m), 1.82–2.76 (7H,m), 3.75–4.38 (4H,m), (2H,s), 5.44–5.95 (2H,m), 6.41–6.86 (3H,m). |

EFFECT OF THE INVENTION

The compounds of the present invention are benzodioxane PGI$_2$ analogues which are long acting and chemically stable.

The compounds of the present invention, as well as PGI$_2$, have cytoprotective effect and/or platelet aggregation inhibitory activity. Especially, the compounds of the present invention have a potent cytoprotective effect and are expected to be used as drugs for treating peptic ulcer. The antiulcer activity of the representative compounds of the present invention against hydrochloric acid ethanol-induced gastric ulcer is examined in the following test.

The Effect Against Hydrochloric Acid Ethanol-Induced Gastric Ulcer

To male JCL-SD rats or CRJ-SD rats (weight: 220 g to 260 g) which have been fasted for 24 hours is administered orally 1 ml of 150 mM hydrochloric acid-60% ethanol. After an hour, the stomachs are excised. The ulcer size is determined by measuring the length of each lesion using a stereoscopic microscope and the sum of individual lesion length is expressed as lesion index. The vehicle (1% to 10% ethanol) and the test compounds are administered orally 30 minutes before the hydrochloric acid-ethanol administration. The percent suppression is calculated from the lesion indexes of treated versus non-treated animals. The results are shown in Table 11.

TABLE II

| Compd. No.* | Dose μg/kg | P.S. (%) | Compd. No.* | Dose μg/kg | P.S. (%) |
|---|---|---|---|---|---|
| (No. 1) (JCL-SD rats) | | | | | |
| Iba-a | 30 | 36 | Ibe-b | 30 | 80 |
| Ibb-a | 30 | 63 | Ibf-b | 30 | 18 |
| Ibc-a | 30 | 29 | Ibh-b | 30 | 58 |
| Ibd-a | 30 | 91 | Ibk-b | 30 | 70 |
| Ibe-a | 30 | 96 | Ibl-b | 30 | 83 |
| Ibf-a | 30 | 50 | Ida-a | 30 | 37 |
| Ibg-a | 30 | 15 | Idd-a | 30 | 32 |
| Ibh-a | 30 | 61 | Ide-a | 30 | 37 |
| Ibi-a | 30 | 41 | Ida-b | 100 | 19 |
| Ibk-a | 30 | 81 | Idb-b | 30 | 25 |
| Ibl-a | 30 | 64 | Ifa-a | 30 | 27 |
| Ibm-a | 30 | 58 | Ifb-a | 30 | 78 |
| Ibo-a | 30 | 63 | Ifd-a | 30 | 66 |
| Iba-b | 100 | 30 | Ife-a | 30 | 91 |
| Ibb-b | 30 | 25 | Iff-a | 30 | 57 |
| Ibc-b | 30 | 14 | Ifi-a | 30 | 52 |
| Ibd-b | 30 | 74 | Ifj-a | 30 | 25 |
| | | | Ifb-b | 30 | 75 |
| (No. 2) (CRJ-SD rats) | | | | | |
| Ibe-a | 30 | 99 | Ibr-a | 30 | 96 |
| Ibu-a | 30 | 98 | | | |

*Each compound number corresponds to the number used in the example.
P.S. means Percent Suppression.
Reference Compound Hoe-892
Dose 300 μg/Kg, Percent Suppression (P.S.) 28%

The compounds of the present invention potently inhibit hydrochloric acid ethanol-induced gastric ulcer.

It is expected that the pharmacological effect of the compounds of the present invention can be applied as useful curative medicine. For example, they have a cytoprotective effect, as well as PG I$_2$, and are expected to be used as curative medicine for ulcerous lesions in esophagus, stomach, duodenum, or anastomosed parts of the stomach.

The compounds of the present invention can be administered orally or parenterally. For oral administration, the compounds are prepared in dosage forms such as tablets, capsules, pills, granules, subtilized granule, solution, or emulsions and for parenteral administration, in forms such as suppositories or injections, e.g., intravenous, intramuscular or subcutaneous injection. In preparing the pharmaceutical preparation of the compounds adequate carriers and fillers are selected from conventionally used carriers and fillers.

The compounds of the present invention may be administered in a dose of about 0.1 to 100 mg per day for an adult.

What we claim is:

1. A compound of the formula:

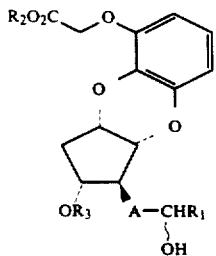

wherein $R_1$ is alkyl, alkenyl, alkynyl, cycloalkyl, cycloalkylalkyl, or phenoxyalkyl; $R_2$ is hydrogen, lower alkyl, or lower alkyl substituted by (1) one or more phenyl which may have one or more substituents selected from the group consisting of methyl, methoxy, bromo and nitro or (2) anthryl; $R_3$ is hydrogen or a hydroxy-protecting group; A is ethylene or vinylene; and the wavy line indicates α or β configuration or their mixture; or a pharmaceutically acceptable salt thereof.

2. A compound claimed in claim 1, wherein $R_2$ is hydrogen or lower alkyl; and $R_3$ is hydrogen.

3. A compound claimed in claim 1, wherein $R_1$ is alkyl, alkenyl or cycloalkyl; $R_2$ is hydrogen or lower alkyl; and $R_3$ is hydrogen.

4. A compound claimed in claim 1, namely, methyl [2-hydroxy-1-(3-hydroxy-5-methyl-1-nonenyl)-2,3,3a,-9a-tetrahydro-1H-cyclopenta[b][1,4]benzodioxin-5-yl]oxyacetate.

5. A compound claimed in claim 1, namely, methyl [2-hydroxy-1-(3-hydroxy-5-methyl-1,8-nonadienyl)-2,3,3a,9a-tetrahydro-1H-cyclopenta[b][1,4]benzodioxin-5-yl]oxyacetate.

6. A compound claimed in claim 1, namely, methyl [2-hydroxy-1-(3-hydroxy-5,9-dimethyl-1,8-decadienyl)-2,3,3a,9a-tetrahydro-1H-cyclopenta[b][1,4]benzodioxin-5-yl]oxyacetate.

7. A compound claimed in claim 1, namely, methyl [2-hydroxy-1-(3-cyclohexyl-3-hydroxypropyl)-2,3,3a,-9a-tetrahydro-1H-cyclopenta[b][1,4]benzodioxin-5-yl]oxyacetate.

8. A compound claimed in claim 1, namely, [2-hydroxy-1-(3-hydroxy-5-methyl-1-nonenyl)-2,3,3a,9a-tetrahydro-1H-cyclopenta[b][1,4]benzodioxin-5-yl]oxyacetic acid.

9. A compound claimed in claim 1, namely, [2-hydroxy-1-(3-hydroxy-5,9-dimethyl-1,8-decadienyl)-2,3,3a,9a-tetrahydro-1H-cyclopenta[b][1,4]benzodioxin-5-yl]oxyacetic acid.